(12) United States Patent
Wurtzel et al.

(10) Patent No.: US 10,059,974 B2
(45) Date of Patent: Aug. 28, 2018

(54) CELLS AND METHODS FOR PRODUCING LUTEIN

(71) Applicant: The Research Foundation of the City University of New York, New York, NY (US)

(72) Inventors: Eleanore T Wurtzel, Great Neck, NY (US); Rena Quinlan, Bronx, NY (US)

( * ) Notice: Subject to any disclaimer, the term of this patent is extended or adjusted under 35 U.S.C. 154(b) by 249 days.

(21) Appl. No.: 14/377,041

(22) PCT Filed: Feb. 5, 2013

(86) PCT No.: PCT/US2013/024746
§ 371 (c)(1),
(2) Date: Aug. 6, 2014

(87) PCT Pub. No.: WO2013/119552
PCT Pub. Date: Aug. 15, 2013

(65) Prior Publication Data
US 2015/0005534 A1    Jan. 1, 2015

Related U.S. Application Data

(60) Provisional application No. 61/595,529, filed on Feb. 6, 2012.

(51) Int. Cl.
| | |
|---|---|
| *C12N 9/90* | (2006.01) |
| *C12P 23/00* | (2006.01) |
| *C07C 403/24* | (2006.01) |
| *C12N 9/02* | (2006.01) |
| *C12N 9/10* | (2006.01) |
| *A23L 33/135* | (2016.01) |
| *A23L 33/145* | (2016.01) |

(52) U.S. Cl.
CPC ............ *C12P 23/00* (2013.01); *A23L 33/135* (2016.08); *A23L 33/145* (2016.08); *C07C 403/24* (2013.01); *C12N 9/001* (2013.01); *C12N 9/0073* (2013.01); *C12N 9/0083* (2013.01); *C12N 9/1085* (2013.01); *C12N 9/90* (2013.01); *C12Y 103/05006* (2013.01); *C12Y 114/13129* (2013.01); *C12Y 114/99045* (2013.01); *C12Y 205/01029* (2013.01); *C12Y 205/01032* (2013.01); *C12Y 505/01018* (2013.01); *C12Y 505/01019* (2013.01)

(58) Field of Classification Search
CPC ...... C12P 23/00; A61K 31/045; C12N 15/825
See application file for complete search history.

(56) References Cited

PUBLICATIONS

Relevant references: The evolution and function of carotenoid hydroxylases in *Arabidopsis*. Kim et al Plant Cell Physiol. Mar. 2009;50(3):463-79.*

\* cited by examiner

*Primary Examiner* — Kagnew H Gebreyesus
(74) *Attorney, Agent, or Firm* — Hoffmann & Baron, LLP

(57) ABSTRACT

Provided herein are recombinant cells (e.g., recombinant bacteria or plant, insect, mammalian, and yeast cells) containing a nucleic acid encoding a CYP97A protein or a nucleic acid encoding a CYP97B protein; a nucleic acid encoding a CYP97C protein; a nucleic acid encoding a geranylgeranyl pyrophosphate synthase protein; a nucleic acid encoding a phytoene synthase protein; a nucleic acid encoding a phytoene desaturase protein; a nucleic acid encoding a lycopene β-cyclase protein; and a nucleic acid encoding a lycopene ε-cyclase protein. Also provided are methods of producing lutein that include culturing these recombinant cells (e.g., recombinant bacteria and yeast cells), and methods of generating these recombinant cells (e.g., recombinant bacteria and yeast cells). Also provided is lutein produced by these methods, and pharmaceutical compositions, food supplements, food products, and cosmetic compositions that contain lutein produced by these methods.

24 Claims, 22 Drawing Sheets
Specification includes a Sequence Listing.

|  | Block 1 | Block 2 | Block 3 | |
|---|---|---|---|---|
| CYP97B1 P. sativum | LLEG-EGRDGQKSVE | DVLPGGHKEDKDGYTI | LVQNKNEEVEKNAGFDPSRSPGALY | Clan B |
| CYP97B2 G. max | LLEG-EGYDGPESIE | DVLPGKEKEEKDGYTI | LVQNKNELESNAGLDPSRSPGALY | |
| CYP97B3 A. thaliana | LIEKETSSGEDTIE | STLPGGHGGENEGHKV | LSTEESKEIEGWAGFDPSRSPGALY | |
| CYP97B4 O. sativa | LIER--GEKGEKYTI | DKLPXGHKGAKEGYET | SVPKEESIEGWAGFDPSRSPGAMY | |
| ST012891 L. esculentum | PDAI-------SGSA | DVLPG-------NYFV | DLE------------------GPV | Clan C |
| TC109838 M. truncatula | ADAV-------NGPA | DELPG-------SYKI | DLD------------------GPV | |
| CYP97C1 A. thaliana | PYAE-------DGSA | DILPG-------NYKV | DID------------------GAI | |
| CYP97C2 O. sativa | TSAL-------SGKP | DVLPG-------NYKI | DLE------------------GPV | |
| TC69886 H. vulgare | TYAL-------SGEP | DVLPG-------NYKV | DLE------------------GPI | |
| CYP97A3 A. thaliana | ANAL-------KGEE | DILG--------EYPI | PLE------------------GPN | Clan A |
| TC101515 M. truncatula | TAAS-------DGED | DVLG--------EYPT | PLD------------------GPN | |
| CYP97A4 O. sativa | KAAS-------DGED | DMLG--------EYPI | PLD------------------GPN | |
| TC76166 H. vulgare | KAAS-------DGED | DMLG--------EYPI | PLD------------------GPN | |

Figure 3

|  | Oxygen-binding | Heme-binding |
|---|---|---|
| CYP97C | | |
| CYP97C2 (*O. sativa*) | AGHETT | FSGGPRKCVG |
| CYP97C1 (*A. thaliana*) | AGHETT | FSGGPRKCVG |
| TC69886 (*H. vulgare*) | AGHETT | FSGGPRKCVG |
| CYP97A | | |
| CYP97A4 (*O. sativa*) | AGHETS | FGGGPRKCVG |
| CYP97A3 (*A. thaliana*) | AGHETS | FGGGPRKCVG |
| TC76166 (*H. vulgare*) | AGHETS | FGGGPRKCVG |

Figure 4

```
O.SATIVA      MSSATSVSAFAMAATSSAAAAAPPPCRLLGSGQAHLRLPPSAAAAAASARRRLLLRCAAS
H.VULGARE     ------------------------------------------------------------
A.THALIANA    ---------------------------MAMAFPLSYTPTITVKPVTYSRRSNFVVFSSSSN
M.TRANCATULA  ------------------------------------------------------------

O.SATIVA      GGNGKGGGGDGSGSDPVLEERRRRRQAELAARIASGEFTAQGPAWIAPLAVGLAKLGPPG
H.VULGARE     ------------------------------------------------------------
A.THALIANA    GRDPLEENSVPNGVKSLEKLQEEKRRAELSARIASGAFTVRKSSFPSTVKNGLSKIGIPS
M.TRANCATULA  ------------------FLKRKDELNCLLKLPQVNSRVKQESGLPSILKKSLSNLGVSN

O.SATIVA      ELAAALLT-KVAGGGGPEIPQAVGSMSAVTGQAFFIPLYDLFLTYGGIFRLNFGPKSFLI
H.VULGARE     ------------------------------------------------------------
A.THALIANA    NVLDFMFDWTGSDQDYPKVPEAKGSIQAVRNEAFFIPLYELFLTYGGIFRLTFGPKSFLI
M.TRANCATULA  EILEFLFG------LYPKIPEAKGSISAIRSEAFFIPLYELYITYGGIFRLNFGPKSFLI

O.SATIVA      VSDPAIAKHILRDNSKAYSKGILAEILEFVMGTGLIPADGEIWRVRRRAIVPAMHQKYVT
H.VULGARE     --------------------------------MGTGLIPADGEVWRVRRRAIVPALHQKYVT
A.THALIANA    VSDPSIAKHILKDNAKAYSKGILAEILDFVMGKGLIPADGEIWRRRRRAIVPALHQKYVA
M.TRANCATULA  VSDPAIAKHILKDNSKAYSKGILAEILDFVMGKGLIPADGEIWRVRRRTIVPALHLKFVA
                                              **.********:** ***:****:* *:*:

O.SATIVA      AMISLFGYASDRLCQKLDKAATDGEDVEMESLFSRLTLDVIGKAVFNYDFDSLSYDNGIV
H.VULGARE     AMIGLFGNASDRLCQKLDKAASDGEDVEMESLFSRLTLDVIGKAVFNYDFDSLSYDNGIV
A.THALIANA    AMISLFGEASDRLCQKLDAAALKGEEVEMESLFSRLTLDIIGKAVFNYDFDSLTNDTGVI
M.TRANCATULA  AMIGLFGQATDRLCQKLDTAASDGEDVEMESLFSRLTLDVIGKAVFNYDFDSLSNDTGII
              ***.***.*:******** **..**:************:.**************: *.*::

O.SATIVA      EAVYVTLREAEMRSTSPIPTWEIPIWKDISPRQKKVNEALALINKTLDELIDICKRLVEE
H.VULGARE     EAVYVTLREAEMRSTSPIPTWEIPIWKDISPRQRKVNEALALINNILDELIATCKRMVDE
A.THALIANA    EAVYTVLREAEDRSVSPIPVWDIPIWKDISPRQRKVATSLKLINDTLDDLIATCKRMVEE
M.TRANCATULA  EAVYTVLREAEDRSISPIPVWDLPIWKDISPRQRKVTAALKLVNDTLNNLIAICKRMVDE
              ****..*****.** ****.*::***********:**   :* *:*. *::** ***:*:*

O.SATIVA      EDLQFHEEYMNEQDP-ITLHFLLASGDDVSSKQLRDDLMTMLIAGHETSAAVLTWTFYLL
H.VULGARE     EDLQFHEEYMNEKDP-SILHFLLASGDDVSSKQLRDDLMTMLIAGHETSAAVLTWTFYLL
A.THALIANA    EELQFHEEYMNERDP-SILHFLLASGDDVSSKQLRDDLMTMLIAGHETSAAVLTWTFYLL
M.TRANCATULA  EELQFHEEYMNEQDPSISFTFLLASGDDVTSKQLRDDLMTMLIAGHETSAAVLTWTFYLL
              *:**********:**   :  ********:******************************

O.SATIVA      SKYPNVMAKLQDEADTVLGDRLPTIEDVKKLKYTTRVINESLRLYPQPPVLIRRSIEEDM
H.VULGARE     SKYPNVMSKLQAEADAVLGDGLPTIDDVKKLKYTTRVINESLRLYPQPPVLIRRSLEDDM
A.THALIANA    TTEPSVVAKLQEEVDSVIGDRFPTIQDMKKLKYTTRVMNESLRLYPQPPVLIRRSIDNDI
M.TRANCATULA  SKEPSVMSKLQEEVDSVLGDRFPTIEDMKKLKYTTRVINESLRLYPQPPVLIRRSIEDDV
              :.  *.*::*** *.*:*:** :***:*:*******:*****************:::*:

O.SATIVA      LGGYPIGRGEDIFISVWNLHHCPKHWDGADVFNPERWPLDGPNPNETNQNFSYLPFGGGP
H.VULGARE     LGEYPIGKGEDIFISIWNLHRCPKHWDDADVFNPERWPLDGPNPNETNQKFSYLPFGGGP
A.THALIANA    LGEYPIKRGEDIFISVWNLHRSPLHWDDAEKFNPERWPLDGPNPNETNQNFSYLPFGGGP
M.TRANCATULA  LGEYPIKRGEDIFISVWNLHRSPTLWNDADKFEPERWPLDGPNPNETNQGFKYLPFGGGP
              ** *** :*******:****: *  *::*: * *****************  *:********

O.SATIVA      RKCVGDMFATFETVVATAMLVRRFDFQMAPGAPPVEMTTGATIHTTEGLKMTVTRRTKPP
H.VULGARE     RKCVGDMFATFETVVATAMLVKRFDFQMAPGAPPVEMTTGATIHTTKGLNMTVTRRIKPP
A.THALIANA    RKCIGDMFASFENVVAIAMLIRRFNFQIAPGAPPVKMTTGATIHTTEGLKLTVTKRTKPL
M.TRANCATULA  RKCIGDMFASYEVVALAMLVRRFNFQMAVGAPPVVMTTGATIHTTQGLNMTVTRRIKPP
              ***:*****::* ***  ***::**:**:* *****.********::***:****:* **

O.SATIVA      VIPNLEMKVISDSPENMSTTTSMPVSAASIASGEDQQGQVSATRI
H.VULGARE     VIPNLEMKIVSDPEGSTSSTASVAVSTASIASGEGQQVEVSTSQV
A.THALIANA    DIPSVPILPMDTSRDEVSSALS-----------------------
M.TRANCATULA  IVPSLQMSTLEVDPSVSISDKTEEIGQKDQVYQAQ----------
              :*.::: ::    ::
```

Figure 5

```
P.sativum     -MVAAPISTVKLTDANLHTRFHSSSSSTPSTLSLPLSLHFHFSSHSKRFSSIRCQSVNGE
G.MAX         MSVDTSSTLSTVTDANLHSRFHSR---------LVPFTHHFSLSQPKRISSIRCQSINTD
A.THALIANA    -MVAAMAFPAAATYPTHFQGGALHLGRTDHCLFGFYPQTISSVNSRRASVSIKCQSTEPK
O.SATIVA      -MAITAATAAAAATPHPWQADASP----------RRHAACPALRGRRRLPVVRCQSSSVD
                 . :       : .                              : ::***  ..

P.sativum     KRKQSSRNVFDNASNLLTSLLSGANLGSMPIAEGAVTDLFDRPLFFSLYDWFLEHGSVYK
G.MAX         KKK-SSRNLLGNASNLLTDLLSGGSIGSMPIAEGAVSDLLGRPLFFSLYDWFLEHGAVYK
A.THALIANA    TNG----NILDNASNLLTNFLSGGSLGSMPTAEGSVSDLFGKPLFLSLYDWFLEHGGIYK
O.SATIVA      DKPKSKRGLLDNASNLLTNLLSGGSLGAMPVAEGAVTDLFGRPLFFSLYDWFLEHGSVYK
                   .:: .:******.:***..:*:** ***:*:**:.:***:*********.:**

P.sativum     LAFGPKAFVVVSDPIVARHILRENAFSYDKGVLADILEPIMGKGLIPADLETWKQRRRVI
G.MAX         LAFGPKAFVVVSDPIVARHILRENAFSYDKGVLADILEPIMGKGLIPADLDTWKQRRRVI
A.THALIANA    LAFGPKAFVVISDPIIARHVLRENAFSYDKGVLAEILEPIMGKGLIPADLDTWKLRRRAI
O.SATIVA      LAFGPKAFVVVSDPIVARHILRENAFCYDKGVLAEILKPIMGKGLIPADLDTWKQRRKVI
              **********:****:***:****** *******:**:*:********:*** **:.*

P.sativum     APGFHTSYLEAMVQLFTSCSERTVLKVNELLEG-EGRDGQKSVELDLEAEFSNLALEIIG
G.MAX         APAFHNSYLEAMVKIFTTCSERTILKFNKLLEG-EGYDGPDSIELDLEAEFSSLALDIIG
A.THALIANA    TPAFHKLYLEAMVKVFSDCSEKMILKSEKLIREKETSSGEDTIELDLEAEFSSLALDIIG
O.SATIVA      TPGFHALFIDAMVGVFTKCSERTIFKLEELIER--GEHGEKYTIVDLEAEFSNLALDIIG
              :*.**    :::*** :*: ***: ::* ::*:.     * .  :*******.***:***

P.sativum     LGVFNYDFGSVTNESPVIKAVYGTLFEAEHRSTFYIPYWKFPLARWIVPRQRKFQDDLKV
G.MAX         LGVFNYDFGSVTKESPVIKAVYGTLFEAEHRSTFYIPYWKIPLARWIVPRQRKFQDDLKV
A.THALIANA    LSVFNYDFGSVTKESPVIKAVYGTLFEAEHRSTFYFPYWNFPPARWIVPRQRKFQSDLKI
O.SATIVA      LGVFNFDFDSVTKESPVIKAVYGTLFEAEHRSTFYIPYWNLPLTRWIVPRQRKFHSDLKV
              *.***:**.***:*********************:***::* :**********:.***:

P.sativum     INTCLDGLIRNAKESRQETDVEKLQQRDYSNLKDASLLRFLVDMRGVDVDDRQLRDDLMT
G.MAX         INTCLDGLIRNAKESRQETDVEKLQQRDYLNLKDASLLRFLVDMRGADVDDRQLRDDLMT
A.THALIANA    INDCLDGLIQNAKETRQETDVEKLQERDYTNLKDASLLRFLVDMRGVDIDDRQLRDDLMT
O.SATIVA      INDCLDSLIKNAKETRQEADVEKLQQRDYSSLKDASLLRFLVDMRGADVDDRQLRDDLMT
              ** ***.**:****:***:******:*** .*************.*:************

P.sativum     MLIAGHETTAAVLTWAVFLLAQNPDKMKKAQAEVDLVLGMGKPTFELLKKLEYIRLIVVE
G.MAX         MLIAGHETTAAVLTWAVFLLAQNPSKMKKAQAEVDLVLGTGRPTFESLKELQYIRLIVVE
A.THALIANA    MLIAGHETTAAVLTWAVFLLSQNPEKIRKAQAEIDAVLGQGPPTYESMKKLEYIRLIVVE
O.SATIVA      MLIAGHETTAAVLTWSVFLLAQNPSKMRKAQAEVDSVLSNETINVDQLKKLEYIRLIIVE
              ***************.****.*** .*:*****:* **.     . : :*:*:*****:**

P.sativum     TLRLYPQPPLLIRRSLKPDVLPGGHKGDKDGYTIPAGTDVFISVYNLHRSPYFWDRPNDF
G.MAX         ALRLYPQPPLLIRRSLKSDVLPGGHKGEKDGYAIPAGTDVFISVYNLHRSPYFWDRPDDF
A.THALIANA    VLRLFPQPPLLIRRTLKPETLPGGHKGEKEGHKVPKGTDIFISVYNLHRSPYFWDNPHDF
O.SATIVA      ALRLYPQPPLLIRRALRPDKLPGGYNGAKEGYEIPAGTDIFLSIYNLHRSPYFWDRPDEF
               .***:*********:*:*.:  ****::* *:*:  :*  ***:*:*:***********.*.:*

P.sativum     EPERFLVQNNNEEVEGWAGFDPSRSPGALYPNEIISDFAFLPFGGGPRKCVGDQFALMES
G.MAX         EPERFLVQNKNEEIEGWAGLDPSRSPGALYPNEVISDFAFLPFGGGPRKCVGDQFALMES
A.THALIANA    EPERFLRTKESNGIEGWAGFDPSRSPGALYPNEIIADFAFLPFGGGPRKCIGDQFALMES
O.SATIVA      EPERFSVPKKDESIEGWAGFDPDRSPGAMYPNEILADFAFLPFGGGPRKCVGDQFALLES
              *****       ::.:  :******.**.*****:::************:*******.**

P.sativum     TVALVCCYRISMWN----------------------------
G.MAX         TVALTMLLQNFDVELKGTPESVELVTGATIHTKNGMWCRLKKRSNLR
A.THALIANA    TVALAMLFQKFDVELRGTPESVELVSGATIHAKNGMWCKLKRRSK--
O.SATIVA      TVALALLLQKFDVELRGSPDEVEMVTGATIHTKSGLWCRVRRRT---
              ****.  :  :
```

Figure 6

```
L.ESCULENTUM    ---FTITMPISVTISSFSLLTNPHHRTTVLRPKNPLQNRSQLTIKSSIDNKKPPSTKPTS
M.TRUNCATULA    --MPSCSCSCSCSLPLSHLSLSSFSKTPLPQKRYPLHPR---ILTKSSTNKNPETTKSTS
A.THALIANA      ------MESSLFSPSSSSYSSLFTAKPTRLLSPKPKFTFSIRSSIEKPKPKLETNSSKSQS
O.SATIVA        MAAAAAAAVPCVPFLCPPPPPLVSPRLRRGHVRLRLRPPRSSGGGGGGGAGGDEPPITTS
H.VULGARE       ------MPAAAFASALASPPPPWAPRPSPRHASLRLPPPRSSGGGGD--------KPTTS
                                                  :               .  *

L.ESCULENTUM    WVSPDWLTKLTRSLTL--GQNDDSNIPIASAELDDVSELLGGALFLPLYRWMNLYGPIYR
M.TRUNCATULA    WVSPDWLTSLSKSLTT--SKNDDSNIPIASAKLDDVSDLLGGALFLPLFKWMNEYGPIYR
A.THALIANA      WVSPDWLTTLTRTLSS--GKNDESGIPIANAKLDDVADLLGGALFLPLYKWMNEYGPIYR
O.SATIVA        WVSPDWLTALSRSVATRLGGGDDSGIPVASAKLDDVRDLLGGALFLPLFKWFREEGPVYR
H.VULGARE       WVSPDWLTSLSRSVLG--RGNDDSGIPVASAKLDDVQDLLGGALFLPLFKWFREEGPVYR
                ********  *::::           .*:*.**:*.*:****  :**********::*:.   **:**

L.ESCULENTUM    LAAGPRNFVIVSDPAIAKHVLKNYG-KYGKGLVAEVSEFLFGSGFAIAEGPLWTARRRAV
M.TRUNCATULA    LAAGPRNFVVVSDPAIAKHVLKNYG-KYGKGLVAEVSEFLFGDGFAIAEGPLWTARRRAV
A.THALIANA      LAAGPRNFVIVSDPAIAKHVLRNYP-KYAKGLVAEVSEFLFGSGFAIAEGPLWTARRRAV
O.SATIVA        LAAGPRDLVVVSDPAVARHVLRGYGSRYEKGLVAEVSEFLFGSGFAIAEGALWTVRRRSV
H.VULGARE       LAAGPRDFVIVSDPAVAKHVLRGYGTRYEKGLVAEVSEFLFGSGFAIAEGALWTVRRRAV
                ******::*:*****:*:***:.*   :* **************.******.***.***:*

L.ESCULENTUM    VPSLHKKYLSVIVDRVFCRCAERMVEKLLPDAISGSAVNMEAKFSQLTLDVIGLALFNYN
M.TRUNCATULA    VPSLHKRYLSIMVDRVFCKCAERLVEKLQADAVNGTAVNMEDKFSQLTLDVIGLSVFNYN
A.THALIANA      VPSLHRRYLSVIVERVFCKCAERLVEKLQPYAEDGSAVNMEAKFSQMTLDVIGLSLFNYN
O.SATIVA        VPSLHKRFLSVMVDRVFCKCAERLVEKLETSALSGKPVNMEARFSQMTLDVIGLSLFNYN
H.VULGARE       VPSLHKRFLSVMVDKVFCKCAERLVEKLETYALSGEPVNMEARFSQMTLDVIGLSLFNYN
                *****::::**::*::****:****:****.  .  *  .* .****:****:*******::****

L.ESCULENTUM    FDSLTTDSPVIDAVYTALKEAELRSTDLLPYWQIKALCKFIPRQIKAENAVSLIRQTVEE
M.TRUNCATULA    FDALNSDSPVIEAVYTALKEAEARSTDLLPYWKIDFLCKIIPRQIKAENAVTVIRKTVED
A.THALIANA      FDSLTTDSPVIEAVYTALKEAELRSTDLLPYWKIDALCKIVPRQVKAEKAVTLIRETVED
O.SATIVA        FDSLTSDSPVIDAVYTALKEAELRSTDLLPYWKIDLLCKIVPRQIKAEKAVNIIRNTVED
H.VULGARE       FDSLTSDSPVIDAVYTALKEAEARSTDLLPYWQIDLLCKIVPRQIKAEKAVNTIRNTVEE
                **:*.:*****:*********  *********:*  :***:.  ***::***:***.**  **:***:

L.ESCULENTUM    LIAKCREIVETEGERINEDEYVNDRDPSILRFLLASREEVSSVQLRDDLLSMLVAGHETT
M.TRUNCATULA    LIEQCKEIVESEGERIDADEYVNDADPSILRFLLASREEVSSVQLRDDLLSMLVAGHETT
A.THALIANA      LIAKCKEIVEREGERINDEEYVNDADPSILRFLLASREEVSSVQLRDDLLSMLVAGHETT
O.SATIVA        LITKCKKIVDAENEQIEGEEYVNEADPSILRFLLASREEVTSVQLRDDLLSMLVAGHETT
H.VULGARE       LIIKCKAIVDAENEQIEGEEYVNEADPSILVFLLASREEVSSLQLRDDLLSMLVAGHETT
                ** :*: **: *.*:*: :****:******:*:*********:*:********************

L.ESCULENTUM    GSVLTWTAYLLSKDPSSLEKAHEEVDRVLGGRSPTYEDMKNLKFLTRCITESLRLYPHPP
M.TRUNCATULA    GSVLTWTLYLLSKDSSSLAKAQEEVDRVLQGRRPTYEDMKDLKFLNRCIIESLRLYPHPP
A.THALIANA      GSVLTWTLYLLSKNSSALRKAQEEVDRVLEGRNPAFEDIKELKYITRCINESMRLYPHPP
O.SATIVA        GSVLTWTIYLLSKDPAALRRAQAEVDRVLQGRPRYEDLKELKYLMRCINESMRLYPHPP
H.VULGARE       GSVLTWTIYLLSKDPVALRRAQDEVDRVLQGRLPRYEDVKELKYLMRCINESMRLYPHPP
                *******  *****.  :*  :*: ****** ** *  :**:*:**::  *** **:*******

L.ESCULENTUM    VLIRRAQVADVLPGNYKVNVGQDIMISVYNIHHSSEVWDRAEEEFDPERFDLEGPVPNETN
M.TRUNCATULA    VLIRRSQIPDELPGDYKIDAGQDIMISVYNIHHSSKVWDRAEEEFLPERFDLDGPVPNETN
A.THALIANA      VLIRRAQVPDILPGNYKVNTGQDIMISVYNIHRSSEVWEKAEEEFLPERFDIDGAIPNETN
O.SATIVA        VLIRRAIVDDVLPGNYKIKAGQDIMISVYNIHRSPEVWDKADDFIPERFDLEGPVPNETN
H.VULGARE       VLIRRALVDDVLPGNYKVKTGQDIMISVYNIHRSPEVWDRADEFIPDRFDLEGPIPNESN
                *****: : *  ***:**::..************:* :** :::*:.*  *:***::*****:*

L.ESCULENTUM    TDFRFIPFSGGPRKCVGDQFALLEATIALAIFVQNFSFELIPDQTISMTTGATIHTTNGL
M.TRUNCATULA    TDFRFIPFRGGPRKGVGDQFALLEATVAFAVFLQHMNFELVPDQNIGMTTGATIHTTNGL
A.THALIANA      TDFKFIPFSGGPRKCVGDQFALMEAIVALAVFLQRLNVELVPDQTISMTTGATIHTTNGL
O.SATIVA        TEYRFIPFSGGPRKCVGDQFALLEAIVALAVVLQKMDIELVPDQKINMTTGATIHTTNGL
H.VULGARE       TDFRFIPFSGGPRKCVGDQFALLEAIVALAIVIQKMDVQLVADQKISMTTGATIHTTNGL
                *:::**** ***** ******::**:**:*:: *.  :*::*  :  :.**.**********
```

Figure 7A

```
L.ESCULENTUM    YMKVKQREKASVLAAAPILSQEKVILILTLYTSLVDYENHHYCVMSYFFSGIIAFFSFFL
M.TRUNCATULA    YMKMSQRLKKLTSTFFSHRWQNLLANNYQQD-----------------------------
A.THALIANA      YMKVSQR-----------------------------------------------------
O.SATIVA        YMNVSLRKVDREPDFALSGSR---------------------------------------
H.VULGARE       YMNVXLRKVEQEADLALSPSG---------------------------------------
                **::   *

L.ESCULENTUM    YIRIYCASFKNNLSMSTRYRGRVRTDQTLCAQDPTLKIYCMYCCISEYAFVVGKKKK
M.TRUNCATULA    --------------------------------------------------------
A.THALIANA      --------------------------------------------------------
O.SATIVA        --------------------------------------------------------
H.VULGARE       --------------------------------------------------------
```

Figure 7B

**CLUSTAL 2.1 Multiple Sequence Alignment of geranylgeranyl pyrophosphate synthase (CrtE) from *A. thaliana*, *O. sativa*, and *C. roseus*.**

```
A. thaliana    --MASVTLGSWIVVHHHNHHHPSSILTKSRSRSCPITLTKPISFRSKRTVSSSSSIVSSS
C. roseus      ------------MRSNLCHPLKNQLPISFFLSGTIRKPIFSCSRLSISAIITKEQTQEES
O. sativa      MHVLAQSTAVAKVAASGCLRRSPNPSVTFQRSPSLLLSPAACRRRCRRGCSVSVDVRCSL
                           :             .  .    .    .      .        . .

A. thaliana    VVTKEDNLRQSEP------SSFDFMSYIITKAELVNKALDSAVPLREPLKIHEAMSYSLL
C. roseus      ESKSKKEVAFSSS------SSFDFKAYMIGKANSVNKALEDAVLVREPLKIHESMRYSLL
O. sativa      GAMVTPELNGGDVGVGVGGGSFDFQRYLSARADAVHDALDRAMPRGFPERLCESMRYSVL
                 ::   ..         .****  *:  :*: *:.**:  *:     *  ::  *:* **:*

A. thaliana    AGGKRVRPVLCIAACELVGGEESTAMPARCAVEMIHTMSLIHDDLPCMDNDDLRRGKPTN
C. roseus      AGGKRVRPMLCIAACELFGGTESVAMPSACAVEMIHTMSLMHDDLPCMDNDDLRRGKPTN
O. sativa      AGGKRVRPVLALAACELVGGDAAAATPVACAVEMIHTMSLIHDDMPCMDDDALRRGRPSN
               ********:*.:*****.**   :.*  * ************:***:****:*: ****:*:*

A. thaliana    HKVFGEDVAVLAGDALLSFSFEHLASATSSDVVSPVRVVRAVGELAKAIGTEGLVAGQVV
C. roseus      HKVFGEDVAVLAGDALLAFAFEHIATATKG--VSSERIVRVVGELAKCIGSEGLVAGQVV
O. sativa      HVAFGEFTALLAGDALHALAFEHVARGCGDHGVPADRTLRAVAELGSASGTGGVAAGQVA
               * .***  .*:******  ::.**:*  .  .    *.. *  :*.*.**...  *:  *:.****.

A. thaliana    DISSEGLDLNDVGLEHLEFIHLHKTAALLEASAVLGAIVGGGSDDEIERLRKFARCIGLL
C. roseus      DVCSEG--IADVGLEHLEFIHIHKTAALLEGSVVLGAIVGGANDEQISKLRKFARCIGLL
O. sativa      DKESEG---LPVSLAMLEYIHVHKTARLLEAAAVSGAIVGGGADAEVERVRRYARCVGLL
               *   ***       *.*   **:**:****  ***.:.*  ******. *  ::.::*:***:***

A. thaliana    FQVVDDILDVTKSSKELGKTAGKDLIADKLTYPKIMGLEKSREFAEKLNREARDQLLGFD
C. roseus      FQVVDDILDVTKSSQELGKTAGKDLVADKVTYPKLLGIDKSREFAEKLNREAQEQLAEFD
O. sativa      FQVVDDVLDMTSTSEQLGKTAGKDVEADKATYPKLLGVDKAREYAADLLAMAEAELDGFD
               ******:**:*.:*.:.:*******:  *** :***::*::*:**:**:.*   *:  :*  **

A. thaliana    SDKVAPLLALANYIAYRQN
C. roseus      PEKAAPLIALANYIAYRDN
O. sativa      AERAAPLRHLARFIAYRQH
                .: *** ** .*****..
                ..                  ..
```

Figure 8

CLUSTAL 2.1 Multiple Sequence Alignment of phytoene synthase (CrtB) from A. thaliana, O. sativa, and P. trichocarpa.

```
A. thaliana     MSSSVAVLWVATSSLNPDPMNNCGLVRVLESSRLFSPCQNQRLNKGKKKQIPTWSSSFVR
O. sativa       MAAITLLRSASLPGLSDALARDAAAVQHVCSSYLPNNKEKKRRWILCSLKYACLGVDPAP
P. trichocarpa  ------------------------------------------------------------

A. thaliana     NRSRRIGVVSSSLVASPSGEIALSSEEKVYNVVLKQAALVNKQLRSSSYDLDVKKPQDVV
O. sativa       GEIARTSPVYSSLTVTPAGEAVISSEQKVYDVVLKQAALLKRHLRPQPHTIPIVPKDLDL
P. trichocarpa  ------------------------------------------------------------

A. thaliana     LPGSLSLLVGEAYDRCGEVCAEYPKTFYLGTLLMTPERRKAIWAIYVWCRRTDELVDGPN
O. sativa       PR----NGLKQAYHRCGEICEEYAKTFYLGTMLMTEDRRRAIWAIYVWCRRTDELVDGPN
P. trichocarpa  --------LEEAYERCRNICAEYAKTFYLGTRLMTEERQKATWAIYVWCRRTDELVDGPN
                  :**.**  ::*  **.****** ***  :*::* ******************

A. thaliana     ASHITPMALDRWEARLEDLFRGRPFDMLAALADTVARYPVDIQPFRDMIEGMRMDLKKS
O. sativa       ASHITPSALDRWEKRLDDLFTGRPYDMLDAALSDTISKFPIDIQPFRDMIEGMRSDLRKT
P. trichocarpa  AVLMSTAVLDRWEERLQDIFDGRPYDMLDAALTDTISKFPLDIKPFRDMIEGMRMDTRKF
                *  ::. .***** **:*:* ***:****:**::::*:**:********** * :*

A. thaliana     RYQNFDDLYLYCYYVAGTVGLMSVPVMGIDPKSKATTESVYNAALALGIANQLTNILRDV
O. sativa       RYKNFDELYMYCYYVAGTVGLMSVPVMGIAPESKATTESVYSAALALGIANQLTNILRDV
P. trichocarpa  RYDNFQELYLYCYYVAGTVGLMSVPVMGIAAESEASAQSIYNAALYLGIGNQLTNILRDV
                **.**::**:****************** .:*:*::*:*.***  ***.*********

A. thaliana     GEDARRGRVYLPQDELAQAGLSDEDIFAGKVTDKWRNFMKMQLKRARMFFDEAEKGVTEL
O. sativa       GEDARRGRIYLPQDELAEAGLSDEDIFNGVVTNKWRSFMKRQIKRARMFFEEAERGVTEL
P. trichocarpa  GEDALRGRVYLPQDELAQFGLCDQDVFARKVTDGWREFMKEQIIRARFYFNLAEEGASKL
                **** ***:********: **.*:*:*   **: **.*** *: ***:*:  **.*.:*

A. thaliana     SAASRWPVWASLLLYRRILDEIEANDYNNFTKRAYVGKVKKIAALPLAYAKSVLKTSSSR
O. sativa       SQASRWPVWASLLLYRQILDEIEANDYNNFTKRAYVGKAKKLLALPVAYGRSLLMPYSLR
P. trichocarpa  EKASRWPVWSSLLVYQKILDAIEDNDYDNFTKRAYVGRTKKLLTLPLAYTKAEMSQPPLL
                 .*******:***:*:.*** **.***:*********: **: :**:**  :  .

A. thaliana     LSI---------------------------------------------------------
O. sativa       NSQK--------------------------------------------------------
P. trichocarpa  DHATQTMANGSKSFATAAKLFDPATRRSVLMLYTWCRHCDDVIDDQTHGFASEAAAEEEA A. thaliana     ------------------------------------------------------------
O. sativa       ------------------------------------------------------------
P. trichocarpa  TQRLARLRTLTLAAFEGAEMQDPAFAAFQEVALTHGITPRMALDHLDGFAMDVAQTRYVT A. thaliana     ------------------------------------------------------------
O. sativa       ------------------------------------------------------------
P. trichocarpa  FEDTLRYCYHVAGVVGLMMARVMGVRDERVLDRACDLGLAFQLTNIARDIIDDAAIDRCY A. thaliana     ------------------------------------------------------------
O. sativa       ------------------------------------------------------------
P. trichocarpa  LPAEWLQDAGLTPENYAARENRAALARVAERLIDAAEPYYISSQAGLHDLPPRCAWAIAT A. thaliana     ------------------------------------------------------------
O. sativa       ------------------------------------------------------------
P. trichocarpa  ARSVYREIGIKVKAAGGSAWDRRQHTSKGEKIAMLMAAPGQVIRAKTTRVTPRPAGLWQR A. thaliana     --
O. sativa       --
P. trichocarpa  PV
```

Figure 9

CLUSTAL 2.1 Multiple Sequence Alignment of phytoene desaturase (CrtI) from E. longus, E. herbicola, and R. sphaeroides

```
E.longus        MNADQNIATGLNFAPANTGERGINPVIAEKYKGRTACVIGSGFGGLALALRLQSHGIQTT
E.herbicola     --------------------------------MKKTVVIGAGFGGLALAIRLQAAGIPTV
R.sphaeroides   -----------------------MPSISPASDADRALVIGSGLGGLAAAMRLGAKGWRVT
                                                 : ***:*:**** *:**   *   ..

E.longus        IVEARDKPGGRAYFWEKDGFTFDAGPTVITDPPCLKELWELTGHDISEDVELMKVHPFYR
E.herbicola     LLEQRDKPGGRAYVWHDQGFTFDAGPTVITDPTALEALFTLAGRRMEDYVRLLPVKPFYR
R.sphaeroides   VIDKLDVPGGRGSSITQEGHRFDLGPTIVTVPQSLRDLWKTCGRDFDADVELKPIDPFYE
                :::   * ****.     .:*. ** ***::* * .*. *:     *: :. *.*  :.***.

E.longus        LNWPDGTNFDYSNVDEELNAEIAKLNPDDVIGYQKFLEYSARVHEEGYVKLGTVPFLDFK
E.herbicola     LCWESGKTLDYANDSAELEAQITQFNPRDVEGYRRFLAYSQAVFQEGYLRLGSVPFLSFR
R.sphaeroides   VRWPDGSHFTVRQSTEAMKAEVARLSPGDVAGYEKFLKDSEKRYWFGYEDLGRRSMHKLW
                : * .*. :   :       ::*::::::.* ** **.:**  *   . **  ** .:. .:

E.longus        SMLKAAPALVKERAWRSVYDMVSSYIKDERLREAFSFHTLLVGGSPMKTSAIYALIHKLE
E.herbicola     DMLRAGPQLLKLQAWQSVYQSVSRFIEDEHLRQAFSFHSLLVGGNPFTTSSIYTLIHALE
R.sphaeroides   DLIKVLPTFGMMRADRTVYQHAALRVKDERLRMALSFHPLFIGGDPFNVTSMYILVSQLE
                .::::. * :   :*   ::**:  .:   ::**:** *:***.*::.**.*:...:::* *:   **

E.longus        KDGGVWWARGGTNRLIAGMVRHFERLGGTMRIGDPVVQVHTQGTKATEVETKSGWKERFD
E.herbicola     REWGVWFPEGGTGALVNGMVKLFTDLGGEIELNARVEELVVADNRVSQVRLADGRIFDTD
R.sphaeroides   KEFGVHYAIGGVAAIAAAMAKVIEGQGGSFRMNTEVDEILVEKGTATGVRLASGEVLRAG
                ::  **  :. **.   :  .*. :  :    **  :.:.  * ::     .: *.  .*    .

E.longus        AVCSNADIMHSYKELLGESDRGRKYAKSLARKSYSPSLFVVHFG---LEGSWPGIAHHMI
E.herbicola     AVASNADVVNTYKKLLGHHPVGQKRAAALERKSMSNSLFVLYFG---LNQPHSQLAHHTI
R.sphaeroides   LVVSNADAGHTYMRLLRNHPRRRWTDAHVKSRRWSMGLFVWYFGTKGTKGMWPDVGHHTI
                 *  **** ::::*  ** .    :         :   : * .*** :**     : . :.** *

E.longus        LFGPRYKELVDDIYKHGVLPQDFSIYLHHPTVTDPSMAPKGMSTFYALVPVAHLG-KMPI
E.herbicola     CFGPRYRELIDEIFTGSALADDFSLYLHSPCVTDPSLAPPGCASFYVLAPVPHLG-NAPL
R.sphaeroides   VNAPRYKGLVEDIFLKGKLAKDMSLYIHRPSITDPTVAPEGDDTFYALSPVPHLKQAQPV
                  .***: *:::*:  . *.:*:*:*:* * *:*** :**  *  :**.* **.**    *:

E.longus        DWDVEGPKFEKAILDEIGRRLIPDIHDRIVTKFSYAPKDFQADLNAHMGSAFSLETVLWQ
E.herbicola     DWAQEGPKLRDRIFDYLEERYMPGLRSQLVTQRIFTPADFHDTLDAHLGSAFSIEPLLTQ
R.sphaeroides   DWQAVAEPYRESVLEVLEQS-MPGIGERIGPSLVFTPETFRDRYLSPWGAGFSIEPRILQ
                **    .  ..  ::: :  . :*.: .:: ..   ::*  *:    : *:.**:*. : *

E.longus        SAYMRGHNRDDVIDNFYLVGAGTHPGAGIPGVVGSAKATAGLMLEDLSVK----------
E.herbicola     SAWFRPHNRDSDIANLYLVGAGTHPGAGIPGVVASAKATASL------------------
R.sphaeroides   SAWFRPHNISEEVANLFLVGAGTHPGAGVPGVIGSAEVMAKLAPDAPRARREAEPAERLA
                **::* **  .. :  *::**********:***:.**.  ::**:. * *

E.longus        --
E.herbicola     --
R.sphaeroides   AE
```

Figure 10

CLUSTAL 2.1 Multiple Sequence Alignment of lycopene beta-cyclase from A. thaliana, O. sativa, and N. tabacum

```
A. thaliana    MDTLLKTPNKLDFFIPQFHGFERLCSNNPYHSRVRLG-VKKRAIKIVSSVVSGSAALLDL
N. tabacum     MDTLLKTPNKLEFLHPVHGFSVKASSFNSVKPHKFGSRKICENWGKGVCVKAKSSALLEL
O. sativa      ----------------MATTALLLRAHPSCKPPPPPSPSPRPTRALVCRAAAAGEALRSL
                                :  . :.   .                .  : .  ** .*

A. thaliana    VPETKKENLDFELPLYDTSKSQVVDLAIVGGGPAGLAVAQQVSEAGLSVCSIDPSPKLIW
N. tabacum     VPETKKENLDFELPMYDPSKGLVVDLAVVGGGPAGLAVAQQVSEAGLSVVSIDPSPKLIW
O. sativa      APPSRPELLSLDLPRYDPARSTPVDLAVVGGGPAGLAVAQRVAEAGLSVCAIDPSPALVW
               .*  ::  * *.::** **.::.  ****:**********:*:****** :***** *:*

A. thaliana    PNNYGVWVDEFEAMDLLDCLDTTWSGAVVYVDEG-VKKDLSRPYGRVNRKQLKSKMLQKC
N. tabacum     PNNYGVWVDEFEAMDLLDCLDATWSGTVVYIDDN-TTKDLDRPYGRVNRKQLKSKMMQKC
O. sativa      PNNYGVWVDEFDAMGLSHCLDAVWPSATVFTHDDGAAKSLHRPYARVARRKLKSTMMDRC
               ***********:**.*  .***:.*...*:  .:. . *.* ***.** *::***.*::*

A. thaliana    ITNGVKFHQSKVTNVVHEEANSTVVCSDGVKIQASVVLDATGFSRCLVQYDKPYNPGYQV
N. tabacum     ILNGVKFHHAKVIKVIHEEAKSMLICNDGVTIQATVVLDATGFSRCLVQYDKPYKPGYQV
O. sativa      VAHGVTFHKARVVKAVHGEASSLLICDDGVAVPATVVLDATGFSRCLVQYDKPYDPGYQV
               : :**.**::.:* :.:* **.* **.* ::*.***  *:*********************.*****

A. thaliana    AYGIVAEVDGHPFDVDKMVFMDWRDKHLDSYPELKERNSKIPTFLYAMPFSSNRIFLEET
N. tabacum     AYGILAEVEEHPFDTSKMVLMDWRDSHLGNNMELKERNRKVPTFLYAMPFSSNKIFLEET
O. sativa      AYGILAEVDGHPFDIDKMLFMDWRDAHLPEGSEIRERNRRIPTFLYAMPFSPTRIFLEET
               ****:***: ****  .**::***** **  .  *::*** :*:**********..:.:******

A. thaliana    SLVARPGLRMEDIQERMAARLKHLGINVKRIEEDERCVIPMGGPLPVLPQRVVGIGGTAG
N. tabacum     SLVARPGLRMDDIQERMVARLNHLGIKVKSIEEDEHCVIPMGGSLPVIPQRVVGTGGTAG
O. sativa      SLVARPGLAMDDIQERMAARLRHLGIRVRAVEEDERCVIPMGGPLPVLPQRVVGIGGTAG
               ******** *:******.****.****:*: :****:*********.****:******* *****

A. thaliana    MVHPSTGYMVARTLAAAPIVANAIVRYLGSPS-SNSLRGDQLSAEVWRDLWPIERRRQRE
N. tabacum     LVHPSTGYMVARTLAAAPVVANAIIHYLGS---EKDLLGNELSAAVWKDLWPIERRRQRE
O. sativa      MVHPSTGYMVARTLATAPIVADAIVRFLDTGSGDSAFAGDALSAEVWRELWPAQRRRQRE
               :*************:**:**:**:::*.:   ..  :  *:  *** **::*** :******

A. thaliana    FFCFGMDILLKLDLDATRRFFDAFFDLQPHYWHGFLSSRLFLPELLVFGLSLFSHASNTS
N. tabacum     FFCFGMDILLKLDLPATRRFFDAFFDLEPRYWHGFLSSRLYLPELIFFGLSLFSRASNTS
O. sativa      FFCFGMDILLKLDLDGTRRFFDAFFDLEPRYWHGFLSSRLFLPELAMFGLSLFAKASNTS
               **************  .***********:*:*********:****  :******:.*****

A. thaliana    RLEIMTKGTVPLAKMINNLVQDRD-
N. tabacum     RIEIMTKGTLPLVNMINNLLQDTE-
O. sativa      RLEIMAKGTAPLAKMIGNLIQDRDR
               *:***:***  **.:**. **:** :
```

Figure 11

CLUSTAL 2.1 Multiple Sequence Alignment of phytoene beta-cyclase from A. thaliana, O. sativa, B. napus, and C. moschata.

```
A. thaliana     MDTLLKTPNKLDFFIPQFHGFERLCSNNPYHSRVRLGVKKRAIKIVSSVVSGSAALLDLV
B. napus        MDTLLRTPNKLEFFIPQFHGFERLS---PHPSRVKLGLKKRSIRIGSTSTS-SSALLDLV
C. moschata     MDTLLKINNKYGFLQQSHGVSEKLRG--GVRSTKIQSREFGFGHRKGRVKWRNSALLELV
O. sativa       ---------------MATTALLLRAHPSCKPPPPPSPSPRPTRALVCRAAAAGEALRSLA
                                                           . **  .*.

A. thaliana     PETKKENLDFELPLYDTSKSQVVDLAIVGGGPAGLAVAQQVSEAGLSVCSIDPSPKLIWP
B. napus        PETKKENLDFDLPLYDTSLNKVVDLAIVGGGPAGLAVAQQVSEAGLSVCSIDPSPKLIWP
C. moschata     PETKKENLEFELPMYDPSKGLVVDLAVVGGGPAGLAVAQQVSEAGLSVCAIDPSPKLIWP
O. sativa       PPSRPELLSLDLPRYDPARSTPVDLAVVGGGPAGLAVAQRVAEAGLSVCAIDPSPALVWP
                * ::  * *.::** **.:  .  ****:***********:*.******:***** *:**

A. thaliana     NNYGVWVDEFEAMDLLDCLDTTWSGAVVYVDEG-VKKDLSRPYGRVNRKQLKSKMLQKCI
B. napus        NNYGVWVDEFEAMDLLDCLDTTWSGAVVYINDG-AEKDLSRPYGRVNRKQLKSKMLQKCI
C. moschata     NNYGVWVDKFEAMDLLDCLDTTWSGAVVFTNGQ-STKDLGRPYGRVNRKQLKSKFLQKCI
O. sativa       NNYGVWVDEFDAMGLSHCLDAVWPSATVFTHDDGAAKSLHRPYARVARRKLKSTMMDRCV
                ********:*:**.*  .***:.*..*.*:  .      *.* ***.** *::***.:::*:

A. thaliana     TNGVKFHQSKVTNVVHEEANSTVVCSDGVKIQASVVLDATGFSRCLVQYDKPYNPGYQVA
B. napus        TNGVRFHQAKVTDVVHEEVNSTVVCSDGVEIQASVVLDATGFSRCLVQYDKPYNPGYQVA
C. moschata     ANGVKFHEAKVVKVIHEEFKSLLICNDGVTIQAAIVLDATGFSRCLVRYDEPYNPGYQVA
O. sativa       AHGVTFHKARVVKAVHGEASSLLICDDGVAVPATVVLDATGFSRCLVQYDKPYDPGYQVA
                ::** **:::*...:* * .* ::*.***  : *::***********:**.**:******

A. thaliana     YGIVAEVDGHPFDVDKMVFMDWRDKHLDSYPELKERNSKIPTFLYAMPFSSNRIFLEETS
B. napus        YGIVAEVDGHPFDVDKMVFMDWRDKHLDAYPEVKERNSKIPTFLYAMPFSSNRIFLEETS
C. moschata     YGILAEVEEHPFDVDKMVFMDWRDSHLDNNMVLKERNSKIPTFLYAMPFSSNRIFLEETS
O. sativa       YGILAEVDGHPFDIDKMLFMDWRDAHLPEGSEIRERNRRIPTFLYAMPFSPTRIFLEETS
                ***:***: ****:***:****** **      ::*** :**********..********

A. thaliana     LVARPGLRMEDIQERMAARLKHLGINVKRIEEDERCVIPMGGPLPVLPQRVVGIGGTAGM
B. napus        LVARPGLKMEDIQERMVARLKHLGINVKRIEEDERCVIPMGGPLPVLPQRVVGIGGTAGM
C. moschata     LVARPGLQMSDIQERMDARLKHLGIKVKSIEEDEHCVIPMGGQLPVLPQRVVGIGGTAGM
O. sativa       LVARPGLAMDDIQERMAARLRHLGIRVRAVEEDERCVIPMGGPLPVLPQRVVGIGGTAGM
                ******* *.****** ***:****.*: ::****:******.*****************

A. thaliana     VHPSTGYMVARTLAAAPIVANAIVRYLGSPS-SNSLRGDQLSAEVWRDLWPIERRRQREF
B. napus        VHPSTGYMVARTLAAAPIVANAIVRYLG------STKGDELSAEVWRDLWPIERRRQREF
C. moschata     VHPSTGYMVARTLAAAPIVAGAIVRCLGS---DGRFRGDEISSEVWRDLWPIERRRQREF
O. sativa       VHPSTGYMVARTLATAPIVADAIVRFLDTGSGDSAFAGDALSAEVWRELWPAQRRRQREF
                **************:*****..***  *.      **  :*:****:***  :*******

A. thaliana     FCFGMDILLKLDLDATRRFFDAFFDLQPHYWHGFLSSRLFLPELLVFGLSLFSHASNTSR
B. napus        FCFGMDILLKLDLDATRRFFDAFFDLEPRYWHGFLSSRLFLPDLVFFGLSLFSHASNTSR
C. moschata     FCFGMDILLKLDLKGTRRLFDAFFDLEPHYWHGFLSSRLFLPELILFGLSLFSHASNASR
O. sativa       FCFGMDILLKLDLDGTRRFFDAFFDLEPRYWHGFLSSRLFLPELAMFGLSFAKASNTSR
                *************. ***:*******:*:**************.* .****::***.**

A. thaliana     LEIMTKGTVPLAKMINNLVQDRD-
B. napus        LEIMTKGTVPLMINN--LVKDRD-
C. moschata     VEIMAKGTPSLVNMIGNLVKDRD-
O. sativa       LEIMAKGTAPLAKMIGNLIQDRDR
                :***:***  .*     *::***
```

Figure 12

CLUSTAL 2.1 Multiple Sequence Alignment of lycopene epsilon-cyclase from A. thaliana, B. napus, and L. sativa

```
A. thaliana    MECVGARNFAAMAVSTFPSWS-CRRKFPVVKRYSYRNIRFGLCSVRASGGGS-SGSESCV
B. napus       MECVGARNLAATAVTAFPSWSSSRKNYPVDNRYSFSNLRCGLCRVKASGGGAGSGIESCV
L. sativa      MECFGARNMTATMAVFTCPRFTDCNIRHKFSLLKQRRFTNLSASSSLRQIKCSAKSDRCV
               ***.****::*   .       .      ...:    .           . : : **

A. thaliana    AVR--EDFADEEDFVKAGGSEILFVQMQQNKDMDEQ--SKLVDKLPPISIGDG--ALDLV
B. napus       AVR--EDFADEEDFVKAGGSEILYVQMQQNKDMDEHEQSKLVDKLPPISTGEGGGALDLV
L. sativa      VDKQGISVADEEDYVKAGGSELFFVQMQRTKSMESQ--SKLSEKLAQIPIGNC--ILDLV
               . :   ..*****:******:::****:.*.*:.:   *** :**. *. *:    ****

A. thaliana    VIGCGPAGLALAAESAKLGLKVGLIGPDLPFTNNYGVWEDEFNDLGLQKCIEHVWRETIV
B. napus       VIGCGPAGLALAAESAKLGLKVGLIGPDLPFTNNYGVWEDEFNDLGLQKCIEHVWRDTLV
L. sativa      VIGCGPAGLALAAESAKLGLNVGLIGPDLPFTNNYGVWQDEFIGLGLEGCIEHSWKDTLV
               ********************.***************:***  .***: **** *::*:*

A. thaliana    YLDDDKPITIGRAYGRVSRRLLHEELLRRCVESGVSYLSSKVDSITEASDGLRLVACDDN
B. napus       YLDDDNPITIGRAYGRVSRRLLHEELLRRCVESGVSYLSSKVESITEAPDGLRLVSCEQN
L. sativa      YLDDADPIRIGRAYGRVHRDLLHEELLRRCVESGVSYLSSKVERITEAPNGYSLIECEGN
               ****  ** ********  *.***************** ****.:*   *:  *: * *

A. thaliana    NVIPCRLATVASGAASGKLLQYEVGGPRVCVQTAYGVEVEVENSPYDPDQMVFMDYRDYT
B. napus       TLVPCRLATVASGAASGKLLQYEVGGPRVCVQTAYGLEVEVEKSPYDPEQMVFMDYRDYT
L. sativa      ITIPCRLATVASGAASGKFLEYELGGPRVCVQTAYGIEVEVENNPYDPDLMVFMDYRDFS
                :**************:*::**:************:*****:.****: ********::

A. thaliana    NEKVRSLEAEYPTFLYAMPMTKSRLFFEETCLASKDVMPFDLLKTKLMLRLDTLGIRILK
B. napus       KEKIRSLEAEYPTFLYAMPMTKTRVFFEETCLASKDVMPFDLLKKKLMLRLETLGIRILK
L. sativa      KHKPESLEAKYPTFLYVMAMSPTKIFFEETCLASREAMPFNLLKSKLMSRLKAMGIRITR
                :.* .****:******.*.*: : :::*********::***:***:*** **.::****  :

A. thaliana    TYEEEWSYIPVGGSLPNTEQKNLAFGAAASMVHPATGYSVVRSLSEAPKYASVIAEILRE
B. napus       TYEEEWSYIPVGGSLPNTEQKNLAFGAAASMVHPATGYSVVRSLSEAPKYASVIANILKH
L. sativa      TYEEEWSYIPVGGSLPNTEQKNLAFGAAASMVHPATGYSVVRSLSEAPNYAAVIAKILRQ
               ************************************************:**:***:**:.

A. thaliana    ETTKQIN-----SNISRQAWDTLWPPERKRQRAFFLFGLALIVQFDTEGIRSFFRTFFRL
B. napus       ETTTSFTRH-INTNISRQAWDTLWPPERKRQRAFFLFGLALIVQLDIEGIRCFFHTFFRL
L. sativa      DQSKEMISLGKYTNISKQAWETLWPLERKRQRAFFLFGLSHIVLMDLEGTRTFFFRTFFRL
               : :..:       :***:***:**** ***********: ** :* ** * **:*****

A. thaliana    PKWMWQGFLGSTLTSGDLVLFALYMFVISPNNLRKGLINHLISDPTGATMIKTYLKV
B. napus       PKWMWRGFLGSTLTSGDLVLFAFYMFIIAPNNLRKGLINHLISDPTGATMIKTYLKV
L. sativa      PKWMWWGFLGSSLSSTDLIIFALYMFVIAPHSLRMELVRHLLSDPTGATMVKAYLTI
               ***** *****:*:* **::**:****::*:.** .*:.**:*******:*:**. :
```

Figure 13

| | | | |
|---|---|---|---|
| Amphipathic α-helix parallel to membrane | Interaction by hydrophobic loop | Interaction by covalently bound membrane lipid | Electrostatic or ionic interactions with membrane lipids |

```
E.coli        ------------------------------------------------------------
L.esculentum  MALCAYAFPGILNRTGVVSDSSKATPLFSGWIHGTDLQFLFQHKLTHEVKKRSRVVQASL E.coli        -----MSFDIAKYPTLALVDSTQELRLLPKESLPKLCDELRRYLLDSVSRSSGHFASGLG
L.esculentum  SESGEYYTQRPPTPILDTVNYPIHMKNLSLKELKQLADELRSDTIFNVSKTGGHLGSSLG
                   : .  * *  *:. . .:: *. :.* :*.****   : .**::.**:.*.**

E.coli        TVELTVALHYVYNTPFDQLIWDVGHQAYPHKILTGRRDKIGTIRQKGGLHPFPWRGESEY
L.esculentum  VVELTVALHYVFNAPQDRILWDVGHQSYPHKILTGRRDKMSTLRQTDGLAGFTKRSESEY
              .**********:*:* *:::*****.*************::*:** .** *. *.****

E.coli        DVLSVGHSSTSISAGIGIAVAAEKEGKNRRTVCVIGDGAITAGMAFEAMNHAGDIRPDML
L.esculentum  DCFGTGHSSTTISAGLGMAVGRDLKGRNNNVIAVIGDGAMTAGQAYEAMNNAGYLDSDMI
              * :..*****:****:*:**. : :*:*...:.******:*** *:****:** : .**:

E.coli        VILNDNE---------MSISENVGALNNHLAQLLSGKLYSSLREGGKKVFSGVP-PIKEL
L.esculentum  VILNDNRQVSLPTATLDGPVAPVGALSSALSRLQSNRPLRELREVAKGVTKQIGGPMHEL
              ******.          .    ****.. *::* *.:   .*** .* * . :  *::**

E.coli        LKRTEEHIKGMVVPG--TLFEELGFNYIGPVDGHDVLGLITTLKNMRDLK--GPQFLHIM
L.esculentum  AAKVDEYARGMISGSGSTLFEELGLYYIGPVDGHNIDDLIAILKEVRSTKTTGPVLIHVV
               :.:*: :.**:       *******: ********::  .**: **::*.  *   ** ::*::

E.coli        TKKGRGYEPAEKDPITFHAVPKFDPSSGCLPKSSGGLPSYSKIFGDWLCETAAKDNKLMA
L.esculentum  TEKGRGYPYAERAADKYHGVAKFDPATGKQFKASAKTQSYTTYFAEALIAEAEADKDIVA
              *:*****  **:    . .:*.*.****:.*   *:*. **:. *.: *    * *:..:*

E.coli        ITPAMREGSGMVEFSRKFPDRYFDVAIAEQHAVTFAAGLAIGGYKPIVAIYSTFLQRAYD
L.esculentum  IHAAMGGGTGMNLFHRRFPTRCFDVGIAEQHAVTFAAGLACEGIKPFCAIYSSFMQRAYD
              *  .** *:** * *:** * *** .************** * **: ****:*:*****

E.coli        QVLHDVAIQKLPVLFAIDRAGIVGADGQTHQGAFDLSYLRCIPEMVIMTPSDENECRQML
L.esculentum  QVVHDVDLQKLPVRFAMDRAGLVGADGPTHCGAFDVTYMACLPNMVVMAPSDEAELFHMV
              **:***  :***** **:*****:*****  * ****::*: *:*:**:*:**** *   :*:

E.coli        YTGYHYNDGPSAVRYPRGNAVGVELTPLEK---LPIGKGIVKRRGEKLAILNFGTLMPEA
L.esculentum  ATAAAIDDRPSCFRYPRGNGIGVELPAGNKGIPLEVGKGRILIEGERVALLGYGSAVQNC
              *.   :* ** ..******.:****.. :*   * :***  :  . .**..:*:*.:*: : :.

E.coli        AKVAESLN-----ATLVDMRFVKPLDEALILEMAASHEALVTEENAIMGGAGSGVNEVL
L.esculentum  LDAAIVLESRGLQVTVADARFCKPLDHALIRSLAKSHEVLITVEEGSIGGFGSHVVQFMA
              ..* *:   .*::.* ** ****.*** .:* ***.:****.:*  .. *: :

E.coli        MAHRKP--VPVLNIGLPDFFIPQGTQEEMRAELGLDAAGMEAKIKAWLA----------
L.esculentum  LDGLLDGKLKWRPIVLPDRYIDHGSPVDQLAEAGLTPSHIAATVFNILGQTREALEVMT
                 :     : ****.*.:*.  : ** ** ...:*.  *.
```

Figure 20

```
E.coli      --------------------MENVILIDHNDCETGIAEKLYTHKKG------ILHRAVSV
Z.mays      MAAAVVDDAGMDAVQKRLMFEDECILVDEQDNVVGHESKYNCHLMEKIDSENLLHRAFSV
                              ::  **:*.:*  .*  .*    *           :****.**

E.coli      YICNSDGKLLLQQRALGKYHSPGLWSNTSCTHPFPGES---------NLSAANRRLREEM
Z.mays      FLFNSKYELLLQQRSATKVTFPLVWTNTCCSHPLYRESELIQENYLGVRNAAQRKLLDEL
            ::  **. :******:    *     *  :*:**.*:**:   **         .**:*:*  :*:

E.coli      GIECP------LSKLLKIYYNVYVGGDLTEHEIAHIFYGISDDEPDLNSLEAMSYKYVSL
Z.mays      GIPAEDAPVDQFTPLGRMLYKAPSDGKWGEHELDYLLFIVRDVKVQPNPDEVADVKYVNR
            ** .         :: * :: *:.  .*.  ***: :::: : * : : *. *. . ***.

E.coli      TELSSEIKFNND-----AFSRWFVYCFP--------YIKNAFLNESNYTNLLI----
Z.mays      DELKELIRKADAGEDGVKISPWFRLVVDNFLMGWWDHVEKGTLGEAVDMETIHKLKE
            **.. *:  :        :* **     .        ::::. *.*:    : :
```

Figure 21

SEQUENCE LISTING

<160> NUMBER OF SEQ ID NOS: 96

<210> SEQ ID NO 1
<211> LENGTH: 644

<212> TYPE: PRT
<213> ORGANISM: O. sativa

<400> SEQUENCE: 1

```
Met Ser Ser Ala Thr Ser Val Ser Ala Phe Ala Met Ala Ala Thr Ser
1               5                   10                  15

Ser Ala Ala Ala Ala Pro Pro Cys Arg Leu Leu Gly Ser Gly
            20              25                  30

Gln Ala His Leu Arg Leu Pro Pro Ser Ala Ala Ala Ala Ala Ser
        35              40                  45

Ala Arg Arg Arg Leu Leu Leu Arg Cys Ala Ala Ser Gly Gly Asn Gly
        50                  55                  60

Lys Gly Gly Gly Gly Asp Gly Ser Gly Ser Asp Pro Val Leu Glu Glu
65                  70                  75                  80

Arg Arg Arg Arg Arg Gln Ala Glu Leu Ala Ala Arg Ile Ala Ser Gly
                    85                  90                  95

Glu Phe Thr Ala Gln Gly Pro Ala Trp Ile Ala Pro Leu Ala Val Gly
            100                 105                 110

Leu Ala Lys Leu Gly Pro Pro Gly Glu Leu Ala Ala Leu Leu Thr
            115                 120                 125

Lys Val Ala Gly Gly Gly Pro Glu Ile Pro Gln Ala Val Gly Ser
130                 135                 140

Met Ser Ala Val Thr Gly Gln Ala Phe Phe Ile Pro Leu Tyr Asp Leu
145                 150                 155                 160

Phe Leu Thr Tyr Gly Gly Ile Phe Arg Leu Asn Phe Gly Pro Lys Ser
                165                 170                 175

Phe Leu Ile Val Ser Asp Pro Ala Ile Ala Lys His Ile Leu Arg Asp
                180                 185                 190

Asn Ser Lys Ala Tyr Ser Lys Gly Ile Leu Ala Glu Ile Leu Glu Phe
            195                 200                 205

Val Met Gly Thr Gly Leu Ile Pro Ala Asp Gly Glu Ile Trp Arg Val
210                 215                 220

Arg Arg Arg Ala Ile Val Pro Ala Met His Gln Lys Tyr Val Thr Ala
225                 230                 235                 240

Met Ile Ser Leu Phe Gly Tyr Ala Ser Asp Arg Leu Cys Gln Lys Leu
                245                 250                 255

Asp Lys Ala Ala Thr Asp Gly Glu Asp Val Glu Met Glu Ser Leu Phe
            260                 265                 270

Ser Arg Leu Thr Leu Asp Val Ile Gly Lys Ala Val Phe Asn Tyr Asp
        275                 280                 285

Phe Asp Ser Leu Ser Tyr Asp Asn Gly Ile Val Glu Ala Val Tyr Val
290                 295                 300

Thr Leu Arg Glu Ala Glu Met Arg Ser Thr Ser Pro Ile Pro Thr Trp
305                 310                 315                 320

Glu Ile Pro Ile Trp Lys Asp Ile Ser Pro Arg Gln Lys Lys Val Asn
                325                 330                 335

Glu Ala Leu Ala Leu Ile Asn Lys Thr Leu Asp Glu Leu Ile Asp Ile
            340                 345                 350

Cys Lys Arg Leu Val Glu Glu Asp Leu Gln Phe His Glu Glu Tyr
        355                 360                 365

Met Asn Glu Gln Asp Pro Ile Thr Leu His Phe Leu Leu Ala Ser Gly
        370                 375                 380

Asp Asp Val Ser Ser Lys Gln Leu Arg Asp Asp Leu Met Thr Met Leu
385                 390                 395                 400
```

Ile Ala Gly His Glu Thr Ser Ala Ala Val Leu Thr Trp Thr Phe Tyr
            405                 410                 415

Leu Leu Ser Lys Tyr Pro Asn Val Met Ala Lys Leu Gln Asp Glu Ala
        420                 425                 430

Asp Thr Val Leu Gly Asp Arg Leu Pro Thr Ile Glu Asp Val Lys Lys
    435                 440                 445

Leu Lys Tyr Thr Thr Arg Val Ile Asn Glu Ser Leu Arg Leu Tyr Pro
450                 455                 460

Gln Pro Pro Val Leu Ile Arg Arg Ser Ile Glu Glu Asp Met Leu Gly
465                 470                 475                 480

Gly Tyr Pro Ile Gly Arg Gly Glu Asp Ile Phe Ile Ser Val Trp Asn
            485                 490                 495

Leu His His Cys Pro Lys His Trp Asp Gly Ala Asp Val Phe Asn Pro
        500                 505                 510

Glu Arg Trp Pro Leu Asp Gly Pro Asn Pro Asn Glu Thr Asn Gln Asn
    515                 520                 525

Phe Ser Tyr Leu Pro Phe Gly Gly Pro Arg Lys Cys Val Gly Asp
530                 535                 540

Met Phe Ala Thr Phe Glu Thr Val Val Ala Thr Ala Met Leu Val Arg
545                 550                 555                 560

Arg Phe Asp Phe Gln Met Ala Pro Gly Ala Pro Val Glu Met Thr
            565                 570                 575

Thr Gly Ala Thr Ile His Thr Thr Glu Gly Leu Lys Met Thr Val Thr
        580                 585                 590

Arg Arg Thr Lys Pro Pro Val Ile Pro Asn Leu Glu Phe Leu Lys Val
    595                 600                 605

Ile Ser Asp Ser Pro Glu Asn Met Ser Thr Thr Ser Met Pro Val
610                 615                 620

Ser Ala Ala Ser Ile Ala Ser Gly Glu Asp Gln Gln Gly Gln Val Ser
625                 630                 635                 640

Ala Thr Arg Ile

<210> SEQ ID NO 2
<211> LENGTH: 1915
<212> TYPE: DNA
<213> ORGANISM: O. sativa

<400> SEQUENCE: 2

```
atgagctcag cgacgtcagt gagtgatttg ccatggcggc tacctcctct cggccgccgc      60
tgctccacct ccgtgccgct tactcggctc cggtcaggca cacctgcgcc ttcctcctta     120
gctgctgagc tgagcttcag ctcgtcgccg cctgacctcc gctgcgccgc ctcgggcggc     180
aacgggaaag gcggtggtgg cgacggctcc ggctccgacc cggttatgag gagcggcggc     240
ggcggcgcca ggctgagctg gcggcgcgca ttgcgtccgg cgagttcacc gcccaaggcc     300
ccgcgtggat tgctcccctc gcgtgggggc ttgccaagct cggcccaccg ggggagctcg     360
ccgccgcgct gctcaccaag gtcgccggtg gcggcggacc ggagataccg caggcggtgg     420
ggtctatgag tgcggtgaca gggcaggctt tcttcatccc gctctatgat ctatccttac     480
ctatggcggc atctttcgcc tcaatttcgg ccctaagtct ttcctcattg tctctgatcc     540
agctatagct aagcacatcc tgagggacaa ctccaaggct tattccaagg gtattctggc     600
agaaaatttta gagtttgtga tgggtacggg tttgatccag ctgatgggga gatttggcgt     660
gttaggaggc gcgccattgt accagcaatg caccagaagt acgttaccgc aatgataagt     720
```

-continued

```
ctcacggata tgatcagatc ggctctgcca gaagttggac aaggcagcac ggatggggag      780
gatgtggaga tggaatcttt gttctctcga ctaacactgg atgtcattgg gaaggcagtc      840
ttcaattatg atttcgactc attgtcttac gataatggaa tagttgaggt agtgtatgtg      900
acactgcgag aagcagaaat gcggagcact tctcctatac caacttggga aatacccata      960
tggaaagata tttccccgcg gcagaagaag gtcaatgaag ctcttgcgct gataaataag     1020
actatgatga actaattgac atctgcaaga gattggtcga ggaagaagat ctgcagtttc     1080
atgaagaata catgaatgag caagacccca ttaccctcca ctccttttgg catctggaga     1140
tgatgtctcc agcacgcaac tccgtgatga tctgatgaca atgacattgc tggccatgag     1200
acctagcagc agtcttgaca tggacatttt atcttctatc taagtatcca aatgtaatgg     1260
ccaaactcca agatgaggct gatactgttc taggtgaccg tttaccaaca attgaggatg     1320
tgaagaaatt gaagtatact actagagtaa ttaacgaatc attgagactc tatccacagc     1380
caccagtttt aattcgtcgc tctattgagg aggatatgct gsgagggtac ccaattggcc     1440
ggggagaaga cattacatat ccgtgtggaa cctacatcat tgcccaaagc attcggatgg     1500
tgcagatgtt tttaatccag aaagatggcc tttggatgga ccaaatccaa atgaaacaaa     1560
ccaaaatttc agttacttgc catttggtgg cggaccaagg aaatgtgtag gtgacatgtt     1620
tgccactttc gagactgtgg tggcaactgc aatgcttgtc aggcgctttg attttcaaat     1680
ggctccagga gctcctccgg ttgagatgac aactggagca acgattcaca caactgaggg     1740
gttgaaaatg actgttactc ggaggacaaa gccacctgta atcccaaacc tagagatgaa     1800
agtcatttct gattcaccag aaaacatgag tactactaca tcaatgcccg tttctgctgc     1860
tagtattgct tcaggagaag atcaacaagg gcaagtctca gcaactcgaa tctga         1915
```

<210> SEQ ID NO 3
<211> LENGTH: 569
<212> TYPE: PRT
<213> ORGANISM: O. sativa

<400> SEQUENCE: 3

```
Met Ala Ile Thr Ala Ala Thr Ala Ala Ala Ala Thr Pro His Pro
1               5                   10                  15

Trp Gln Ala Asp Ala Ser Pro Arg Arg His Ala Ala Cys Pro Ala Leu
                20                  25                  30

Arg Gly Arg Arg Arg Leu Pro Val Val Arg Cys Gln Ser Ser Ser Val
            35                  40                  45

Asp Asp Lys Pro Lys Ser Lys Arg Gly Leu Leu Asp Asn Ala Ser Asn
        50                  55                  60

Leu Leu Thr Asn Leu Leu Ser Gly Gly Ser Leu Gly Ala Met Pro Val
65                  70                  75                  80

Ala Glu Gly Ala Val Thr Asp Leu Phe Gly Arg Pro Leu Phe Phe Ser
                85                  90                  95

Leu Tyr Asp Trp Phe Leu Glu His Gly Ser Val Tyr Lys Leu Ala Phe
                100                 105                 110

Gly Pro Lys Ala Phe Val Val Ser Asp Pro Ile Val Ala Arg His
            115                 120                 125

Ile Leu Arg Glu Asn Ala Phe Cys Tyr Asp Lys Gly Val Leu Ala Glu
        130                 135                 140

Ile Leu Lys Pro Ile Met Gly Lys Gly Leu Ile Pro Ala Asp Leu Asp
145                 150                 155                 160
```

Thr Trp Lys Gln Arg Arg Lys Val Ile Thr Pro Gly Phe His Ala Leu
            165                 170                 175

Phe Ile Asp Ala Met Val Gly Val Phe Thr Lys Cys Ser Glu Arg Thr
            180                 185                 190

Phe Lys Leu Glu Glu Leu Ile Glu Arg Gly Glu His Gly Glu Lys Tyr
            195                 200                 205

Thr Ile Val Asp Leu Glu Ala Glu Phe Ser Asn Leu Ala Leu Asp Ile
            210                 215                 220

Ile Gly Leu Gly Val Phe Asn Phe Asp Phe Asp Ser Val Thr Lys Glu
225                 230                 235                 240

Ser Pro Val Ile Lys Ala Val Tyr Gly Thr Leu Phe Glu Ala Glu His
                245                 250                 255

Arg Ser Thr Phe Tyr Ile Pro Tyr Trp Asn Leu Pro Leu Thr Arg Trp
            260                 265                 270

Ile Val Pro Arg Gln Arg Lys Phe His Ser Asp Leu Lys Val Ile Asn
            275                 280                 285

Asp Cys Leu Asp Ser Leu Ile Lys Asn Ala Lys Glu Thr Arg Gln Glu
            290                 295                 300

Ala Asp Val Glu Lys Leu Gln Gln Arg Asp Tyr Ser Ser Leu Lys Asp
305                 310                 315                 320

Ala Ser Leu Leu Arg Phe Leu Val Asp Met Arg Gly Ala Asp Val Asp
                325                 330                 335

Asp Arg Gln Leu Arg Asp Asp Leu Met Thr Met Leu Ile Ala Gly His
            340                 345                 350

Glu Thr Thr Ala Ala Val Leu Thr Trp Ser Val Phe Leu Leu Ala Gln
            355                 360                 365

Asn Pro Ser Lys Met Arg Lys Ala Gln Ala Glu Val Asp Ser Val Leu
            370                 375                 380

Ser Asn Glu Thr Ile Asn Val Asp Gln Leu Lys Leu Glu Tyr Ile Arg
385                 390                 395                 400

Leu Ile Ile Val Glu Ala Leu Arg Leu Tyr Pro Gln Pro Pro Leu Leu
                405                 410                 415

Ile Arg Arg Ala Leu Arg Pro Asp Lys Leu Pro Gly Gly Tyr Asn Gly
            420                 425                 430

Ala Lys Glu Gly Tyr Glu Ile Pro Ala Gly Thr Asp Ile Phe Leu Ser
            435                 440                 445

Ile Tyr Asn Leu His Arg Ser Pro Tyr Phe Trp Asp Arg Pro Asp Glu
            450                 455                 460

Phe Glu Pro Glu Arg Phe Ser Val Pro Lys Lys Asp Glu Ser Ile Glu
465                 470                 475                 480

Gly Trp Ala Gly Phe Asp Pro Asp Arg Ser Pro Gly Ala Met Tyr Pro
                485                 490                 495

Asn Glu Ile Leu Ala Asp Phe Ala Phe Leu Pro Phe Gly Gly Gly Pro
            500                 505                 510

Arg Lys Cys Val Gly Asp Gln Phe Ala Leu Leu Glu Ser Thr Val Ala
            515                 520                 525

Leu Ala Leu Leu Leu Gln Lys Phe Asp Val Glu Leu Arg Gly Ser Pro
530                 535                 540

Asp Glu Val Glu Met Val Thr Gly Ala Thr Ile His Thr Lys Ser Gly
545                 550                 555                 560

Leu Trp Cys Arg Val Arg Arg Thr
            565

<210> SEQ ID NO 4
<211> LENGTH: 1706
<212> TYPE: DNA
<213> ORGANISM: O. sativa

<400> SEQUENCE: 4

```
atggcgatca ccgcggccac cgccgccgcc gccgccacgc cccacccgtg gcaggccgac    60
gcctcgccgc gtcgccacgc cgcgtgcacg ctctccgcgg gaggaggcgc ctcccgtcgt   120
caggtgccag tcgtccagcg tcgacgacaa gcccaagtcc aagcgggacc tgctagacaa   180
cgccagcaac ctgctcacca acctgctcag cggcgsgaga tcggcgcgat gcccgtcgcc   240
gagggcgccg tcaccgacct cttcggccgg ccactcttca ctcgctctac gactcttcct   300
cgagcatggc tttgtgtaca aactcgcttt tggacccaag gcatttgttg ttrctccgat   360
ccaattgttg ctagacatat cctgcgagaa aatgatttct gttatgataa gggagttctt   420
gctgaaattt taaaaccaat aatggggaag ggtcttatac ctgctgacct tgatacctca   480
agcaaaggag aaaagttata cccccgggt tccatgcctt attcatagat gctatggtgg   540
gagtatttac taagtgttca gagagaacaa tatttaagct tgaagagctt attgaaaggg   600
gcgaacatgg ggaaaagtat accatagtgg accttgaagc tgagttttct aatttggctc   660
tcgacataat tggcttgggc gtgttcaatt ttgattttga ttcggttacc aaagaatctc   720
ctgtgatcaa ggcagtatac ggaactcttt ttgaagctga gcacagatcc acttttacat   780
tccctattgg aatcttcctt taactagatg gatagttcca aggcaacgca agttccacag   840
tgacctcaag gttattaatg attgccttga tagtctcata aaaaatgcaa agagacaag   900
acaggaagct gatgtcgaaa agatccagca aagagattac tcatcattga aggatgccag   960
cttgctgagg ttccttgttg atatgcgggg agctgatgtt gacgatcgcc agcttcgaga  1020
tgaccttatg acaatgctta ttgctgggca tgaaacaact gctgctgttt tgacatggtc  1080
tgttttcta ctagcccaga atccctccaa gatgagaaaa gcacaggcag aggttgattc  1140
tgtactcagc aatgagacaa ttaatgtgga ccagctcaag aaattggagt acataagact  1200
gataattgtt gaagctcttc gcttgtatcc ccagccacca ttgttaatca ggcgtgctct  1260
gcggccagat aaattgccag gtgggtacaa tggtgcaaaa gaaggatatg aaataccagc  1320
tggaaccgat atatttcttt cgatatacaa cctccataga tctccatact tttgggatcg  1380
gccagatgag tttgaaccag agagattttc agtaccaaaa aaggatgaga gcatagaagg  1440
gtgggctgat tgatcctga ccggagtcct ggtgctatgt atcctaacga gattttagca  1500
gactttgctt tccttcctat ggcggaggac cccgcaaatg cgtgggagac cagttttgcac  1560
tcctagagtc gacagtagcc ctggccctgc tattgcaaaa gtttgatgtg gagctgcgag  1620
gatcacccga tgaagtggag atggtgacag gcgcaacaat tcacacgaag agcgggttat  1680
ggtgcagagt gaggagaagg acctga                                        1706
```

<210> SEQ ID NO 5
<211> LENGTH: 553
<212> TYPE: PRT
<213> ORGANISM: O. sativa

<400> SEQUENCE: 5

Ala Val Pro Cys Val Pro Phe Leu Cys Pro Pro Pro Pro Leu Val
1               5                   10                  15

Ser Pro Arg Leu Arg Arg Gly His Val Arg Leu Arg Leu Arg Pro Pro
            20                  25                  30

-continued

```
Arg Ser Ser Gly Gly Gly Gly Gly Ala Gly Gly Asp Ala Pro
        35              40              45

Pro Ile Thr Thr Ser Trp Val Ser Pro Asp Trp Leu Thr Ala Leu Ser
50                  55                  60

Arg Ser Val Ala Thr Arg Leu Gly Gly Gly Asp Asp Ser Gly Ile Pro
65              70                  75                  80

Val Ala Ser Ala Lys Leu Asp Asp Val Arg Asp Leu Leu Gly Gly Ala
                85                  90                  95

Leu Phe Leu Pro Phe Lys Trp Phe Arg Ala Ala Gly Pro Val Tyr Arg
            100                 105                 110

Leu Ala Ala Gly Pro Arg Asp Leu Val Val Ser Asp Pro Ala Val
            115                 120                 125

Ala Arg His Val Leu Arg Gly Tyr Gly Ser Arg Tyr Ala Lys Gly Leu
130                 135                 140

Val Ala Ala Val Ser Ala Phe Leu Phe Gly Ser Gly Phe Ala Ile Ala
145                 150                 155                 160

Ala Gly Ala Leu Trp Thr Val Arg Arg Ser Val Val Pro Ser Leu
            165                 170                 175

His Lys Arg Phe Leu Ser Val Met Val Asp Arg Val Phe Cys Lys Cys
            180                 185                 190

Ala Ala Arg Leu Val Ala Lys Leu Ala Thr Ser Ala Leu Ser Gly Lys
        195                 200                 205

Pro Val Asn Met Ala Ala Arg Phe Ser Gln Met Thr Leu Asp Val Ile
    210                 215                 220

Gly Leu Ser Leu Phe Asn Tyr Asn Phe Asp Ser Leu Thr Ser Asp Ser
225                 230                 235                 240

Pro Val Ile Asp Ala Val Tyr Thr Ala Leu Lys Ala Ala Leu Arg
            245                 250                 255

Ser Thr Asp Leu Leu Pro Tyr Trp Lys Ile Asp Leu Leu Cys Lys Ile
            260                 265                 270

Val Pro Arg Gln Ile Lys Ala Ala Lys Ala Val Asn Ile Ile Arg Asn
    275                 280                 285

Thr Val Ala Asp Leu Ile Thr Lys Cys Lys Lys Val Asp Ala Ala Asn
290                 295                 300

Ala Gln Ile Ala Gly Ala Ala Tyr Val Asn Ala Ala Asp Pro Ser Ile
305                 310                 315                 320

Leu Arg Phe Leu Leu Ala Ser Arg Ala Ala Val Thr Ser Val Gln Leu
            325                 330                 335

Arg Asp Asp Leu Leu Ser Met Leu Val Ala Gly His Ala Thr Thr Gly
            340                 345                 350

Ser Val Leu Thr Trp Thr Ile Tyr Leu Leu Ser Lys Asp Pro Ala Ala
        355                 360                 365

Leu Arg Arg Ala Gln Ala Ala Val Asp Arg Val Leu Gln Gly Arg Leu
370                 375                 380

Pro Arg Tyr Ala Asp Leu Lys Ala Leu Lys Tyr Leu Met Arg Cys Ile
385                 390                 395                 400

Asn Ala Ser Met Arg Leu Tyr Pro His Pro Pro Val Leu Ile Arg Arg
            405                 410                 415

Ala Ile Val Asp Asp Val Leu Pro Gly Asn Tyr Lys Ile Lys Ala Gly
            420                 425                 430

Gln Asp Ile Met Ile Ser Val Tyr Asn Ile Phe Ile Arg Ser Pro Ala
        435                 440                 445

Val Trp Asp Arg Ala Asp Asp Phe Ile Pro Ala Arg Phe Asp Leu Ala
```

|   |   |   | 450 |   |   |   | 455 |   |   |   | 460 |   |   |
|---|---|---|---|---|---|---|---|---|---|---|---|---|---|

Gly Pro Val Pro Asn Ala Thr Asn Thr Ala Tyr Arg Phe Ile Pro Phe
465                 470                 475                 480

Ser Gly Gly Pro Arg Lys Cys Val Gly Asp Gln Phe Ala Leu Leu Ala
                485                 490                 495

Ala Ile Val Ala Leu Ala Val Val Leu Gln Lys Met Asp Ile Ala Leu
            500                 505                 510

Val Pro Asp Gln Lys Ile Asn Met Thr Thr Gly Ala Thr Ile His Thr
        515                 520                 525

Thr Asn Gly Leu Tyr Met Asn Val Ser Leu Pro Ile Val Asp Arg Ala
    530                 535                 540

Pro Asp Phe Ala Leu Ser Gly Ser Arg
545                 550

<210> SEQ ID NO 6
<211> LENGTH: 1655
<212> TYPE: DNA
<213> ORGANISM: O. sativa

<400> SEQUENCE: 6

```
gccgtcccgt gcgtaccatt cctgtgcccg cctcctccgc cattggtctc gccgcgtctc      60
cgccgtggcc acgtacgcct ccgcctgcgg ccgccaagga gcagcggcgg tggaggcgga     120
ggcggagcgg gggagacgag ccgcccatca ccacctcgtg ggtgagcccc gactggctca     180
cggcgctctc ccgctcggtg gcaacccgcc tcsgcggggg agacgactcg gggatccccg     240
tcgcctccgc caagctcgac gacgtgcmga cctcctcgga ggcgcgctct tcctccactc     300
ttcaagtggt tccgcgagga aggccccgtc taccgcctcg cggcggggcc gcgggatctc     360
gtcgtcgtca gcgatcccgc cgttgccagg cacgtgctgc gtgggtacgg ttcgaggtac     420
gagaaggggc tcgtcgccga ggtttccgag ttcctcttcg gctccgggtt cgccatcgcc     480
gagggcgcta tctggacggt gagacgtcga tcagttgtac catctctaca caaacgattt     540
ctctcggtga tggttgacag agttattgta aatgtgctga gagattagtg gagaagattg     600
agacatctgc tttaagtgga aaccgtaaat atggaagcaa ggttctctca atgactttta     660
gatgtgattt tttgtccttg ttcaattaca attttgattc cctcacatca gatagccctg     720
ttattgatgc tgtttacaag cactcaagga agcagaactt cgttctacag atctttttacc    780
atactggaag attgatttgc tgtgcaagat tgttcctaga caaataaaag cagaaaaggc     840
agttaacatc atcaggaata ccgttgagga cctaattacc aaatgcaaga agattgtaga     900
tgctgagaat gaacaaattg agggtgagga atatgtaaat gaggcagacc ctagcatcct     960
gcgattccta cttgctagcc gtgaagaggt aaccagtgtg cagttacgtg atgatctatt    1020
gcaatgttag ttgctggtca tgaaacaaca ggctctgtac tgacgtggac tatttatctt    1080
ctcagtaagg atccagcagc gctgaggaga gctcaagcag aggttgaccg tgttctacaa    1140
ggtagactcc ccagatatga agatctaaaa gagctgaagt acttgatgcg ctgtatataat   1200
gagtctatgc ggctttatcc acacccacct gggttgatac ggcgagccat agttgatgat    1260
gtgcttcccg gaaactataa gatcaaagct ggtcaagata ttatgatttc agtgtacaat    1320
atacacaggt cacctgaggt ttgggacaga gctgatgata tattcctgag agatttgatt    1380
tagagggacc tgttccaaat gagacaaaca ctgaatacag atttatccca ttcagtggag    1440
gtcctcggaa atgtgttgga gatcagtttg ctctcttgga agcaattgtg gcacttgctg    1500
ttgtgttgca gaagatggac attgagcttg tgccagatca aaaaattaac atgactactg    1560
```

```
gggccacaat tcatacaacc aatggcctgt atatgaatgt aagtctgcgt aaagttgaca    1620
gggaacctga ttttgcactc agtgggtcca gatga                              1655

<210> SEQ ID NO 7
<211> LENGTH: 595
<212> TYPE: PRT
<213> ORGANISM: A. thaliana

<400> SEQUENCE: 7

Met Ala Met Ala Phe Pro Leu Ser Tyr Thr Pro Thr Ile Thr Val Lys
1               5                   10                  15

Pro Val Thr Tyr Ser Arg Arg Ser Asn Phe Val Phe Ser Ser Ser
            20                  25                  30

Ser Asn Gly Arg Asp Pro Leu Glu Glu Asn Ser Val Pro Asn Gly Val
        35                  40                  45

Lys Ser Leu Glu Lys Leu Gln Glu Lys Arg Arg Ala Glu Leu Ser
50                  55                  60

Ala Arg Ile Ala Ser Gly Ala Phe Thr Val Arg Lys Ser Ser Phe Pro
65                  70                  75                  80

Ser Thr Val Lys Asn Gly Leu Ser Lys Ile Gly Ile Pro Ser Asn Val
                85                  90                  95

Leu Asp Phe Met Phe Asp Trp Thr Gly Ser Asp Gln Asp Tyr Pro Lys
            100                 105                 110

Val Pro Glu Ala Lys Gly Ser Ile Gln Ala Val Arg Asn Glu Ala Phe
        115                 120                 125

Phe Ile Pro Leu Tyr Glu Leu Phe Leu Thr Tyr Gly Gly Ile Phe Arg
    130                 135                 140

Leu Thr Phe Gly Pro Lys Ser Phe Leu Ile Val Ser Asp Pro Ser Ile
145                 150                 155                 160

Ala Lys His Ile Leu Lys Asp Asn Ala Lys Ala Tyr Ser Lys Gly Ile
                165                 170                 175

Leu Ala Glu Ile Leu Asp Phe Val Met Gly Lys Gly Leu Ile Pro Ala
            180                 185                 190

Asp Gly Glu Ile Trp Arg Arg Arg Arg Ala Ile Val Pro Ala Leu
        195                 200                 205

His Gln Lys Tyr Val Ala Ala Met Ile Ser Leu Phe Gly Glu Ala Ser
    210                 215                 220

Asp Arg Leu Cys Gln Lys Leu Asp Ala Ala Leu Lys Gly Glu Glu
225                 230                 235                 240

Val Glu Met Glu Ser Leu Phe Ser Arg Leu Thr Leu Asp Ile Ile Gly
                245                 250                 255

Lys Ala Val Phe Asn Tyr Asp Phe Asp Ser Leu Thr Asn Asp Thr Gly
            260                 265                 270

Val Ile Glu Ala Val Tyr Thr Val Leu Arg Glu Ala Glu Asp Arg Ser
        275                 280                 285

Val Ser Pro Ile Pro Val Trp Asp Ile Pro Ile Trp Lys Asp Ile Ser
    290                 295                 300

Pro Arg Gln Arg Lys Val Ala Thr Ser Leu Lys Leu Ile Asn Asp Thr
305                 310                 315                 320

Leu Asp Asp Leu Ile Ala Thr Cys Lys Arg Met Val Glu Glu Glu
                325                 330                 335

Leu Gln Phe His Glu Glu Tyr Met Asn Glu Arg Asp Pro Ser Ile Leu
            340                 345                 350
```

| | | | | | | | | | | | |
|---|---|---|---|---|---|---|---|---|---|---|---|
|His|Phe|Leu|Leu|Ala|Ser|Gly|Asp|Val|Ser|Ser|Lys|Gln|Leu|Arg|
| | | |355| | | |360| | | |365| | | |

His Phe Leu Leu Ala Ser Gly Asp Val Ser Ser Lys Gln Leu Arg
            355                 360                 365

Asp Asp Leu Met Thr Met Leu Ile Ala Gly His Glu Thr Ser Ala Ala
        370                 375                 380

Val Leu Thr Trp Thr Phe Tyr Leu Leu Thr Thr Glu Pro Ser Val Val
385                 390                 395                 400

Ala Lys Leu Gln Glu Glu Val Asp Ser Val Ile Gly Asp Arg Phe Pro
                405                 410                 415

Thr Ile Gln Asp Met Lys Lys Leu Lys Tyr Thr Thr Arg Val Met Asn
            420                 425                 430

Glu Ser Leu Arg Leu Tyr Pro Gln Pro Pro Val Leu Ile Arg Arg Ser
        435                 440                 445

Ile Asp Asn Asp Ile Leu Gly Glu Tyr Pro Ile Lys Arg Gly Glu Asp
    450                 455                 460

Ile Phe Ile Ser Val Trp Asn Leu His Arg Ser Pro Leu His Trp Asp
465                 470                 475                 480

Asp Ala Glu Lys Phe Asn Pro Glu Arg Trp Pro Leu Asp Gly Pro Asn
                485                 490                 495

Pro Asn Glu Thr Asn Gln Asn Phe Ser Tyr Leu Pro Phe Gly Gly Gly
            500                 505                 510

Pro Arg Lys Cys Ile Gly Asp Met Phe Ala Ser Phe Glu Asn Val Val
        515                 520                 525

Ala Ile Ala Met Leu Ile Arg Arg Phe Asn Phe Gln Ile Ala Pro Gly
    530                 535                 540

Ala Pro Pro Val Lys Met Thr Thr Gly Ala Thr Ile His Thr Thr Glu
545                 550                 555                 560

Gly Leu Lys Leu Thr Val Thr Lys Arg Thr Lys Pro Leu Asp Ile Pro
                565                 570                 575

Ser Val Pro Ile Leu Pro Met Asp Thr Ser Arg Asp Glu Val Ser Ser
            580                 585                 590

Ala Leu Ser
        595

<210> SEQ ID NO 8
<211> LENGTH: 2070
<212> TYPE: DNA
<213> ORGANISM: A. thaliana

<400> SEQUENCE: 8

```
gctctgtgat tgagttttt attttgcggt ggcgttgtat ggctatggcc tttcctcttt      60
cttatactcc gacgattact gttaaaccag taacgtactc tcggagatcg aactttgtag     120
ttttctcgtc gagttctaat ggacgagatc ctttagagga gaattcagta cctaatggtg     180
tgaaaagctt ggagaagctt caagaagaga agcgtcgtgc tgagttatct gctaggattg     240
cttctggagc tttcactgta cggaaatcta gttttccatc tacagtgaag aatggtttat     300
ctaagattgg aataccaagc aatgttcttg atttcatgtt tgattggact ggttctgacc     360
aagactaccc caaggttcct gaggctaaag ctcgattca ggcggtccgg aacgaagctt      420
tcttcatccc tttgtatgag cttttcctta cttatggtgg aattttcagg ttgacctttg     480
ggcctaagtc attcttgatc gtgtcggatc cttctattgc taaacatata ttgaaggaca     540
atgcaaaagc ttactccaag gggattttag ctgaaattct agattttgtg atgggaaaag     600
gactcattcc tgctgatggg gagatatggc gtagacgaag gcgtgccatt gttcctgcat     660
tgcatcaaaa gtatgtagca gctatgatta gtttattcgg agaagcttca gataggcttt     720
```

```
gtcagaagct tgatgctgct gcattgaaag gggaagaagt agagatggaa tcactcttct    780
ctcgtttgac acttgatatt attggcaagg cggttttcaa ttacgacttt gactccctta    840
ctaatgatac cggtgtgatc gaggcagtgt acactgttct aagagaagct gaagacagaa    900
gtgtttcacc tattcctgtt tgggacatac ccatttggaa agatatttcc ccacgtcaga    960
ggaaagttgc tacttccttg aaattaatca atgacacact tgatgatttg attgcaacat   1020
gcaagagaat ggtagaagaa gaggagttgc agtttcacga ggagtatatg aacgaaagag   1080
atcctagcat ccttcacttt cttttagctt caggagatga tgtctctagt aagcagcttc   1140
gtgatgactt gatgacaatg cttatagccg gacatgaaac atcggcggca gtattaacat   1200 ggaccttta cctttaaca acggaaccaa gtgtagttgc caaacttcaa gaagaggttg   1260
attctgtaat tggagataga ttcccaacca tacaagatat gaaaaagctg aaatacacta   1320
ctcgagtcat gaatgagtca ttgagattat atccacaacc accagtactg atccgtcgtt   1380
ctatagataa tgatatactt ggagagtatc cgataaaaag gggagaggat atcttcatct   1440
cggtttggaa tctacatcga agtcctctgc attgggatga tgcagagaag ttcaatcccg   1500
agagatggcc tttggatgga ccaaacccaa atgagacaaa ccaaaacttc agttacttac   1560
ctttcggtgg aggaccgcgg aaatgtatag gcgacatgtt tgcttccttt gagaatgtgg   1620
tagcaatcgc aatgcttatt cgaagattta acttcagat tgcaccagga gctcctccgg   1680
tgaaaatgac tacaggagct acaatacaca ccacagaagg attgaaattg acagtaacaa   1740
agaggacaaa acctctggac ataccatccg taccgatact tccaatggat acttcacggg   1800
atgaagtttc atctgctctt tcttaagtct tcatctttac aaaactgaaa acaaacaagc   1860
tcagatgaag aagcaaaaat cttgtgttag aacagcaaat gttgaattgt tggaacatga   1920 ccaatgctttt ctgattattt atctgcactg taaaatgcag acaagtaaaa tgagaagatt   1980
tattattctt tggaaaaaaa aatgttttg tctgcacagt gaagataata taacttctgg   2040
gttctatgta agttcaaata ttttctagga                                      2070
```

<210> SEQ ID NO 9
<211> LENGTH: 551
<212> TYPE: PRT
<213> ORGANISM: M. truncatula

<400> SEQUENCE: 9

```
Phe Leu Lys Arg Lys Asp Glu Leu Asn Cys Leu Leu Lys Leu Pro Gln
1               5                   10                  15

Val Asn Ser Arg Val Lys Gln Glu Ser Gly Leu Pro Ser Ile Leu Lys
            20                  25                  30

Lys Ser Leu Ser Asn Leu Gly Val Ser Asn Glu Ile Leu Glu Phe Leu
        35                  40                  45

Phe Gly Leu Tyr Pro Lys Ile Pro Glu Ala Lys Gly Ser Ile Ser Ala
    50                  55                  60

Ile Arg Ser Glu Ala Phe Phe Ile Pro Leu Tyr Glu Leu Tyr Ile Thr
65                  70                  75                  80

Tyr Gly Gly Ile Phe Arg Leu Asn Phe Gly Pro Lys Ser Phe Leu Ile
                85                  90                  95

Val Ser Asp Pro Ala Ile Ala Lys His Ile Leu Lys Asp Asn Ser Lys
            100                 105                 110

Ala Tyr Ser Lys Gly Ile Leu Ala Glu Ile Leu Asp Phe Val Met Gly
        115                 120                 125
```

```
Lys Gly Leu Ile Pro Ala Asp Gly Glu Ile Trp Arg Val Arg Arg
130                 135                 140

Thr Ile Val Pro Ala Leu His Leu Lys Phe Val Ala Ala Met Ile Gly
145                 150                 155                 160

Leu Phe Gly Gln Ala Thr Asp Arg Leu Cys Gln Lys Leu Asp Thr Ala
                165                 170                 175

Ala Ser Asp Gly Glu Asp Val Glu Met Glu Ser Leu Phe Ser Arg Leu
                180                 185                 190

Thr Leu Asp Val Ile Gly Lys Ala Val Phe Asn Tyr Asp Phe Asp Ser
                195                 200                 205

Leu Ser Asn Asp Thr Gly Ile Ile Glu Ala Val Tyr Thr Val Leu Arg
210                 215                 220

Glu Ala Glu Asp Arg Ser Ile Ser Pro Ile Pro Val Trp Asp Leu Pro
225                 230                 235                 240

Ile Trp Lys Asp Ile Ser Pro Arg Gln Arg Lys Val Thr Ala Ala Leu
                245                 250                 255

Lys Leu Val Asn Asp Thr Leu Asn Asn Leu Ile Ala Ile Cys Lys Arg
                260                 265                 270

Met Val Asp Glu Glu Leu Gln Phe His Glu Glu Tyr Met Asn Glu
                275                 280                 285

Gln Asp Pro Ser Ile Ser Phe Thr Phe Leu Leu Ala Ser Gly Asp Asp
290                 295                 300

Val Thr Ser Lys Gln Leu Arg Asp Asp Leu Met Thr Met Leu Ile Ala
305                 310                 315                 320

Gly His Glu Thr Ser Ala Ala Val Leu Thr Trp Thr Phe Tyr Leu Leu
                325                 330                 335

Ser Lys Glu Pro Ser Val Met Ser Lys Leu Gln Glu Glu Val Asp Ser
                340                 345                 350

Val Leu Gly Asp Arg Phe Pro Thr Ile Glu Asp Met Lys Lys Leu Lys
                355                 360                 365

Tyr Thr Thr Arg Val Ile Asn Glu Ser Leu Arg Leu Tyr Pro Gln Pro
370                 375                 380

Pro Val Leu Ile Arg Arg Ser Ile Glu Asp Asp Val Leu Gly Glu Tyr
385                 390                 395                 400

Pro Ile Lys Arg Gly Glu Asp Ile Phe Ile Ser Val Trp Asn Leu His
                405                 410                 415

Arg Ser Pro Thr Leu Trp Asn Asp Ala Asp Lys Phe Glu Pro Glu Arg
                420                 425                 430

Trp Pro Leu Asp Gly Pro Asn Pro Asn Glu Thr Asn Gln Gly Phe Lys
                435                 440                 445

Tyr Leu Pro Phe Gly Gly Pro Arg Lys Cys Ile Gly Asp Met Phe
450                 455                 460

Ala Ser Tyr Glu Val Val Ala Leu Ala Met Leu Val Arg Arg Phe
465                 470                 475                 480

Asn Phe Gln Met Ala Val Gly Ala Pro Pro Val Val Met Thr Thr Gly
                485                 490                 495

Ala Thr Ile His Thr Thr Gln Gly Leu Asn Met Thr Val Thr Arg Arg
                500                 505                 510

Ile Lys Pro Pro Ile Val Pro Ser Leu Gln Met Ser Thr Leu Glu Val
                515                 520                 525

Asp Pro Ser Val Ser Ile Ser Asp Lys Thr Glu Glu Ile Gly Gln Lys
530                 535                 540

Asp Gln Val Tyr Gln Ala Gln
```

-continued 545            550

<210> SEQ ID NO 10
<211> LENGTH: 551
<212> TYPE: PRT
<213> ORGANISM: M. truncatula

<400> SEQUENCE: 10

Phe Leu Lys Arg Lys Asp Glu Leu Asn Cys Leu Leu Lys Leu Pro Gln
1               5                   10                  15

Val Asn Ser Arg Val Lys Gln Glu Ser Gly Leu Pro Ser Ile Leu Lys
            20                  25                  30

Lys Ser Leu Ser Asn Leu Gly Val Ser Asn Glu Ile Leu Glu Phe Leu
        35                  40                  45

Phe Gly Leu Tyr Pro Lys Ile Pro Glu Ala Lys Gly Ser Ile Ser Ala
    50                  55                  60

Ile Arg Ser Glu Ala Phe Phe Ile Pro Leu Tyr Glu Leu Tyr Ile Thr
65                  70                  75                  80

Tyr Gly Gly Ile Phe Arg Leu Asn Phe Gly Pro Lys Ser Phe Leu Ile
                85                  90                  95

Val Ser Asp Pro Ala Ile Ala Lys His Ile Leu Lys Asp Asn Ser Lys
            100                 105                 110

Ala Tyr Ser Lys Gly Ile Leu Ala Glu Ile Leu Asp Phe Val Met Gly
        115                 120                 125

Lys Gly Leu Ile Pro Ala Asp Gly Glu Ile Trp Arg Val Arg Arg Arg
    130                 135                 140

Thr Ile Val Pro Ala Leu His Leu Lys Phe Val Ala Ala Met Ile Gly
145                 150                 155                 160

Leu Phe Gly Gln Ala Thr Asp Arg Leu Cys Gln Lys Leu Asp Thr Ala
                165                 170                 175

Ala Ser Asp Gly Glu Asp Val Glu Met Glu Ser Leu Phe Ser Arg Leu
            180                 185                 190

Thr Leu Asp Val Ile Gly Lys Ala Val Phe Asn Tyr Asp Phe Asp Ser
        195                 200                 205

Leu Ser Asn Asp Thr Gly Ile Ile Glu Ala Val Tyr Thr Val Leu Arg
    210                 215                 220

Glu Ala Glu Asp Arg Ser Ile Ser Pro Ile Pro Val Trp Asp Leu Pro
225                 230                 235                 240

Ile Trp Lys Asp Ile Ser Pro Arg Gln Arg Lys Val Thr Ala Ala Leu
                245                 250                 255

Lys Leu Val Asn Asp Thr Leu Asn Asn Leu Ile Ala Ile Cys Lys Arg
            260                 265                 270

Met Val Asp Glu Glu Leu Gln Phe His Glu Glu Tyr Met Asn Glu
        275                 280                 285

Gln Asp Pro Ser Ile Ser Phe Thr Phe Leu Leu Ala Ser Gly Asp Asp
    290                 295                 300

Val Thr Ser Lys Gln Leu Arg Asp Asp Leu Met Thr Met Leu Ile Ala
305                 310                 315                 320

Gly His Glu Thr Ser Ala Ala Val Leu Thr Trp Thr Phe Tyr Leu Leu
                325                 330                 335

Ser Lys Glu Pro Ser Val Met Ser Lys Leu Gln Glu Glu Val Asp Ser
            340                 345                 350

Val Leu Gly Asp Arg Phe Pro Thr Ile Glu Asp Met Lys Lys Leu Lys
        355                 360                 365

-continued

```
Tyr Thr Thr Arg Val Ile Asn Glu Ser Leu Arg Leu Tyr Pro Gln Pro
370                 375                 380

Pro Val Leu Ile Arg Arg Ser Ile Glu Asp Asp Val Leu Gly Glu Tyr
385                 390                 395                 400

Pro Ile Lys Arg Gly Glu Asp Ile Phe Ile Ser Val Trp Asn Leu His
                405                 410                 415

Arg Ser Pro Thr Leu Trp Asn Asp Ala Asp Lys Phe Glu Pro Glu Arg
            420                 425                 430

Trp Pro Leu Asp Gly Pro Asn Pro Asn Glu Thr Asn Gln Gly Phe Lys
        435                 440                 445

Tyr Leu Pro Phe Gly Gly Gly Pro Arg Lys Cys Ile Gly Asp Met Phe
450                 455                 460

Ala Ser Tyr Glu Val Val Val Ala Leu Ala Met Leu Val Arg Arg Phe
465                 470                 475                 480

Asn Phe Gln Met Ala Val Gly Ala Pro Pro Val Val Met Thr Thr Gly
                485                 490                 495

Ala Thr Ile His Thr Thr Gln Gly Leu Asn Met Thr Val Thr Arg Arg
                500                 505                 510

Ile Lys Pro Pro Ile Val Pro Ser Leu Gln Met Ser Thr Leu Glu Val
            515                 520                 525

Asp Pro Ser Val Ser Ile Ser Asp Lys Thr Glu Glu Ile Gly Gln Lys
        530                 535                 540

Asp Gln Val Tyr Gln Ala Gln
545                 550

<210> SEQ ID NO 11
<211> LENGTH: 434
<212> TYPE: PRT
<213> ORGANISM: H. vulgare

<400> SEQUENCE: 11

Met Gly Thr Gly Leu Ile Pro Ala Asp Gly Glu Val Trp Arg Val Arg
1               5                   10                  15

Arg Arg Ala Ile Val Pro Ala Leu His Gln Lys Tyr Val Thr Ala Met
                20                  25                  30

Ile Gly Leu Phe Gly Asn Ala Ser Asp Arg Leu Cys Gln Lys Leu Asp
            35                  40                  45

Lys Ala Ala Ser Asp Gly Glu Asp Val Glu Met Glu Ser Leu Phe Ser
        50                  55                  60

Arg Leu Thr Leu Asp Val Ile Gly Lys Ala Val Phe Asn Tyr Asp Phe
65                  70                  75                  80

Asp Ser Leu Ser Tyr Asp Asn Gly Ile Val Glu Ala Val Tyr Val Thr
                85                  90                  95

Leu Arg Glu Ala Glu Met Arg Ser Thr Ser Pro Ile Pro Thr Trp Glu
                100                 105                 110

Ile Pro Ile Trp Lys Asp Ile Ser Pro Arg Gln Arg Lys Val Asn Glu
            115                 120                 125

Ala Leu Ala Leu Ile Asn Asn Ile Leu Asp Glu Leu Ile Ala Thr Cys
        130                 135                 140

Lys Arg Met Val Asp Glu Glu Asp Leu Gln Phe His Glu Glu Tyr Met
145                 150                 155                 160

Asn Glu Lys Asp Pro Ser Ile Leu His Phe Leu Leu Ala Ser Gly Asp
                165                 170                 175

Asp Val Ser Ser Lys Gln Leu Arg Asp Asp Leu Met Thr Met Leu Ile
                180                 185                 190
```

Ala Gly His Glu Thr Ser Ala Ala Val Leu Thr Trp Thr Phe Tyr Leu
        195                 200                 205

Leu Ser Lys Tyr Pro Asn Val Met Ser Lys Leu Gln Ala Glu Ala Asp
        210                 215                 220

Ala Val Leu Gly Asp Gly Leu Pro Thr Ile Asp Asp Val Lys Lys Leu
225                 230                 235                 240

Lys Tyr Thr Thr Arg Val Ile Asn Glu Ser Leu Arg Leu Tyr Pro Gln
                245                 250                 255

Pro Pro Val Leu Ile Arg Arg Ser Leu Glu Asp Asp Met Leu Gly Glu
            260                 265                 270

Tyr Pro Ile Gly Lys Gly Glu Asp Ile Phe Ile Ser Ile Trp Asn Leu
        275                 280                 285

His Arg Cys Pro Lys His Trp Asp Asp Ala Asp Val Phe Asn Pro Glu
    290                 295                 300

Arg Trp Pro Leu Asp Gly Pro Asn Pro Asn Glu Thr Asn Gln Lys Phe
305                 310                 315                 320

Ser Tyr Leu Pro Phe Gly Gly Pro Arg Lys Cys Val Gly Asp Met
                325                 330                 335

Phe Ala Thr Phe Glu Thr Val Val Ala Thr Ala Met Leu Val Lys Arg
            340                 345                 350

Phe Asp Phe Gln Met Ala Pro Gly Ala Pro Val Glu Met Thr Thr
        355                 360                 365

Gly Ala Thr Ile His Thr Thr Lys Gly Leu Asn Met Thr Val Thr Arg
    370                 375                 380

Arg Ile Lys Pro Pro Val Ile Pro Asn Leu Glu Met Lys Ile Val Ser
385                 390                 395                 400

Asp Pro Glu Gly Ser Thr Ser Ser Thr Ala Ser Val Ala Val Ser Thr
                405                 410                 415

Ala Ser Ile Ala Ser Gly Glu Gly Gln Gln Val Glu Val Ser Thr Ser
            420                 425                 430

Gln Val

<210> SEQ ID NO 12
<211> LENGTH: 434
<212> TYPE: PRT
<213> ORGANISM: H. vulgare

<400> SEQUENCE: 12

Met Gly Thr Gly Leu Ile Pro Ala Asp Gly Glu Val Trp Arg Val Arg
1               5                   10                  15

Arg Arg Ala Ile Val Pro Ala Leu His Gln Lys Tyr Val Thr Ala Met
            20                  25                  30

Ile Gly Leu Phe Gly Asn Ala Ser Asp Arg Leu Cys Gln Lys Leu Asp
        35                  40                  45

Lys Ala Ala Ser Asp Gly Glu Asp Val Glu Met Glu Ser Leu Phe Ser
    50                  55                  60

Arg Leu Thr Leu Asp Val Ile Gly Lys Ala Val Phe Asn Tyr Asp Phe
65                  70                  75                  80

Asp Ser Leu Ser Tyr Asp Asn Gly Ile Val Glu Ala Val Tyr Val Thr
                85                  90                  95

Leu Arg Glu Ala Glu Met Arg Ser Thr Ser Pro Ile Pro Thr Trp Glu
            100                 105                 110

Ile Pro Ile Trp Lys Asp Ile Ser Pro Arg Gln Arg Lys Val Asn Glu
        115                 120                 125

```
Ala Leu Ala Leu Ile Asn Asn Ile Leu Asp Glu Leu Ile Ala Thr Cys
        130                 135                 140

Lys Arg Met Val Asp Glu Glu Asp Leu Gln Phe His Glu Glu Tyr Met
145                 150                 155                 160

Asn Glu Lys Asp Pro Ser Ile Leu His Phe Leu Leu Ala Ser Gly Asp
                165                 170                 175

Asp Val Ser Ser Lys Gln Leu Arg Asp Asp Leu Met Thr Met Leu Ile
            180                 185                 190

Ala Gly His Glu Thr Ser Ala Ala Val Leu Thr Trp Thr Phe Tyr Leu
        195                 200                 205

Leu Ser Lys Tyr Pro Asn Val Met Ser Lys Leu Gln Ala Glu Ala Asp
    210                 215                 220

Ala Val Leu Gly Asp Gly Leu Pro Thr Ile Asp Asp Val Lys Lys Leu
225                 230                 235                 240

Lys Tyr Thr Thr Arg Val Ile Asn Glu Ser Leu Arg Leu Tyr Pro Gln
                245                 250                 255

Pro Pro Val Leu Ile Arg Arg Ser Leu Glu Asp Asp Met Leu Gly Glu
            260                 265                 270

Tyr Pro Ile Gly Lys Gly Glu Asp Ile Phe Ile Ser Ile Trp Asn Leu
        275                 280                 285

His Arg Cys Pro Lys His Trp Asp Asp Ala Asp Val Phe Asn Pro Glu
    290                 295                 300

Arg Trp Pro Leu Asp Gly Pro Asn Pro Asn Glu Thr Asn Gln Lys Phe
305                 310                 315                 320

Ser Tyr Leu Pro Phe Gly Gly Pro Arg Lys Cys Val Gly Asp Met
                325                 330                 335

Phe Ala Thr Phe Glu Thr Val Val Ala Thr Ala Met Leu Val Lys Arg
            340                 345                 350

Phe Asp Phe Gln Met Ala Pro Gly Ala Pro Pro Val Glu Met Thr Thr
        355                 360                 365

Gly Ala Thr Ile His Thr Thr Lys Gly Leu Asn Met Thr Val Thr Arg
    370                 375                 380

Arg Ile Lys Pro Pro Val Ile Pro Asn Leu Glu Met Lys Ile Val Ser
385                 390                 395                 400

Asp Pro Glu Gly Ser Thr Ser Ser Thr Ala Ser Val Ala Val Ser Thr
                405                 410                 415

Ala Ser Ile Ala Ser Gly Glu Gly Gln Gln Val Glu Val Ser Thr Ser
            420                 425                 430

Gln Val

<210> SEQ ID NO 13
<211> LENGTH: 552
<212> TYPE: PRT
<213> ORGANISM: P. sativum

<400> SEQUENCE: 13

Met Val Ala Ala Pro Ile Ser Thr Val Lys Leu Thr Asp Ala Asn Leu
1               5                   10                  15

His Thr Arg Phe His Ser Ser Ser Ser Thr Pro Thr Leu Ser
                20                  25                  30

Leu Pro Leu Ser Leu His Phe His Phe Ser Ser His Ser Lys Arg Phe
            35                  40                  45

Ser Ser Ile Arg Cys Gln Ser Val Asn Gly Glu Lys Arg Lys Gln Ser
        50                  55                  60
```

```
Ser Arg Asn Val Phe Asp Asn Ala Ser Asn Leu Leu Thr Ser Leu Leu
 65                  70                  75                  80

Ser Gly Ala Asn Leu Gly Ser Met Pro Ile Ala Glu Gly Ala Val Thr
                 85                  90                  95

Asp Leu Phe Asp Arg Pro Leu Phe Phe Ser Leu Tyr Asp Trp Phe Leu
            100                 105                 110

Glu His Gly Ser Val Tyr Lys Leu Ala Phe Gly Pro Lys Ala Phe Val
        115                 120                 125

Val Val Ser Asp Pro Ile Val Ala Arg His Ile Leu Arg Glu Asn Ala
130                 135                 140

Phe Ser Tyr Asp Lys Gly Val Leu Ala Asp Ile Leu Glu Pro Ile Met
145                 150                 155                 160

Gly Lys Gly Leu Ile Pro Ala Asp Leu Glu Thr Trp Lys Gln Arg Arg
                165                 170                 175

Arg Val Ile Ala Pro Gly Phe His Thr Ser Tyr Leu Glu Ala Met Val
            180                 185                 190

Gln Leu Phe Thr Ser Cys Ser Glu Arg Thr Val Leu Lys Val Asn Glu
        195                 200                 205

Leu Leu Glu Gly Glu Gly Arg Asp Gly Gln Lys Ser Val Glu Leu Asp
210                 215                 220

Leu Glu Ala Glu Phe Ser Asn Leu Ala Leu Glu Ile Ile Gly Leu Gly
225                 230                 235                 240

Val Phe Asn Tyr Asp Phe Gly Ser Val Thr Asn Glu Ser Pro Val Ile
                245                 250                 255

Lys Ala Val Tyr Gly Thr Leu Phe Glu Ala Glu His Arg Ser Thr Phe
            260                 265                 270

Tyr Ile Pro Tyr Trp Lys Phe Pro Leu Ala Arg Trp Ile Val Pro Arg
        275                 280                 285

Gln Arg Lys Phe Gln Asp Asp Leu Lys Val Ile Asn Thr Cys Leu Asp
290                 295                 300

Gly Leu Ile Arg Asn Ala Lys Glu Ser Arg Gln Glu Thr Asp Val Glu
305                 310                 315                 320

Lys Leu Gln Gln Arg Asp Tyr Ser Asn Leu Lys Asp Ala Ser Leu Leu
                325                 330                 335

Arg Phe Leu Val Asp Met Arg Gly Val Asp Val Asp Arg Gln Leu
            340                 345                 350

Arg Asp Asp Leu Met Thr Met Leu Ile Ala Gly His Glu Thr Thr Ala
        355                 360                 365

Ala Val Leu Thr Trp Ala Val Phe Leu Leu Ala Gln Asn Pro Asp Lys
        370                 375                 380

Met Lys Lys Ala Gln Ala Glu Val Asp Leu Val Leu Gly Met Gly Lys
385                 390                 395                 400

Pro Thr Phe Glu Leu Leu Lys Lys Leu Glu Tyr Ile Arg Leu Ile Val
                405                 410                 415

Val Glu Thr Leu Arg Leu Tyr Pro Gln Pro Leu Leu Ile Arg Arg
            420                 425                 430

Ser Leu Lys Pro Asp Val Leu Pro Gly Gly His Lys Gly Asp Lys Asp
        435                 440                 445

Gly Tyr Thr Ile Pro Ala Gly Thr Asp Val Phe Ile Ser Val Tyr Asn
        450                 455                 460

Leu His Arg Ser Pro Tyr Phe Trp Asp Arg Pro Asn Asp Phe Glu Pro
465                 470                 475                 480
```

```
Glu Arg Phe Leu Val Gln Asn Asn Asn Glu Glu Val Glu Gly Trp Ala
                485                 490                 495

Gly Phe Asp Pro Ser Arg Ser Pro Gly Ala Leu Tyr Pro Asn Glu Ile
            500                 505                 510

Ile Ser Asp Phe Ala Phe Leu Pro Phe Gly Gly Gly Pro Arg Lys Cys
            515                 520                 525

Val Gly Asp Gln Phe Ala Leu Met Glu Ser Thr Val Ala Leu Val Cys
            530                 535                 540

Cys Tyr Arg Ile Ser Met Trp Asn
545                 550

<210> SEQ ID NO 14
<211> LENGTH: 1926
<212> TYPE: DNA
<213> ORGANISM: P. sativum

<400> SEQUENCE: 14
```

| | | | | | |
|---|---|---|---|---|---|
| catcacttac | cactaactga | aacttgcaag | caccattctc | aacttaacac | cgtcgtcacc | 60 |
| gccatggttg | ccgcccctat | ctcaaccgtc | aaacttaccg | atgccaatct | tcacaccaga | 120 |
| tttcattcct | cttcttcttc | tacaccatcc | accctcagtc | ttccactctc | tcttcatttt | 180 |
| cacttttctt | ctcactccaa | acgcttttct | tctatcagat | gtcaatcggt | taatggtgaa | 240 |
| aagcgaaaac | aaagtagtag | aaatgtgttt | gacaatgcta | gcaacctcct | tacaagcttg | 300 |
| ttaagtggtg | caaatttagg | gtccatgccc | atagctgaag | gtgccgtcac | agatctgttt | 360 |
| gaccggccgc | tgtttttctc | actatatgat | tggttcttag | agcatggttc | tgtgtataaa | 420 |
| ctggcgtttg | gaccgaaagc | atttgttgtt | gtatcagatc | ccattgttgc | aagacatatt | 480 |
| ctgcgagaaa | atgcattttc | ttatgacaag | ggagtacttg | ctgatatcct | agaaccaatt | 540 |
| atgggaaaag | gactcatacc | tgcagacctt | gagacatgga | agcaaaggag | aagagtgatt | 600 |
| gctccgggtt | tccatacctc | atacttggaa | gctatggtac | aactattcac | ttcatgttca | 660 |
| gaaagaactg | tgttaaaggt | caatgagctt | cttgaaggag | aggggcgtga | tggacagaag | 720 |
| tcagttgaat | tggaccttga | ggcagaattt | caaatttgg | ctcttgagat | tattgggcta | 780 |
| ggtgtgttca | actatgactt | tggttctgtc | accaatgaat | ctcccgttat | taaggctgtc | 840 |
| tatggcactc | ttttgaagc | cgaacataga | tccactttct | atattccata | ttggaaattt | 900 |
| ccattagcaa | ggtggattgt | gcccaggcaa | aggaagtttc | aggatgacct | taaagtcatt | 960 |
| aatacttgtc | ttgatggact | tatcagaaat | gcaaagaga | gcaggcagga | aacagatgtt | 1020 |
| gagaaactgc | agcaaaggga | ttactcaaat | ttgaaggatg | caagtcttct | gcgtttccta | 1080 |
| gttgatatgc | ggggagttga | tgttgatgat | cgtcagttga | gggatgattt | aatgacaatg | 1140 |
| cttattgctg | gtcatgagac | gacggctgca | gttcttacat | gggcagtttt | cctgctagct | 1200 |
| caaaatcctg | acaaaatgaa | gaaggctcaa | gcagaggtag | atttggtgct | ggggatgggg | 1260 |
| aagccaactt | tgaattgct | taaaaagttg | gagtacatta | ggttaattgt | tgtgagact | 1320 |
| cttcgattat | atccacaacc | acctctgctg | attagacgtt | cactcaaacc | tgatgttttg | 1380 |
| ccaggtggac | ataaaggtga | caaagatggt | tatacaattc | ctgctgggac | tgatgtcttc | 1440 |
| atttctgtat | ataatctcca | tcgatctcca | tattttgggg | accgccctaa | tgacttcgag | 1500 |
| cctgaacgat | ttctagtgca | aaacaataat | gaagaagttg | aagggtgggc | tggttttgac | 1560 |
| ccatctcgaa | gtcctggagc | cttgtatcca | aacgagatta | tatcagattt | tgcattcttg | 1620 |
| cctttttggtg | gtggaccacg | aaaatgcgtt | ggagaccaat | ttgctctcat | ggaatccact | 1680 |

-continued

```
gtagcgctag tatgctgcta cagaatttcg atgtggaact gaaggggacc cctgaatcgg   1740
ttgaactagt tactggggca actatccata ccaaaaatgg attgtggtgc aatttgagga   1800
agagatctag tttacattga catgttaact gcaacatttt tcttatgcag aatgatgtac   1860
aaaatattta tcatttaaaa tgacattaac attgaatagt gtctaataca gctaaagggt   1920
atttac                                                             1926
```

<210> SEQ ID NO 15
<211> LENGTH: 576
<212> TYPE: PRT
<213> ORGANISM: G. max

<400> SEQUENCE: 15

```
Met Ser Val Asp Thr Ser Ser Thr Leu Ser Thr Val Thr Asp Ala Asn
1               5                   10                  15

Leu His Ser Arg Phe His Ser Arg Leu Val Pro Phe Thr His His Phe
            20                  25                  30

Ser Leu Ser Gln Pro Lys Arg Ile Ser Ile Arg Cys Gln Ser Ile
        35                  40                  45

Asn Thr Asp Lys Lys Ser Ser Arg Asn Leu Leu Gly Asn Ala Ser
50                  55                  60

Asn Leu Leu Thr Asp Leu Leu Ser Gly Gly Ser Ile Gly Ser Met Pro
65                  70                  75                  80

Ile Ala Glu Gly Ala Val Ser Asp Leu Leu Gly Arg Pro Leu Phe Phe
                85                  90                  95

Ser Leu Tyr Asp Trp Phe Leu Glu His Gly Ala Val Tyr Lys Leu Ala
            100                 105                 110

Phe Gly Pro Lys Ala Phe Val Val Ser Asp Pro Ile Val Ala Arg
        115                 120                 125

His Ile Leu Arg Glu Asn Ala Phe Ser Tyr Asp Lys Gly Val Leu Ala
130                 135                 140

Asp Ile Leu Glu Pro Ile Met Gly Lys Gly Leu Ile Pro Ala Asp Leu
145                 150                 155                 160

Asp Thr Trp Lys Gln Arg Arg Val Ile Ala Pro Ala Phe His Asn
                165                 170                 175

Ser Tyr Leu Glu Ala Met Val Lys Ile Phe Thr Thr Cys Ser Glu Arg
            180                 185                 190

Thr Ile Leu Lys Phe Asn Lys Leu Glu Gly Glu Gly Tyr Asp Gly
        195                 200                 205

Pro Asp Ser Ile Glu Leu Asp Leu Glu Ala Glu Phe Ser Ser Leu Ala
    210                 215                 220

Leu Asp Ile Ile Gly Leu Gly Val Phe Asn Tyr Asp Phe Gly Ser Val
225                 230                 235                 240

Thr Lys Glu Ser Pro Val Ile Lys Ala Val Tyr Gly Thr Leu Phe Glu
                245                 250                 255

Ala Glu His Arg Ser Thr Phe Tyr Ile Pro Tyr Trp Lys Ile Pro Leu
            260                 265                 270

Ala Arg Trp Ile Val Pro Arg Gln Arg Lys Phe Gln Asp Asp Leu Lys
        275                 280                 285

Val Ile Asn Thr Cys Leu Asp Gly Leu Ile Arg Asn Ala Lys Glu Ser
    290                 295                 300

Arg Gln Glu Thr Asp Val Glu Lys Leu Gln Gln Arg Asp Tyr Leu Asn
305                 310                 315                 320

Leu Lys Asp Ala Ser Leu Leu Arg Phe Leu Val Asp Met Arg Gly Ala
```

```
                    325                 330                 335
Asp Val Asp Asp Arg Gln Leu Arg Asp Asp Leu Met Thr Met Leu Ile
                340                 345                 350
Ala Gly His Glu Thr Thr Ala Ala Val Leu Thr Trp Ala Val Phe Leu
                355                 360                 365
Leu Ala Gln Asn Pro Ser Lys Met Lys Lys Ala Gln Ala Glu Val Asp
    370                 375                 380
Leu Val Leu Gly Thr Gly Arg Pro Thr Phe Glu Ser Leu Lys Glu Leu
385                 390                 395                 400
Gln Tyr Ile Arg Leu Ile Val Val Glu Ala Leu Arg Leu Tyr Pro Gln
                405                 410                 415
Pro Pro Leu Leu Ile Arg Arg Ser Leu Lys Ser Asp Val Leu Pro Gly
                420                 425                 430
Gly His Lys Gly Glu Lys Asp Gly Tyr Ala Ile Pro Ala Gly Thr Asp
                435                 440                 445
Val Phe Ile Ser Val Tyr Asn Leu His Arg Ser Pro Tyr Phe Trp Asp
    450                 455                 460
Arg Pro Asp Asp Phe Glu Pro Glu Arg Phe Leu Val Gln Asn Lys Asn
465                 470                 475                 480
Glu Glu Ile Glu Gly Trp Ala Gly Leu Asp Pro Ser Arg Ser Pro Gly
                485                 490                 495
Ala Leu Tyr Pro Asn Glu Val Ile Ser Asp Phe Ala Phe Leu Pro Phe
                500                 505                 510
Gly Gly Gly Pro Arg Lys Cys Val Gly Asp Gln Phe Ala Leu Met Glu
                515                 520                 525
Ser Thr Val Ala Leu Thr Met Leu Leu Gln Asn Phe Asp Val Glu Leu
    530                 535                 540
Lys Gly Thr Pro Glu Ser Val Glu Leu Val Thr Gly Ala Thr Ile His
545                 550                 555                 560
Thr Lys Asn Gly Met Trp Cys Arg Leu Lys Lys Arg Ser Asn Leu Arg
                565                 570                 575

<210> SEQ ID NO 16
<211> LENGTH: 1831
<212> TYPE: DNA
<213> ORGANISM: G. max

<400> SEQUENCE: 16
caacactcgc agtaccgcca tgagtgtcga cacttcctcc accctctcca ccgtcaccga    60
tgccaatctt cactccagat ttcattctcg tcttgttcca ttcactcatc atttctcact   120
ttctcaaccc aaacggattt cttcaatcag atgccaatca attaataccg ataagaagaa   180
atcaagtaga aatctgctgg gcaatgcaag taacctcctc acggacttat taagtggtgg   240
aagtataggg tctatgccca tagctgaagg tgcagtctca gatctgcttg gtcgacctct   300
cttttctca ctgtatgatt ggttcttgga gcatggtgcg gtgtataaac ttgcctttgg   360
accaaaagca tttgttgttg tatcagatcc catagttgct agacatattc tgcgagaaaa   420
tgcattttct tatgacaagg gagtacttgc tgatatcctt gaaccaataa tgggcaaagg   480
actcatacca gcagaccttg atacttggaa gcaaaggaga gagtcattg ctccggcttt    540
ccataactca tacttggaag ctatggttaa atattcaca acttgttcag aaagaacaat    600
attgaagttt aataagcttc ttgaaggaga gggttatgat ggacctgact caattgaatt   660
ggatcttgag gcagagtttt ctagtttggc tcttgatatt attgggcttg gtgtgttcaa   720
```

```
ctatgactttt ggttctgtca ccaaagaatc tccagttatt aaggcagtct atggcactct    780
ttttgaagct gaacacagat ccactttcta cattccatat tggaaaattc cattggcaag    840
gtggatagtc ccaaggcaaa gaaagtttca ggatgaccta aaggtcatca atacttgtct    900
tgatggactt atcagaaatg caaagagag cagacaggaa acagatgttg agaaattgca    960
gcagagggat tacttaaatt tgaaggatgc aagtcttctg cgtttcctgg ttgatatgcg   1020
gggagctgat gttgatgatc gtcagttgag ggatgattta atgacaatgc ttattgccgg   1080
tcatgaaaca acggctgcag ttcttacttg ggcagttttc ctcctagctc aaaatcctag   1140
caaaatgaag aaggctcaag cagaggtaga tttggtgctg ggtacgggga ggccaacttt   1200
tgaatcactt aaggaattgc agtacattag attgattgtt gtggaggctc ttcgtttata   1260
cccccaacca cctttgctga ttagacgttc actcaaatct gatgttttac caggtgggca   1320
caaaggtgaa aaagatggtt atgcaattcc tgctgggact gatgtcttca tttctgtata   1380
taatctccat agatctccat attttgggga ccgccctgat gacttcgaac cagagagatt   1440
tcttgtgcaa acaagaatg aagaaattga aggatgggct ggtcttgatc catctcgaag   1500
tcccggagcc ttgtatccga acgaggttat atcggatttt gcattcttac cttttggtgg   1560
cggaccacga aaatgtgttg gggaccaatt tgctctgatg gagtccactg tagcgttgac   1620
tatgctgctc cagaattttg acgtggaact aaaagggacc cctgaatcgg tggaactagt   1680
tactggggca actattcata ccaaaaatgg aatgtggtgc agattgaaga agagatctaa   1740
tttacgttga catatgtact gtggccattt ttcttataca gaataatgta tattattatt   1800
ctttgagaat aatatgaata aattcctaga c                                  1831
```

<210> SEQ ID NO 17
<211> LENGTH: 580
<212> TYPE: PRT
<213> ORGANISM: A. thaliana

<400> SEQUENCE: 17

```
Met Val Ala Ala Met Ala Phe Pro Ala Ala Thr Tyr Pro Thr His
1               5                   10                  15

Phe Gln Gly Gly Ala Leu His Leu Gly Arg Thr Asp His Cys Leu Phe
            20                  25                  30

Gly Phe Tyr Pro Gln Thr Ile Ser Ser Val Asn Ser Arg Arg Ala Ser
        35                  40                  45

Val Ser Ile Lys Cys Gln Ser Thr Glu Pro Lys Thr Asn Gly Asn Ile
    50                  55                  60

Leu Asp Asn Ala Ser Asn Leu Leu Thr Asn Phe Leu Ser Gly Gly Ser
65                  70                  75                  80

Leu Gly Ser Met Pro Thr Ala Glu Gly Ser Val Ser Asp Leu Phe Gly
                85                  90                  95

Lys Pro Leu Phe Leu Ser Leu Tyr Asp Trp Phe Leu Glu His Gly Gly
            100                 105                 110

Ile Tyr Lys Leu Ala Phe Gly Pro Lys Ala Phe Val Val Ile Ser Asp
        115                 120                 125

Pro Ile Ile Ala Arg His Val Leu Arg Glu Asn Ala Phe Ser Tyr Asp
    130                 135                 140

Lys Gly Val Leu Ala Glu Ile Leu Glu Pro Ile Met Gly Lys Gly Leu
145                 150                 155                 160

Ile Pro Ala Asp Leu Asp Thr Trp Lys Leu Arg Arg Arg Ala Ile Thr
                165                 170                 175
```

```
Pro Ala Phe His Lys Leu Tyr Leu Glu Ala Met Val Lys Val Phe Ser
            180                 185                 190

Asp Cys Ser Glu Lys Met Ile Leu Lys Ser Glu Lys Leu Ile Arg Glu
            195                 200                 205

Lys Glu Thr Ser Ser Gly Glu Asp Thr Ile Glu Leu Asp Leu Glu Ala
            210                 215                 220

Glu Phe Ser Ser Leu Ala Leu Asp Ile Ile Gly Leu Ser Val Phe Asn
225                 230                 235                 240

Tyr Asp Phe Gly Ser Val Thr Lys Glu Ser Pro Val Ile Lys Ala Val
            245                 250                 255

Tyr Gly Thr Leu Phe Glu Ala Glu His Arg Ser Thr Phe Tyr Phe Pro
            260                 265                 270

Tyr Trp Asn Phe Pro Pro Ala Arg Trp Ile Val Pro Arg Gln Arg Lys
            275                 280                 285

Phe Gln Ser Asp Leu Lys Ile Ile Asn Asp Cys Leu Asp Gly Leu Ile
            290                 295                 300

Gln Asn Ala Lys Glu Thr Arg Gln Glu Thr Asp Val Glu Lys Leu Gln
305                 310                 315                 320

Glu Arg Asp Tyr Thr Asn Leu Lys Asp Ala Ser Leu Leu Arg Phe Leu
                    325                 330                 335

Val Asp Met Arg Gly Val Asp Ile Asp Asp Arg Gln Leu Arg Asp Asp
                340                 345                 350

Leu Met Thr Met Leu Ile Ala Gly His Glu Thr Thr Ala Ala Val Leu
                355                 360                 365

Thr Trp Ala Val Phe Leu Leu Ser Gln Asn Pro Glu Lys Ile Arg Lys
        370                 375                 380

Ala Gln Ala Glu Ile Asp Ala Val Leu Gly Gln Gly Pro Pro Thr Tyr
385                 390                 395                 400

Glu Ser Met Lys Lys Leu Glu Tyr Ile Arg Leu Ile Val Val Glu Val
                    405                 410                 415

Leu Arg Leu Phe Pro Gln Pro Pro Leu Leu Ile Arg Arg Thr Leu Lys
                420                 425                 430

Pro Glu Thr Leu Pro Gly Gly His Lys Gly Glu Lys Glu Gly His Lys
                435                 440                 445

Val Pro Lys Gly Thr Asp Ile Phe Ile Ser Val Tyr Asn Leu His Arg
450                 455                 460

Ser Pro Tyr Phe Trp Asp Asn Pro His Asp Phe Glu Pro Glu Arg Phe
465                 470                 475                 480

Leu Arg Thr Lys Glu Ser Asn Gly Ile Glu Gly Trp Ala Gly Phe Asp
                    485                 490                 495

Pro Ser Arg Ser Pro Gly Ala Leu Tyr Pro Asn Glu Ile Ile Ala Asp
                500                 505                 510

Phe Ala Phe Leu Pro Phe Gly Gly Pro Arg Lys Cys Ile Gly Asp
                515                 520                 525

Gln Phe Ala Leu Met Glu Ser Thr Val Ala Leu Ala Met Leu Phe Gln
                530                 535                 540

Lys Phe Asp Val Glu Leu Arg Gly Thr Pro Glu Ser Val Glu Leu Val
545                 550                 555                 560

Ser Gly Ala Thr Ile His Ala Lys Asn Gly Met Trp Cys Lys Leu Lys
                    565                 570                 575

Arg Arg Ser Lys
                580
```

<210> SEQ ID NO 18
<211> LENGTH: 1921
<212> TYPE: DNA
<213> ORGANISM: A. thaliana

<400> SEQUENCE: 18

| | | | | | |
|---|---|---|---|---|---|
| atctaacttt | agagcttctc | ttttcatttg | aagatggtag | cagccatggc | ttttcctgcc | 60 |
| gctgctactt | atcccaccca | tttccaaggc | ggcgctcttc | atctgggtag | gaccgatcat | 120 |
| tgcctcttcg | gtttctaccc | tcaaaccatt | tcctctgtga | attctcggag | agcttctgtt | 180 |
| tccatcaagt | gccaatctac | ggagccaaag | acgaatggta | acatattgga | caatgcgagc | 240 |
| aaccttttga | caaattttttt | aagtggtgga | agtttgggt | caatgcctac | tgctgaaggc | 300 |
| tctgtctctg | atttgtttgg | aaagcctctc | tttttatctc | tttacgactg | gttcttggag | 360 |
| catggaggaa | tttataaact | tgcgtttggt | ccaaaagcct | tgttgtcat | ctcagatccc | 420 |
| attattgcaa | ggcatgtcct | ccgggaaaat | gcttttctt | atgacaaggg | agttcttgct | 480 |
| gagatcttag | agccgattat | gggaaaaggg | ttaataccgg | ctgatctaga | tacgtggaag | 540 |
| ttaagaagaa | gagctatcac | tcccgcattc | cataaattgt | atctagaggc | catggtcaaa | 600 |
| gtatttagtg | actgttcgga | gaaaatgata | ttgaaatctg | agaaactcat | aagggagaaa | 660 |
| gaaacttcaa | gcggggagga | caccattgag | ttggatctgg | aagcagaatt | ctcgagtctg | 720 |
| gctcttgata | ttataggtct | tagcgtgttc | aactacgatt | ttggctctgt | cacaaaagag | 780 |
| tcccctgtga | tcaaggcagt | ttatggaact | cttttcgagg | cagagcatcg | gtctactttc | 840 |
| tacttcccctt | attggaactt | tcctccagct | agatggatag | ttccgaggca | acgaaagttc | 900 |
| caaagcgatc | tgaagattat | aaacgattgc | cttgatggcc | tcattcaaaa | tgctaaagag | 960 |
| acaagacagg | aaacagatgt | tgagaagctc | caggaaaggg | actacactaa | tctcaaggat | 1020 |
| gcaagtcttt | tgcggttctt | agtcgatatg | cgcggtgttg | acattgatga | ccggcagctg | 1080 |
| agggatgact | tgatgactat | gctaattgct | ggtcatgaga | caacagcagc | agtacttact | 1140 |
| tgggctgttt | tccttctgtc | acaaaatcct | gaaaaaatta | ggaaagctca | agctgagatt | 1200 |
| gatgctgtgc | ttggtcaagg | tccacccact | tatgaatcaa | tgaaaaagct | cgagtacata | 1260 |
| cgactgatcg | ttgtagaagt | ccttcgtctc | tttcctcagc | cacctttgct | catcagacgc | 1320 |
| actctcaaac | cagaaacatt | acccggagga | cacaaggggg | aaaagaaagg | tcataaagtt | 1380 |
| ccaaaaggga | ctgatatctt | catttctgtg | tataatctcc | atagatctcc | atacttttgg | 1440 |
| gataatcccc | acgatttttga | gcctgagagg | tttttaagaa | caaggagag | caatggaatt | 1500 |
| gaaggatggg | ctggctttga | tccatctcgt | agccccgggg | cactatatcc | gaatgagata | 1560 |
| atagcagact | ttgcattctt | accatttggt | ggaggaccaa | gaaaatgcat | tggagaccag | 1620 |
| tttgcactaa | tggaatcgac | cgtcgcacta | gctatgttgt | ttcagaaatt | cgatgtggag | 1680 |
| ctgcgtggaa | cgccagaatc | tgttgaactc | gtgagcggcg | caacgattca | tgccaaaaat | 1740 |
| gggatgtggt | gcaaactaaa | gagaagatca | aagtgaaatt | tatggatagg | caaaagact | 1800 |
| caatttttaac | ttgaaggaag | ctgagtgtaa | atgagagatg | atatgcttat | gattcactaa | 1860 |
| acgtacattc | ttgagatttt | gaaaatgcaa | aaaagctaat | acagagattg | gatctgttgg | 1920 |
| t | | | | | | 1921 |

<210> SEQ ID NO 19
<211> LENGTH: 651
<212> TYPE: PRT
<213> ORGANISM: L. esculentum

<400> SEQUENCE: 19

```
Phe Thr Ile Thr Met Pro Ile Ser Val Thr Ile Ser Ser Phe Ser Leu
1               5                   10                  15

Leu Thr Asn Pro His His Arg Thr Thr Val Leu Arg Pro Lys Asn Pro
            20                  25                  30

Leu Gln Asn Arg Ser Gln Leu Thr Ile Lys Ser Ser Ile Asp Asn Lys
        35                  40                  45

Lys Pro Pro Ser Thr Lys Pro Thr Ser Trp Val Ser Pro Asp Trp Leu
    50                  55                  60

Thr Lys Leu Thr Arg Ser Leu Thr Leu Gly Gln Asn Asp Asp Ser Asn
65                  70                  75                  80

Ile Pro Ile Ala Ser Ala Glu Leu Asp Asp Val Ser Glu Leu Leu Gly
                85                  90                  95

Gly Ala Leu Phe Leu Pro Leu Tyr Arg Trp Met Asn Leu Tyr Gly Pro
            100                 105                 110

Ile Tyr Arg Leu Ala Ala Gly Pro Arg Asn Phe Val Ile Val Ser Asp
        115                 120                 125

Pro Ala Ile Ala Lys His Val Leu Lys Asn Tyr Gly Lys Tyr Gly Lys
    130                 135                 140

Gly Leu Val Ala Glu Val Ser Glu Phe Leu Phe Gly Ser Gly Phe Ala
145                 150                 155                 160

Ile Ala Glu Gly Pro Leu Trp Thr Ala Arg Arg Arg Ala Val Val Pro
                165                 170                 175

Ser Leu His Lys Lys Tyr Leu Ser Val Ile Val Asp Arg Val Phe Cys
            180                 185                 190

Arg Cys Ala Glu Arg Met Val Glu Lys Leu Leu Pro Asp Ala Ile Ser
        195                 200                 205

Gly Ser Ala Val Asn Met Glu Ala Lys Phe Ser Gln Leu Thr Leu Asp
    210                 215                 220

Val Ile Gly Leu Ala Leu Phe Asn Tyr Asn Phe Asp Ser Leu Thr Thr
225                 230                 235                 240

Asp Ser Pro Val Ile Asp Ala Val Tyr Thr Ala Leu Lys Glu Ala Glu
                245                 250                 255

Leu Arg Ser Thr Asp Leu Leu Pro Tyr Trp Gln Ile Lys Ala Leu Cys
            260                 265                 270

Lys Phe Ile Pro Arg Gln Ile Lys Ala Glu Asn Ala Val Ser Leu Ile
        275                 280                 285

Arg Gln Thr Val Glu Glu Leu Ile Ala Lys Cys Arg Glu Ile Val Glu
    290                 295                 300

Thr Glu Gly Glu Arg Ile Asn Glu Asp Glu Tyr Val Asn Asp Arg Asp
305                 310                 315                 320

Pro Ser Ile Leu Arg Phe Leu Leu Ala Ser Arg Glu Glu Val Ser Ser
                325                 330                 335

Val Gln Leu Arg Asp Asp Leu Leu Ser Met Leu Val Ala Gly His Glu
            340                 345                 350

Thr Thr Gly Ser Val Leu Thr Trp Thr Ala Tyr Leu Leu Ser Lys Asp
        355                 360                 365

Pro Ser Ser Leu Glu Lys Ala His Glu Glu Val Asp Arg Val Leu Gly
    370                 375                 380

Gly Arg Ser Pro Thr Tyr Glu Asp Met Lys Asn Leu Lys Phe Leu Thr
385                 390                 395                 400

Arg Cys Ile Thr Glu Ser Leu Arg Leu Tyr Pro His Pro Pro Val Leu
                405                 410                 415
```

Ile Arg Arg Ala Gln Val Ala Asp Val Leu Pro Gly Asn Tyr Lys Val
                420                 425                 430

Asn Val Gly Gln Asp Ile Met Ile Ser Val Tyr Asn Ile His His Ser
            435                 440                 445

Ser Glu Val Trp Asp Arg Ala Glu Phe Asp Pro Glu Arg Phe Asp
450                 455                 460

Leu Glu Gly Pro Val Pro Asn Glu Thr Asn Thr Asp Phe Arg Phe Ile
465                 470                 475                 480

Pro Phe Ser Gly Gly Pro Arg Lys Cys Val Gly Asp Gln Phe Ala Leu
                485                 490                 495

Leu Glu Ala Thr Ile Ala Leu Ala Ile Phe Val Gln Asn Phe Ser Phe
            500                 505                 510

Glu Leu Ile Pro Asp Gln Thr Ile Ser Met Thr Thr Gly Ala Thr Ile
        515                 520                 525

His Thr Thr Asn Gly Leu Tyr Met Lys Val Lys Gln Arg Glu Lys Ala
    530                 535                 540

Ser Val Leu Ala Ala Ala Pro Ile Leu Ser Gln Glu Lys Val Ile Leu
545                 550                 555                 560

Ile Leu Thr Leu Tyr Thr Ser Leu Val Asp Tyr Glu Asn His His Tyr
                565                 570                 575

Cys Val Met Ser Tyr Phe Phe Ser Gly Ile Ile Ala Phe Phe Ser Phe
            580                 585                 590

Phe Leu Tyr Ile Arg Ile Tyr Cys Ala Ser Phe Lys Asn Asn Leu Ser
        595                 600                 605

Met Ser Thr Arg Tyr Arg Gly Arg Val Arg Thr Asp Gln Thr Leu Cys
    610                 615                 620

Ala Gln Asp Pro Thr Leu Lys Ile Tyr Cys Met Tyr Cys Cys Ile Ser
625                 630                 635                 640

Glu Tyr Ala Phe Val Val Gly Lys Lys Lys
                645                 650

<210> SEQ ID NO 20
<211> LENGTH: 1967
<212> TYPE: DNA
<213> ORGANISM: L. esculentum

<400> SEQUENCE: 20
ttcaccatca ccatgccaat ttcggtcacc atttcttcct ctctcttct cactaaccct      60 caccaccgga ccaccgtgct ccgcccaaaa aacccactcc aaaatcgttc acaactcacc    120
attaaatcct ccattgacaa caagaaacca ccttcaacta agcctacttc atgggtcagt    180
ccagattggc ttactaaact taccaggtca cttactttag ccaaaatgaa tgattctaac   240
atacccattg cgagtgctga gcttgatgat gtttcggaac ttctgggcgg tgctctttt    300 cttccattgt atagatggat gaatttgtat ggacctattt atcgtcttgc tgctgggccg    360
aggaattttg ttattgttag tgatcctgct attgctaagc atgttttgaa gaattatggg   420
aagtatggga aagggcttgt tgctgaagtt tctgagtttt gtttggttc tggttttgct    480 attgctgaag gtcctctttg acggcaaggc gaagggctg tggttccatc tcttcacaag   540
aagtacttgt cagtaatagt tgatcgggtc ttttgcagat gtgctgagag aatggtggaa   600 aaactttac ctgatgcaat ttctggctct gcagtgaata tggaggcaaa gttttctcaa   660
ctaacacttg atgttattgg ccttgcactc ttcaattaca attttgattc ccttactact   720
gacagtccag ttattgatgc agtttacact gcactaaaag aagcagaact ccgttcaact   780

```
gatttgttgc catattggca gatcaaagct ttatgtaagt tcatcccacg acaaataaag      840
gctgagaatg cagtgtcatt aatcagacaa acagttgaag aacttattgc aaagtgcaga      900
gagattgtag aaactgaggg tgagaggatt aatgaagatg agtacgtgaa tgatagagat      960
ccaagcatcc ttcgattctt gcttgctagc cgtgaggagg tttcaagtgt acaacttcga     1020
gatgatcttc tgtcaatgct agttgctggg catgaaacca caggttcagt tttgacttgg     1080
acggcatacc tgctgagtaa ggatccttcc tctttggaaa aagcacatga ggaagtagac     1140
agagttttgg gaggacgctc tccgacttat gaagacatga agaatctcaa gttcttaaca     1200
cggtgcataa ctgagtcact cagactctat ccacatccac ctgtcctaat aagaagagct     1260
caagtagctg atgtcctccc cgggaattac aaagtcaatg ttggtcagga tataatgatt     1320
tcggtatata acattcatca ttcttcagag gtatgggata gagctgaaga atttgatcct     1380
gaaagattcg acttggaagg tcccgtccca aatgaaacaa atactgactt tagattcatc     1440
ccgtttagtg gagggccacg aaaatgcgtt ggtgatcaat ttgccttgtt ggaagctaca     1500
attgctctcg cgatatttgt acagaacttc tcattcgagt tgattccaga tcaaactatt     1560
agcatgacta ctggagcaac cattcatacg acaaacggtt tatacatgaa agtgaagcaa     1620
agggagaaag catctgtttt ggctgctgca ccgtaaattt tgtcacagga gaaagtaatc     1680
ttgattcttt gaacattata tacatctttg gtagactatg agaatcatca ttattgcgtt     1740
atgtcctatt ttttctctgg cattattgcc ttttttttctt tctttctata tattagaata     1800
tattgcgcct ctttcaaaaa taacctctct atgtctacga ggtataggggg tagagtgtag     1860 cgtacagatc aaactctctg cgcccaagat cctaccttga aaatatactg tatgtattgt     1920
tgtatatcag aatatgcctt ttaagttgtt ggaaaaaaaa aaaaaaa                    1967

<210> SEQ ID NO 21
<211> LENGTH: 563
<212> TYPE: PRT
<213> ORGANISM: M. truncatula

<400> SEQUENCE: 21

Met Pro Ser Cys Ser Cys Ser Cys Ser Cys Ser Leu Pro Leu Ser His
1               5                   10                  15

Leu Ser Leu Ser Ser Phe Ser Lys Thr Pro Leu Pro Gln Lys Arg Tyr
            20                  25                  30

Pro Leu His Pro Arg Ile Leu Thr Lys Ser Ser Thr Asn Lys Asn Pro
        35                  40                  45

Glu Thr Thr Lys Ser Thr Ser Trp Val Ser Pro Asp Trp Leu Thr Ser
    50                  55                  60

Leu Ser Lys Ser Leu Thr Thr Ser Lys Asn Asp Asp Ser Asn Ile Pro
65                  70                  75                  80

Ile Ala Ser Ala Lys Leu Asp Asp Val Ser Asp Leu Leu Gly Gly Ala
                85                  90                  95

Leu Phe Leu Pro Leu Phe Lys Trp Met Asn Glu Tyr Gly Pro Ile Tyr
            100                 105                 110

Arg Leu Ala Ala Gly Pro Arg Asn Phe Val Val Ser Asp Pro Ala
        115                 120                 125

Ile Ala Lys His Val Leu Lys Asn Tyr Gly Lys Tyr Gly Lys Gly Leu
    130                 135                 140

Val Ala Glu Val Ser Glu Phe Leu Phe Gly Asp Gly Phe Ala Ile Ala
145                 150                 155                 160
```

```
Glu Gly Pro Leu Trp Thr Ala Arg Arg Ala Val Pro Ser Leu
            165                 170             175
His Lys Arg Tyr Leu Ser Ile Met Val Asp Arg Val Phe Cys Lys Cys
            180                 185                 190
Ala Glu Arg Leu Val Glu Lys Leu Gln Ala Asp Ala Val Asn Gly Thr
            195                 200                 205
Ala Val Asn Met Glu Asp Lys Phe Ser Gln Leu Thr Leu Asp Val Ile
210             215                 220
Gly Leu Ser Val Phe Asn Tyr Asn Phe Asp Ala Leu Asn Ser Asp Ser
225                 230                 235                 240
Pro Val Ile Glu Ala Val Tyr Thr Ala Leu Lys Glu Ala Glu Ala Arg
                245                 250                 255
Ser Thr Asp Leu Leu Pro Tyr Trp Lys Ile Asp Phe Leu Cys Lys Ile
                260                 265                 270
Ile Pro Arg Gln Ile Lys Ala Glu Asn Ala Val Thr Val Ile Arg Lys
                275                 280                 285
Thr Val Glu Asp Leu Ile Glu Gln Cys Lys Glu Ile Val Glu Ser Glu
                290                 295                 300
Gly Glu Arg Ile Asp Ala Asp Glu Tyr Val Asn Asp Ala Asp Pro Ser
305                 310                 315                 320
Ile Leu Arg Phe Leu Leu Ala Ser Arg Glu Glu Val Ser Ser Val Gln
                325                 330                 335
Leu Arg Asp Asp Leu Leu Ser Met Leu Val Ala Gly His Glu Thr Thr
                340                 345                 350
Gly Ser Val Leu Thr Trp Thr Leu Tyr Leu Leu Ser Lys Asp Ser Ser
                355                 360                 365
Ser Leu Ala Lys Ala Gln Glu Glu Val Asp Arg Val Leu Gln Gly Arg
            370                 375                 380
Arg Pro Thr Tyr Glu Asp Met Lys Asp Leu Lys Phe Leu Asn Arg Cys
385                 390                 395                 400
Ile Ile Glu Ser Leu Arg Leu Tyr Pro His Pro Val Leu Ile Arg
                405                 410                 415
Arg Ser Gln Ile Pro Asp Glu Leu Pro Gly Asp Tyr Lys Ile Asp Ala
                420                 425                 430
Gly Gln Asp Ile Met Ile Ser Val Tyr Asn Ile His His Ser Ser Lys
            435                 440                 445
Val Trp Asp Arg Ala Glu Glu Phe Leu Pro Glu Arg Phe Asp Leu Asp
            450                 455                 460
Gly Pro Val Pro Asn Glu Thr Asn Thr Asp Phe Arg Phe Ile Pro Phe
465                 470                 475                 480
Arg Gly Gly Pro Arg Lys Gly Val Gly Asp Gln Phe Ala Leu Leu Glu
                485                 490                 495
Ala Thr Val Ala Phe Ala Val Phe Leu Gln His Met Asn Phe Glu Leu
                500                 505                 510
Val Pro Asp Gln Asn Ile Gly Met Thr Thr Gly Ala Thr Ile His Thr
                515                 520                 525
Thr Asn Gly Leu Tyr Met Lys Met Ser Gln Arg Leu Lys Lys Leu Thr
                530                 535                 540
Ser Thr Phe Phe Ser His Arg Trp Gln Asn Leu Leu Ala Asn Asn Tyr
545                 550                 555                 560

Gln Gln Asp

<210> SEQ ID NO 22
```

<211> LENGTH: 1814
<212> TYPE: DNA
<213> ORGANISM: M. truncatula

<400> SEQUENCE: 22

```
cgtaaaccca aaacaatgc catcatgttc atgttcatgt tcatgttcac tccctctctc      60
tcatctttct ctctcttcct tctccaaaac accactccca caaaaacgtt atccacttca    120
tcctcgtatc ttaacaaaat cctcaactaa caaaaaccct gaaacaacaa aatccacttc    180
atgggtaagt ccagattggc tcacatcact ttcaaaatcc ttaacaacat caaaaaatga    240
tgattccaac attcctatag caagtgctaa gcttgatgat gtttctgatc ttttgggtgg    300
tgctcttttt cttcctttgt ttaaatggat gaatgagtat ggtcctattt atcgtttagc    360
tgctggtcca agaaactttg ttgttgttag tgatcctgct attgctaaac atgttcttaa    420
gaattatggt aaatatggta aggtcttgt tgctgaggtt tctgagtttt tgtttgggga    480
tggttttgct attgctgaag gacctctttg gacggcaagg cgcagggctg tggttccatc    540
tcttcacaaa cggtacttgt ctattatggt ggatagggtg ttctgtaaat gtgcagagag    600
attagtagag aagctacaag ccgatgcagt taatggaact gctgttaaca tggaagacaa    660
gttttctcag ttaacccttg atgttattgg tttatccgtg ttcaactaca actttgacgc    720
actaaattca gatagtcctg ttattgaagc cgtttacact gcactgaaag aggcggaggc    780
tcggtcaacc gatcttttgc cctattggaa gattgatttt ctttgtaaga taatcccgag    840
acaaataaag gctgaaaatg ctgttactgt tatcaggaaa actgtagaag accttattga    900
acaatgtaaa gagattgtag agtccgaggg tgaaagaatt gatgctgatg aatatgtgaa    960
tgacgctgac cctagtattc ttcgattttt gcttgccagc agagaagagg tttctagtgt   1020
gcaattaagg gatgatcttt tgtcaatgtt agttgctggt catgagacca ccggttcggt   1080
gctgacttgg acactttatc ttctaagtaa ggattcttcc tcattggcaa agctcaaga    1140
agaggtagac agagttttac agggaaggcg tcctacctat gaagatatga agatcttaa    1200
gttcttgaat cgctgtatta tcgagtcact ccgactttat ccacatcctc ctgtattgat   1260
aagaagatct caaattcctg atgagcttcc gggtgattac aaaatcgatg ccggtcaaga   1320
tattatgatt tctgtgtaca acatacatca ttcttctaag gtttgggata gagctgaaga   1380
gtttttgcc agaaagattt gtttggatgg tccagtacca aatgaaacaa atacagattt   1440
cagattcatt ccattcaggg gaggccctcg aaagggtgtc ggtgatcagt ttgcattatt   1500
ggaagctacc gttgctttg cagttttttt acagcacatg aactttgagc tggtacctga   1560
tcagaatatt ggcatgacta cgggagcaac aatacataca acaaatggct tgtacatgaa   1620
aatgagccaa cggttgaaaa agttgacatc cactttttt tcacataggt ggcaaaattt   1680
attggctaat aactatcagc aagattaaat tattttttg agagaagcaa tattaaattc   1740
ttaagaggct tatttgtgcc atttcgtaca ccccaagtaa gtagtaaata tcgcatttga   1800
tagaaaatat ttct                                                     1814
```

<210> SEQ ID NO 23
<211> LENGTH: 539
<212> TYPE: PRT
<213> ORGANISM: A. thaliana

<400> SEQUENCE: 23

Met Glu Ser Ser Leu Phe Ser Pro Ser Ser Ser Tyr Ser Ser Leu
1               5                   10                  15

-continued

```
Phe Thr Ala Lys Pro Thr Arg Leu Leu Ser Pro Lys Pro Lys Phe Thr
             20                  25                  30
Phe Ser Ile Arg Ser Ser Ile Glu Lys Pro Lys Pro Lys Leu Glu Thr
         35                  40                  45
Asn Ser Ser Lys Ser Gln Ser Trp Val Ser Pro Asp Trp Leu Thr Thr
 50                  55                  60
Leu Thr Arg Thr Leu Ser Ser Gly Lys Asn Asp Glu Ser Gly Ile Pro
 65                  70                  75                  80
Ile Ala Asn Ala Lys Leu Asp Asp Val Ala Asp Leu Leu Gly Gly Ala
                 85                  90                  95
Leu Phe Leu Pro Leu Tyr Lys Trp Met Asn Glu Tyr Gly Pro Ile Tyr
            100                 105                 110
Arg Leu Ala Ala Gly Pro Arg Asn Phe Val Ile Val Ser Asp Pro Ala
            115                 120                 125
Ile Ala Lys His Val Leu Arg Asn Tyr Pro Lys Tyr Ala Lys Gly Leu
        130                 135                 140
Val Ala Glu Val Ser Glu Phe Leu Phe Gly Ser Gly Phe Ala Ile Ala
145                 150                 155                 160
Glu Gly Pro Leu Trp Thr Ala Arg Arg Arg Ala Val Val Pro Ser Leu
                165                 170                 175
His Arg Arg Tyr Leu Ser Val Ile Val Glu Arg Val Phe Cys Lys Cys
            180                 185                 190
Ala Glu Arg Leu Val Glu Lys Leu Gln Pro Tyr Ala Glu Asp Gly Ser
        195                 200                 205
Ala Val Asn Met Glu Ala Lys Phe Ser Gln Met Thr Leu Asp Val Ile
210                 215                 220
Gly Leu Ser Leu Phe Asn Tyr Asn Phe Asp Ser Leu Thr Thr Asp Ser
225                 230                 235                 240
Pro Val Ile Glu Ala Val Tyr Thr Ala Leu Lys Glu Ala Glu Leu Arg
                245                 250                 255
Ser Thr Asp Leu Leu Pro Tyr Trp Lys Ile Asp Ala Leu Cys Lys Ile
            260                 265                 270
Val Pro Arg Gln Val Lys Ala Glu Lys Ala Val Thr Leu Ile Arg Glu
        275                 280                 285
Thr Val Glu Asp Leu Ile Ala Lys Cys Lys Glu Ile Val Glu Arg Glu
290                 295                 300
Gly Glu Arg Ile Asn Asp Glu Glu Tyr Val Asn Asp Ala Asp Pro Ser
305                 310                 315                 320
Ile Leu Arg Phe Leu Leu Ala Ser Arg Glu Glu Val Ser Ser Val Gln
                325                 330                 335
Leu Arg Asp Asp Leu Leu Ser Met Leu Val Ala Gly His Glu Thr Thr
            340                 345                 350
Gly Ser Val Leu Thr Trp Thr Leu Tyr Leu Leu Ser Lys Asn Ser Ser
        355                 360                 365
Ala Leu Arg Lys Ala Gln Glu Glu Val Asp Arg Val Leu Glu Gly Arg
    370                 375                 380
Asn Pro Ala Phe Glu Asp Ile Lys Glu Leu Lys Tyr Ile Thr Arg Cys
385                 390                 395                 400
Ile Asn Glu Ser Met Arg Leu Tyr Pro His Pro Val Leu Ile Arg
                405                 410                 415
Arg Ala Gln Val Pro Asp Ile Leu Pro Gly Asn Tyr Lys Val Asn Thr
            420                 425                 430
Gly Gln Asp Ile Met Ile Ser Val Tyr Asn Ile His Arg Ser Ser Glu
```

|  |  | 435 |  |  | 440 |  |  | 445 |  |  |  |
|---|---|---|---|---|---|---|---|---|---|---|---|

Val Trp Glu Lys Ala Glu Phe Leu Pro Glu Arg Phe Asp Ile Asp
450                 455                 460

Gly Ala Ile Pro Asn Glu Thr Asn Thr Asp Phe Lys Phe Ile Pro Phe
465                 470                 475                 480

Ser Gly Gly Pro Arg Lys Cys Val Gly Asp Gln Phe Ala Leu Met Glu
                485                 490                 495

Ala Ile Val Ala Leu Ala Val Phe Leu Gln Arg Leu Asn Val Glu Leu
            500                 505                 510

Val Pro Asp Gln Thr Ile Ser Met Thr Thr Gly Ala Thr Ile His Thr
        515                 520                 525

Thr Asn Gly Leu Tyr Met Lys Val Ser Gln Arg
530                 535

<210> SEQ ID NO 24
<211> LENGTH: 1620
<212> TYPE: DNA
<213> ORGANISM: A. thaliana

<400> SEQUENCE: 24

| | |
|---|---|
| atggagtctt cactcttttc tccatcttcc tcttcttact cttctctctt cactgcaaaa | 60 |
| cctacgcgtc ttttatcacc aaaacccaaa ttcacattct ccatcagatc ctccattgag | 120 |
| aaacccaaac ccaaactcga gaccaattca tcgaaatccc aatcatgggt cagtcccgat | 180 |
| tggctcacaa cactcactcg tacccttttcc tcaggaaaaa acgacgagtc aggtatacca | 240 |
| atcgcgaacg cgaagctcga cgatgtcgct gatctcctcg gaggtgctct cttcttacct | 300 |
| ctctacaaat ggatgaatga gtacggaccc atttaccgtc tcgctgctgg tcctcgtaat | 360 |
| ttcgtaattg tgagcgaccc agcgatagct aaacatgttt tgaggaatta tccaaagtac | 420 |
| gctaaaggct tagtcgctga agtctctgaa tttctatttg gttcgggttt cgctatcgct | 480 |
| gaaggacctc tttggacagc gaggcgtaga gcggtggttc atcgcttca caggaggtat | 540 |
| tgtctctgtga ttgtggagag agtattctgc aaatgtgcag agaggcttgt tgagaagttg | 600 |
| cagccttatg cagaagacgg aagtgctgtg aatatggaag cgaagttctc tcagatgaca | 660 |
| cttgatgtca ttgggttgtc tcttttaac tacaatttcg attctttgac tactgatagt | 720 |
| cctgtcattg aagctgttta cactgctctt aaagaagctg agcttcgttc tactgatctt | 780 |
| ctgccatatt ggaagatcga tgcattgtgt aagatagtcc cgagacaggt gaaagctgaa | 840 |
| aaggctgtaa cttgtgataag ggaaactgtt gaagacctta ttgctaagtg taaagaaatt | 900 |
| gtcgaaagag aaggcgaaag aatcaatgat gaggagtatg taaatgatgc tgacccaagt | 960 |
| atcctgcgtt tcttgcttgc aagcagagaa gaggtatcaa gtgtgcagtt acgggatgat | 1020 |
| cttctctcaa tgctcgtagc gggtcatgaa accactggat ctgtcctcac ttggacactt | 1080 |
| tatctcctaa gtaagaactc atctgcatta aggaaagcac aagaagaagt agacagagtg | 1140 |
| ttagaaggaa gaaacccggc tttcgaggat ataaggagt tgaagtacat cactcgttgt | 1200 |
| ataaacgagt caatgcgtct ctatcctcat cctcctgtct tgataagaag agctcaagtt | 1260 |
| cctgacattc ttcctgggaa ctataaggtc aataccggac aagacattat gatttcagtc | 1320 |
| tataacatcc atcgttcttc cgaggtatgg gaaaaagctg aggaatttct gcctgaacga | 1380 |
| ttcgacatag atggcgcaat ccctaacgaa acaaacactg atttcaaatt catcccattc | 1440 |
| agtggagggc ctagaaaatg tgtaggcgat cagtttgcat tgatggaggc aattgtggca | 1500 |
| ctcgcggtgt ttcttcagcg gttaaacgtt gagctggttc ctgatcagac cattagcatg | 1560 | accacaggag caaccataca caccaccaat ggattgtata tgaaggtgag ccaaaggtaa    1620

<210> SEQ ID NO 25
<211> LENGTH: 371
<212> TYPE: PRT
<213> ORGANISM: A. thaliana

<400> SEQUENCE: 25

Met Ala Ser Val Thr Leu Gly Ser Trp Ile Val His His Asn
1               5                   10                  15

His His His Pro Ser Ser Ile Leu Thr Lys Ser Arg Ser Cys
            20                  25                  30

Pro Ile Thr Leu Thr Lys Pro Ile Ser Phe Arg Ser Lys Arg Thr Val
            35                  40                  45

Ser Ser Ser Ser Ser Ile Val Ser Ser Ser Val Val Thr Lys Glu Asp
50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Ser Tyr Ser Leu Leu
            100                 105                 110

Ala Gly Gly Lys Arg Val Arg Pro Val Leu Cys Ile Ala Ala Cys Glu
        115                 120                 125

Leu Val Gly Gly Glu Glu Ser Thr Ala Met Pro Ala Arg Cys Ala Val
130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ser
            180                 185                 190

Phe Glu His Leu Ala Ser Ala Thr Ser Ser Asp Val Val Ser Pro Val
        195                 200                 205

Arg Val Val Arg Ala Val Gly Glu Leu Ala Lys Ala Ile Gly Thr Glu
210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
        275                 280                 285

Ile Gly Leu Leu Phe Gln Val Val Asp Ile Leu Asp Val Thr Lys
        290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Lys Ser Arg Glu Phe
                325                 330                 335

Ala Glu Lys Leu Asn Arg Glu Ala Arg Asp Gln Leu Leu Gly Phe Asp
            340                 345                 350

Ser Asp Lys Val Ala Pro Leu Leu Ala Leu Ala Asn Tyr Ile Ala Tyr
        355                 360                 365

Arg Gln Asn
    370

<210> SEQ ID NO 26
<211> LENGTH: 1242
<212> TYPE: DNA
<213> ORGANISM: A. thaliana

<400> SEQUENCE: 26

```
ggtgagaatt tcagatttca gaaatcgcca tggcttcagt gactctaggt tcatggattg      60
ttgttcacca ccacaatcat catcatccat cttcaatcct taccaaatcc agatccagat     120
cttgtcctat aactcttact aaacccatct cctttcgatc aaaacgcacc gtttcatcat     180
cttcttcaat cgtttcttct tccgttgtta caaaagaaga caatctacgc caatctgaac     240
catcctcttt cgatttcatg tcgtacatca tcaccaaagc cgaattagtc aacaaagctt     300
tagattcagc tgttcctctc cgtgagccac tcaagatcca cgaagcgatg agttactctc     360
ttctcgccgg tggcaaaaga gttagaccag ttctctgcat cgctgcttgt gaactcgtcg     420
gaggtgaaga atcaaccgct atgccagcac gttgcgccgt cgagatgatt cacaccatgt     480
cgttgatcca cgacgatctc ccttgtatgg ataacgacga tctccgccgt ggaaaaccga     540
ccaaccacaa agtgtttggt gaagacgtcg ctgttttagc cggagacgcg cttctctctt     600
tctctttcga gcatttagct tcggcgacga gttctgatgt tgtttctccg gtgagagtgg     660
ttcgagccgt tggagaattg gctaaagcga taggaacaga agggttagtg gcgggtcaag     720
tcgtggatat tagtagtgaa gggttagatt taaacgacgt cggtttagag catttggagt     780
ttatccattt gcataaaacg gcggcgttgc ttgaagcttc tgctgttttg ggagctattg     840
ttggtggagg aagtgatgat gagattgaga ggttaagaaa gtttgcgaga tgtattggtt     900
tgttgtttca ggtggttgat gatatcttgg atgtgacgaa atcgtcgaaa gagttaggga     960
aaactgctgg gaaagatttg attgctgata agttgacgta tcctaagatt atgggtttgg    1020
agaaatcgag agagtttgct gagaaattga atagagaggc tcgtgatcag cttttagggt    1080
ttgattctga taaggttgct cctttgttgg ctttggctaa ttacattgcc tatagacaga    1140
actgatttgt gttcgattcc ttttgtcggg aatcattatt agattggaat tgtagaaatc    1200
tcggacaggt tctctagagt ttgttggtgt aatcgtatcc gg                        1242
```

<210> SEQ ID NO 27
<211> LENGTH: 376
<212> TYPE: PRT
<213> ORGANISM: O. sativa

<400> SEQUENCE: 27

Met His Val Leu Ala Gln Ser Thr Ala Val Ala Lys Val Ala Ala Ser
1               5                   10                  15

Gly Cys Leu Arg Arg Ser Pro Asn Pro Ser Val Thr Phe Gln Arg Ser
            20                  25                  30

Pro Ser Leu Leu Leu Ser Pro Ala Ala Cys Arg Arg Cys Arg Arg
        35                  40                  45

Gly Cys Ser Val Ser Val Asp Val Arg Cys Ser Leu Gly Ala Met Val
    50                  55                  60

Thr Pro Glu Leu Asn Gly Gly Asp Val Gly Val Gly Val Gly Gly
65                  70                  75                  80

Ser Phe Asp Phe Gln Arg Tyr Leu Ser Ala Arg Ala Asp Ala Val His
                85                  90                  95

```
Asp Ala Leu Asp Arg Ala Met Pro Arg Gly Phe Pro Glu Arg Leu Cys
            100                 105                 110
Glu Ser Met Arg Tyr Ser Val Leu Ala Gly Gly Lys Arg Val Arg Pro
            115                 120                 125
Val Leu Ala Leu Ala Ala Cys Glu Leu Val Gly Gly Asp Ala Ala Ala
            130                 135                 140
Ala Thr Pro Val Ala Cys Ala Val Glu Met Ile His Thr Met Ser Leu
145                 150                 155                 160
Ile His Asp Asp Met Pro Cys Met Asp Asp Ala Leu Arg Arg Gly
                165                 170                 175
Arg Pro Ser Asn His Val Ala Phe Gly Glu Phe Thr Ala Leu Leu Ala
            180                 185                 190
Gly Asp Ala Leu His Ala Leu Ala Phe Glu His Val Ala Arg Gly Cys
            195                 200                 205
Gly Asp His Gly Val Pro Ala Asp Arg Thr Leu Arg Ala Val Ala Glu
            210                 215                 220
Leu Gly Ser Ala Ser Gly Thr Gly Gly Val Ala Ala Gly Gln Val Ala
225                 230                 235                 240
Asp Lys Glu Ser Glu Gly Leu Pro Val Ser Leu Ala Met Leu Glu Tyr
            245                 250                 255
Ile His Val His Lys Thr Ala Arg Leu Leu Glu Ala Ala Ala Val Ser
            260                 265                 270
Gly Ala Ile Gly Gly Gly Ala Asp Ala Glu Val Glu Arg Val Arg
            275                 280                 285
Arg Tyr Ala Arg Cys Val Gly Leu Leu Phe Gln Val Val Asp Asp Val
            290                 295                 300
Leu Asp Met Thr Ser Thr Ser Glu Gln Leu Gly Lys Thr Ala Gly Lys
305                 310                 315                 320
Asp Val Glu Ala Asp Lys Ala Thr Tyr Pro Lys Leu Leu Gly Val Asp
            325                 330                 335
Lys Ala Arg Glu Tyr Ala Ala Asp Leu Leu Ala Met Ala Glu Ala Glu
            340                 345                 350
Leu Asp Gly Phe Asp Ala Glu Arg Ala Ala Pro Leu Arg His Leu Ala
            355                 360                 365
Arg Phe Ile Ala Tyr Arg Gln His
            370                 375

<210> SEQ ID NO 28
<211> LENGTH: 1131
<212> TYPE: DNA
<213> ORGANISM: O. sativa

<400> SEQUENCE: 28
atgcacgtcc tcgctcaatc cacggccgtg gccaaggtcg ccgcctccgg ctgcctccga      60
cgaagcccga accctccgt gacgttccag agatcccctt cccttcttct ctcgccggcc      120
gcgtgccgcc gccgctgccg ccgcgggtgc tccgtctccg tcgacgtgag gtgctccctg     180
ggcgccatgg tcacgccgga gctgaacggc ggcgacgtcg gcgtcggcgt cggcggtggt     240
agcttcgact tcagcggta tctgtctgcc agggccgacg ccgtgcacga cgcgctggac     300
cgggccatgc cgcgcggctt cccggagcgg ctctgcgagt ccatgcgcta ctccgtcctc    360
gccggcggca gcgggtgcg ccccgtgctc gcgctggccg cgtgcgagct cgtcggcggg    420
gacgccgcgg cggccacgcc cgtcgcctgc gcggtcgaga tgatccacac catgtcgctc    480
```

```
atccacgacg acatgccgtg catggacgac gacgccctcc gccggggccg cccctccaac    540
cacgtcgcct tcggcgagtt caccgccctc ctcgccggcg acgcgctcca cgccctcgcg    600
ttcgagcacg tggcgcgcgg ctgcggcgac cacggcgtcc ccgcggaccg cacgctccgg    660
gcggtcgccg agctcgggag cgcctcgggc accggcgggg tcgccgccgg gcaggtcgcc    720
gacaaggaga gcgagggcct ccccgtcagc ctcgccatgc tggagtacat ccacgtgcac    780
aagacggcga ggctcctcga ggccgccgcc gtgtccggcg ccatcgtcgg cggggggcgcg    840
gacgccgagg tggagagggt ccggcggtac gcgcgctgcg tcgggctcct cttccaggtg    900
gtcgacgacg tgctcgacat gacgagcaca tcggagcagc tcgggaagac ggccgggaag    960
gacgtcgagg ccgacaaggc cacttacccg aagctgctcg gcgtcgacaa ggcccgcgag   1020
tacgccgccg acctcctcgc catggccgag gcggagctcg acgggttcga cgccgagcgc   1080
gccgcgccgc tgcgacacct cgcgcggttc atcgcctaca ggcagcatta a            1131
```

<210> SEQ ID NO 29
<211> LENGTH: 357
<212> TYPE: PRT
<213> ORGANISM: Catharanthus roseus

<400> SEQUENCE: 29

```
Met Arg Ser Asn Leu Cys His Pro Leu Lys Asn Gln Leu Pro Ile Ser
1               5                   10                  15

Phe Phe Leu Ser Gly Thr Ile Arg Lys Pro Ile Phe Ser Cys Ser Arg
            20                  25                  30

Leu Ser Ile Ser Ala Ile Ile Thr Lys Glu Gln Thr Gln Glu Glu Ser
        35                  40                  45

Glu Ser Lys Ser Lys Lys Glu Val Ala Phe Ser Ser Ser Ser Ser Phe
    50                  55                  60

Asp Phe Lys Ala Tyr Met Ile Gly Lys Ala Asn Ser Val Asn Lys Ala
65                  70                  75                  80

Leu Glu Asp Ala Val Leu Val Arg Glu Pro Leu Lys Ile His Glu Ser
                85                  90                  95

Met Arg Tyr Ser Leu Leu Ala Gly Gly Lys Arg Val Arg Pro Met Leu
            100                 105                 110

Cys Ile Ala Ala Cys Glu Leu Phe Gly Gly Thr Glu Ser Val Ala Met
        115                 120                 125

Pro Ser Ala Cys Ala Val Glu Met Ile His Thr Met Ser Leu Met His
    130                 135                 140

Asp Asp Leu Pro Cys Met Asp Asn Asp Leu Arg Arg Gly Lys Pro
145                 150                 155                 160

Thr Asn His Lys Val Phe Gly Glu Asp Val Ala Val Leu Ala Gly Asp
                165                 170                 175

Ala Leu Leu Ala Phe Ala Phe Glu His Ile Ala Thr Ala Thr Lys Gly
            180                 185                 190

Val Ser Ser Glu Arg Ile Val Arg Val Val Gly Glu Leu Ala Lys Cys
        195                 200                 205

Ile Gly Ser Glu Gly Leu Val Ala Gly Gln Val Val Asp Val Cys Ser
    210                 215                 220

Glu Gly Ile Ala Asp Val Gly Leu Glu His Leu Glu Phe Ile His Ile
225                 230                 235                 240

His Lys Thr Ala Ala Leu Leu Glu Gly Ser Val Val Leu Gly Ala Ile
                245                 250                 255

Val Gly Gly Ala Asn Asp Glu Gln Ile Ser Lys Leu Arg Lys Phe Ala
```

```
                260             265             270
Arg Cys Ile Gly Leu Leu Phe Gln Val Val Asp Asp Ile Leu Asp Val
            275                 280             285

Thr Lys Ser Ser Gln Glu Leu Gly Lys Thr Ala Gly Lys Asp Leu Val
        290                 295             300

Ala Asp Lys Val Thr Tyr Pro Lys Leu Leu Gly Ile Asp Lys Ser Arg
305             310                 315                 320

Glu Phe Ala Glu Lys Leu Asn Arg Glu Ala Gln Glu Gln Leu Ala Glu
                325                 330                 335

Phe Asp Pro Glu Lys Ala Ala Pro Leu Ile Ala Leu Ala Asn Tyr Ile
            340                 345             350

Ala Tyr Arg Asp Asn
        355

<210> SEQ ID NO 30
<211> LENGTH: 1271
<212> TYPE: DNA
<213> ORGANISM: Catharanthus roseus

<400> SEQUENCE: 30
gaattcaatt acaacatggg ttccagccca atcaatttat tgtttggaga atggcagatc    60
cagttctatg cgctctaatc tttgtcaccc tctcaaaaat caacttccca tttctttttt   120
tctttcgggc acaatccgaa agcccatttt cagttgttct cgtctctcaa tttctgccat   180
tataacgaaa gaacaaaccc aagaagagag cgaaagcaaa agcaagaaag aggtagcctt   240
ttcttcctca tcttcatttg atttcaaggc atatatgatt ggaaaggcca attctgttaa   300
taaggcattg gaagatgcag tcttggttag ggaacctttg aaaattcatg aatctatgag   360
gtactcactt ctagctggtg gtaaaagagt tcgtcctatg ctctgtattg ctgcttgtga   420 acttttggt ggaacagaat ctgttgccat gccttctgct tgtgctgttg agatgattca   480
tactatgtct ctgatgcacg atgaccttcc ctgtatggaa aatgatgatt tgagaagagg   540
gaagccgaca aatcataagg ttttgggga ggatgttgct gttttagctg gggatgccct   600
tcttgcattt gcctttgaac atatagcaac tgctaccaaa ggtgtctctt ccgaaagaat   660
tgtgagagta gttggggaat ggctaagtg tattggttca gaagggctgg tggctggaca   720
ggttgttgat gtgtgctctg agggcattgc tgatgtaggg cttgagcatt tagagttcat   780
ccatattcac aagactgcag ctttattaga agggtctgtg gttttagggg caattgtggg   840
tggtgctaat gatgaacaaa tttccaaatt gaggaaattt gctaggtgta ttgggttgtt   900
gtttcaggtt gtagatgata ttcttgatgt tactaaatct tctcaagaat taggaaaaac   960
tgcagggaaa gacttggtgg cagataaggt cacttatcct aaacttcttg gtattgataa  1020
gtccagagaa tttgctgaga gttgaatag agaagctcaa gaacaacttg ctgagtttga  1080
tcctgaaaag gctgctccat taattgctct agcaaattac atagcctaca gagataacta  1140
ataatatgtt gttaagtta taagagaatt tcacattaa gatagactat accaatagaa  1200
ttagatattg ttgtcacaca agatatgagc tggtaattct ttcacattgt taatggaaat  1260
gatccgaatt c                                                      1271

<210> SEQ ID NO 31
<211> LENGTH: 423
<212> TYPE: PRT
<213> ORGANISM: A. thaliana

<400> SEQUENCE: 31
```

-continued

```
Met Ser Ser Ser Val Ala Val Leu Trp Val Ala Thr Ser Ser Leu Asn
1               5                   10                  15

Pro Asp Pro Met Asn Asn Cys Gly Leu Val Arg Val Leu Glu Ser Ser
            20                  25                  30

Arg Leu Phe Ser Pro Cys Gln Asn Gln Arg Leu Asn Lys Gly Lys Lys
        35                  40                  45

Lys Gln Ile Pro Thr Trp Ser Ser Phe Val Arg Asn Arg Ser Arg
50                  55                  60

Arg Ile Gly Val Val Ser Ser Leu Val Ala Ser Pro Ser Gly Glu
65              70                  75                  80

Ile Ala Leu Ser Ser Glu Glu Lys Val Tyr Asn Val Val Leu Lys Gln
                85                  90                  95

Ala Ala Leu Val Asn Lys Gln Leu Arg Ser Ser Ser Tyr Asp Leu Asp
                100                 105                 110

Val Lys Lys Pro Gln Asp Val Val Leu Pro Gly Ser Leu Ser Leu Leu
            115                 120                 125

Val Gly Glu Ala Tyr Asp Arg Cys Gly Glu Val Cys Ala Glu Tyr Pro
130                 135                 140

Lys Thr Phe Tyr Leu Gly Thr Leu Leu Met Thr Pro Glu Arg Arg Lys
145                 150                 155                 160

Ala Ile Trp Ala Ile Tyr Val Trp Cys Arg Arg Thr Asp Glu Leu Val
                165                 170                 175

Asp Gly Pro Asn Ala Ser His Ile Thr Pro Met Ala Leu Asp Arg Trp
            180                 185                 190

Glu Ala Arg Leu Glu Asp Leu Phe Arg Gly Arg Pro Phe Asp Met Leu
        195                 200                 205

Asp Ala Ala Leu Ala Asp Thr Val Ala Arg Tyr Pro Val Asp Ile Gln
210                 215                 220

Pro Phe Arg Asp Met Ile Glu Gly Met Arg Met Asp Leu Lys Lys Ser
225                 230                 235                 240

Arg Tyr Gln Asn Phe Asp Asp Leu Tyr Leu Tyr Cys Tyr Tyr Val Ala
            245                 250                 255

Gly Thr Val Gly Leu Met Ser Val Pro Val Met Gly Ile Asp Pro Lys
            260                 265                 270

Ser Lys Ala Thr Thr Glu Ser Val Tyr Asn Ala Ala Leu Ala Leu Gly
        275                 280                 285

Ile Ala Asn Gln Leu Thr Asn Ile Leu Arg Asp Val Gly Glu Asp Ala
290                 295                 300

Arg Arg Gly Arg Val Tyr Leu Pro Gln Asp Glu Leu Ala Gln Ala Gly
305                 310                 315                 320

Leu Ser Asp Glu Asp Ile Phe Ala Gly Lys Val Thr Asp Lys Trp Arg
            325                 330                 335

Asn Phe Met Lys Met Gln Leu Lys Arg Ala Arg Met Phe Phe Asp Glu
        340                 345                 350

Ala Glu Lys Gly Val Thr Glu Leu Ser Ala Ala Ser Arg Trp Pro Val
        355                 360                 365

Trp Ala Ser Leu Leu Leu Tyr Arg Arg Ile Leu Asp Glu Ile Glu Ala
370                 375                 380

Asn Asp Tyr Asn Asn Phe Thr Lys Arg Ala Tyr Val Gly Lys Val Lys
385                 390                 395                 400

Lys Ile Ala Ala Leu Pro Leu Ala Tyr Ala Lys Ser Val Leu Lys Thr
            405                 410                 415
```

Ser Ser Ser Arg Leu Ser Ile
            420

<210> SEQ ID NO 32
<211> LENGTH: 1769
<212> TYPE: DNA
<213> ORGANISM: A. thaliana

<400> SEQUENCE: 32

| | |
|---|---|
| cttccgaccg tgtacatata ttacagtaag cgttgcaaca caacttcttg aggatcttct | 60 |
| cacattaatg ggtcaaacct tttgctcttc cttttgatta atttagtgtt tgacaatctc | 120 |
| ctcctccttc tccttcttct tcaaagtttt gtcgcagtat ctattgttct tacagagaga | 180 |
| aaggaaagct ttagtctttt accagtttga tccaattctg ggtttcactg aaaaaaagtt | 240 |
| gggagtttga ttcttctaac tgtagaagaa acagagtcaa cagaagaaaa ctaaaaaagt | 300 |
| tgagatttt ctctcacgcg ctcaagaact tgagtatgtc ttcttctgta gcagtgttat | 360 |
| gggttgctac ttcttctcta aatccagacc caatgaacaa ttgtggttg gtaagggttc | 420 |
| tagaatcttc tagactgttc tctccttgtc agaatcagag actaaacaaa ggtaagaaga | 480 |
| agcagatacc aacttggagt tcttcttttg taaggaaccg aagtagaaga attggtgttg | 540 |
| tgtcttcaag cttagtagca agtccttctg gagagatagc tctttcatct gaagagaagg | 600 |
| tttacaatgt tgtgttgaaa caagctgctt tggtgaacaa acagctaagg tcttcttctt | 660 |
| atgaccttga tgtgaagaaa ccacaagatg ttgttcttcc tgggagtttg agtttgttgg | 720 |
| tgggtgaagc ttatgatcga tgcggtgaag tttgcgctga atatcctaag acgttttatc | 780 |
| ttggaacttt gcttatgaca cccgaaaggc gaaaggcgat ttgggcaatc tacgtttggt | 840 |
| gtagaagaac tgatgaactt gtggatgggc caaatgcttc acatataact cccatggctt | 900 |
| tagatagatg ggaagcaagg ttagaagatc ttttccgtgg tcgtcctttc gatatgcttg | 960 |
| atgctgctct cgctgataca gttgctagat acccggtcga tattcagcca tttcgagaca | 1020 |
| tgatcgaagg aatgagaatg gacttgaaga aatcgagata ccagaacttc gatgatctat | 1080 |
| accttactg ctactacgtc gctggaaccg tcggattgat gagcgttccg gttatgggaa | 1140 |
| tcgatcctaa gtcgaaagca acaaccgaaa gtgtttacaa cgctgccttg gcccttggta | 1200 |
| tagccaatca gcttactaac atactcagag acgtaggcga agatgcgaga agaggaaggg | 1260 |
| tttatctgcc tcaggatgaa ttggctcagg ctggtctttc agatgaagac atattcgccg | 1320 |
| gaaaagtaac tgataaatgg agaaacttca tgaaaatgca gcttaaacga gcaagaatgt | 1380 |
| tcttcgacga agctgagaaa ggcgtcaccg agctcagtgc cgctagcaga tggcctgtat | 1440 |
| gggcttcatt gctattgtac aggagaatac tggacgagat tgaagcgaat gattacaaca | 1500 |
| attttactaa gagagcttat gtggggaaag tcaagaaaat tgcagctttg ccattggctt | 1560 |
| atgctaaatc agtactaaag acttcaagtt caagactatc gatatgagag cgagaggaaa | 1620 |
| gtggaacaaa acaacctaa gagcgctttt tgtgattaag aaaaaactta ggctcgaatt | 1680 |
| tcttatgtta actaatatat acatattaat ggggaagcaa attcttataa tgttacatta | 1740 |
| tctttctgaa tgtaaaaaag tattttttt | 1769 |

<210> SEQ ID NO 33
<211> LENGTH: 420
<212> TYPE: PRT
<213> ORGANISM: O. sativa

<400> SEQUENCE: 33

```
Met Ala Ala Ile Thr Leu Leu Arg Ser Ala Ser Leu Pro Gly Leu Ser
1               5                   10                  15

Asp Ala Leu Ala Arg Asp Ala Ala Val Gln His Val Cys Ser Ser
            20                  25                  30

Tyr Leu Pro Asn Asn Lys Glu Lys Arg Arg Trp Ile Leu Cys Ser
        35                  40                  45

Leu Lys Tyr Ala Cys Leu Gly Val Asp Pro Ala Pro Gly Glu Ile Ala
50                  55                  60

Arg Thr Ser Pro Val Tyr Ser Ser Leu Thr Val Thr Pro Ala Gly Glu
65                  70                  75                  80

Ala Val Ile Ser Ser Glu Gln Lys Val Tyr Asp Val Val Leu Lys Gln
                85                  90                  95

Ala Ala Leu Leu Lys Arg His Leu Arg Pro Gln Pro His Thr Ile Pro
            100                 105                 110

Ile Val Pro Lys Asp Leu Asp Leu Pro Arg Asn Gly Leu Lys Gln Ala
        115                 120                 125

Tyr His Arg Cys Gly Glu Ile Cys Glu Glu Tyr Ala Lys Thr Phe Tyr
    130                 135                 140

Leu Gly Thr Met Leu Met Thr Glu Asp Arg Arg Arg Ala Ile Trp Ala
145                 150                 155                 160

Ile Tyr Val Trp Cys Arg Arg Thr Asp Glu Leu Val Asp Gly Pro Asn
                165                 170                 175

Ala Ser His Ile Thr Pro Ser Ala Leu Asp Arg Trp Glu Lys Arg Leu
            180                 185                 190

Asp Asp Leu Phe Thr Gly Arg Pro Tyr Asp Met Leu Asp Ala Ala Leu
        195                 200                 205

Ser Asp Thr Ile Ser Lys Phe Pro Ile Asp Ile Gln Pro Phe Arg Asp
    210                 215                 220

Met Ile Glu Gly Met Arg Ser Asp Leu Arg Lys Thr Arg Tyr Lys Asn
225                 230                 235                 240

Phe Asp Glu Leu Tyr Met Tyr Cys Tyr Tyr Val Ala Gly Thr Val Gly
                245                 250                 255

Leu Met Ser Val Pro Val Met Gly Ile Ala Pro Glu Ser Lys Ala Thr
            260                 265                 270

Thr Glu Ser Val Tyr Ser Ala Ala Leu Ala Leu Gly Ile Ala Asn Gln
        275                 280                 285

Leu Thr Asn Ile Leu Arg Asp Val Gly Glu Asp Ala Arg Arg Gly Arg
    290                 295                 300

Ile Tyr Leu Pro Gln Asp Glu Leu Ala Glu Ala Gly Leu Ser Asp Glu
305                 310                 315                 320

Asp Ile Phe Asn Gly Val Val Thr Asn Lys Trp Arg Ser Phe Met Lys
                325                 330                 335

Arg Gln Ile Lys Arg Ala Arg Met Phe Phe Glu Glu Ala Glu Arg Gly
            340                 345                 350

Val Thr Glu Leu Ser Gln Ala Ser Arg Trp Pro Val Trp Ala Ser Leu
        355                 360                 365

Leu Leu Tyr Arg Gln Ile Leu Asp Glu Ile Glu Ala Asn Asp Tyr Asn
    370                 375                 380

Asn Phe Thr Lys Arg Ala Tyr Val Gly Lys Ala Lys Lys Leu Leu Ala
385                 390                 395                 400

Leu Pro Val Ala Tyr Gly Arg Ser Leu Leu Met Pro Tyr Ser Leu Arg
                405                 410                 415

Asn Ser Gln Lys
```

<210> SEQ ID NO 34
<211> LENGTH: 1263
<212> TYPE: DNA
<213> ORGANISM: O. sativa

<400> SEQUENCE: 34

```
atggcggcca tcacgctcct acgttcagcg tctcttccgg gcctctccga cgccctcgcc      60
cgggacgctg ctgccgtcca acatgtctgc tcctcctacc tgcccaacaa caaggagaag     120
aagaggaggt ggatcctctg ctcgctcaag tacgcctgcc ttggcgtcga ccctgccccg     180
ggcgagattg cccggacctc gccggtgtac tccagcctca ccgtcacccc tgctggagag     240
gccgtcatct cctcggagca gaaggtgtac gacgtcgtcc tcaagcaggc agcattgctc     300
aaacgccacc tgcgcccaca accacacacc attcccatcg ttcccaagga cctggacctg     360
ccaagaaacg gcctcaagca ggcctatcat cgctgcggag agatctgcga ggagtatgcc     420
aagacctttt accttggaac tatgctcatg acggaggacc gacggcgcgc catatgggcc     480
atctatgtgt ggtgtaggag gacagatgag cttgtagatg gaccaaatgc ctcgcacatc     540
acaccgtcag ccctggaccg gtgggagaag aggcttgatg atctcttcac ggacgccccc     600
tacgacatgc ttgatgctgc actttctgat accatctcca agtttcctat agatattcag     660
cctttcaggg acatgataga agggatgcgg tcagacctca gaaagactag atacaagaac     720
ttcgacgagc tctacatgta ctgctactat gttgctggaa ctgtggggct aatgagtgtt     780
cctgtgatgg gtattgcacc cgagtcgaag gcaacaactg aaagtgtgta cagtgctgct     840
ttggctctcg gcattgcaaa ccagctcaca aatatactcc gtgacgttgg agaggacgcg     900
agaagaggga ggatatattt accacaagat gaacttgcag aggcagggct ctctgatgag     960
gacatcttca atggcgttgt gactaacaaa tggagaagct tcatgaagag acagatcaag    1020
agagctagga tgttttttga ggaggcagag agaggggtga ccgagctcag ccaggcaagc    1080
cggtggccgg tctgggcgtc tctgttgtta taccggcaaa tccttgacga gatagaagca    1140
aacgattaca caacttcac aaagagggcg tacgttggga aggcgaagaa attgctagcg    1200
cttccagttg catatggtag atcattgctg atgccctact cactgagaaa tagccagaag    1260
tag                                                                 1263
```

<210> SEQ ID NO 35
<211> LENGTH: 284
<212> TYPE: PRT
<213> ORGANISM: P. trichocarpa

<400> SEQUENCE: 35

```
Leu Glu Glu Ala Tyr Glu Arg Cys Arg Asn Ile Cys Ala Glu Tyr Ala
1               5                   10                  15
Lys Thr Phe Tyr Leu Gly Thr Arg Leu Met Thr Glu Glu Arg Gln Lys
            20                  25                  30
Ala Thr Trp Ala Ile Tyr Val Trp Cys Arg Arg Thr Asp Glu Leu Val
        35                  40                  45
Asp Gly Pro Asn Ala Val Leu Met Ser Thr Ala Val Leu Asp Arg Trp
    50                  55                  60
Glu Glu Arg Leu Gln Asp Ile Phe Asp Gly Arg Pro Tyr Asp Met Leu
65                  70                  75                  80
Asp Ala Ala Leu Thr Asp Thr Ile Ser Lys Phe Pro Leu Asp Ile Lys
                85                  90                  95
```

```
Pro Phe Arg Asp Met Ile Glu Gly Met Arg Met Asp Thr Arg Lys Phe
            100                 105                 110

Arg Tyr Asp Asn Phe Gln Glu Leu Tyr Leu Tyr Cys Tyr Val Ala
        115                 120                 125

Gly Thr Val Gly Leu Met Ser Val Pro Val Met Gly Ile Ala Ala Glu
        130                 135                 140

Ser Glu Ala Ser Ala Gln Ser Ile Tyr Asn Ala Ala Leu Tyr Leu Gly
145                 150                 155                 160

Ile Gly Asn Gln Leu Thr Asn Ile Leu Arg Asp Val Gly Glu Asp Ala
                165                 170                 175

Leu Arg Gly Arg Val Tyr Leu Pro Gln Asp Glu Leu Ala Gln Phe Gly
        180                 185                 190

Leu Cys Asp Gln Asp Val Phe Ala Arg Lys Val Thr Asp Gly Trp Arg
        195                 200                 205

Glu Phe Met Lys Glu Gln Ile Ile Arg Ala Arg Phe Tyr Phe Asn Leu
    210                 215                 220

Ala Glu Glu Gly Ala Ser Lys Leu Glu Lys Ala Ser Arg Trp Pro Val
225                 230                 235                 240

Trp Ser Ser Leu Leu Val Tyr Gln Lys Ile Leu Asp Ala Ile Glu Asp
                245                 250                 255

Asn Asp Tyr Asp Asn Phe Thr Lys Arg Ala Tyr Val Gly Arg Thr Lys
                260                 265                 270

Lys Leu Leu Thr Leu Pro Leu Ala Tyr Thr Lys Ala
        275                 280

<210> SEQ ID NO 36
<211> LENGTH: 852
<212> TYPE: DNA
<213> ORGANISM: P. trichocarpa

<400> SEQUENCE: 36
cttgaagaag cctatgaaag gtgcagaaac atttgcgccg aatatgccaa gactttctat        60
ctaggaactc ggctgatgac agaggagcga cagaaagcca catgggcaat ttatgtatgg       120
tgcaggagga cagatgagct ggtcgatgga cctaatgcag tgctcatgag cactgctgtt       180
cttgataggt gggaagagag gctgcaagac atctttgatg acgccccta tgacatgctc        240 gatgctgcac ttactgatac aatttccaag ttcccttag acattaagcc ttttagggac        300
atgattgaag gtatgagaat ggatacgaga aaattccgtt acgataattt tcaagagctc       360
tatctttatt gctattacgt tgcgggcaca gtcggcctaa tgagcgttcc agtgatggga       420
attgcagcag aatctgaagc ttctgctcaa gtatttata atgcggcact gtacttgggt        480
attggaaacc agcttacaaa cattcttaga gatgtgggag aggatgcttt gagagggaga       540
gtttatctac acaagatga gcttgcacag tttgggctat cgaccaaga tgttttcgca         600 agaaaagtca ctgatggatg agagagttc atgaaggagc agataataag gcaagattc         660 tatttcaacc ttgcagaaga aggggcttca aagcttgaaa aggctagccg gtggccagta       720
tggtcatccc tactagtata ccaaaaaatc ttggatgcaa ttgaggataa tgattatgat       780
aacttcacaa aacagctta tgttggaaga acaaagaaac ttctcacatt gcccctggca        840
tacacaaaag ct                                                           852

<210> SEQ ID NO 37
<211> LENGTH: 526
<212> TYPE: PRT
```

<213> ORGANISM: E. longus

<400> SEQUENCE: 37

```
Met Asn Ala Asp Gln Asn Ile Ala Thr Gly Leu Asn Phe Ala Pro Ala
1               5                   10                  15

Asn Thr Gly Glu Arg Gly Ile Asn Pro Val Ile Ala Glu Lys Tyr Lys
            20                  25                  30

Gly Arg Thr Ala Cys Val Ile Gly Ser Gly Phe Gly Gly Leu Ala Leu
        35                  40                  45

Ala Leu Arg Leu Gln Ser His Gly Ile Gln Thr Thr Ile Val Glu Ala
50                  55                  60

Arg Asp Lys Pro Gly Gly Arg Ala Tyr Phe Trp Glu Lys Asp Gly Phe
65                  70                  75                  80

Thr Phe Asp Ala Gly Pro Thr Val Ile Thr Asp Pro Pro Cys Leu Lys
                85                  90                  95

Glu Leu Trp Glu Leu Thr Gly His Asp Ile Ser Glu Asp Val Glu Leu
            100                 105                 110

Met Lys Val His Pro Phe Tyr Arg Leu Asn Trp Pro Asp Gly Thr Asn
        115                 120                 125

Phe Asp Tyr Ser Asn Val Asp Glu Glu Leu Asn Ala Glu Ile Ala Lys
130                 135                 140

Leu Asn Pro Asp Asp Val Ile Gly Tyr Gln Lys Phe Leu Glu Tyr Ser
145                 150                 155                 160

Ala Arg Val His Glu Glu Gly Tyr Val Lys Leu Gly Thr Val Pro Phe
                165                 170                 175

Leu Asp Phe Lys Ser Met Leu Lys Ala Ala Pro Ala Leu Val Lys Glu
            180                 185                 190

Arg Ala Trp Arg Ser Val Tyr Asp Met Val Ser Ser Tyr Ile Lys Asp
        195                 200                 205

Glu Arg Leu Arg Glu Ala Phe Ser Phe His Thr Leu Leu Val Gly Gly
210                 215                 220

Ser Pro Met Lys Thr Ser Ala Ile Tyr Ala Leu Ile His Lys Leu Glu
225                 230                 235                 240

Lys Asp Gly Gly Val Trp Trp Ala Arg Gly Gly Thr Asn Arg Leu Ile
                245                 250                 255

Ala Gly Met Val Arg His Phe Glu Arg Leu Gly Gly Thr Met Arg Ile
            260                 265                 270

Gly Asp Pro Val Val Gln Val His Thr Gln Gly Thr Lys Ala Thr Glu
        275                 280                 285

Val Glu Thr Lys Ser Gly Trp Lys Glu Arg Phe Asp Ala Val Cys Ser
290                 295                 300

Asn Ala Asp Ile Met His Ser Tyr Lys Glu Leu Leu Gly Glu Ser Asp
305                 310                 315                 320

Arg Gly Arg Lys Tyr Ala Lys Ser Leu Ala Arg Lys Ser Tyr Ser Pro
                325                 330                 335

Ser Leu Phe Val Val His Phe Gly Leu Glu Gly Ser Trp Pro Gly Ile
            340                 345                 350

Ala His His Met Ile Leu Phe Gly Pro Arg Tyr Lys Glu Leu Val Asp
        355                 360                 365

Asp Ile Tyr Lys His Gly Val Leu Pro Gln Asp Phe Ser Ile Tyr Leu
370                 375                 380

His His Pro Thr Val Thr Asp Pro Ser Met Ala Pro Lys Gly Met Ser
385                 390                 395                 400
```

```
Thr Phe Tyr Ala Leu Val Pro Val Ala His Leu Gly Lys Met Pro Ile
            405                 410                 415
Asp Trp Asp Val Glu Gly Pro Lys Phe Glu Lys Ala Ile Leu Asp Glu
        420                 425                 430
Ile Gly Arg Arg Leu Ile Pro Asp Ile His Asp Arg Ile Val Thr Lys
    435                 440                 445
Phe Ser Tyr Ala Pro Lys Asp Phe Gln Ala Asp Leu Asn Ala His Met
450                 455                 460
Gly Ser Ala Phe Ser Leu Glu Thr Val Leu Trp Gln Ser Ala Tyr Met
465                 470                 475                 480
Arg Gly His Asn Arg Asp Asp Val Ile Asp Asn Phe Tyr Leu Val Gly
            485                 490                 495
Ala Gly Thr His Pro Gly Ala Gly Ile Pro Gly Val Val Gly Ser Ala
        500                 505                 510
Lys Ala Thr Ala Gly Leu Met Leu Glu Asp Leu Ser Val Lys
    515                 520                 525
```

<210> SEQ ID NO 38
<211> LENGTH: 1581
<212> TYPE: DNA
<213> ORGANISM: E. longus

<400> SEQUENCE: 38

```
atgaacgccg atcaaaacat cgctacaggg ctcaactttg cgccagccaa tactggcgag    60
cgcggcatta atccggtgat cgccgaaaaa tacaaaggcc gcaccgcctg tgtgatcggt   120
tccggttttg cggcttggc gctagcactg cggctgcaat cgcatggcat tcaaacgacc   180
atcgtcgaag cgcgcgacaa gcccggtggc cgcgcctatt tctgggaaaa agacggcttt   240
accttcgatg ctggccccac ggtcatcacc gacccgccgt gtttgaaaga actgtgggag   300
ctgaccggcc acgacatttc cgaagatgtc gagctgatga aggttcaccc tttctaccgc   360
ctcaactggc ccgatggcac aaacttcgat tattcgaacg ttgatgagga attgaacgcc   420
gaaatcgcga agctcaatcc tgacgatgtg atcggctatc aaaaattcct cgaatattcg   480
gcgcgcgtgc acgaggaagg ctatgtgaag cttggcacgg tgccgttcct cgatttcaag   540
tcgatgctga agccgccccc tgcccttgtt aaagagcgcg catggcgcag cgtttacgat   600
atggtctcaa gctacatcaa ggatgagcgc ctgcgcgaag cgttcagctt ccacacgctg   660
cttgtcggcg gctcgccgat gaagaccagc gccatttatg cgttgatcca aagcttgaa    720
aaagacggcg tgtctggtg ggcgcgcggc gggaccaacc ggttgatcgc cggaatggtg   780
cgccattttg aacgcctcgg cggcacgatg cgcatcggcg atccggtggt tcaggtccac   840
acccaaggga ccaaagcgac cgaggttgaa acgaagagcg ttggaaaga gcgctttgac   900
gcggtgtgtt caaacgccga catcatgcac tcttacaagg aacttctggg cgaatccgac   960
cgtggcagaa aatacgctaa gtcattggct cgcaaaagct attcgccttc gctattcgtc  1020
gtacactttg ggcttgaggg gtcgtggccc ggtattgccc accacatgat cctgtttggc  1080
ccacgttaca aggaactggt cgacgacatc tacaagcacg gcgttctgcc gcaggatttt  1140
tcgatctatc ttcaccaccc gaccgtcacc gacccatcga tggcgcccaa gggcatgagc  1200
acattctacg cgcttgtccc cgtcgcccac cttggcaaga tgccgattga ttgggacgtc  1260
gaaggaccca gtttgaaaa ggcgattttg gacgagatcg gtcgccgcct gatccccgac  1320
atccacgacc ggatcgtcac caaattcagc tacgcaccaa aggactttca ggcagacctc  1380
aacgcccata tggcagcgc gttcagcctt gagacggtcc tgtggcaaag cgcctacatg  1440
```

-continued

```
cgcggccaca accgcgacga tgtgatcgac aatttctacc tcgtgggcgc agggacacac    1500
ccgggcgctg gtatcccgg  agtggtcggt agcgcgaagg caacggcggg gctgatgctt   1560
gaagatctgt cggtcaaata a                                              1581
```

<210> SEQ ID NO 39
<211> LENGTH: 486
<212> TYPE: PRT
<213> ORGANISM: E. herbicola

<400> SEQUENCE: 39

```
Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110

Phe Asn Pro Arg Asp Val Glu Gly Tyr Arg Arg Phe Leu Ala Tyr Ser
        115                 120                 125

Gln Ala Val Phe Gln Glu Gly Tyr Leu Arg Leu Gly Ser Val Pro Phe
    130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
            180                 185                 190

Asn Pro Phe Thr Thr Ser Ser Ile Tyr Thr Leu Ile His Ala Leu Glu
        195                 200                 205

Arg Glu Trp Gly Val Trp Phe Pro Glu Gly Gly Thr Gly Ala Leu Val
    210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
        275                 280                 285

Val Gly Gln Lys Arg Ala Ala Ala Leu Glu Arg Lys Ser Met Ser Asn
    290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                325                 330                 335

Glu Ile Phe Thr Gly Ser Ala Leu Ala Asp Asp Phe Ser Leu Tyr Leu
```

|     |     |     | 340 |     |     |     | 345 |     |     |     | 350 |     |     |
| --- | --- | --- | --- | --- | --- | --- | --- | --- | --- | --- | --- | --- | --- |
| His | Ser | Pro | Cys | Val | Thr | Asp | Pro | Ser | Leu | Ala | Pro | Pro | Gly | Cys | Ala |
|     |     |     | 355 |     |     |     | 360 |     |     |     | 365 |     |     |

Ser Phe Tyr Val Leu Ala Pro Val Pro His Leu Gly Asn Ala Pro Leu
    370                    375                  380

Asp Trp Ala Gln Glu Gly Pro Lys Leu Arg Asp Arg Ile Phe Asp Tyr
385                    390                    395                400

Leu Glu Glu Arg Tyr Met Pro Gly Leu Arg Ser Gln Leu Val Thr Gln
            405                    410                    415

Arg Ile Phe Thr Pro Ala Asp Phe His Asp Thr Leu Asp Ala His Leu
            420                    425                    430

Gly Ser Ala Phe Ser Ile Glu Pro Leu Leu Thr Gln Ser Ala Trp Phe
            435                    440                    445

Arg Pro His Asn Arg Asp Ser Asp Ile Ala Asn Leu Tyr Leu Val Gly
            450                    455                    460

Ala Gly Thr His Pro Gly Ala Gly Ile Pro Gly Val Val Ala Ser Ala
465                    470                    475                480

Lys Ala Thr Ala Ser Leu
            485

<210> SEQ ID NO 40
<211> LENGTH: 1459
<212> TYPE: DNA
<213> ORGANISM: E. herbicola

<400> SEQUENCE: 40

| | | |
|---|---|---|
| atgaaaaaaa ccgttgtgat tggcgcaggc tttggtggcc tggcgctggc gattcgcctg | 60 |
| caggcggcag ggatcccaac cgtactgctg gagcagcggg acaagcccgg cggtcgggcc | 120 |
| tacgtctggc atgaccaggg ctttaccttt gacgccgggc cgacggtgat caccgatcct | 180 |
| accgcgcttg aggcgctgtt caccctggcc ggcaggcgca tggaggatta cgtcaggctg | 240 |
| ctgccggtaa aaccccttcta ccgactctgc tgggagtccg ggaagaccct cgactatgct | 300 |
| aacgacagcg ccgagcttga ggcgcagatt acccagttca accccgcga cgtcgagggc | 360 |
| taccggcgct ttctggctta ctcccaggcg gtattccagg agggatattt cgcgcctcggc | 420 |
| agcgtgccgt tcctctcttt cgcgacacat gctgcgcgccg gccgcagct gcttaagctc | 480 |
| caggcgtggc agagcgtcta ccagtcggtt cgcgctttta ttgaggatga gcatctgcgg | 540 |
| caggccttct cgttccactc cctgctggta ggcggcaacc ccttcaccac ctcgtccatc | 600 |
| tacaccctga tccacgccct tgagcgggag tgggggggtct ggttccctga gggcggcacc | 660 |
| ggggcgctgg tgaacggcat ggtgaagctg tttaccgatc tgggcgggga gatcgaactc | 720 |
| aacgcccggg tcgaagagct ggtggtggcc gataaccgcg taagccaggt ccggctggcg | 780 |
| gatggtcgga tctttgacac cgacgccgta gcctcgaacg ctgacgtggt gaacacctat | 840 |
| aaaaagctgc tcggccacca tccggtgggg cagaagcggg cggcagcgct ggagcgcaag | 900 |
| agcatgagca actcgctgtt gtgctctac ttcggcctga accagcctca ttcccagctg | 960 |
| gcgcaccata ccatctgttt tggtcccccgc taccgggagc tgatcgacga gatctttacc | 1020 |
| ggcagcgcgc tggcggatga cttctcgctc tacctgcact cgccctgcgt gaccgatccc | 1080 |
| tcgctcgcgc ctcccggctg cgccagcttc tacgtgctgg ccccggtgcc gcatcttggc | 1140 |
| aacgcgccgc tggactgggc gcaggagggg ccgaagctgc gcgaccgcat ctttgactac | 1200 |
| cttgaagagc gctatatgcc cggcctgcgt agccagctgg tgacccagcg gatctttacc | 1260 |

-continued

```
ccggcagact tccacgacac gctggatgcg catctgggat cggccttctc catcgagccg      1320
ctgctgaccc aaagcgcctg gttccgcccg cacaaccgcg acagcgacat tgccaacctc      1380
tacctggtgg gcgcaggtac tcaccctggg gcgggcattc ctggcgtagt ggcctcggcg      1440
aaagccaccg ccagcctga                                                    1459

<210> SEQ ID NO 41
<211> LENGTH: 518
<212> TYPE: PRT
<213> ORGANISM: R. sphaeroides

<400> SEQUENCE: 41

Met Pro Ser Ile Ser Pro Ala Ser Asp Ala Asp Arg Ala Leu Val Ile
1               5                   10                  15

Gly Ser Gly Leu Gly Gly Leu Ala Ala Ala Met Arg Leu Gly Ala Lys
                20                  25                  30

Gly Trp Arg Val Thr Val Ile Asp Lys Leu Asp Val Pro Gly Gly Arg
            35                  40                  45

Gly Ser Ser Ile Thr Gln Glu Gly His Arg Phe Asp Leu Gly Pro Thr
        50                  55                  60

Ile Val Thr Val Pro Gln Ser Leu Arg Asp Leu Trp Lys Thr Cys Gly
65                  70                  75                  80

Arg Asp Phe Asp Ala Asp Val Glu Leu Lys Pro Ile Asp Pro Phe Tyr
                85                  90                  95

Glu Val Arg Trp Pro Asp Gly Ser His Phe Thr Val Arg Gln Ser Thr
            100                 105                 110

Glu Ala Met Lys Ala Glu Val Ala Arg Leu Ser Pro Gly Asp Val Ala
        115                 120                 125

Gly Tyr Glu Lys Phe Leu Lys Asp Ser Glu Lys Arg Tyr Trp Phe Gly
    130                 135                 140

Tyr Glu Asp Leu Gly Arg Arg Ser Met His Lys Leu Trp Asp Leu Ile
145                 150                 155                 160

Lys Val Leu Pro Thr Phe Gly Met Met Arg Ala Asp Arg Thr Val Tyr
                165                 170                 175

Gln His Ala Ala Leu Arg Val Lys Asp Glu Arg Leu Arg Met Ala Leu
            180                 185                 190

Ser Phe His Pro Leu Phe Ile Gly Gly Asp Pro Phe Asn Val Thr Ser
        195                 200                 205

Met Tyr Ile Leu Val Ser Gln Leu Glu Lys Glu Phe Gly Val His Tyr
    210                 215                 220

Ala Ile Gly Gly Val Ala Ile Ala Ala Met Ala Lys Val Ile
225                 230                 235                 240

Glu Gly Gln Gly Gly Ser Phe Arg Met Asn Thr Glu Val Asp Glu Ile
                245                 250                 255

Leu Val Glu Lys Gly Thr Ala Thr Gly Val Arg Leu Ala Ser Gly Glu
            260                 265                 270

Val Leu Arg Ala Gly Leu Val Val Ser Asn Ala Asp Ala Gly His Thr
        275                 280                 285

Tyr Met Arg Leu Leu Arg Asn His Pro Arg Arg Trp Thr Asp Ala
    290                 295                 300

His Val Lys Ser Arg Arg Trp Ser Met Gly Leu Phe Val Trp Tyr Phe
305                 310                 315                 320

Gly Thr Lys Gly Thr Lys Gly Met Trp Pro Asp Val Gly His His Thr
                325                 330                 335
```

```
Ile Val Asn Ala Pro Arg Tyr Lys Gly Leu Val Glu Asp Ile Phe Leu
            340                 345                 350

Lys Gly Lys Leu Ala Lys Asp Met Ser Leu Tyr Ile His Arg Pro Ser
            355                 360                 365

Ile Thr Asp Pro Thr Val Ala Pro Glu Gly Asp Asp Thr Phe Tyr Ala
            370                 375                 380

Leu Ser Pro Val Pro His Leu Lys Gln Ala Gln Pro Val Asp Trp Gln
385                 390                 395                 400

Ala Val Ala Glu Pro Tyr Arg Glu Ser Val Leu Glu Val Leu Glu Gln
                405                 410                 415

Ser Met Pro Gly Ile Gly Glu Arg Ile Gly Pro Ser Leu Val Phe Thr
            420                 425                 430

Pro Glu Thr Phe Arg Asp Arg Tyr Leu Ser Pro Trp Gly Ala Gly Phe
            435                 440                 445

Ser Ile Glu Pro Arg Ile Leu Gln Ser Ala Trp Phe Arg Pro His Asn
            450                 455                 460

Ile Ser Glu Glu Val Ala Asn Leu Phe Leu Val Gly Ala Gly Thr His
465                 470                 475                 480

Pro Gly Ala Gly Val Pro Gly Val Ile Gly Ser Ala Glu Val Met Ala
                485                 490                 495

Lys Leu Ala Pro Asp Ala Pro Arg Ala Arg Glu Ala Glu Pro Ala
            500                 505                 510

Glu Arg Leu Ala Ala Glu
            515

<210> SEQ ID NO 42
<211> LENGTH: 2834
<212> TYPE: DNA
<213> ORGANISM: R. sphaeroides

<400> SEQUENCE: 42
ttgtaaacct gactagacag tctattgtat ggggcatgtt gacaagcact gcaggagttc      60
gcgccatgcc ctcgatctcg cccgcctccg acgccgaccg cgccttgtg atcggctccg       120 gactgggggg ccttgcggct gcgatgcgcc tcggcgccaa gggctggcgc gtgacggtca      180
tcgacaagct cgacgttccg ggcggccgcg gctcctcgat cacgcaggag gggcaccggt      240
tcgatctggg acccaccatc gtgacggtgc cgcagagcct cgcgacctg tggaagacct       300 gcgggcggga cttcgacgcc gatgtcgagc tgaagccgat cgatccgttc tacgaggtgc      360
gctggccgga cgggtcgcac ttcacggtgc cagtcgac cgaggcgatg aaggccgagg        420
tcgcgcgcct ctcgcccggc gatgtggcgg atacgagaa gttcctgaag acagcgaaa        480 agcgctactg gttcggttac gaggatctcg gccgccgctc gatgcacaag ctgtgggatc      540
tcatcaaggt gctgcccacc ttcgggatga tgcgggccga ccgtacggtc taccagcacg      600
ccgcgcttcg ggtgaaggac gagcggctgc gcatggcgct ctcgttccac ccgctcttca      660
tcggcggcga ccccttcaac gtgacctcga tgtatatcct tgtgagccag ctcgagaagg      720
agttcggcgt ccattatgcc atcggcggcg tggcggccat cgccgcggcc atggcgaagg      780
tgatcgaggg gcagggcggc agcttccgca tgaacaccga ggtggacgag atcctcgtcg      840
agaagggcac cgccaccggt gtgcggctcg cctcgggcga ggtgctgcgg cgggtctcg       900 tggtctcgaa tgcggatgcg ggccatacct acatgcggct tctgcgtaac catccgcgcc      960
gccgctggac cgacgcccat gtgaagagcc ggcgctggtc gatggggctg ttcgtctggt     1020
atttcggaac gaagggggacg aagggcatgt ggcccgacgt cggccaccac acgatcgtca    1080
```

```
atgcgccgcg ctacaagggg ctggtcgagg acatcttcct caagggcaag ctcgcgaagg    1140
acatgagcct ctatatccac cggccctcga tcaccgatcc gaccgtggcg cccgaggggg    1200
atgacacgtt ctatgcgctc tcgcccgtgc cgcatctgaa acaggcgcaa ccggtggact    1260
ggcaggctgt ggccgagccc taccgcgaaa gcgtgctcga ggtgctcgaa cagtcgatgc    1320
cggggatcgg ggaacggatc gggccctcgc tcgtcttcac ccccgagacc ttccgcgacc    1380
gctacctcag cccctggggc gcgggcttct cgatcgagcc gcggatcctg cagtcggcct    1440
ggttccggcc gcacaacatt tccgaggagg tggcgaacct gttcctcgtg ggcgcgggca    1500
cccatccggg tgcgggcgtg cccggcgtga tcggttcggc cgaagtgatg gccaagcttg    1560
cccccgatgc gccacgtgcg cgccgcgagg ccgaacctgc tgaaaggctt gccgcggaat    1620
gattgcctct gccgatctcg atgcctgccg ggagatgatc cgcaccggct cctattcctt    1680
ccatgccgcg tcccgcctgc tgcccgagcg cgtgcgcgcg ccgtcgctgg cgctctatgc    1740
cttctgccgc gtggccgacg atgcggtcga cgaggcggtg aacgatggac agcgcgagga    1800
ggatgccgag gtcaagcgcc gcgccgtcct gagcctgcgc gaccggctgg acctcgtcta    1860
tggcggccgc ccgcgcaatg cgccggccga ccgcgccttc gccgcggtgg tcgaggagtt    1920
cgagatgccc cgggcgctgc cgaggcgct gctcgagggg ctcgcctggg acgcggtggg    1980
gcggagctac gacagtttct cgggcgtgct cgactattcg gcgcgggtgg ccgcggcggt    2040
gggggcgatg atgtgcgtcc tcatgcgggt gcgcgatccc gacgtgctgg cccgggcctg    2100
cgatctgggc ctcgccatgc agctcaccaa catcgcccgc gacgtgggga ccgacgcgcg    2160
ctcgggacgg atctatctgc cgcgcgactg gatggaggag gaggggctgc cggtcgagga    2220
gttcctcgcc cggccggtgg tcgacgaccc catccgcgcg gtgacgcacc gcctgctgcg    2280
cgcggccgac cggctctatc tgcgttcgga agcgggggtc tgcggcctgc ctctggcctg    2340
ccggcccggc atctatgccg cgcgccacat ctatgcgggt atcggcgacg agatcgcgcg    2400
gaacggctat gacagcgtga cgcgccgcgc cttcaccacg cggcgccaga agctcgtctg    2460
gctcgggctc tcttccacac gcgcggccct cagcccgttc ggccccggct gcgccacgct    2520
gcatgcggcc cccgagcccg aagtggcctt cctcgtcaat gccgccgccc gggcccggcc    2580
gcagcgcggc cgctccgagg cgctgatctc ggttctggcc cagctcgagg cgcaggatcg    2640
gcagatctcg cggcagcgac tggggaaccg gccaacccg atctaggttc tcatgccggt    2700
ataccggagt aacgatgatg aacatggact gggctctttt cctcaccttc ctcgctgcct    2760
gcggcgcgcc cgcgacgacg ggggcgttgc tgaagcccga tgaatggtac gacaatctga    2820
acaagccctg gtgg                                                     2834
```

<210> SEQ ID NO 43
<211> LENGTH: 501
<212> TYPE: PRT
<213> ORGANISM: A. thaliana

<400> SEQUENCE: 43

Met Asp Thr Leu Leu Lys Thr Pro Asn Lys Leu Asp Phe Phe Ile Pro
1               5                   10                  15

Gln Phe His Gly Phe Glu Arg Leu Cys Ser Asn Asn Pro Tyr His Ser
            20                  25                  30

Arg Val Arg Leu Gly Val Lys Lys Arg Ala Ile Lys Ile Val Ser Ser
        35                  40                  45

Val Val Ser Gly Ser Ala Ala Leu Leu Asp Leu Val Pro Glu Thr Lys

```
             50                  55                  60
Lys Glu Asn Leu Asp Phe Glu Leu Pro Leu Tyr Asp Thr Ser Lys Ser
 65                  70                  75                  80

Gln Val Val Asp Leu Ala Ile Val Gly Gly Pro Ala Gly Leu Ala
                     85                  90                  95

Val Ala Gln Gln Val Ser Glu Ala Gly Leu Ser Val Cys Ser Ile Asp
                100                 105                 110

Pro Ser Pro Lys Leu Ile Trp Pro Asn Asn Tyr Gly Val Trp Val Asp
                115                 120                 125

Glu Phe Glu Ala Met Asp Leu Leu Asp Cys Leu Asp Thr Thr Trp Ser
                130                 135                 140

Gly Ala Val Val Tyr Val Asp Glu Gly Val Lys Lys Asp Leu Ser Arg
145                 150                 155                 160

Pro Tyr Gly Arg Val Asn Arg Lys Gln Leu Lys Ser Lys Met Leu Gln
                165                 170                 175

Lys Cys Ile Thr Asn Gly Val Lys Phe His Gln Ser Lys Val Thr Asn
                180                 185                 190

Val Val His Glu Glu Ala Asn Ser Thr Val Val Cys Ser Asp Gly Val
                195                 200                 205

Lys Ile Gln Ala Ser Val Val Leu Asp Ala Thr Gly Phe Ser Arg Cys
210                 215                 220

Leu Val Gln Tyr Asp Lys Pro Tyr Asn Pro Gly Tyr Gln Val Ala Tyr
225                 230                 235                 240

Gly Ile Val Ala Glu Val Asp Gly His Pro Phe Asp Val Asp Lys Met
                245                 250                 255

Val Phe Met Asp Trp Arg Asp Lys His Leu Asp Ser Tyr Pro Glu Leu
                260                 265                 270

Lys Glu Arg Asn Ser Lys Ile Pro Thr Phe Leu Tyr Ala Met Pro Phe
                275                 280                 285

Ser Ser Asn Arg Ile Phe Leu Glu Gly Thr Ser Leu Val Ala Arg Pro
                290                 295                 300

Gly Leu Arg Met Glu Asp Ile Gln Glu Arg Met Ala Ala Arg Leu Lys
305                 310                 315                 320

His Leu Gly Ile Asn Val Lys Arg Ile Glu Glu Asp Glu Arg Cys Val
                325                 330                 335

Ile Pro Met Gly Gly Pro Leu Pro Val Leu Pro Gln Arg Val Val Gly
                340                 345                 350

Ile Gly Gly Thr Ala Gly Met Val His Pro Ser Thr Gly Tyr Met Val
                355                 360                 365

Ala Arg Thr Leu Ala Ala Ala Pro Ile Val Ala Asn Ala Ile Val Arg
                370                 375                 380

Tyr Leu Gly Ser Pro Ser Ser Asn Ser Leu Arg Gly Asp Gln Leu Ser
385                 390                 395                 400

Ala Glu Val Trp Arg Asp Leu Trp Pro Ile Glu Arg Arg Arg Gln Arg
                405                 410                 415

Glu Phe Phe Cys Phe Gly Met Asp Ile Leu Leu Lys Leu Asp Leu Asp
                420                 425                 430

Ala Thr Arg Arg Phe Phe Asp Ala Phe Phe Asp Leu Gln Pro His Tyr
                435                 440                 445

Trp His Gly Phe Leu Ser Ser Arg Leu Phe Leu Pro Glu Leu Leu Val
                450                 455                 460

Phe Gly Leu Ser Leu Phe Ser His Ala Ser Asn Thr Ser Arg Leu Glu
465                 470                 475                 480
```

Ile Met Thr Lys Gly Thr Val Pro Leu Ala Lys Met Ile Asn Asn Leu
                485                 490                 495

Val Gln Asp Arg Asp
            500

```
<210> SEQ ID NO 44
<211> LENGTH: 1964
<212> TYPE: DNA
<213> ORGANISM: A. thaliana

<400> SEQUENCE: 44
gagtttgaaa gatttgcttt tgtgttcaaa atccactctt ttatcttatt acattttgcc      60
tctagttttg gatttacaag agttggtgaa acacaatgca gcacaaagta ttaattttaa     120
tgaactagta gtaacaattt gatttcacaa ggattcaggt tatgatctgt ggtttataca     180
caattatcca acgacttgca atgcggatat actactggtc aagaaccaaa gaacagatgt     240
acttatatgt ctaagtttct ggtccttagt ctctatcttg taccaaattg ttgatcatct     300
tagcaagagg aacagtcccc tttgtcatga tctccaatct tgaggtattg gaagcgtgtg     360
agaagagcga caacccgaag accaacagtt ccgggagaaa cagcctggaa gacaagaatc     420
cgtgccagta atgaggttgc agatcaaaga atgcatcaaa gaaccttcta gtagcgtcta     480
aatcgagttt cagcagaata tccattccaa aacagaagaa ctccctctgt ctacgccgtt     540
cgataggcca caagtctctc caaacctcag cagagagttg atctcctctc aggctattac     600
tacttggtga accgaggtat ctcacaatgg catttgcaac tattggtgca gctgcaagag     660
tcctagcaac catgtaacca gttgaaggat gaaccattcc tgctgtccca ccaatcccca     720
caacccgttg aggtaagact ggtaaaggac cgcccatcgg gatcacacaa cgctcgtctt     780
cctcaatcct cttcacattg atccccagat gtttcagtct agcagccatt ctttcttgga     840
tatcttccat tctcagacca ggtctagcaa ctaaagaagt tcttcaagaa aatattcggt     900
tggaagaaaa tggcatagcg tacaagaacg ttgggatctt gctgttccgt tctttcagct     960
caggatatga gtccagatgt ttgtctctcc aatccatgaa caccattttg tctacatcga    1020
atgggtgacc atcaacttca gctacaatcc cgtaagctac ttggtaccca gggttgtaag    1080
gtttgtcata ctgaaccaag catcgggaaa acccagtggc atcaagaacc acggaagcct    1140
gaatctttac accgtcactg cagaccacag tggagtttgc ctcctcgtga accacattag    1200
tgaccttaga ctgatgaaat ttaacaccgt tggtaataca tttctgaagc attttggatt    1260
tgagctgttt ccggttaact ctcccataag gccggctcaa atccttcttg acaccttcat    1320
cgacatagac aacagcacca gaccatgtgg tatccaggca gtctagtaaa tccatagcct    1380
caaactcatc aacccaaact ccataattgt taggccatat gagcttagga gaaggatcaa    1440
tggaacaaac agagagtcca gcttcagaaa cctgctgagc cacggctaaa ccagcaggac    1500
caccaccaac aatagccaaa tcaacaactt gactcttgga agtgtcgtac aaaggaagct    1560
caaagtcaag attctccttc ttagtttcag gaacaagatc caaagagca gcgctaccac     1620
tcactacact agagacaatt ttgatagccc ttttcttcac accaagccta acccttgaat    1680
ggtatggatt gttactgcat aatctctcaa acccatgaaa ctgagggatg aaaaaatcga    1740
gcttgttggg tgttttcaac agagtatcca tcgaattccc ccaaaatcga gaaaacacc     1800
aaaaggatat aattcaaaaa tcaccggaca cgatttctaa ccagagggat tgagaaaatg    1860
gaatactaaa ttgctagaga aaagatgaac gaagaccaca aaacttaccc agaagcagta    1920
```
gcttcatgga gatggagaca attatcttct tcccagaaag agag                              1964

<210> SEQ ID NO 45
<211> LENGTH: 489
<212> TYPE: PRT
<213> ORGANISM: O. sativa

<400> SEQUENCE: 45

```
Met Ala Thr Thr Ala Leu Leu Leu Arg Ala His Pro Ser Cys Lys Pro
1               5                   10                  15

Pro Pro Pro Pro Ser Pro Ser Pro Arg Pro Thr Arg Ala Leu Val Cys
                20                  25                  30

Arg Ala Ala Ala Gly Glu Ala Leu Arg Ser Leu Ala Pro Pro Ser
                35                  40                  45

Arg Pro Glu Leu Leu Ser Leu Asp Leu Pro Arg Tyr Asp Pro Ala Arg
    50                  55                  60

Ser Thr Pro Val Asp Leu Ala Val Val Gly Gly Pro Ala Gly Leu
65                  70                  75                  80

Ala Val Ala Gln Arg Val Ala Glu Ala Gly Leu Ser Val Cys Ala Ile
                    85                  90                  95

Asp Pro Ser Pro Ala Leu Val Trp Pro Asn Asn Tyr Gly Val Trp Val
                100                 105                 110

Asp Glu Phe Asp Ala Met Gly Leu Ser His Cys Leu Asp Ala Val Trp
            115                 120                 125

Pro Ser Ala Thr Val Phe Thr His Asp Asp Gly Ala Ala Lys Ser Leu
    130                 135                 140

His Arg Pro Tyr Ala Arg Val Ala Arg Arg Lys Leu Lys Ser Thr Met
145                 150                 155                 160

Met Asp Arg Cys Val Ala His Gly Val Thr Phe His Lys Ala Arg Val
                165                 170                 175

Val Lys Ala Val His Gly Glu Ala Ser Ser Leu Leu Ile Cys Asp Asp
                    180                 185                 190

Gly Val Ala Val Pro Ala Thr Val Val Leu Asp Ala Thr Gly Phe Ser
            195                 200                 205

Arg Cys Leu Val Gln Tyr Asp Lys Pro Tyr Asp Pro Gly Tyr Gln Val
    210                 215                 220

Ala Tyr Gly Ile Leu Ala Glu Val Asp Gly His Pro Phe Asp Ile Asp
225                 230                 235                 240

Lys Met Leu Phe Met Asp Trp Arg Asp Ala His Leu Pro Glu Gly Ser
                245                 250                 255

Glu Ile Arg Glu Arg Asn Arg Arg Ile Pro Thr Phe Leu Tyr Ala Met
                    260                 265                 270

Pro Phe Ser Pro Thr Arg Ile Phe Leu Glu Glu Thr Ser Leu Val Ala
            275                 280                 285

Arg Pro Gly Leu Ala Met Asp Asp Ile Gln Glu Arg Met Ala Ala Arg
    290                 295                 300

Leu Arg His Leu Gly Ile Arg Val Arg Ala Val Glu Glu Asp Glu Arg
305                 310                 315                 320

Cys Val Ile Pro Met Gly Gly Pro Leu Pro Val Leu Pro Gln Arg Val
                325                 330                 335

Val Gly Ile Gly Gly Thr Ala Gly Met Val His Pro Ser Thr Gly Tyr
                    340                 345                 350

Met Val Ala Arg Thr Leu Ala Thr Ala Pro Ile Val Ala Asp Ala Ile
            355                 360                 365
```

```
Val Arg Phe Leu Asp Thr Gly Ser Gly Asp Ser Ala Phe Ala Gly Asp
    370             375                 380

Ala Leu Ser Ala Glu Val Trp Arg Glu Leu Trp Pro Ala Gln Arg Arg
385             390                 395                 400

Arg Gln Arg Glu Phe Phe Cys Phe Gly Met Asp Ile Leu Leu Lys Leu
                405             410                 415

Asp Leu Asp Gly Thr Arg Arg Phe Phe Asp Ala Phe Phe Asp Leu Glu
            420             425                 430

Pro Arg Tyr Trp His Gly Phe Leu Ser Ser Arg Leu Phe Leu Pro Glu
        435             440                 445

Leu Ala Met Phe Gly Leu Ser Leu Phe Ala Lys Ala Ser Asn Thr Ser
450             455                 460

Arg Leu Glu Ile Met Ala Lys Gly Thr Ala Pro Leu Ala Lys Met Ile
465             470                 475                 480

Gly Asn Leu Ile Gln Asp Arg Asp Arg
                485
```

<210> SEQ ID NO 46
<211> LENGTH: 1470
<212> TYPE: DNA
<213> ORGANISM: O. sativa

<400> SEQUENCE: 46

```
tcacctatct ctgtcctgga tgaggttgcc gatcatcttg gcgagagggg cggtgccctt      60
ggccatgatc tcgaggcgcg acgtgttgga ggccttggcg aagagggaga ggccgaacat     120
ggcgagctcc ggcaagaaga gcctcgacga caggaagccg tgccagtagc gcggctccag     180
gtcgaagaag gcgtcgaaga tcgccgcgt gccgtcgagg tcgagcttga ggaggatgtc      240
catgccgaag cagaagaact ccctctgcct cctcctctgc gccggccaca gctcccatcca    300
cacctccgcc gacagcgcgt cgccggcgaa cgcgctgtcg ccgctgccgg tgtcgaggaa     360
gcgcacgatg gcgtccgcca cgatgggcgc agtggcgagg gtgcgcgcca ccatgtagcc     420
cgtggacggg tgcaccatcc ggcggtgcc gccgatgccg acgacccgct gcgggagcac      480
cgggagcggg ccgcccatgg ggatgacgca ccgctcgtcc tcctccacgg cgcggacgcg     540
tatcccgagg tggcgcagcc tcgccgccat gcgctcctgg atgtcgtcca tggcgaggcc     600
cgggcgcgcc acgagggagg tctcctcgag gaagatcctc gtcggggaga agggcatggc     660
gtagaggaac gtcgggatgc ggcggttgcg ctccctgatc tcggacccct cggggaggtg     720
cgcgtcgcgc cagtccatga acagcatctt gtcgatgtcg aacgggtgtc cgtccacctc     780
ggcgaggatg ccataggcga cctggtaccc cgggtcgtac ggcttgtcgt actggacgag     840
gcaccgggag aacccgtgg cgtcgagcac gacggtggcc gggacggcga cgccgtcgtc      900
gcagatgagg agggaggatg cctcgccgtg gacggccttg acgaccctgg ccttgtggaa     960
cgtgacgcca tgggcgacgc agcggtccat catggtggac ttgagcttgc ggcgggcgac    1020
gcgggcgtag gggcggtgga gcgacttggc ggcgccgtcg tcgtgggtga agacggtggc    1080
ggagggccag acggcgtcga ggcagtggga gagtcccatg gcgtcgaact cgtcgaccca    1140
gacgccgtag ttgttgggcc agacgagggc ggggagggg tcgatggcgc agacggagag    1200
gcccgcctcc gcgacgcgct gcgcgacggc gaggccggcg gggccgccgc cgacgacggc    1260
gaggtcgacg gggtggagc gggcggggtc gtagcggggg aggtcgaggg agagcagctc    1320
ggggcgtgac ggcggggcca gcgaccgcag cgcctcgccg gcggcggcgg cgcggcagac    1380
gagcgcgcgc gtgggcgcg gcgacggcga gggagggga gggggcttgc aggagggggtg    1440
```
ggcgcggagg aggagggcgg tggtggccat                                    1470

<210> SEQ ID NO 47
<211> LENGTH: 500
<212> TYPE: PRT
<213> ORGANISM: N. tabacum

<400> SEQUENCE: 47

Met Asp Thr Leu Leu Lys Thr Pro Asn Lys Leu Glu Phe Leu His Pro
1               5                   10                  15

Val His Gly Phe Ser Val Lys Ala Ser Ser Phe Asn Ser Val Lys Pro
            20                  25                  30

His Lys Phe Gly Ser Arg Lys Ile Cys Glu Asn Trp Gly Lys Gly Val
        35                  40                  45

Cys Val Lys Ala Lys Ser Ala Leu Leu Glu Leu Val Pro Glu Thr
    50                  55                  60

Lys Lys Glu Asn Leu Asp Phe Glu Leu Pro Met Tyr Asp Pro Ser Lys
65                  70                  75                  80

Gly Leu Val Val Asp Leu Ala Val Gly Gly Pro Ala Gly Leu
                85                  90                  95

Ala Val Ala Gln Gln Val Ser Glu Ala Gly Leu Ser Val Val Ser Ile
            100                 105                 110

Asp Pro Ser Pro Lys Leu Ile Trp Pro Asn Asn Tyr Gly Val Trp Val
        115                 120                 125

Asp Glu Phe Glu Ala Met Asp Leu Leu Asp Cys Leu Asp Ala Thr Trp
    130                 135                 140

Ser Gly Thr Val Val Tyr Ile Asp Asp Asn Thr Thr Lys Asp Leu Asp
145                 150                 155                 160

Arg Pro Tyr Gly Arg Val Asn Arg Lys Gln Leu Lys Ser Lys Met Met
                165                 170                 175

Gln Lys Cys Ile Leu Asn Gly Val Lys Phe His His Ala Lys Val Ile
            180                 185                 190

Lys Val Ile His Glu Glu Ala Lys Ser Met Leu Ile Cys Asn Asp Gly
        195                 200                 205

Val Thr Ile Gln Ala Thr Val Val Leu Asp Ala Thr Gly Phe Ser Arg
    210                 215                 220

Cys Leu Val Gln Tyr Asp Lys Pro Tyr Lys Pro Gly Tyr Gln Val Ala
225                 230                 235                 240

Tyr Gly Ile Leu Ala Glu Val Glu His Pro Phe Asp Thr Ser Lys
                245                 250                 255

Met Val Leu Met Asp Trp Arg Asp Ser His Leu Gly Asn Asn Met Glu
            260                 265                 270

Leu Lys Glu Arg Asn Arg Lys Val Pro Thr Phe Leu Tyr Ala Met Pro
        275                 280                 285

Phe Ser Ser Asn Lys Ile Phe Leu Glu Glu Thr Ser Leu Val Ala Arg
    290                 295                 300

Pro Gly Leu Arg Met Asp Asp Ile Gln Glu Arg Met Val Ala Arg Leu
305                 310                 315                 320

Asn His Leu Gly Ile Lys Val Lys Ser Ile Glu Glu Asp Glu His Cys
                325                 330                 335

Val Ile Pro Met Gly Gly Ser Leu Pro Val Ile Pro Gln Arg Val Val
            340                 345                 350

Gly Thr Gly Gly Thr Ala Gly Leu Val His Pro Ser Thr Gly Tyr Met
        355                 360                 365

```
Val Ala Arg Thr Leu Ala Ala Pro Val Val Ala Asn Ala Ile Ile
        370                 375                 380

His Tyr Leu Gly Ser Glu Lys Asp Leu Leu Gly Asn Glu Leu Ser Ala
385                 390                 395                 400

Ala Val Trp Lys Asp Leu Trp Pro Ile Glu Arg Arg Gln Arg Glu
                405                 410                 415

Phe Phe Cys Phe Gly Met Asp Ile Leu Leu Lys Leu Asp Leu Pro Ala
            420                 425                 430

Thr Arg Arg Phe Phe Asp Ala Phe Phe Asp Leu Glu Pro Arg Tyr Trp
            435                 440                 445

His Gly Phe Leu Ser Ser Arg Leu Tyr Leu Pro Glu Leu Ile Phe Phe
        450                 455                 460

Gly Leu Ser Leu Phe Ser Arg Ala Ser Asn Thr Ser Arg Ile Glu Ile
465                 470                 475                 480

Met Thr Lys Gly Thr Leu Pro Leu Val Asn Met Ile Asn Asn Leu Leu
                485                 490                 495

Gln Asp Thr Glu
        500
```

<210> SEQ ID NO 48
<211> LENGTH: 1614
<212> TYPE: DNA
<213> ORGANISM: N. tabacum

<400> SEQUENCE: 48

```
ggaactttct tgaaatcctg tttgtagttt tcaaaaaaaa ttgaacccct gttggaagat      60
atggatacat tgttgaaaac cccaaataag cttgagtttc tgcacccagt tcatggattt     120
tctgttaaag ctagctcctt taactctgta agcccccata agtttggttc taggaaaatt     180
tgtgaaaatt ggggtaaagg ggtttgtgtt aaggctaaga gtagtgccct tttggagctt     240
gtacctgaga ccaaaaagga aaatcttgat tttgagcttc ctatgtatga cccttcaaaa     300
ggtcttgttg tagatctagc tgtggttggt ggtggacccg ctggacttgc agttgcacag     360
caggtttcgg aggctggact atcggttgtt tcaatcgatc catcgccgaa attgatatgg     420
cccaataact atggtgtttg ggtggatgaa tttgaggcca tggatttgtt ggattgcctc     480
gacgccacat ggtcaggtac tgttgtttat attgatgaca atacaactaa agatcttgat     540
agaccttatg aagggttaa tcggaaacaa cttaagtcca aaatgatgca gaaatgcata     600
ctaaacggtg ttaaattcca ccacgccaaa gttataaagg taattcacga ggaagctaaa     660
tctatgctga tttgcaatga tggtgtaact attcaggcaa cggtggtgct tgatgcaact     720
ggcttctcaa gatgtcttgt tcagtatgat aagccatata acctggata tcaagtagct     780
tatggcatat tggcagaagt ggaggaacat ccctttgata caagtaagat ggttctcatg     840
gattggcgag attcgcatct tggtaataat atggagctga aggagagaaa tagaaaagtt     900
ccaactttt  tgtatgccat gccattttca tcaaataaaa tatttcttga agaaacctca     960
cttgttgctc gtcctggatt acgtatggac gatattcaag aaagaatggt ggctcgttta    1020
aatcacttgg gtataaaagt taagagcatt gaagaggacg agcattgtgt aattccgatg    1080
ggaggctccc ttcctgtaat acctcagaga gttgttggaa ctggtggtac agctggtctg    1140
gttcatccct caacaggtta tatggtagca aggaccctag ctgcagctcc ggtcgtcgct    1200
aatgcaataa ttcactacct tggttctgag aagacctttt aggtaatga gttatctgca    1260
gctgtttgga agatttgtg gcccatagaa aggagacgtc aacgagagtt cttttgtttc    1320
```

```
ggtatggata ttcttctgaa gcttgattta cccgctacaa gaaggttttt cgatgccttt    1380
tttgatctag aacctcgtta ttggcatggc ttcttgtcat ctcgcctgta tcttcctgag    1440
cttatatttt tcgggctgtc cctttctct cgcgcttcaa atacttctag aatagagatt    1500
atgacaaagg gaactcttcc tttggtaaat atgatcaaca atttgttaca ggatacagaa    1560
tgacttacca ggaatcttgt tcaatattac atagcatgtg ttaatacact gctc          1614

<210> SEQ ID NO 49
<211> LENGTH: 524
<212> TYPE: PRT
<213> ORGANISM: A. thaliana

<400> SEQUENCE: 49

Met Glu Cys Val Gly Ala Arg Asn Phe Ala Ala Met Ala Val Ser Thr
1               5                   10                  15

Phe Pro Ser Trp Ser Cys Arg Arg Lys Phe Pro Val Val Lys Arg Tyr
                20                  25                  30

Ser Tyr Arg Asn Ile Arg Phe Gly Leu Cys Ser Val Arg Ala Ser Gly
            35                  40                  45

Gly Gly Ser Ser Gly Ser Glu Ser Cys Val Ala Val Arg Glu Asp Phe
        50                  55                  60

Ala Asp Glu Glu Asp Phe Val Lys Ala Gly Gly Ser Glu Ile Leu Phe
65                  70                  75                  80

Val Gln Met Gln Gln Asn Lys Asp Met Asp Glu Gln Ser Lys Leu Val
                85                  90                  95

Asp Lys Leu Pro Pro Ile Ser Ile Gly Asp Gly Ala Leu Asp Leu Val
            100                 105                 110

Val Ile Gly Cys Gly Pro Ala Gly Leu Ala Leu Ala Ala Glu Ser Ala
        115                 120                 125

Lys Leu Gly Leu Lys Val Gly Leu Ile Gly Pro Asp Leu Pro Phe Thr
    130                 135                 140

Asn Asn Tyr Gly Val Trp Glu Asp Glu Phe Asn Asp Leu Gly Leu Gln
145                 150                 155                 160

Lys Cys Ile Glu His Val Trp Arg Glu Thr Ile Val Tyr Leu Asp Asp
                165                 170                 175

Asp Lys Pro Ile Thr Ile Gly Arg Ala Tyr Gly Arg Val Ser Arg Arg
            180                 185                 190

Leu Leu His Glu Glu Leu Leu Arg Arg Cys Val Glu Ser Gly Val Ser
        195                 200                 205

Tyr Leu Ser Ser Lys Val Asp Ser Ile Thr Glu Ala Ser Asp Gly Leu
    210                 215                 220

Arg Leu Val Ala Cys Asp Asp Asn Asn Val Ile Pro Cys Arg Leu Ala
225                 230                 235                 240

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val Glu
            260                 265                 270

Val Glu Asn Ser Pro Tyr Asp Pro Asp Gln Met Val Phe Met Asp Tyr
        275                 280                 285

Arg Asp Tyr Thr Asn Glu Lys Val Arg Ser Leu Glu Ala Glu Tyr Pro
    290                 295                 300

Thr Phe Leu Tyr Ala Met Pro Met Thr Lys Ser Arg Leu Phe Phe Glu
305                 310                 315                 320
```

```
Glu Thr Cys Leu Ala Ser Lys Asp Val Met Pro Phe Asp Leu Leu Lys
            325                 330                 335
Thr Lys Leu Met Leu Arg Leu Asp Thr Leu Gly Ile Arg Ile Leu Lys
        340                 345                 350
Thr Tyr Glu Glu Trp Ser Tyr Ile Pro Val Gly Gly Ser Leu Pro
    355                 360                 365
Asn Thr Glu Gln Lys Asn Leu Ala Phe Gly Ala Ala Ser Met Val
370                 375                 380
His Pro Ala Thr Gly Tyr Ser Val Val Arg Ser Leu Ser Glu Ala Pro
385                 390                 395                 400
Lys Tyr Ala Ser Val Ile Ala Glu Ile Leu Arg Glu Thr Thr Lys
            405                 410                 415
Gln Ile Asn Ser Asn Ile Ser Arg Gln Ala Trp Asp Thr Leu Trp Pro
        420                 425                 430
Pro Glu Arg Lys Arg Gln Arg Ala Phe Phe Leu Phe Gly Leu Ala Leu
    435                 440                 445
Ile Val Gln Phe Asp Thr Glu Gly Ile Arg Ser Phe Arg Thr Phe
450                 455                 460
Phe Arg Leu Pro Lys Trp Met Trp Gln Gly Phe Leu Gly Ser Thr Leu
465                 470                 475                 480
Thr Ser Gly Asp Leu Val Leu Phe Ala Leu Tyr Met Phe Val Ile Ser
            485                 490                 495
Pro Asn Asn Leu Arg Lys Gly Leu Ile Asn His Leu Ile Ser Asp Pro
        500                 505                 510
Thr Gly Ala Thr Met Ile Lys Thr Tyr Leu Lys Val
        515                 520

<210> SEQ ID NO 50
<211> LENGTH: 1860
<212> TYPE: DNA
<213> ORGANISM: A. thaliana

<400> SEQUENCE: 50
acaaaaggaa ataattagat tcctctttct gcttgctata ccttgataga acaatataac     60
aatggtgtaa gtcttctcgc tgtattcgaa attatttgga ggaggaaaat ggagtgtgtt    120
ggggctagga atttcgcagc aatggcggtt tcaacatttc cgtcatggag ttgtcgaagg    180
aaatttccag tggttaagag atacagctat aggaatattc gtttcggttt gtgtagtgtc    240
agagctagcg gcggcggaag ttccggtagt gagagttgtg tagcggtgag agaagatttc    300
gctgacgaag aagattttgt gaaagctggt ggttctgaga ttctatttgt tcaaatgcag    360
cagaacaaag atatggatga acagtctaag cttgttgata agttgcctcc tatatcaatt    420
ggtgatggtg ctttggatca tgtggttatt ggttgtggtc ctgctggttt agccttggct    480
gcagaatcag ctaagcttgg attaaaagtt ggactcattg gtccagatct tccttttact    540
aacaattacg tgtttggga agatgaattc aatgatcttg gctgcaaaa atgtattgag     600 catgtttgga gagagactat tgtgtatctg gatgatgaca agcctattac cattggccgt    660
gcttatggaa gagttagtcg acgtttgctc catgaggagc ttttgaggag gtgtgtcgag    720
tcaggtgtct cgtaccttag ctcgaaagtt gacagcataa cagaagcttc tgatggcctt    780
agacttgttg cttgtgacga caataacgtc attccctgca ggcttgccac tgttgcttct    840
ggagcagctt cgggaaagct cttgcaatac gaagttggtg gacctagagt ctgtgtgcaa    900
actgcatacg gcgtggaggt tgaggtggaa aatagtccat atgatccaga tcaaatggtt    960
```

-continued

```
ttcatggatt acagagatta tactaacgag aaagttcgga gcttagaagc tgagtatcca   1020
acgtttctgt acgccatgcc tatgacaaag tcaagactct tcttcgagga gacatgtttg   1080
gcctcaaaag atgtcatgcc ctttgatttg ctaaaaacga agctcatgtt aagattagat   1140
acactcggaa ttcgaattct aaagacttac gaagaggagt ggtcctatat cccagttggt   1200
ggttccttgc caaacaccga acaaaagaat ctcgcctttg gtgctgccgc tagcatggta   1260
catcccgcaa caggctattc agttgtgaga tctttgtctg aagctccaaa atatgcatca   1320
gtcatcgcag agatactaag agaagagact accaaacaga tcaacagtaa tatttcaaga   1380
caagcttggg atactttatg gccaccagaa aggaaaagac agagagcatt ctttctcttt   1440
ggtcttgcac tcatagttca attcgatacc gaaggcatta aagcttcttc ccgtactttc   1500
ttccgccttc caaatggat gtggcaaggg tttctaggat caacattaac atcaggagat   1560
ctcgttctct ttgctttata catgttcgtc atttcaccaa acaatttgag aaaaggtctc   1620
atcaatcatc tcatctctga tccaaccgga gcaaccatga taaaaaccta tctcaaagta   1680
tgatttactt atcaactctt aggtttgtgt atatatatgt tgatttatct gaataatcga   1740
tcaaagaatg gtatgtgggt tactaggaag ttggaaacaa acatgtatag aatctaagga   1800
gtgatcgaaa tggagatgga aacgaaaaga aaaaaatcag tctttgtttt gtggttagtg   1860
```

<210> SEQ ID NO 51
<211> LENGTH: 533
<212> TYPE: PRT
<213> ORGANISM: L. sativa

<400> SEQUENCE: 51

```
Met Glu Cys Phe Gly Ala Arg Asn Met Thr Ala Thr Met Ala Val Phe
1               5                   10                  15

Thr Cys Pro Arg Phe Thr Asp Cys Asn Ile Arg His Lys Phe Ser Leu
            20                  25                  30

Leu Lys Gln Arg Arg Phe Thr Asn Leu Ser Ala Ser Ser Ser Leu Arg
        35                  40                  45

Gln Ile Lys Cys Ser Ala Lys Ser Asp Arg Cys Val Val Asp Lys Gln
    50                  55                  60

Gly Ile Ser Val Ala Asp Glu Glu Asp Tyr Val Lys Ala Gly Gly Ser
65                  70                  75                  80

Glu Leu Phe Phe Val Gln Met Gln Arg Thr Lys Ser Met Glu Ser Gln
                85                  90                  95

Ser Lys Leu Ser Glu Lys Leu Ala Gln Ile Pro Ile Gly Asn Cys Ile
            100                 105                 110

Leu Asp Leu Val Val Ile Gly Cys Gly Pro Ala Gly Leu Ala Leu Ala
        115                 120                 125

Ala Glu Ser Ala Lys Leu Gly Leu Asn Val Gly Leu Ile Gly Pro Asp
    130                 135                 140

Leu Pro Phe Thr Asn Asn Tyr Gly Val Trp Gln Asp Glu Phe Ile Gly
145                 150                 155                 160

Leu Gly Leu Glu Gly Cys Ile Glu His Ser Trp Lys Asp Thr Leu Val
                165                 170                 175

Tyr Leu Asp Asp Ala Asp Pro Ile Arg Ile Gly Arg Ala Tyr Gly Arg
            180                 185                 190

Val His Arg Asp Leu Leu His Glu Glu Leu Leu Arg Arg Cys Val Glu
        195                 200                 205

Ser Gly Val Ser Tyr Leu Ser Ser Lys Val Glu Arg Ile Thr Glu Ala
    210                 215                 220
```

```
Pro Asn Gly Tyr Ser Leu Ile Glu Cys Glu Gly Asn Ile Thr Ile Pro
225                 230                 235                 240

Cys Arg Leu Ala Thr Val Ala Ser Gly Ala Ser Gly Lys Phe Leu
            245                 250                 255

Glu Tyr Glu Leu Gly Gly Pro Arg Val Cys Val Gln Thr Ala Tyr Gly
        260                 265                 270

Ile Glu Val Glu Val Glu Asn Asn Pro Tyr Asp Pro Asp Leu Met Val
            275                 280                 285

Phe Met Asp Tyr Arg Asp Phe Ser Lys His Lys Pro Glu Ser Leu Glu
290                 295                 300

Ala Lys Tyr Pro Thr Phe Leu Tyr Val Met Ala Met Ser Pro Thr Lys
305                 310                 315                 320

Ile Phe Phe Glu Glu Thr Cys Leu Ala Ser Arg Glu Ala Met Pro Phe
            325                 330                 335

Asn Leu Leu Lys Ser Lys Leu Met Ser Arg Leu Lys Ala Met Gly Ile
            340                 345                 350

Arg Ile Thr Arg Thr Tyr Glu Glu Trp Ser Tyr Ile Pro Val Gly
            355                 360                 365

Gly Ser Leu Pro Asn Thr Glu Gln Lys Asn Leu Ala Phe Gly Ala Ala
370                 375                 380

Ala Ser Met Val His Pro Ala Thr Gly Tyr Ser Val Val Arg Ser Leu
385                 390                 395                 400

Ser Glu Ala Pro Asn Tyr Ala Ala Val Ile Ala Lys Ile Leu Arg Gln
                405                 410                 415

Asp Gln Ser Lys Glu Met Ile Ser Leu Gly Lys Tyr Thr Asn Ile Ser
            420                 425                 430

Lys Gln Ala Trp Glu Thr Leu Trp Pro Leu Glu Arg Lys Arg Gln Arg
            435                 440                 445

Ala Phe Phe Leu Phe Gly Leu Ser His Ile Val Leu Met Asp Leu Glu
450                 455                 460

Gly Thr Arg Thr Phe Phe Arg Thr Phe Phe Arg Leu Pro Lys Trp Met
465                 470                 475                 480

Trp Trp Gly Phe Leu Gly Ser Ser Leu Ser Ser Thr Asp Leu Ile Ile
            485                 490                 495

Phe Ala Leu Tyr Met Phe Val Ile Ala Pro His Ser Leu Arg Met Glu
                500                 505                 510

Leu Val Arg His Leu Leu Ser Asp Pro Thr Gly Ala Thr Met Val Lys
            515                 520                 525

Ala Tyr Leu Thr Ile
    530
```

<210> SEQ ID NO 52
<211> LENGTH: 1780
<212> TYPE: DNA
<213> ORGANISM: L. sativa

<400> SEQUENCE: 52

```
gaaacaaatg acgtgaaagt tcttcaaaat tgaattaatt gtaatcctga aaacttgatt      60
tgtgatagaa gaatcaatgg agtgctttgg agctcgaaac atgacggcaa caatggcggt     120
ttttacgtgc cctagattca cggactgtaa tatcaggcac aaattttcgt tactgaaaca     180
acgaagattt actaatttat cagcatcgtc ttcgttgcgt caaattaagt gcagcgctaa     240
aagcgaccgt tgtgtagtgg ataaacaagg gattccgta gcagacgaag aagattatgt      300
```

```
gaaggccggt ggatcggagc tgtttttttgt tcaaatgcag cggactaagt ccatggaaag    360
ccagtctaaa cttccgaaa agctagcaca gataccaatt ggaaattgca tacttgatct     420
ggttgtaatc ggttgtggcc ctgctggcct tgctcttgct gcagagtcag ccaaactagg    480
gttgaacgtt ggactcattg gccctgatct tccttttaca aacaattatg gtgtttggca    540
ggatgaattt ataggtcttg gacttgaagg atgcattgaa cattcttgga agatactct    600
tgtataccctt gatgatgctg atcccatccg cataggtcgt gcatatggca gagttcatcg    660
tgatttactt catgaagagt tgttaagaag gtgtgtggaa tcaggtgttt catatctaag    720
ctccaaagta gaaagaatca ctgaagctcc aaatggctat agtctcattg aatgtgaagg    780
caatatcacc attccatgca ggcttgctac tgttgcatca ggggcagctt cagggaaatt    840
tctggagtat gaacttgggg gtccccgtgt ttgtgtccaa acagcttatg gtatagaggt    900
tgaggttgaa acaaccccct atgatccaga tctaatggtg ttcatggatt atagagactt    960
ctcaaaacat aaaccggaat ctttagaagc aaaatatccg actttcctct atgtcatggc   1020
catgtctcca acaaaaatat tcttcgagga aacttgttta gcttcaagag aagccatgcc   1080
tttcaatctt ctaaagtcca aactcatgtc acgattaaag gcaatgggta tccgaataac   1140
aagaacgtac gaagaggaat ggtcgtatat ccccgtaggt ggatcgttac ctaatacaga   1200
acaaaagaat ctcgcatttg gtgctgcagc tagtatggtg caccctgcca cagggtattc   1260
agttgttcga tctttgtcag aagctcctaa ttatgcagca gtcattgcta agattttaag   1320
acaagatcaa tctaaagaga tgatttctct tggaaaatac actaacattt caaaacaagc   1380
atgggaaaca ttgtggccac ttgaaaggaa aagacagcga gccttctttc tattcggact   1440
atcacacatc gtgctaatgg atctagaggg aacacgtaca ttttccgta ctttctttcg   1500
tttgcccaaa tggatgtggt ggggattttt ggggtcttct ttatcttcaa cggatttgat   1560
aatatttgcg ctttatatgt ttgtgatagc acctcacagc ttgagaatgg aactggttag   1620
acatctactt tctgatccga caggggcaac tatggtaaaa gcatatctca ctatatagat   1680
ttagattata taaataatac ccatatcttg catatatata agcccttattt atttctttg    1740
tatccttaca acaacatact cgttaattat atgttttta                           1780
```

<210> SEQ ID NO 53
<211> LENGTH: 534
<212> TYPE: PRT
<213> ORGANISM: B. napus

<400> SEQUENCE: 53

```
Met Glu Cys Val Gly Ala Arg Asn Leu Ala Ala Thr Ala Val Thr Ala
1               5                   10                  15

Phe Pro Ser Trp Ser Ser Ser Arg Lys Asn Tyr Pro Val Asp Asn Arg
            20                  25                  30

Tyr Ser Phe Ser Asn Leu Arg Cys Gly Leu Cys Arg Val Lys Ala Ser
        35                  40                  45

Gly Gly Gly Ala Gly Ser Gly Ile Glu Ser Cys Val Ala Val Arg Glu
    50                  55                  60

Asp Phe Ala Asp Glu Glu Asp Phe Val Lys Ala Gly Ser Glu Ile
65                  70                  75                  80

Leu Tyr Val Gln Met Gln Gln Asn Lys Asp Met Asp Glu His Glu Gln
                85                  90                  95

Ser Lys Leu Val Asp Lys Leu Pro Pro Ile Ser Thr Gly Glu Gly Gly
            100                 105                 110
```

```
Gly Ala Leu Asp Leu Val Val Ile Gly Cys Gly Pro Ala Gly Leu Ala
            115                 120                 125

Leu Ala Ala Glu Ser Ala Lys Leu Gly Leu Lys Val Gly Leu Ile Gly
130                 135                 140

Pro Asp Leu Pro Phe Thr Asn Asn Tyr Gly Val Trp Glu Asp Glu Phe
145                 150                 155                 160

Asn Asp Leu Gly Leu Gln Lys Cys Ile Glu His Val Trp Arg Asp Thr
                165                 170                 175

Leu Val Tyr Leu Asp Asp Asp Asn Pro Ile Thr Ile Gly Arg Ala Tyr
            180                 185                 190

Gly Arg Val Ser Arg Arg Leu Leu His Glu Glu Leu Leu Arg Arg Cys
        195                 200                 205

Val Glu Ser Gly Val Ser Tyr Leu Ser Ser Lys Val Glu Ser Ile Thr
    210                 215                 220

Glu Ala Pro Asp Gly Leu Arg Leu Val Ser Cys Glu Gln Asn Thr Leu
225                 230                 235                 240

Val Pro Cys Arg Leu Ala Thr Val Ala Ser Gly Ala Ala Ser Gly Lys
                245                 250                 255

Leu Leu Gln Tyr Glu Val Gly Gly Pro Arg Val Cys Val Gln Thr Ala
            260                 265                 270

Tyr Gly Leu Glu Val Glu Val Glu Lys Ser Pro Tyr Asp Pro Glu Gln
        275                 280                 285

Met Val Phe Met Asp Tyr Arg Asp Tyr Thr Lys Glu Lys Ile Arg Ser
    290                 295                 300

Leu Glu Ala Glu Tyr Pro Thr Phe Leu Tyr Ala Met Pro Met Thr Lys
305                 310                 315                 320

Thr Arg Val Phe Phe Glu Glu Thr Cys Leu Ala Ser Lys Asp Val Met
                325                 330                 335

Pro Phe Asp Leu Leu Lys Lys Lys Leu Met Leu Arg Leu Glu Thr Leu
            340                 345                 350

Gly Ile Arg Ile Leu Lys Thr Tyr Glu Glu Glu Trp Ser Tyr Ile Pro
        355                 360                 365

Val Gly Gly Ser Leu Pro Asn Thr Glu Gln Lys Asn Leu Ala Phe Gly
    370                 375                 380

Ala Ala Ala Ser Met Val His Pro Ala Thr Gly Tyr Ser Val Val Arg
385                 390                 395                 400

Ser Leu Ser Glu Ala Pro Lys Tyr Ala Ser Val Ile Ala Asn Ile Leu
                405                 410                 415

Lys His Glu Thr Thr Ser Phe Thr Arg His Ile Asn Thr Asn Ile
            420                 425                 430

Ser Arg Gln Ala Trp Asp Thr Leu Trp Pro Pro Glu Arg Lys Arg Gln
        435                 440                 445

Arg Ala Phe Phe Leu Phe Gly Leu Ala Leu Ile Val Gln Leu Asp Ile
    450                 455                 460

Glu Gly Ile Arg Cys Phe Phe Thr Phe Arg Leu Pro Lys Trp
465                 470                 475                 480

Met Trp Arg Gly Phe Leu Gly Ser Thr Leu Thr Ser Gly Asp Leu Val
                485                 490                 495

Leu Phe Ala Phe Tyr Met Phe Ile Ile Ala Pro Asn Asn Leu Arg Lys
            500                 505                 510

Gly Leu Ile Asn His Leu Ile Ser Asp Pro Thr Gly Ala Thr Met Ile
        515                 520                 525

Lys Thr Tyr Leu Lys Val
```

<210> SEQ ID NO 54
<211> LENGTH: 2422
<212> TYPE: DNA
<213> ORGANISM: B. napus

<400> SEQUENCE: 54

```
atggagtgtg ttggtgctcg caatctcgct gcaacggcgg tcacagcttt tccgtcctgg      60
agttcttcgc gtaaaaacta tcccgtggat aatagataca gctttagtaa tctccggtgc     120
ggtttgtgta gagtcaaagc tagcggcggc ggagcaggtt ccggtataga gagttgcgtg     180
gcggtgagag aggacttcgc cgacgaggaa gacttcgtga aggctggtgg ttcggagatt     240
ctatacgttc aaatgcagca gaacaaagac atggatgaac atgaacagtc taagcttgtt     300
gataaggtaa gtcaacgttt tgccgttgac ttgtttgtga agataacgaa ctatctatct     360
cctttgatct tacatttgct tcagacagtt cacgtctgag ttttgaagcc tttgtcttat     420
tgattgtgtg tgtgtgtgtt ttttttttta atataacagt tacctcctat atcaactggt     480
gaaggtggtg gtgcttttga cctagtggtt attgggtgtg gtcctgctgg tttagccttg     540
gcggctgaat cagctaagtt aggacttaaa gttggactga ttggtcctga ccttcctttc     600
actaacaact acggtgtttg gaagatgag ttcaacggta atgatctagc agttactatc     660
tccatggtca tattataata aatctatttt gtgtttattg ttttactctt tgcagatctt     720
ggcttgcaaa aatgtattga gcatgtttgg agagataccc ttgtgtatct ggacgatgac     780
aatcctatta ccattggtcg tgcttatgga agagttagtc gacgtttact tcacgaggag     840
ctcttgagga ggtaattaaa aaaatgctcc cactcttcag agagacattt cactagagtt     900
attattgttc atctcctgac aattgatttt ctgataggtg tgtggagtca ggtgtctcgt     960
atcttagctc caaagttgag agcataacag aagctcctga tggccttagg cttgttttcct    1020
gtgaacagaa caccccttgtt ccgtgcaggt actctttctt aagtccaaca aaaacgtgct    1080
tgggtacagt gtcaatggtt ccgacattct agacaaatgc aggcttgcca ctgttgcttc    1140
tggagcagct tctgggaagc tcttgcaata cgaagttgga ggacctagag tctgtgtcca    1200
aactgcttac ggcttggagg ttgaggtata gtaatcaaat tatgatattc cagagtaatt    1260
aatacacata ttcctgtaag gaattgtat taatctctgt ttgaaaactc tttgtaggtg    1320
gaaaagagtc catatgatcc agagcagatg gtgttcatgg attacagaga ttatacaaaa    1380
gagaaaatcc ggagcttaga agctgaatat ccaacgtttc tctacgccat gcctatgaca    1440
aagacaagag tcttctttga ggttccttct ctcttcttct gttttaatca ttttttagcac    1500
taaaagtcta ttgcttatta ttggctggag ttttctttgca ggagacatgt cttgcttcaa    1560
aagatgtcat gccctttgat ctgctaaaaa agaagctcat gttgagatta gagacactcg    1620
gaatccgaat actaaagact tatgaagagg taaatctata taacaaaaa gaagtagagc    1680
ttcacttgtt gagcaaacaa tataaacttc tttggttggt gcataaaaaa caggaatggt    1740
cttatatccc agtaggtggt tccttgccga acacggaaca aaagaatctc gcctttggtg    1800
ctgcagctag catggtacat cctgcaacag gctattcagt tgtgagatct ttgtctgaag    1860
ctccaaaata cgcatcagtc atcgctaata tactaaaaca tgagaccact acttccttca    1920
ccagacacat caacaccaat atttcaagac aaggtgaggc tctatataaa ccaccactga    1980
gttcacatct ttcagacaat ttataaaaac ttgtgagctt gttattctgt gccagcttgg    2040
gatactttat ggccaccaga aaggaaacga caaagagcat tctttctctt tggtcttgcg    2100
```

```
ctcatagttc aactcgacat cgaaggcatt agatgcttct tccacacttt cttccgcctt    2160
ccaaaatggt aagccatcga ctgatattct tgattcagtt aacaaacaat gtatggaaaa    2220
atcaagaaag tgatgttttt gttttctttt gctcaggatg tggagagggt ttctaggatc    2280
aacattaaca tcaggagacc tcgttctgtt tgctttctac atgttcatca ttgcaccaaa    2340
caacttgaga aaggtctca tcaatcatct tatctctgat ccaaccggag caaccatgat    2400
taaaacctat cttaaagtat ga                                             2422
```

<210> SEQ ID NO 55
<211> LENGTH: 307
<212> TYPE: PRT
<213> ORGANISM: E. herbicola

<400> SEQUENCE: 55

```
Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205

Ser Thr Arg Glu Thr Leu His Ala Phe Ala Leu Asp Phe Gly Gln Ala
    210                 215                 220

Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
                245                 250                 255

Ala Asp Ala Ala Arg Gln Lys Leu Arg Glu His Ile Asp Ser Ala Asp
            260                 265                 270

Lys His Leu Thr Phe Ala Cys Pro Gln Gly Gly Ala Ile Arg Gln Phe
        275                 280                 285

Met His Leu Trp Phe Gly His His Leu Ala Asp Trp Ser Pro Val Met
    290                 295                 300

Lys Ile Ala
```

-continued

```
305

<210> SEQ ID NO 56
<211> LENGTH: 924
<212> TYPE: DNA
<213> ORGANISM: E. herbicola

<400> SEQUENCE: 56
atggtgagtg gcagtaaagc gggcgtttcg cctcatcgcg aaatagaagt aatgagacaa      60
tccattgacg atcacctggc tggcctgtta cctgaaaccg acagccagga tatcgtcagc     120
cttgcgatgc gtgaaggcgt catggcaccc ggtaaacgga tccgtccgct gctgatgctg     180
ctggccgccc gcgacctccg ctaccagggc agtatgccta cgctgctcga tctcgcctgc     240
gccgttgaac tgacccatac cgcgtcgctg atgctcgacg acatgccctg catggacaac     300
gccgagctgc gccgcggtca gcccactacc cacaaaaaat tggtgagag cgtggcgatc      360 cttgcctccg ttgggctgct ctctaaagcc tttggtctga tcgccgccac cggcgatctg     420
ccgggggaga ggcgtgccca gcggtcaac gagctctcta ccgccgtggg cgtgcagggc      480
ctggtactgg ggcagtttcg cgatcttaac gatgccgccc tcgaccgtac ccctgacgct     540
atcctcagca ccaaccacct caagaccggc attctgttca gcgcgatgct gcagatcgtc     600
gccattgctt ccgcctcgtc gccgagcacg cgagagacgc tgcacgcctt cgccctcgac     660
ttcggccagg cgtttcaact gctggacgat ctgcgtgacg atcacccgga accggtaaa      720 gatcgcaata aggacgcggg aaaatcgacg ctggtcaacc ggctgggcgc agacgcggcc     780
cggcaaaagc tgcgcgagca tattgattcc gccgacaaac acctcacttt tgcctgtccg     840
cagggcggcg ccatccgaca gtttatgcat ctgtggtttg gccatcacct tgccgactgg     900
tcaccggtca tgaaaatcgc ctga                                           924

<210> SEQ ID NO 57
<211> LENGTH: 309
<212> TYPE: PRT
<213> ORGANISM: E. herbicola

<400> SEQUENCE: 57

Met Ser Gln Pro Pro Leu Leu Asp His Ala Thr Gln Thr Met Ala Asn
1               5                   10                  15

Gly Ser Lys Ser Phe Ala Thr Ala Ala Lys Leu Phe Asp Pro Ala Thr
            20                  25                  30

Arg Arg Ser Val Leu Met Leu Tyr Thr Trp Cys Arg His Cys Asp Asp
        35                  40                  45

Val Ile Asp Asp Gln Thr His Gly Phe Ala Ser Glu Ala Ala Ala Glu
    50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
            100                 105                 110

Leu Asp Gly Phe Ala Met Asp Val Ala Gln Thr Arg Tyr Val Thr Phe
        115                 120                 125

Glu Asp Thr Leu Arg Tyr Cys Tyr His Val Ala Gly Val Val Gly Leu
    130                 135                 140

Met Met Ala Arg Val Met Gly Val Arg Asp Glu Arg Val Leu Asp Arg
145                 150                 155                 160
```

```
Ala Cys Asp Leu Gly Leu Ala Phe Gln Leu Thr Asn Ile Ala Arg Asp
            165                 170                 175

Ile Ile Asp Asp Ala Ala Ile Asp Arg Cys Tyr Leu Pro Ala Glu Trp
        180                 185                 190

Leu Gln Asp Ala Gly Leu Thr Pro Glu Asn Tyr Ala Arg Glu Asn
        195                 200                 205

Arg Ala Ala Leu Ala Arg Val Ala Glu Arg Leu Ile Asp Ala Ala Glu
    210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
                260                 265                 270

Thr Ser Lys Gly Glu Lys Ile Ala Met Leu Met Ala Ala Pro Gly Gln
            275                 280                 285

Val Ile Arg Ala Lys Thr Thr Arg Val Thr Pro Arg Pro Ala Gly Leu
        290                 295                 300

Trp Gln Arg Pro Val
305

<210> SEQ ID NO 58
<211> LENGTH: 930
<212> TYPE: DNA
<213> ORGANISM: E. herbicola

<400> SEQUENCE: 58
atgagccaac cgccgctgct tgaccacgcc acgcagacca tggccaacgg ctcgaaaagt      60
tttgccaccg ctgcgaagct gttcgacccg gccacccgcc gtagcgtgct gatgctctac    120
acctggtgcc gccactgcga tgacgtcatt gacgaccaga cccacggctt cgccagcgag    180
gccgcggcgg aggaggaggc cacccagcgc ctggcccggc tgcgcacgct gaccctggcg    240
gcgtttgaag gggccgagat gcaggatccg gccttcgctg cctttcagga ggtggcgctg    300
acccacggta ttacgccccg catggcgctc gatcacctcg acggctttgc gatggacgtg    360
gctcagaccc gctatgtcac ctttgaggat acgctgcgct actgctatca cgtggcgggc    420
gtggtgggtc tgatgatggc cagggtgatg ggcgtgcggg atgagcgggt gctggatcgc    480
gcctgcgatc tggggctggc cttccagctg acgaatatcg cccgggatat tattgacgat    540
gcggctattg accgctgcta tctgcccgcc gagtggctgc aggatgccgg gctgaccccg    600
gagaactatg ccgcgcggga gaatcgggcc gcgctggcgc gggtggcgga gcggcttatt    660
gatgccgcag agccgtacta catctcctcc caggccgggc tacacgatct gccgccgcgc    720
tgcgcctggg cgatcgccac cgcccgcagc gtctaccggg agatcggtat taaggtaaaa    780
gcggcgggag gcagcgcctg ggatcgccgc cagcacacca gcaaaggtga aaaaattgcc    840
atgctgatgg cggcaccggg gcaggttatt cgggcgaaga cgacgagggt gacgccgcgt    900
ccggccggtc tttggcagcg tcccgtttag                                     930

<210> SEQ ID NO 59
<211> LENGTH: 386
<212> TYPE: PRT
<213> ORGANISM: E. herbicola

<400> SEQUENCE: 59
```

```
Met Arg Asp Leu Ile Leu Val Gly Gly Leu Ala Asn Gly Leu Ile
1               5                   10                  15

Ala Trp Arg Leu Arg Gln Arg Tyr Pro Gln Leu Asn Leu Leu Ile
            20                  25                  30

Glu Ala Gly Glu Gln Pro Gly Gly Asn His Thr Trp Ser Phe His Glu
        35                  40                  45

Asp Asp Leu Thr Pro Gly Gln His Ala Trp Leu Ala Pro Leu Val Ala
50                  55                  60

His Ala Trp Pro Gly Tyr Glu Val Gln Phe Pro Asp Leu Arg Arg Arg
65                  70                  75                  80

Leu Ala Arg Gly Tyr Tyr Ser Ile Thr Ser Glu Arg Phe Ala Glu Ala
                85                  90                  95

Leu His Gln Ala Leu Gly Glu Asn Ile Trp Leu Asn Cys Ser Val Ser
            100                 105                 110

Glu Val Leu Pro Asn Ser Val Arg Leu Ala Asn Gly Glu Ala Leu Leu
        115                 120                 125

Ala Gly Ala Val Ile Asp Gly Arg Gly Val Thr Ala Ser Ser Ala Met
130                 135                 140

Gln Thr Gly Tyr Gln Leu Phe Leu Gly Gln Gln Trp Arg Leu Thr Gln
145                 150                 155                 160

Pro His Gly Leu Thr Val Pro Ile Leu Met Asp Ala Thr Val Ala Gln
                165                 170                 175

Gln Gln Gly Tyr Arg Phe Val Tyr Thr Leu Pro Leu Ser Ala Asp Thr
            180                 185                 190

Leu Leu Ile Glu Asp Thr Arg Tyr Ala Asn Val Pro Gln Arg Asp Asp
        195                 200                 205

Asn Ala Leu Arg Gln Thr Val Thr Asp Tyr Ala His Ser Lys Gly Trp
210                 215                 220

Gln Leu Ala Gln Leu Glu Arg Glu Thr Gly Cys Leu Pro Ile Thr
225                 230                 235                 240

Leu Ala Gly Asp Ile Gln Ala Leu Trp Ala Asp Ala Pro Gly Val Pro
                245                 250                 255

Arg Ser Gly Met Arg Ala Gly Leu Phe His Pro Thr Thr Gly Tyr Ser
            260                 265                 270

Leu Pro Leu Ala Val Ala Leu Ala Asp Ala Ile Ala Asp Ser Pro Arg
        275                 280                 285

Leu Gly Ser Val Pro Leu Tyr Gln Leu Thr Arg Gln Phe Ala Glu Arg
290                 295                 300

His Trp Arg Arg Gln Gly Phe Phe Arg Leu Leu Asn Arg Met Leu Phe
305                 310                 315                 320

Leu Ala Gly Arg Glu Glu Asn Arg Trp Arg Val Met Gln Arg Phe Tyr
                325                 330                 335

Gly Leu Pro Glu Pro Thr Val Glu Arg Phe Tyr Ala Gly Arg Leu Ser
            340                 345                 350

Leu Phe Asp Lys Ala Arg Ile Leu Thr Gly Lys Pro Pro Val Pro Leu
        355                 360                 365

Gly Glu Ala Trp Arg Ala Ala Leu Asn His Phe Pro Asp Arg Arg Asp
370                 375                 380

Lys Gly
385

<210> SEQ ID NO 60
<211> LENGTH: 1161
<212> TYPE: DNA
```

<213> ORGANISM: E. herbicola

<400> SEQUENCE: 60

| | | | | | |
|---|---|---|---|---|---|
| gtgagggatc | tgattttagt | cggcggcggc | ctggccaacg | ggctgatcgc | ctggcgtctg | 60 |
| cgccagcgct | acccgcagct | taacctgctg | ctgatcgagg | ccggggagca | gcccggcggg | 120 |
| aaccatacct | ggtcattcca | tgaagacgat | ctgactcccg | ggcagcacgc | ctggctggcc | 180 |
| ccgctggtgg | cccacgcctg | gccgggctat | gaggtgcagt | ttcccgatct | tcgccgtcgc | 240 |
| ctcgcgcgcg | gctactactc | cattacctca | gagcgctttg | ccgaggccct | gcatcaggcg | 300 |
| ctgggggaga | acatctggct | aaactgttcg | gtgagcgagg | tgttacccaa | tagcgtgcgc | 360 |
| cttgccaacg | gtgaggcgct | gcttgccgga | gcggtgattg | acggacgcgg | cgtgaccgcc | 420 |
| agttcggcga | tgcaaaccgg | ctatcagctc | tttcttggtc | agcagtggcg | gctgacacag | 480 |
| ccccacggcc | tgaccgtacc | gatcctgatg | gatgccacgg | tggcgcagca | gcagggctat | 540 |
| cgctttgtct | acacgctgcc | gctctccgcc | gacacgctgc | tgatcgagga | tacgcgctac | 600 |
| gccaatgtcc | cgcagcgtga | tgataatgcc | ctacgccaga | cggttaccga | ctatgctcac | 660 |
| agcaaagggt | ggcagctggc | ccagcttgaa | cgcgaggaga | ccggctgtct | gccgattacc | 720 |
| ctggcgggtg | acatccaggc | tctgtgggcc | gatgcgccgg | gcgtgccgcg | ctcgggaatg | 780 |
| cgggctgggc | tatttcaccc | taccactggc | tattcgctgc | cgctggcggt | ggcccttgcc | 840 |
| gacgcgattg | ccgacagccc | gcggctgggc | agcgttccgc | tctatcagct | cacccggcag | 900 |
| tttgccgaac | gccactggcg | caggcaggga | ttcttccgcc | tgctgaaccg | gatgcttttc | 960 |
| ctggccgggc | gcgaggagaa | ccgctggcgg | gtgatgcagc | gcttttatgg | gctgccggag | 1020 |
| cccaccgtag | agcgctttta | cgccggtcgg | ctctctctct | ttgataaggc | ccgcattttg | 1080 |
| acgggcaagc | caccggttcc | gctgggcgaa | gcctggcggg | cggcgctgaa | ccattttcct | 1140 |
| gacagacgag | ataaaggatg | a | | | | 1161 |

<210> SEQ ID NO 61
<211> LENGTH: 25
<212> TYPE: DNA
<213> ORGANISM: Artificial Sequence
<220> FEATURE:
<223> OTHER INFORMATION: synthetic

<400> SEQUENCE: 61
accgcatatg gccgtcccgt gcgta 25

<210> SEQ ID NO 62
<211> LENGTH: 28
<212> TYPE: DNA
<213> ORGANISM: Artificial Sequence
<220> FEATURE:
<223> OTHER INFORMATION: synthetic sequence

<400> SEQUENCE: 62
gagaggtacc tcatctggac ccactgag 28

<210> SEQ ID NO 63
<211> LENGTH: 27
<212> TYPE: DNA
<213> ORGANISM: Artificial Sequence
<220> FEATURE:
<223> OTHER INFORMATION: synthetic sequence

<400> SEQUENCE: 63
gagagaattc aatggccgcc ggtctgt 27

-continued

<210> SEQ ID NO 64
<211> LENGTH: 26
<212> TYPE: DNA
<213> ORGANISM: Artificial Sequence
<220> FEATURE:
<223> OTHER INFORMATION: synthetic sequence

<400> SEQUENCE: 64
accgaagctt tcagatggtc cggccg                                          26

<210> SEQ ID NO 65
<211> LENGTH: 41
<212> TYPE: DNA
<213> ORGANISM: Artificial Sequence
<220> FEATURE:
<223> OTHER INFORMATION: synthetic sequence

<400> SEQUENCE: 65
accgctcgag gccaccatga gctcagcgac gtcagtgagt g                         41

<210> SEQ ID NO 66
<211> LENGTH: 35
<212> TYPE: DNA
<213> ORGANISM: Artificial Sequence
<220> FEATURE:
<223> OTHER INFORMATION: synthetic sequence

<400> SEQUENCE: 66
gagatctaga tcagattcga gttgctgaga cttgc                                35

<210> SEQ ID NO 67
<211> LENGTH: 31
<212> TYPE: DNA
<213> ORGANISM: Artificial Sequence
<220> FEATURE:
<223> OTHER INFORMATION: synthetic sequence

<400> SEQUENCE: 67
gagactcgag aatccatctc gaatccctag c                                    31

<210> SEQ ID NO 68
<211> LENGTH: 30
<212> TYPE: DNA
<213> ORGANISM: Artificial Sequence
<220> FEATURE:
<223> OTHER INFORMATION: synthetic sequence

<400> SEQUENCE: 68
accgtctaga tcatctggac ccactgagtg                                      30

<210> SEQ ID NO 69
<211> LENGTH: 34
<212> TYPE: DNA
<213> ORGANISM: Artificial Sequence
<220> FEATURE:
<223> OTHER INFORMATION: synthetic sequence

<400> SEQUENCE: 69
accgctcgag gccaccatgg ccgccggtct gtcc                                 34

<210> SEQ ID NO 70
<211> LENGTH: 29
<212> TYPE: DNA
<213> ORGANISM: Artificial Sequence
<220> FEATURE:

<223> OTHER INFORMATION: synthetic sequence

<400> SEQUENCE: 70
gagatctaga tcagatggtc cggccgatt                               29

<210> SEQ ID NO 71
<211> LENGTH: 33
<212> TYPE: DNA
<213> ORGANISM: Artificial Sequence
<220> FEATURE:
<223> OTHER INFORMATION: synthetic sequence

<400> SEQUENCE: 71
accgtctaga atgagctcag cgacgtcagt gag                          33

<210> SEQ ID NO 72
<211> LENGTH: 33
<212> TYPE: DNA
<213> ORGANISM: Artificial Sequence
<220> FEATURE:
<223> OTHER INFORMATION: synthetic sequence

<400> SEQUENCE: 72
gagaggatcc gattcgagtt gctgagactt gcc                          33

<210> SEQ ID NO 73
<211> LENGTH: 34
<212> TYPE: DNA
<213> ORGANISM: Artificial Sequence
<220> FEATURE:
<223> OTHER INFORMATION: synthetic sequence

<400> SEQUENCE: 73
accgtctaga atggccgccg ccgccgccgc cgcc                         34

<210> SEQ ID NO 74
<211> LENGTH: 36
<212> TYPE: DNA
<213> ORGANISM: Artificial Sequence
<220> FEATURE:
<223> OTHER INFORMATION: synthetic sequence

<400> SEQUENCE: 74
gagatgatca tctggaccca ctgagtgcaa aatcag                       36

<210> SEQ ID NO 75
<211> LENGTH: 28
<212> TYPE: DNA
<213> ORGANISM: Artificial Sequence
<220> FEATURE:
<223> OTHER INFORMATION: synthetic sequence

<400> SEQUENCE: 75
accgtctaga atggccgccg gtctgtcc                                28

<210> SEQ ID NO 76
<211> LENGTH: 28
<212> TYPE: DNA
<213> ORGANISM: Artificial Sequence
<220> FEATURE:
<223> OTHER INFORMATION: synthetic sequence

<400> SEQUENCE: 76
gagaggatcc gatggtccgg ccgattcg                                28

<210> SEQ ID NO 77
<211> LENGTH: 39
<212> TYPE: DNA
<213> ORGANISM: Artificial Sequence
<220> FEATURE:
<223> OTHER INFORMATION: synthetic sequence

<400> SEQUENCE: 77
accgctcgag gcaacaatga gctcagcgac gtcagtgag    39

<210> SEQ ID NO 78
<211> LENGTH: 33
<212> TYPE: DNA
<213> ORGANISM: Artificial Sequence
<220> FEATURE:
<223> OTHER INFORMATION: synthetic sequence

<400> SEQUENCE: 78
gagagaattc gattcgagtt gctgagactt gcc    33

<210> SEQ ID NO 79
<211> LENGTH: 34
<212> TYPE: DNA
<213> ORGANISM: Artificial Sequence
<220> FEATURE:
<223> OTHER INFORMATION: synthetic sequence

<400> SEQUENCE: 79
accgctcgag atggccgccg ccgccgccgc cgcc    34

<210> SEQ ID NO 80
<211> LENGTH: 36
<212> TYPE: DNA
<213> ORGANISM: Artificial Sequence
<220> FEATURE:
<223> OTHER INFORMATION: synthetic sequence

<400> SEQUENCE: 80
gagagaattc tctggaccca ctgagtgcaa aatcag    36

<210> SEQ ID NO 81
<211> LENGTH: 28
<212> TYPE: DNA
<213> ORGANISM: Artificial Sequence
<220> FEATURE:
<223> OTHER INFORMATION: synthetic sequence

<400> SEQUENCE: 81
accgctcgag atggccgccg gtctgtcc    28

<210> SEQ ID NO 82
<211> LENGTH: 28
<212> TYPE: DNA
<213> ORGANISM: Artificial Sequence
<220> FEATURE:
<223> OTHER INFORMATION: synthetic sequence

<400> SEQUENCE: 82
gagagaattc gatggtccgg ccgattcg    28

<210> SEQ ID NO 83
<211> LENGTH: 33
<212> TYPE: DNA
<213> ORGANISM: Artificial Sequence
<220> FEATURE:
<223> OTHER INFORMATION: synthetic sequence -continued

<400> SEQUENCE: 83
accgctcgag atgagctcag cgacgtcagt gag            33

<210> SEQ ID NO 84
<211> LENGTH: 33
<212> TYPE: DNA
<213> ORGANISM: Artificial Sequence
<220> FEATURE:
<223> OTHER INFORMATION: synthetic sequence

<400> SEQUENCE: 84
gagagaattc gattcgagtt gctgagactt gcc            33

<210> SEQ ID NO 85
<211> LENGTH: 21
<212> TYPE: DNA
<213> ORGANISM: Artificial Sequence
<220> FEATURE:
<223> OTHER INFORMATION: synthetic sequence

<400> SEQUENCE: 85
accgccatgg ccgccgccgc c            21

<210> SEQ ID NO 86
<211> LENGTH: 28
<212> TYPE: DNA
<213> ORGANISM: Artificial Sequence
<220> FEATURE:
<223> OTHER INFORMATION: synthetic sequence

<400> SEQUENCE: 86
gagagaattc tctggaccca ctgagtgc            28

<210> SEQ ID NO 87
<211> LENGTH: 29
<212> TYPE: DNA
<213> ORGANISM: Artificial Sequence
<220> FEATURE:
<223> OTHER INFORMATION: synthetic sequence

<400> SEQUENCE: 87
accgtcatga tggccgccgg tctgtccgg            29

<210> SEQ ID NO 88
<211> LENGTH: 30
<212> TYPE: DNA
<213> ORGANISM: Artificial Sequence
<220> FEATURE:
<223> OTHER INFORMATION: synthetic sequence

<400> SEQUENCE: 88
gagagaattc gatggtccgg ccgattcgcg            30

<210> SEQ ID NO 89
<211> LENGTH: 620
<212> TYPE: PRT
<213> ORGANISM: E. coli

<400> SEQUENCE: 89

Met Ser Phe Asp Ile Ala Lys Tyr Pro Thr Leu Ala Leu Val Asp Ser
1               5                   10                  15

Thr Gln Glu Leu Arg Leu Leu Pro Lys Glu Ser Leu Pro Lys Leu Cys
                20                  25                  30

Asp Glu Leu Arg Arg Tyr Leu Leu Asp Ser Val Ser Arg Ser Ser Gly

```
            35                  40                  45
His Phe Ala Ser Gly Leu Gly Thr Val Glu Leu Thr Val Ala Leu His
 50                  55                  60
Tyr Val Tyr Asn Thr Pro Phe Asp Gln Leu Ile Trp Asp Val Gly His
 65                  70                  75                  80
Gln Ala Tyr Pro His Lys Ile Leu Thr Gly Arg Arg Asp Lys Ile Gly
                 85                  90                  95
Thr Ile Arg Gln Lys Gly Gly Leu His Pro Phe Pro Trp Arg Gly Glu
            100                 105                 110
Ser Glu Tyr Asp Val Leu Ser Val Gly His Ser Ser Thr Ser Ile Ser
        115                 120                 125
Ala Gly Ile Gly Ile Ala Val Ala Ala Glu Lys Glu Gly Lys Asn Arg
    130                 135                 140
Arg Thr Val Cys Val Ile Gly Asp Gly Ala Ile Thr Ala Gly Met Ala
145                 150                 155                 160
Phe Glu Ala Met Asn His Ala Gly Asp Ile Arg Pro Asp Met Leu Val
                165                 170                 175
Ile Leu Asn Asp Asn Glu Met Ser Ile Ser Glu Asn Val Gly Ala Leu
            180                 185                 190
Asn Asn His Leu Ala Gln Leu Leu Ser Gly Lys Leu Tyr Ser Ser Leu
        195                 200                 205
Arg Glu Gly Gly Lys Lys Val Phe Ser Gly Val Pro Pro Ile Lys Glu
    210                 215                 220
Leu Leu Lys Arg Thr Glu Glu His Ile Lys Gly Met Val Val Pro Gly
225                 230                 235                 240
Thr Leu Phe Glu Glu Leu Gly Phe Asn Tyr Ile Gly Pro Val Asp Gly
                245                 250                 255
His Asp Val Leu Gly Leu Ile Thr Thr Leu Lys Asn Met Arg Asp Leu
            260                 265                 270
Lys Gly Pro Gln Phe Leu His Ile Met Thr Lys Lys Gly Arg Gly Tyr
        275                 280                 285
Glu Pro Ala Glu Lys Asp Pro Ile Thr Phe His Ala Val Pro Lys Phe
    290                 295                 300
Asp Pro Ser Ser Gly Cys Leu Pro Lys Ser Ser Gly Gly Leu Pro Ser
305                 310                 315                 320
Tyr Ser Lys Ile Phe Gly Asp Trp Leu Cys Glu Thr Ala Ala Lys Asp
                325                 330                 335
Asn Lys Leu Met Ala Ile Thr Pro Ala Met Arg Glu Gly Ser Gly Met
            340                 345                 350
Val Glu Phe Ser Arg Lys Phe Pro Asp Arg Tyr Phe Asp Val Ala Ile
        355                 360                 365
Ala Glu Gln His Ala Val Thr Phe Ala Ala Gly Leu Ala Ile Gly Gly
    370                 375                 380
Tyr Lys Pro Ile Val Ala Ile Tyr Ser Thr Phe Leu Gln Arg Ala Tyr
385                 390                 395                 400
Asp Gln Val Leu His Asp Val Ala Ile Gln Lys Leu Pro Val Leu Phe
                405                 410                 415
Ala Ile Asp Arg Ala Gly Ile Val Gly Ala Asp Gly Gln Thr His Gln
            420                 425                 430
Gly Ala Phe Asp Leu Ser Tyr Leu Arg Cys Ile Pro Glu Met Val Ile
        435                 440                 445
Met Thr Pro Ser Asp Glu Asn Glu Cys Arg Gln Met Leu Tyr Thr Gly
    450                 455                 460
```

```
Tyr His Tyr Asn Asp Gly Pro Ser Ala Val Arg Tyr Pro Arg Gly Asn
465                 470                 475                 480

Ala Val Gly Val Glu Leu Thr Pro Leu Glu Lys Leu Pro Ile Gly Lys
            485                 490                 495

Gly Ile Val Lys Arg Arg Gly Glu Lys Leu Ala Ile Leu Asn Phe Gly
        500                 505                 510

Thr Leu Met Pro Glu Ala Ala Lys Val Ala Glu Ser Leu Asn Ala Thr
    515                 520                 525

Leu Val Asp Met Arg Phe Val Lys Pro Leu Asp Glu Ala Leu Ile Leu
530                 535                 540

Glu Met Ala Ala Ser His Glu Ala Leu Val Thr Val Glu Glu Asn Ala
545                 550                 555                 560

Ile Met Gly Gly Ala Gly Ser Gly Val Asn Glu Val Leu Met Ala His
                565                 570                 575

Arg Lys Pro Val Pro Val Leu Asn Ile Gly Leu Pro Asp Phe Phe Ile
            580                 585                 590

Pro Gln Gly Thr Gln Glu Met Arg Ala Glu Leu Gly Leu Asp Ala
            595                 600                 605

Ala Gly Met Glu Ala Lys Ile Lys Ala Trp Leu Ala
    610                 615                 620

<210> SEQ ID NO 90
<211> LENGTH: 1863
<212> TYPE: DNA
<213> ORGANISM: E. coli

<400> SEQUENCE: 90
atgagttttg atattgccaa atacccgacc ctggcactgg tcgactccac ccaggagtta      60
cgactgttgc cgaaagagag tttaccgaaa ctctgcgacg aactgcgccg ctatttactc     120
gacagcgtga gccgttccag cgggcacttc gcctccgggc tgggcacggt cgaactgacc     180
gtggcgctgc actatgtcta acacccccg tttgaccaat tgatttggga tgtggggcat     240
caggcttatc cgcataaaat tttgaccgga cgccgcgaca aaatcggcac catccgtcag     300
aaaggcggtc tgcacccgtt cccgtggcgc ggcgaaagcg aatatgacgt attaagcgtc     360
gggcattcat caacctccat cagtgccgga attggtattg cggttgctgc gaaaaagaa     420 ggcaaaaatc gccgcaccgt ctgtgtcatt ggcgatggcg cgattaccgc aggcatggcg     480
tttgaagcga tgaatcacgc gggcgatatc cgtcctgata tgctggtgat tctcaacgac     540
aatgaaatgt cgatttccga aaatgtcggc gcgctcaaca accatctggc acagctgctt     600
tccggtaagc tttactcttc actgcgcgaa ggcgggaaaa agttttctc tggcgtgccg     660 ccaattaaag agctgctcaa acgcaccgaa gaacatatta aaggcatggt agtgcctggc     720
acgttgtttg aagagctggg ctttaactac atcggcccgg tgacggtca cgatgtgctg     780 gggcttatca ccacgctaaa gaacatgcgc gacctgaaag cccgcagtt cctgcatatc     840 atgaccaaaa aaggtcgtgg ttatgaaccg gcagaaaaag acccgatcac tttccacgcc     900
gtgcctaaat ttgatccctc cagcggttgt tgccgaaaa gtagcggcgg tttgccgagc     960
tattcaaaaa tctttggcga ctggttgtgc gaaacggcag cgaaagacaa caagctgatg    1020
gcgattactc cggcgatgcg tgaaggttcc ggcatggtcg agttttcacg taaattcccg    1080
gatcgctact cgacgtggc aattgccgag caacacgcgg tgacctttgc tgcgggtctg    1140
gcgattggtg ggtacaaacc cattgtcgcg atttactcca ctttcctgca acgcgcctat    1200
```

-continued

```
gatcaggtgc tgcatgacgt ggcgattcaa aagcttccgg tcctgttcgc catcgaccgc    1260
gcgggcattg ttggtgctga cggtcaaacc catcagggtg cttttgatct ctcttacctg    1320
cgctgcatac cggaaatggt cattatgacc ccgagcgatg aaaacgaatg tcgccagatg    1380
ctctataccg gctatcacta taacgatggc ccgtcagcgg tgcgctaccc gcgtggcaac    1440
gcggtcggcg tggaactgac gccgctggaa aaactaccaa ttggcaaagg cattgtgaag    1500
cgtcgtggcg agaaactggc gatccttaac tttggtacgc tgatgccaga agcggcgaaa    1560
gtcgccgaat cgctgaacgc cacgctggtc gatatgcgtt ttgtgaaacc gcttgatgaa    1620
gcgttaattc tggaaatggc cgccagccat gaagcgctgg tcaccgtaga agaaaacgcc    1680
attatgggcg gcgcaggcag cggcgtgaac gaagtgctga tggcccatcg taaaccagta    1740
cccgtgctga acattggcct gccggacttc tttattccgc aaggaactca ggaagaaatg    1800
cgcgccgaac tcggcctcga tgccgctggt atggaagcca aatcaaggc ctggctggca    1860 taa                                                                  1863
```

<210> SEQ ID NO 91
<211> LENGTH: 719
<212> TYPE: PRT
<213> ORGANISM: L. esculentum

<400> SEQUENCE: 91

```
Met Ala Leu Cys Ala Tyr Ala Phe Pro Gly Ile Leu Asn Arg Thr Gly
1               5                   10                  15

Val Val Ser Asp Ser Ser Lys Ala Thr Pro Leu Phe Ser Gly Trp Ile
            20                  25                  30

His Gly Thr Asp Leu Gln Phe Leu Phe Gln His Lys Leu Thr His Glu
        35                  40                  45

Val Lys Lys Arg Ser Arg Val Val Gln Ala Ser Leu Ser Glu Ser Gly
    50                  55                  60

Glu Tyr Tyr Thr Gln Arg Pro Pro Thr Pro Ile Leu Asp Thr Val Asn
65                  70                  75                  80

Tyr Pro Ile His Met Lys Asn Leu Ser Leu Lys Glu Leu Lys Gln Leu
                85                  90                  95

Ala Asp Glu Leu Arg Ser Asp Thr Ile Phe Asn Val Ser Lys Thr Gly
            100                 105                 110

Gly His Leu Gly Ser Ser Leu Gly Val Val Glu Leu Thr Val Ala Leu
        115                 120                 125

His Tyr Val Phe Asn Ala Pro Gln Asp Arg Ile Leu Trp Asp Val Gly
    130                 135                 140

His Gln Ser Tyr Pro His Lys Ile Leu Thr Gly Arg Arg Asp Lys Met
145                 150                 155                 160

Ser Thr Leu Arg Gln Thr Asp Gly Leu Ala Gly Phe Thr Lys Arg Ser
                165                 170                 175

Glu Ser Glu Tyr Asp Cys Phe Gly Thr Gly His Ser Ser Thr Thr Ile
            180                 185                 190

Ser Ala Gly Leu Gly Met Ala Val Gly Arg Asp Leu Lys Gly Arg Asn
        195                 200                 205

Asn Asn Val Ile Ala Val Ile Gly Asp Gly Ala Met Thr Ala Gly Gln
    210                 215                 220

Ala Tyr Glu Ala Met Asn Asn Ala Gly Tyr Leu Asp Ser Asp Met Ile
225                 230                 235                 240

Val Ile Leu Asn Asp Asn Arg Gln Val Ser Leu Pro Thr Ala Thr Leu
                245                 250                 255
```

```
Asp Gly Pro Val Ala Pro Val Gly Ala Leu Ser Ser Ala Leu Ser Arg
            260                 265                 270

Leu Gln Ser Asn Arg Pro Leu Arg Glu Leu Arg Glu Val Ala Lys Gly
        275                 280                 285

Val Thr Lys Gln Ile Gly Gly Pro Met His Glu Leu Ala Ala Lys Val
    290                 295                 300

Asp Glu Tyr Ala Arg Gly Met Ile Ser Gly Ser Gly Ser Thr Leu Phe
305                 310                 315                 320

Glu Glu Leu Gly Leu Tyr Tyr Ile Gly Pro Val Asp Gly His Asn Ile
                325                 330                 335

Asp Asp Leu Ile Ala Ile Leu Lys Glu Val Arg Ser Thr Lys Thr Thr
            340                 345                 350

Gly Pro Val Leu Ile His Val Val Thr Glu Lys Gly Arg Gly Tyr Pro
        355                 360                 365

Tyr Ala Glu Arg Ala Ala Asp Lys Tyr His Gly Val Ala Lys Phe Asp
    370                 375                 380

Pro Ala Thr Gly Lys Gln Phe Lys Ala Ser Ala Lys Thr Gln Ser Tyr
385                 390                 395                 400

Thr Thr Tyr Phe Ala Glu Ala Leu Ile Ala Glu Ala Glu Ala Asp Lys
                405                 410                 415

Asp Ile Val Ala Ile His Ala Ala Met Gly Gly Gly Thr Gly Met Asn
            420                 425                 430

Leu Phe His Arg Arg Phe Pro Thr Arg Cys Phe Asp Val Gly Ile Ala
        435                 440                 445

Glu Gln His Ala Val Thr Phe Ala Ala Gly Leu Ala Cys Glu Gly Ile
    450                 455                 460

Lys Pro Phe Cys Ala Ile Tyr Ser Ser Phe Met Gln Arg Ala Tyr Asp
465                 470                 475                 480

Gln Val Val His Asp Val Asp Leu Gln Lys Leu Pro Val Arg Phe Ala
                485                 490                 495

Met Asp Arg Ala Gly Leu Val Gly Ala Asp Gly Pro Thr His Cys Gly
            500                 505                 510

Ala Phe Asp Val Thr Tyr Met Ala Cys Leu Pro Asn Met Val Val Met
        515                 520                 525

Ala Pro Ser Asp Glu Ala Glu Leu Phe His Met Val Ala Thr Ala Ala
    530                 535                 540

Ala Ile Asp Asp Arg Pro Ser Cys Phe Arg Tyr Pro Arg Gly Asn Gly
545                 550                 555                 560

Ile Gly Val Glu Leu Pro Ala Gly Asn Lys Gly Ile Pro Leu Glu Val
                565                 570                 575

Gly Lys Gly Arg Ile Leu Ile Glu Gly Glu Arg Val Ala Leu Leu Gly
            580                 585                 590

Tyr Gly Ser Ala Val Gln Asn Cys Leu Asp Ala Ala Ile Val Leu Glu
        595                 600                 605

Ser Arg Gly Leu Gln Val Thr Val Ala Asp Ala Arg Phe Cys Lys Pro
    610                 615                 620

Leu Asp His Ala Leu Ile Arg Ser Leu Ala Lys Ser His Glu Val Leu
625                 630                 635                 640

Ile Thr Val Glu Glu Gly Ser Ile Gly Gly Phe Gly Ser His Val Val
                645                 650                 655

Gln Phe Met Ala Leu Asp Gly Leu Leu Asp Gly Lys Leu Lys Trp Arg
            660                 665                 670
```

```
Pro Ile Val Leu Pro Asp Arg Tyr Ile Asp His Gly Ser Pro Val Asp
            675                 680                 685

Gln Leu Ala Glu Ala Gly Leu Thr Pro Ser His Ile Ala Ala Thr Val
        690                 695                 700

Phe Asn Ile Leu Gly Gln Thr Arg Glu Ala Leu Glu Val Met Thr
705                 710                 715

<210> SEQ ID NO 92
<211> LENGTH: 179
<212> TYPE: PRT
<213> ORGANISM: E. coli

<400> SEQUENCE: 92

Met Glu Asn Val Ile Leu Ile Asp His Asn Asp Cys Glu Thr Gly Ile
1               5                   10                  15

Ala Glu Lys Leu Tyr Thr His Lys Lys Gly Ile Leu His Arg Ala Val
            20                  25                  30

Ser Val Tyr Ile Cys Asn Ser Asp Gly Lys Leu Leu Leu Gln Gln Arg
        35                  40                  45

Ala Leu Gly Lys Tyr His Ser Pro Gly Leu Trp Ser Asn Thr Ser Cys
    50                  55                  60

Thr His Pro Phe Pro Gly Glu Ser Asn Leu Ser Ala Ala Asn Arg Arg
65                  70                  75                  80

Leu Arg Glu Glu Met Gly Ile Glu Cys Pro Leu Ser Lys Leu Leu Lys
                85                  90                  95

Ile Tyr Tyr Asn Val Tyr Val Gly Gly Asp Leu Thr Glu His Glu Ile
            100                 105                 110

Ala His Ile Phe Tyr Gly Ile Ser Asp Asp Glu Pro Asp Leu Asn Ser
        115                 120                 125

Leu Glu Ala Met Ser Tyr Lys Tyr Val Ser Leu Thr Glu Leu Ser Ser
    130                 135                 140

Glu Ile Lys Phe Asn Asn Asp Ala Phe Ser Arg Trp Phe Val Tyr Cys
145                 150                 155                 160

Phe Pro Tyr Ile Lys Asn Ala Phe Leu Asn Glu Ser Asn Tyr Thr Asn
                165                 170                 175

Leu Leu Ile

<210> SEQ ID NO 93
<211> LENGTH: 545
<212> TYPE: DNA
<213> ORGANISM: E. coli

<400> SEQUENCE: 93
ctaaatcaat aaattggtat aattactctc attcaggaaa gcattttaa tatatgggaa      60 acaatagacg aaccaacgag aaaaagcatc gttattgaat tttatttcag aacttaactc    120
tgtcaaggaa acatatttat aactcatagc ttccaaacta tttaaatctg gctcatcatc    180
actaatacca tagaaaatat gtgcaatctc atgttctgtt aaatcaccgc cgacataaac    240
attatagtag atctttaata gtttagataa ggggcattct atccccattt cctcccttaa    300
tcttctgtta gctgcagata aattcgattc tcccgggaag ggatgtgtac aagaggtatt    360
gctccaaagg ccgggagaat gatattttcc aagtgctctt tgctgtaaca ataattttcc    420
atcgctatta catatataaa cagaaacagc ccgatgtaaa atacctttt tgtgggtata     480 taatttttcg gcaatccccg tttcacaatc attatggtca attaaaataa cattctccat    540
aaatt                                                                545
```

<210> SEQ ID NO 94
<211> LENGTH: 237
<212> TYPE: PRT
<213> ORGANISM: Z. mays

<400> SEQUENCE: 94

Met Ala Ala Ala Val Val Asp Asp Ala Gly Met Asp Ala Val Gln Lys
1               5                   10                  15

Arg Leu Met Phe Glu Asp Glu Cys Ile Leu Val Asp Glu Gln Asp Asn
            20                  25                  30

Val Val Gly His Glu Ser Lys Tyr Asn Cys His Leu Met Glu Lys Ile
        35                  40                  45

Asp Ser Glu Asn Leu Leu His Arg Ala Phe Ser Val Phe Leu Phe Asn
    50                  55                  60

Ser Lys Tyr Glu Leu Leu Leu Gln Gln Arg Ser Ala Thr Lys Val Thr
65                  70                  75                  80

Phe Pro Leu Val Trp Thr Asn Thr Cys Cys Ser His Pro Leu Tyr Arg
                85                  90                  95

Glu Ser Glu Leu Ile Gln Glu Asn Tyr Leu Gly Val Arg Asn Ala Ala
            100                 105                 110

Gln Arg Lys Leu Leu Asp Glu Leu Gly Ile Pro Ala Glu Asp Ala Pro
        115                 120                 125

Val Asp Gln Phe Thr Pro Leu Gly Arg Met Leu Tyr Lys Ala Pro Ser
    130                 135                 140

Asp Gly Lys Trp Gly Glu His Glu Leu Asp Tyr Leu Leu Phe Ile Val
145                 150                 155                 160

Arg Asp Val Lys Val Gln Pro Asn Pro Asp Glu Val Ala Asp Val Lys
                165                 170                 175

Tyr Val Asn Arg Asp Glu Leu Lys Glu Leu Ile Arg Lys Ala Asp Ala
            180                 185                 190

Gly Glu Asp Gly Val Lys Ile Ser Pro Trp Phe Arg Leu Val Val Asp
        195                 200                 205

Asn Phe Leu Met Gly Trp Trp Asp His Val Glu Lys Gly Thr Leu Gly
    210                 215                 220

Glu Ala Val Asp Met Glu Thr Ile His Lys Leu Lys Glu
225                 230                 235

<210> SEQ ID NO 95
<211> LENGTH: 1095
<212> TYPE: DNA
<213> ORGANISM: Z. mays

<400> SEQUENCE: 95
cgcacacccc ggcagccgca aacgccttcg ccgtcgcgtc ccgctcctcc gcccgcccga        60 cgcgaccct  aggacctgga gagagaggtc ggcatggctg ccgcagtggt cgacgacgct       120
ggtatggacg ccgtccagaa agcgcctcatg ttcgaagacg aatgcatttt ggtggacgag      180
caggacaatg ttgttggcca tgagtcaaag tacaactgcc atttgatgga aaagattgat       240
tctgagaatc tgctacatag ggcattcagt gtgttccttt tcaactcaaa atatgagctg       300
ctacttcagc aaaggtccgc gacaaaggtt acctttcctt tagtttggac caatacctgc       360
tgcagccacc ctctgtaccg tgagtctgag cttatccagg agaactacct tggtgtgaga       420
aatgcagcac agaggaagct actggatgag ctgggcatcc cagcagaaga tgccccagtt       480
gaccaattca cccctctggg ccgaatgctt tacaaggcac catctgacgg gaaatggggg       540

```
gagcatgagc ttgactacct gctgttcatc gtccgggacg tgaaggtgca gccgaaccca      600
gatgaagtcg ctgacgtgaa gtacgtgaac cgcgacgagc tcaaggagct catccggaag      660
gctgacgctg gcgaggacgg ggtgaagatc tcccccctgg tcaggctggt ggtggacaac      720
ttcctcatgg gctggtggga ccatgtcgag aaaggcaccc tcggcgaggc cgtggacatg      780
gagaccatcc ataagctgaa ggagtgaggg gccgccggcc ggccggctcc gatgacctca      840
ccacctgttg atgttgctgc tgctgctgca ctgcatgttt atcaaaagtt atcgctcctg      900
ctcgcggaaa gtgagcttga ctgttgccgg ggtggaagtg tcgttttgga ctgaagatga      960
gtgccgcgga ggggtttgtt gtttgtttgt ttgtttgttc ggtgaccgaa tcgcgagttg     1020
gacgcctgtt taatccgtgc ttatacatcg tctgagtaaa cagcaataag agggacatcc     1080
gtaagctctt tccgt                                                      1095
```

<210> SEQ ID NO 96
<211> LENGTH: 2567
<212> TYPE: DNA
<213> ORGANISM: L. esculentum

<400> SEQUENCE: 96

```
catcttcata acaacatttt tagtgacagt agcaccaaca caccccacta gaattttctt       60
gaagtaaacc cctttttttca agaatcaaga aaccacttat aaaatttgtg ggttttcatt     120
gaaacaaagg aaaaaaaaca gttgaattga ctaatcatgg ctttgtgtgc ttatgcattt     180
cctgggattt tgaacaggac tggtgtggtt tcagattctt ctaaggcaac ccctttgttc     240
tctggatgga ttcatggaac agatctgcag ttttttgttcc aacacaagct tactcatgag     300
gtcaagaaaa ggtcacgtgt ggttcaggct tccttatcag aatctggaga atactacaca     360
cagagaccgc caacgcctat tttggacact gtgaactatc ccattcatat gaaaaatctg     420
tctctgaagg aacttaaaca actagcagat gaactaaggt cagatacaat tttcaatgta     480
tcaaagactg ggggtcacct tggctcaagt cttggtgttg ttgagctgac tgttgctctt     540
cattatgtct tcaatgcacc gcaagatagg attctctggg atgttggtca tcagtcttat     600
ctcacaaaat cttgactggt agaagggaca agatgtcgac attaaggcag acagatggtc     660
ttgcaggatt tactaagcga tcggagagtg aatatgattg ctttggcacc ggccacagtt     720
ccaccaccat ctcagcaggc ctagggatgg ctgttggtag agatctaaaa ggaagaaaca     780
acaatgttat tgccgtaata ggtgatggtg ccatgacagc aggtcaagct tatgaagcca     840
tgaataatgc tggttacctg gactctgaca tgattgttat cttaaacgac aatagacaag     900
tttctttacc tactgctact ctggatgggc cagttgctcc tgttggagct ctaagtagtg     960
ctttgagcag gttacagtct aataggcctc tcagagaact aagagaagtc gcaaagggag    1020
ttactaagca gattggtggt cctatgcatg agcttgctgc aaaagttgat gaatatgctc    1080
gtggcatgat tagtggttct ggatcaacat tgtttgaaga acttggactt tactatattg    1140
gtcctgtgga tggtcacaac attgatgatc taattgcgat tctcaaagag gttagaagta    1200
ctaaaacaac aggtccagta ctgatccatg ttgtcactga gaaggcaga ggttatccat    1260 atgctgagag agctgcagat aagtatcatg agttgccaa gtttgatcca gcaacaggaa     1320
agcaattcaa agccagtgcc aagacacagt cctatacaac atattttgcc gaggctttaa     1380
ttgcagaagc agaagcagat aaagacattg ttgcaatcca tgctgccatg ggggtggga     1440 ccggaatgaa cctttttccat cgtcgcttcc aacaaggtg ttttgatgtt ggaatagcag     1500
```

-continued

```
aacaacatgc agtaaccttt gctgctggat tggcttgtga aggcattaaa cctttctgtg  1560
caatctattc gtctttcatg cagagggctt atgaccaggt agtgcatgac gttgatttgc  1620
aaaagctgcc cgtgaggttt gcaatggaca gagcaggtct tgttggagca gatggtccaa  1680
cacattgtgg tgcatttgat gttacttaca tggcatgtct tcctaacatg gttgtaatgg  1740
ctccttctga tgaagcggag ctatttcaca tggtagcaac tgctgccgcc attgatgaca  1800
gaccaagttg ttttagatac caagaggaa atgggatcgg tgtagagctt ccggctggaa  1860
acaaaggaat tcctcttgag gttggtaaag gtaggatatt gattgagggg gagagagtgg  1920
ctctattggg atatggctca gcagtgcaga actgtttgga tgctgctatt gtgctagaat  1980
cccgcggctt acaagtaaca gttgcagatg cacgtttctg caaaccactg gaccatgccc  2040
tcataaggag ccttgcaaaa tcacatgaag tgctaatcac tgtcgaagaa ggatcaattg  2100
gaggttttgg atctcatgtt gttcagttca tggcttaga tgggcttctt gatggcaagt  2160
tgaagtggag accaatagtt cttcctgatc gatacattga ccatggatct cctgttgatc  2220
agttggcgga agctggccta acaccatctc acattgcagc aacagtattt aacatacttg  2280
gacaaaccag agaggctcta gaggtcatga cataagatgg aagaagcgta gaaagatata  2340
tagtatattg taaaatatag ttttaggtca tgacataagc agattaacat atactttatc  2400
ctccaaaata tgtttaaagt ttccatggct gagttcaagc cctcctctta gtctccacca  2460
tgacttatga ttaactcata tggtttctga ttgtgtaacc ggttcttgat ttttcgagtt  2520
atgaagatga atgaaaatga aagattttac tttcaaaaaa aaaaaaa                2567
```

CELLS AND METHODS FOR PRODUCING LUTEIN

CROSS REFERENCE TO RELATED APPLICATION

This application claims the benefit of U.S. Provisional Application No. 61/595,529, filed Feb. 6, 2012, which is incorporated herein by reference.

FEDERALLY SPONSORED RESEARCH

This invention was made with Government support under grant number GM081160 awarded by the National Institutes of Health. The Government has certain rights in the invention.

FIELD OF THE INVENTION

The invention relates to methods of producing lutein and microbiology.

BACKGROUND OF THE INVENTION

Carotenoids are a large class of isoprenoid pigments synthesized by all photosynthetic organisms, as well as some bacteria, fungi, and aphids (Cuttriss et al., Adv. Botanical Res. Part A 58:1-36, 2011). In plants, carotenoids serve essential roles in photosynthesis and photoprotection (Jahns et al., Biochim. Biophys. Acta Bioenergetics 1817:182-193, 2012), and are precursors to apocarotenoids that function in stress and developmental responses (Walter et al., Planta 232:1-17, 2010).

Plant-derived carotenoids also provide nutritional benefits to humans. For example, lutein is a natural part of the human diet when fruits and vegetables are consumed. Lutein-fortified foods are available for individuals lacking sufficient lutein intake. While there is no recommended daily allowance for lutein, the positive effects of lutein can be observed at dietary intake levels of 6-10 mg/day. In addition to its use in nutraceuticals and fortified food products, lutein can be used to treat age-related macular degeneration and other eye diseases, or as an antioxidant (e.g., used as an antioxidant in cosmetic agents).

SUMMARY OF THE INVENTION

The invention is based, in part, on the discovery that the co-expression of a CYP97A and a CYP97C enzyme in a bacterium that is capable of producing α-carotene, is capable of producing a significantly increased amount of lutein, and the discovery that CYP97A and CYP97C proteins interact within a plant cell.

In view of these discoveries, provided herein are recombinant bacteria and yeast cells that are capable of producing a significantly increased amount of lutein, methods of making lutein that include culturing these recombinant bacteria or yeast cells, and methods of making these recombinant bacteria and yeast cells. Also provided is lutein produced by the methods described herein, and pharmaceutical compositions, food supplements, food products, and cosmetic compositions that contain lutein produced by the methods described herein.

Provided herein are recombinant cells (e.g., a recombinant bacterium or yeast cell) that contain: a nucleic acid encoding a CYP97A protein or a nucleic acid encoding a CYP97B protein; a nucleic acid encoding a CYP97C protein; a nucleic acid encoding a geranylgeranyl pyrophosphate synthase protein; a nucleic acid encoding a phytoene synthase protein; a nucleic acid encoding a phytoene desaturase protein; a nucleic acid encoding a lycopene β-cyclase protein; and a nucleic acid encoding a lycopene ε-cyclase protein.

In some embodiments, the recombinant cells (e.g., a recombinant bacterium or yeast cell) further contain a nucleic acid encoding a D-1-deoxyxylulose 5-phosphate synthase protein; and/or a nucleic acid encoding an isopentenyl pyrophosphate isomerase protein.

In some embodiments, the recombinant cell (e.g., the recombinant bacterium or yeast cell) contains a nucleic acid encoding a CYP97A protein (e.g., a CYP97A protein containing a sequence at least 80% identical to SEQ ID NO: 1).

In some embodiments, the recombinant cell (e.g., the recombinant bacterium or yeast cell) contains a nucleic acid encoding a CYP97B protein (e.g., a CYP97B protein containing a sequence at least 80% identical to SEQ ID NO: 3.

In some embodiments, the CYP97C protein contains a sequence at least 80% identical to SEQ ID NO: 5. In some embodiments, the geranylgeranyl pyrophosphate synthase protein contains a sequence at least 80% identical to SEQ ID NO: 57. In some embodiments, the phytoene synthase protein comprises a sequence at least 80% identical to SEQ ID NO: 59. In some embodiments, the phytoene desaturase protein comprises a sequence at least 80% identical to SEQ ID NO: 39. In some embodiments, the lycopene β-cyclase protein contains a sequence at least 80% identical to SEQ ID NO: 45 or SEQ ID NO: 63. In some embodiments, the lycopene ε-cyclase protein comprises a sequence at least 80% identical to SEQ ID NO: 51.

In some embodiments, one or more (e.g., 2, 3, 4, 5, 6, 7, 8, 9, or 10) of the nucleic acid encoding a CYP97A protein or the nucleic acid encoding a CYP97B protein; the nucleic acid encoding a CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene β-cyclase protein; the nucleic acid encoding a lycopene ε-cyclase protein; the nucleic acid encoding a D-1-deoxyxylulose 5-phosphate synthase protein; and the nucleic acid encoding an isopentenyl pyrophosphate isomerase protein is integrated in a chromosome in the cell (e.g., the bacterium or the yeast cell).

In some embodiments, one or more (e.g., 2, 3, 4, 5, 6, 7, 8, 9, or 10) of the nucleic acid encoding a CYP97A protein or the nucleic acid encoding a CYP97B protein; the nucleic acid encoding a CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene β-cyclase protein; the nucleic acid encoding a lycopene ε-cyclase protein; the nucleic acid encoding a D-1-deoxyxylulose 5-phosphate synthase protein; and the nucleic acid encoding an isopentenyl pyrophosphate isomerase protein is operably expressed from an inducible promoter present within the chromosome. In some embodiments, the chromosome in the cell (e.g., the bacterium or yeast cell) further contains a selection marker.

In some embodiments, one or more of the nucleic acid encoding a CYP97A protein or the nucleic acid encoding a CYP97B protein; the nucleic acid encoding a CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene β-cyclase protein; the nucleic acid encoding a lycopene ε-cyclase protein, the nucleic acid encoding a D-1-deoxyxylulose 5-phosphate synthase protein; and the nucleic acid encoding an isopentenyl pyrophosphate isomerase protein is present within a vector. In some embodiments, the vector is a plasmid or an artificial chromosome. In some embodiments, the vector contains at least one inducible promoter. In some embodiments, the vector contains at least one selection marker.

Also provided are methods of producing lutein that include culturing any of the recombinant cells described herein (e.g., any of the recombinant bacterium or yeast cells described herein) under conditions that allow for the production of lutein. Some embodiments further include extracting the lutein from the cell (e.g., the bacterial cell or yeast cell). In some embodiments, the cell (e.g., the bacterium or yeast cell) is cultured in a liquid medium. Some embodiments further include isolating lutein from the liquid medium.

Also provided is lutein produced by any of the methods described herein. Also provided are pharmaceutical compositions, food supplements, food products, and cosmetic compositions containing lutein produced by any of the methods described herein.

Also provided are methods of generating a recombinant cell (e.g., a recombinant bacterium or yeast cell) that include introducing a nucleic acid encoding a CYP97A protein or a nucleic acid encoding a CYP97B protein; a nucleic acid encoding a CYP97C protein; a nucleic acid encoding a geranylgeranyl pyrophosphate synthase protein; a nucleic acid encoding a phytoene synthase protein; a nucleic acid encoding a phytoene desaturase protein; a nucleic acid encoding a lycopene β-cyclase protein; and a nucleic acid encoding a lycopene ε-cyclase protein. Some embodiments further include introducing a nucleic acid encoding a D-1-deoxyxylulose 5-phosphate synthase protein; and/or a nucleic acid encoding an isopentenyl pyrophosphate isomerase protein. In some embodiments, the introducing is performed by transformation.

By the term "CYP97A protein" is meant a CYP97A protein from *O. sativa*, a member of the CYP97A protein family, or a CYP97A protein derived from the CYP97A protein from *O. sativa* or a member of the CYP97A protein family, that has the ability to hydroxylate the β-ring of α-carotene. Non-limiting examples of CYP97A proteins are described herein. Additional examples of CYP97A proteins are known in the art.

By the term "nucleic acid encoding a CYP97A protein" can be any nucleic acid that contains a sequence that encodes a CYP97A protein. Non-limiting examples of nucleic acids encoding a CYP97A protein are described herein. Additional examples of nucleic acids encoding a CYP97A protein are known in the art.

By the term "CYP97B protein" is meant a CYP97B protein from *O. sativa*, a member of the CYP97B protein family, or a CYP97B protein derived from the CYP97B protein from *O. sativa or a member of the CYP97*B protein family, that has the ability to hydroxylate the β-ring of α-carotene. Non-limiting examples of CYP97B proteins are described herein. Additional examples of CYP97B proteins are known in the art.

By the term "nucleic acid encoding a CYP97B protein" can be any nucleic acid that contains a sequence that encodes a CYP97B protein. Non-limiting examples of nucleic acids encoding a CYP97B protein are described herein. Additional examples of nucleic acids encoding a CYP97B protein are known in the art.

By the term "CYP97C protein" is meant a CYP97C protein from *O. sativa*, a member of the CYP97C protein family, or a CYP97C protein derived from the CYP97C protein from *O. sativa* or a member of the CYP97C protein family, that has the ability to hydroxylate the ε-ring of α-carotene. Non-limiting examples of CYP97C proteins are described herein. Additional examples of CYP97C proteins are known in the art.

By the term "nucleic acid encoding a CYP97C protein" can be any nucleic acid that contains a sequence that encodes a CYP97C protein. Non-limiting examples of nucleic acids encoding a CYP97C protein are described herein. Additional examples of nucleic acids encoding a CYP97C protein are known in the art.

By the term "geranylgeranyl pyrophosphate synthase protein" is meant a geranylgeranyl pyrophosphate synthase protein from *E. herbicola*, a member of the geranylgeranyl pyrophosphate synthase protein family, or a geranylgeranyl pyrophosphate synthase protein derived from the geranylgeranyl pyrophosphate synthase protein from *E. herbicola* or a member of the geranylgeranyl pyrophosphate synthase protein family, that has the ability to produce geranylgeranyl pyrophosphate from farnesyl pyrophosphate (FPP) and isopentenyl pyrophosphate (IPP). Non-limiting examples of geranylgeranyl pyrophosphate synthase proteins are described herein. Additional examples of geranylgeranyl pyrophosphate synthase proteins are known in the art.

By the term "nucleic acid encoding a geranylgeranyl pyrophosphate synthase protein" can be any nucleic acid that contains a sequence that encodes a geranylgeranyl pyrophosphate synthase protein. Non-limiting examples of nucleic acids encoding a geranylgeranyl pyrophosphate synthase protein are described herein. Additional examples of nucleic acids encoding a geranylgeranyl pyrophosphate synthase protein are known in the art.

By the term "phytoene synthase protein" is meant a phytoene synthase protein from *E. herbicola*, a member of the phytoene synthase protein family, or a phytoene synthase protein derived from the phytoene synthase protein from *E. herbicola* or a member of the phytoene synthase protein family, that has the ability to convert geranylgeranyl pyrophosphate to phytoene. Non-limiting examples of phytoene synthase proteins are described herein. Additional examples of phytoene synthase proteins are known in the art.

By the term "nucleic acid encoding a phytoene synthase protein" can be any nucleic acid that contains a sequence that encodes a phytoene synthase protein. Non-limiting examples of nucleic acids encoding a phytoene synthase protein are described herein. Additional examples of nucleic acids encoding a phytoene synthase protein are known in the art.

By the term "phytoene desaturase protein" is meant a phytoene synthase protein from *E. herbicola*, a member of the phytoene desaturase protein family, or a phytoene desaturase protein derived from the phytoene desaturase protein from *E. herbicola* or a member of the phytoene desaturase protein family, that has the ability to convert phytoene to lycopene. Non-limiting examples of phytoene desaturase proteins are described herein. Additional examples of phytoene desaturase proteins are known in the art.

By the term "nucleic acid encoding a phytoene desaturase protein" can be any nucleic acid that contains a sequence that encodes a phytoene desaturase protein. Non-limiting examples of nucleic acids encoding a phytoene desaturase protein are described herein. Additional examples of nucleic acids encoding a phytoene desaturase protein are known in the art.

By the term "lycopene β-cyclase protein" is meant a lycopene β-cyclase protein from *A. thaliana*, a member of the lycopene β-cyclase protein family, or a lycopene β-cyclase protein derived from the lycopene β-cyclase protein from *A. thaliana* or a member of the lycopene β-cyclase protein family, that has the ability to convert lycopene to β-carotene. Non-limiting examples of lycopene β-cyclase proteins are described herein. Additional examples of lycopene β-cyclase proteins are known in the art.

By the term "nucleic acid encoding a lycopene β-cyclase protein" can be any nucleic acid that contains a sequence that encodes a lycopene β-cyclase protein. Non-limiting examples of nucleic acids encoding a lycopene β-cyclase protein are described herein. Additional examples of nucleic acids encoding a lycopene β-cyclase protein are known in the art.

By the term "lycopene ε-cyclase protein" is meant a lycopene ε-cyclase protein from *A. thaliana*, a member of the lycopene ε-cyclase protein family, or a lycopene ε-cyclase protein derived from the lycopene ε-cyclase protein from *A. thaliana* or a member of the lycopene ε-cyclase protein family, that has the ability to convert lycopene to α-carotene (in combination with a lycopene β-cyclase protein). Non-limiting examples of lycopene ε-cyclase proteins are described herein. Additional examples of lycopene ε-cyclase proteins are known in the art.

By the term "nucleic acid encoding a lycopene ε-cyclase protein" can be any nucleic acid that contains a sequence that encodes a lycopene ε-cyclase protein. Non-limiting examples of nucleic acids encoding a lycopene ε-cyclase protein are described herein. Additional examples of nucleic acids encoding a lycopene ε-cyclase protein are known in the art.

By the term "D-1-deoxyxylulose 5-phosphate synthase protein" is meant a D-1-deoxyxylulose 5-phosphate synthase protein from *E. coli*, a member of the D-1-deoxyxylulose 5-phosphate synthase protein family, or a D-1-deoxyxylulose 5-phosphate synthase protein derived from the D-1-deoxyxylulose 5-phosphate synthase protein from *E coli* or a member of the D-1-deoxyxylulose 5-phosphate synthase protein family, that has the ability to produce D-1-deoxyxylulose 5-phosphate from pyruvate and glyceraldehyde 3-phosphate. Non-limiting examples of D-1-deoxyxylulose 5-phosphate synthase proteins are described herein. Additional examples of D-1-deoxyxylulose 5-phosphate synthase proteins are known in the art.

By the term "nucleic acid encoding a D-1-deoxyxylulose 5-phosphate synthase protein" can be any nucleic acid that contains a sequence that encodes a D-1-deoxyxylulose 5-phosphate synthase protein. Non-limiting examples of nucleic acids encoding a D-1-deoxyxylulose 5-phosphate synthase protein are described herein. Additional examples of nucleic acids encoding a D-1-deoxyxylulose 5-phosphate synthase protein are known in the art.

By the term "isopentenyl pyrophosphate isomerase protein" is meant an isopentenyl pyrophosphate isomerase protein from *E. coli*, a member of the isopentenyl pyrophosphate isomerase protein family, or an isopentenyl pyrophosphate isomerase protein derived from the isopentenyl pyrophosphate isomerase protein from *E. coli* or a member of the isopentenyl pyrophosphate isomerase protein family, that has the ability to convert isopentenyl pyrophosphate to dimethylallyl diphosphate. Non-limiting examples of isopentenyl pyrophosphate isomerase proteins are described herein. Additional examples of isopentenyl pyrophosphate isomerase proteins are known in the art.

By the term "nucleic acid encoding an isopentenyl pyrophosphate isomerase protein" can be any nucleic acid that contains a sequence that encodes an isopentenyl pyrophosphate isomerase protein. Non-limiting examples of nucleic acids encoding an isopentenyl pyrophosphate isomerase protein are described herein. Additional examples of nucleic acids encoding an isopentenyl pyrophosphate isomerase protein are known in the art.

By the term "lutein" is meant a molecule of the structure:

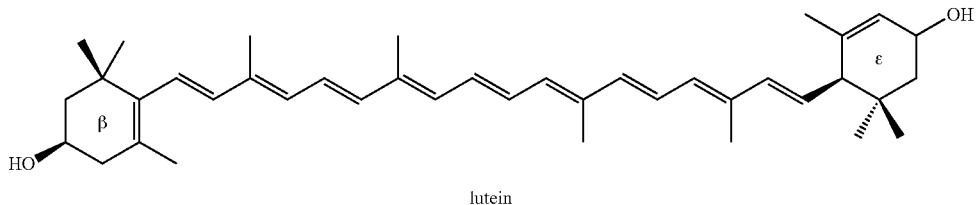

lutein

Lutein has three chiral centers and therefore, 8 sterioisomers. The principal natural stereoisomer of lutein is (3R,3'R,6'R)-β,ε-carotene-3,3'-diol. However, as used herein, the term "lutein" includes (3R,3'R,6'R)-β,ε-carotene-3,3'-diol and the other seven sterioisomers of lutein (e.g., (3S,3'S,6'S)-β,ε-carotene-3,3'-diol; (3R,3'S,6'S)-β,ε-carotene-3,3'-diol; (3S,3'R,6'S)-ε,ε-carotene-3,3'-diol; (3S,3'S,6'R)-β,ε-carotene-3,3'-diol; (3R,3'R,6'S)-β,ε-carotene-3,3'-diol; and (3R,3'S,6'R)-β,ε-carotene-3,3'-diol.

By the term "bacterium" or "bacteria" is meant any bacterial cell or cells from any species that is/are capable of expressing one or more nucleic acids (e.g., one or more (e.g., 2, 3, 4, 5, 6, 7, or 8) of a nucleic acid encoding a CYP97A protein, a nucleic acid encoding a CYP97C protein, a nucleic acid encoding a geranylgeranyl pyrophosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene β-cyclase protein) that encode one or more heterologous proteins (e.g., one or more (e.g., 2, 3, 4, 5, 6, 7, or 8) of a CYP97A protein, a CYP97B protein, a CYP97C protein, a geranylgeranyl pyrophosphate synthase protein, a phytoene synthase protein, a phytoene desaturase protein, a lycopene β-cyclase protein, and a lycopene ε-cyclase protein). Non-limiting examples of bacteria are described herein. Additional examples of bacteria are known in the art.

By the term "recombinant cell" or "recombinant cells" is meant a cell (e.g., eukaryotic or prokaryotic cells, e.g., bacteria, yeast cells, mammalian cells, and insect cells) that contains/contain one or more nucleic acids (e.g., one or more (e.g., one or more (e.g., 2, 3, 4, 5, 6, 7, or 8) of a nucleic acid encoding a CYP97A protein, a nucleic acid encoding a CYP97C protein, a nucleic acid encoding a geranylgeranyl pyrophosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene ε-cyclase protein) that encode one or more heterologous proteins (e.g., one or more (e.g., 2, 3, 4, 5, 6, 7, or 8) of a CYP97A protein, a CYP97B protein, a CYP97C protein, a geranylgeranyl pyrophosphate synthase protein, a phytoene synthase protein, a phytoene desaturase protein, a lycopene β-cyclase protein, and a lycopene ε-cyclase protein). Various embodiments of recombinant cells are described herein. Methods of generating recombinant cells are described herein. Additional methods for generating recombinant cells are known in the art.

By the term "recombinant bacterium" or "recombinant bacteria" is meant a bacterial cell or cells that contains/contain one or more nucleic acids (e.g., one or more (e.g., one or more (e.g., 2, 3, 4, 5, 6, 7, or 8) of a nucleic acid encoding a CYP97A protein, a nucleic acid encoding a CYP97C protein, a nucleic acid encoding a geranylgeranyl pyrophosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene ε-cyclase protein) that encode one or more heterologous proteins (e.g., one or more (e.g., 2, 3, 4, 5, 6, 7, or 8) of a CYP97A protein, a CYP97B protein, a CYP97C protein, a geranylgeranyl pyrophosphate synthase protein, a phytoene synthase protein, a phytoene desaturase protein, a lycopene β-cyclase protein, and a lycopene ε-cyclase protein). Various embodiments of recombinant bacteria are described herein. Methods of generating recombinant bacteria are described herein. Additional methods for generating recombinant bacteria are known in the art.

By the term "yeast cell" or "yeast cells" is meant any yeast cell or cells from any species that is/are capable of expressing one or more nucleic acids (e.g., one or more (e.g., 2, 3, 4, 5, 6, 7, or 8) of a nucleic acid encoding a CYP97A protein, a nucleic acid encoding a CYP97C protein, a nucleic acid encoding a geranylgeranyl pyrophosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene ε-cyclase protein) that encode one or more heterologous proteins (e.g., one or more (e.g., 2, 3, 4, 5, 6, 7, or 8) of a CYP97A protein, a CYP97B protein, a CYP97C protein, a geranylgeranyl pyrophosphate synthase protein, a phytoene synthase protein, a phytoene desaturase protein, a lycopene β-cyclase protein, and a lycopene ε-cyclase protein). Non-limiting examples of yeast cells are described herein. Additional examples of yeast cells are known in the art.

By the term "recombinant yeast cell" is meant a yeast cell that contains one or more nucleic acids (e.g., one or more (e.g., one or more (e.g., 2, 3, 4, 5, 6, 7, or 8) of a nucleic acid encoding a CYP97A protein, a nucleic acid encoding a CYP97C protein, a nucleic acid encoding a geranylgeranyl pyrophosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene ε-cyclase protein) that encode one or more heterologous proteins (e.g., one or more (e.g., 2, 3, 4, 5, 6, 7, or 8) of a CYP97A protein, a CYP97B protein, a CYP97C protein, a geranylgeranyl pyrophosphate synthase protein, a phytoene synthase protein, a phytoene desaturase protein, a lycopene β-cyclase protein, and a lycopene ε-cyclase protein). Various embodiments of recombinant yeast cells are described herein. Methods of generating recombinant yeast cells are described herein. Additional methods for generating recombinant yeast cells are known in the art.

By the term "inducible promoter" or "inducible promoter sequence" is meant a nucleic acid sequence that is located proximal (e.g., downstream) of a nucleic acid sequence encoding a polypeptide that is capable of modulating (e.g., increasing or decreasing) the expression of the polypeptide within a cell (e.g., a bacterium or a yeast cell) upon exposure to an inducing agent (e.g., a small molecule) or a change in physical conditions (e.g., temperature). An inducible promoter can be located within a vector (e.g., a plasmid or an artificial chromosome) or can be integrated in a chromosome (e.g., a bacterial chromosome or a yeast chromosome). Non-limiting examples of inducible promoters are described herein.

Additional examples of inducible promoters are known in the art.

By the term "selection marker" is meant a nucleic acid sequence that encodes a polypeptide that is capable of conferring protection against cell death or inducing cell death in a cell containing the nucleic acid (e.g., a bacterium or yeast cell), that is exposed to a selective agent (e.g., an antibiotic).

By the term "yeast artificial chromosome" is meant a DNA construct that can be genetically modified to contain a heterologous DNA sequence (e.g., a DNA sequence as large as 3000 kb), that contains telomeric, centromeric, and origin of replication (replication origin) sequences.

By the term "bacterial artificial chromosome" is a DNA construct that can be genetically modified to contain a heterologous DNA sequence (e.g., a DNA sequence as large as 300 kb), that contains an origin of replication sequence (Ori), and may contain one or more helicases (e.g., parA, parB, and parC).

By the term "vector" is meant any nucleic acid construct that can be utilized to deliver one or more nucleic acids to a target cell (e.g., a bacterium or yeast cell). Non-limiting examples of vectors include plasmids (e.g., yeast integrating plasmids and yeast episomal plasmids), cosmids, bacterial artificial chromosomes, and yeast artificial chromosomes. Additional examples of plasmids that can be used in the present methods are described in Wang et al., *Crit. Rev. Biotechnol.* 17:227-272, 1997.

By the term "pharmaceutical composition" is meant a composition that is administered to a subject for the treatment (e.g., prophylactic treatment) of a subject that has a disorder or a subject that has an increased risk of developing a disorder.

By the term "food supplement" is meant a composition that is taken by a subject (e.g., taken orally) that is meant to improve a subject's nutrition. In some embodiments, a food supplement can contain lutein produced using the methods described herein.

By the term "food product" is meant any composition that can be orally consumed by a subject (e.g., a solid or liquid). In some embodiments, a food product can be supplemented or fortified with lutein produced using the methods described herein.

By the term "cosmetic composition" is meant a composition that is applied to the skin, hair, or nails of a subject. In some embodiments, a cosmetic composition can contain lutein produced using the methods described herein. In some embodiments, a cosmetic composition can also contain one or more additional moisturizers, fragrances, sunscreen, pigments, or lubricants.

Other definitions appear in context throughout this disclosure. Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 3 is comparison of the conserved P450 domain in the three clans of the CYP97 family showing three sequence blocks that distinguish members of Clan B (CYP97B proteins) from those in Clans A (CYP97A proteins) and Clan C (CYP97C proteins).

FIG. 4 is a comparison of the conserved oxygen and heme-binding motifs for CYP97A and CYP97C enzymes of rice compared with those of other plant species.

FIG. 5 is a multiple sequence alignment showing the comparison of CYP97A protein sequences from a variety of species (SEQ ID NOS: 1, 7, 9, and 11).

FIG. 6 is a multiple sequence alignment showing the comparison of CYP97B protein sequences from a variety of species (SEQ ID NOS: 3, 13, 15, and 17).

FIGS. 7A and 7B is a multiple sequence alignment showing the comparison of CYP97C protein sequences from a variety of species (SEQ ID NOS: 5, 19, 21, and 23).

FIG. 8 is a multiple sequence alignment showing the conservation of geranyl pyrophosphate synthase (CrtE) from *A. thaliana, O. sativa*, and *C. roseus* (SEQ ID NOS: 25, 27, and 29).

FIG. 9 is a multiple sequence alignment showing the conservation of phytoene synthase (CrtB) from *A. thaliana, O. sativa*, and *P. trichocarpa* (SEQ ID NOS: 31, 33, and 35).

FIG. 10 is a multiple sequence alignment showing the conservation of phytoene desaturase (CrtI) from *A. thaliana, O. sativa*, and *P. trichocarpa* (SEQ ID NOS: 37, 39, and 41).

FIG. 11 is a multiple sequence alignment showing the conservation of lycopene β-cyclase (CrtY) from *A. thaliana, O. sativa*, and *N. tabacum* (SEQ ID NOS: 45, 47, and 49).

FIG. 12 is a multiple sequence alignment showing the conservation of lycopene β-cyclase from *A. thaliana, O. sativa, B. napus*, and *C. moschata* (SEQ ID NO: 45, 47, 65, and 66).

FIG. 13 is a multiple sequence alignment showing the conservation of lycopene ε-cyclase from *A. thaliana, B. napus*, and *L. sativa* (SEQ ID NO: 51, 53, and 55).

FIG. 20 is a multiple sequence alignment showing the comparison of D-1-deoxyxylulose 5-phosphate synthase protein sequences from two exemplary species (SEQ ID NOS: 95 and 97).

FIG. 21 is a multiple sequence alignment showing the comparison of isopentenyl pyrophosphate isomerase protein sequences from two exemplary species (SEQ ID NOS: 99 and 101).

DETAILED DESCRIPTION OF THE INVENTION

Figure 1:
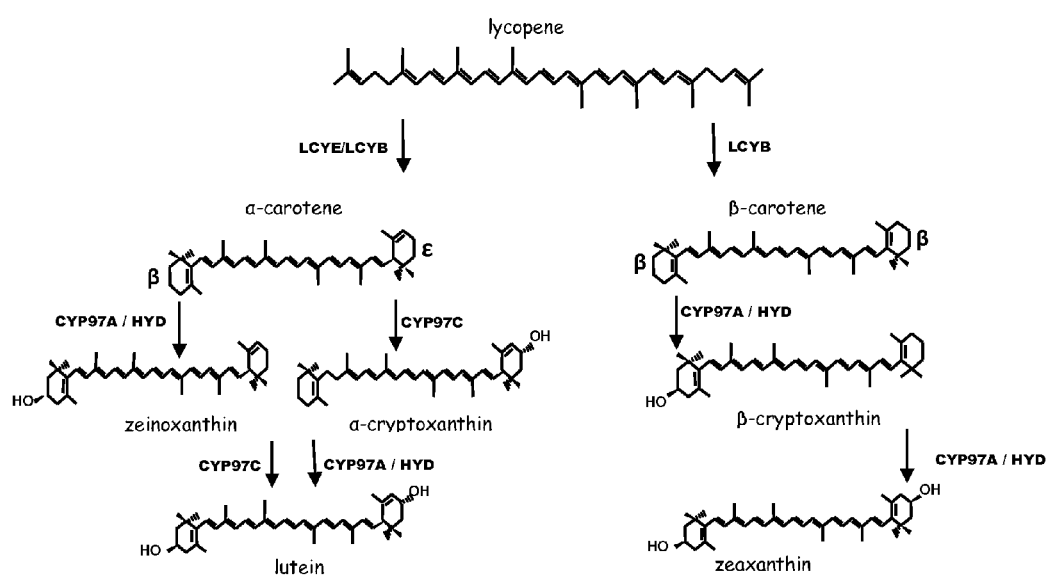
FIG. 1 is schematic showing the biosynthetic pathways that transform lycopene into lutein and zeaxanthin.

The invention is based, in part, on the discovery that the co-expression of a CYP97A protein and a CYP97C protein in a bacterium that is capable of producing α-carotene, is capable of producing a significantly increased amount of lutein, and the discovery that CYP97A and CYP97C proteins interact within a plant cell.

In view of these discoveries, provided herein are recombinant bacteria and yeast cells that are capable of producing a significantly increased amount of lutein, methods of making lutein that include culturing these recombinant bacteria or yeast cells, and methods of making these recombinant bacteria and yeast cells. Also provided is lutein produced by the methods described herein, and pharmaceutical compositions, food supplements, food products, and cosmetic compositions that contain lutein produced by the methods described herein.

Various embodiments of these recombinant bacteria and yeast cells, and methods are described herein.

Lutein

Lutein has the structure of:

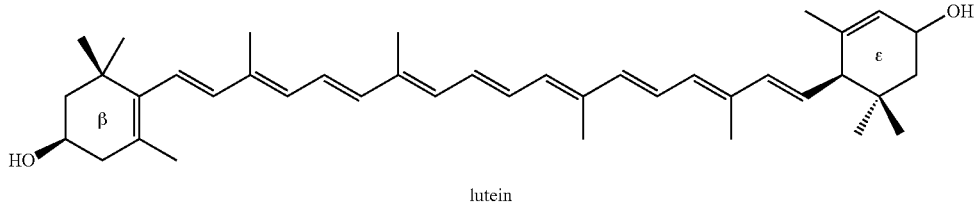

lutein

Lutein has three chiral centers and therefore, 8 sterioisomers. The principal natural stereoisomer of lutein is (3R, 3'R,6'R)-β,ε-carotene-3,3'-diol. The other seven sterioisomers of lutein are: (3S,3'S,6'S)-β,ε-carotene-3,3'-diol; (3R, 3'S,6'S)-β,ε-carotene-3,3'-diol; (3S,3'R,6'S)-β,ε-carotene-3, 3'-diol; (3S,3'S,6'R)-β,ε-carotene-3,3'-diol; (3R,3'R,6'S)-β, ε-carotene-3,3'-diol; and (3R,3'S,6'R)-β,ε-carotene-3,3'-diol.

The lutein produced by the methods described herein can further be modified. For example, the lutein produced by the methods described herein can be chemically- or enzymatically modified in vitro, or be further modified in the cell (e.g., a bacterial, yeast, mammalian, or insect cell) by one or more additional enzymes.

CYP97A

Non-limiting examples of CYP97A proteins are described herein (see, FIGS. 2-5). Additional examples of CYP97A proteins are known in the art. Methods for determining the ability of a CYP97A protein to hydroxylate the β-ring of α-carotene are described herein. Additional methods for determining the ability of CYP97A protein to hydroxylate the β-ring of α-carotene are known in the art.

Wild type CYP97A proteins are known to share a number of conserved residues, including for example, the conserved amino acid residues shown in FIG. 3 (see, Clan A), and the conserved amino acid residues present in the oxygen-binding motif and the heme-binding motif (see, FIG. 4). The conserved heme-binding motif corresponds to amino acids 534 to 543 (FGGGPRKCVG) in CYP97A4 from *O. sativa* (SEQ ID NO: 1). The conserved oxygen-binding motif in wild type CYP97A proteins has a consensus sequence of AGHETS, and the conserved heme-binding motif in wild type CYP97A proteins has a consensus sequence of FGGGPRKCV/IG (see, FIG. 4). Wild type CYP97A proteins are also conserved at a number of other residues (see, for example, the aligned wild type CYP97A sequences in FIG. 5).

In some embodiments, a CYP97A protein can contain one or more (e.g., two, three, four, five, six, seven, eight, nine, or ten) additions, insertions, substitution, or deletions as compared to a corresponding wild type CYP97A protein. For example, a CYP97A protein can contain one or more substitutions at amino acid positions that are not present within the conserved heme-binding motif or within the oxygen-binding motif, or at amino acid positions that are not conserved among wild type CYP97A proteins (see, e.g., the amino acid positions that are not conserved in FIG. 5). A CYP97A protein can be at least 80% identical (e.g., at least 85%, 90%, 95%, or 100%) identical to a wild type CYP97A protein (e.g., SEQ NO: 1, 7, 9, and 11).

a mathematical algorithm. The percent identity between two amino acid sequences is determined using the Needleman and Wunsch ((1970) J. Mol. Biol. 48:444-453) algorithm, which has been incorporated into the GAP program in the GCG software package (available at the GCG website), using either a Blossum 62 matrix or a PAM250 matrix, and a gap weight of 16 and a length weight of 1. The percent CYP97A4 protein O. sativa (SEQ ID NO: 1)

```
MSSATSVSAFAMAATSSAAAAAPPPCRLLGSGQAHL
RLPPSAAAAAASARRRLLLRCAASGGNGKGGGDGS
GSDPVLEERRRRQAELAARIASGEFTAQGPAWIAP
LAVGLAKLGPPGELAAALLTKVAGGGGPEIPQAVGS
MSAVTGQAFFIPLYDLFLTYGGIFRLNFGPKSFLIV
SDPAIAKHILRDNSKAYSKGILAEILEFVMGTGLIP
ADGEIWRVRRRAIVPAMHQKYVTAMISLFGYASDRL
CQKLDKAATDGEDVEMESLFSRLTLDVIGKAVFNYD
FDSLSYDNGIVEAVYVTLREAEMRSTSPIPTWEIPI
WKDISPRQKKVNEALALINKTLDELIDICKRLVEEE
DLQFHEEYMNEQDPITLHFLLASGDDVSSKQLRDDL
MTMLIAGHETSAAVLTWTFYLLSKYPNVMAKLQDEA
DTVLGDRLPTIEDVKKLKYTTRVINESLRLYPQPPV
LIRRSIEEDMLGGYPIGRGEDIFISVWNLHHCPKHW
DGADVFNPERWPLDGPNPNETNQNFSYLPFGGGPRK
CVGDMFATFETVVATAMLVRRFDFQMAPGAPPVEMT
TGATIHTTEGLKMTVTRRTKPPVIPNLEMKVISDSP
ENMSTTTSMPVSAASIASGEDQQGQVSATRI
```

CYP97A3 protein A. thaliana (SEQ ID NO: 7)

```
  1 mamafplsyt ptitvkpvty srrsnfvvfs sssngrdple ensvpngvks leklqeekrr
 61 aelsariasg aftvrkssfp stvknglski gipsnvldfm fdwtgsdqdy pkvpeakgsi
121 qavrneaffi plyelfltyg gifrltfgpk sflivsdpsi akhilkdnak ayskgilaei
181 ldfvmgkgli padgeiwrrr rraivpalhq kyvaamislf geasdrlcqk ldaaalkgee
241 vemeslfsrl tldiigkavf nydfdsltnd tgvieavytv lreaedrsvs pipvwdipiw
301 kdisprqrkv atslklindt lddliatckr mveeeelqfh eeymnerdps ilhfllasgd
361 dvsskqlrdd lmtmliaghe tsaavltwtf yllttepsvv aklqeevdsv igdrfptiqd
421 mkklkyttrv mneslrlypq ppvlirrsid ndilgeypik rgedifisvw nlhrsplhwd
481 daekfnperw pldgpnpnet nqnfsylpfg ggprkcigdm fasfenvvai amlirrfnfq
541 iapgappvkm ttgatihtte glkltvtkrt kpldipsvpi lpmdtsrdev ssals
```

TC101515 M. truncatula (SEQ ID NO: 9)

```
FLKRKDELNCLLKLPQVNSRVKQESGLPSILKKSLSNLGVSNEILEFLFGLYPKIPEAKG
SISAIRSEAFFIPLYELYITYGGIFRLNFGPKSFLIVSDPAIAKHILKDNSKAYSKGILA
EILDFVMGKGLIPADGEIWRVRRRTIVPALHLKFVAAMIGLFGQATDRLCQKLDTAASDG
EDVEMESLFSRLTLDVIGKAVFNYDFDSLSNDTGIIEAVYTVLREAEDRSISPIPVWDLP
IWKDISPRQRKVTAALKLVNDTLNNLIAICKRMVDEEELQPHEEYMNEQDPSISFTFLLA
SGDDVTSKQLRDDLMTMLIAGHETSAAVLTWTFYLLSKEPSVMSKLQEEVDSVLGDRFPT
IEDMKKLKYTTRVINESLRLYPQPPVLIRRSIEDDVLGEYPIKRGEDIFISVWNLHRSPT
LWNDADKFEPERWPLDGPNPNETNQGFKYLPFGGGPRKCIGDMFASYEVVVALAMLVRRF
NFQMAVGAPPVVMTTGATIHTTQGLNMTVTRRIKPPIVPSLQMSTLEVDPSVSISDKTEE
IGQKDQVYQAQ
```

TC76166 H. vulgare (SEQ ID NO: 11)

```
MGTGLIPADGEVWRVRRRAIVPALHQKYVTAMIGLFGNASDRLCQKLDKAASDGEDVEMESLFSRLTL
DVIGKAVFNYDFDSLSYDNGIVEAVYVTLREAEMRSTSPIPTWEIPIWKDISPRQRKVNEALALINNI
LDELIATCKRMVDEEDLQFHEEYMNEKDPSILHFLLASGDDVSSKQLRDDLMTMLIAGHETSAAVLTW
TFYLLSKYPNVMSKLQAEADAVLGDGLPTIDDVKKLKYTTRVINESLRLYPQPPVLIRRSLEDDMLGE
YPIGKGEDIFISIWNLHRCPKHWDDADVFNPERWPLDGPNPNETNQKFSYLPFGGGPRKCVGDMFATF
ETVVATAMLVKRFDFQMAPGAPPVEMTTGATIHTTKGLNMTVTRRIKPPVIPNLEMKIVSDPEGSTSS
TASVAVSTASIASGEGQQVEVSTSQV
```

In some embodiments, a nucleic acid encoding a CYP97A protein can be any nucleic acid containing a nucleic acid sequence that is at least 80% (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type CYP97A protein (e.g., SEQ ID NO: 2, 8, 10, and 12). In some embodiments, the CYP97A protein contains the sequence of a wild type CYP97A protein (e.g., a protein containing the sequence of SEQ ID NO: 1, 7, 9, or 11).

The comparison of sequences and determination of percent identity between two sequences is accomplished using identity between two nucleotide sequences is determined using the GAP program in the GCG software package (available at GCG website), using a NWSgapdna.CMP matrix and a gap weight of 40 and a length weight of 1.

In general, percent identity between amino acid sequences referred to herein is determined using the BLAST 2.0 program, which is available to the public at NCBI website. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., *Nucleic Acids Res.* 25:3389-3402, 1997.

Figure 2:
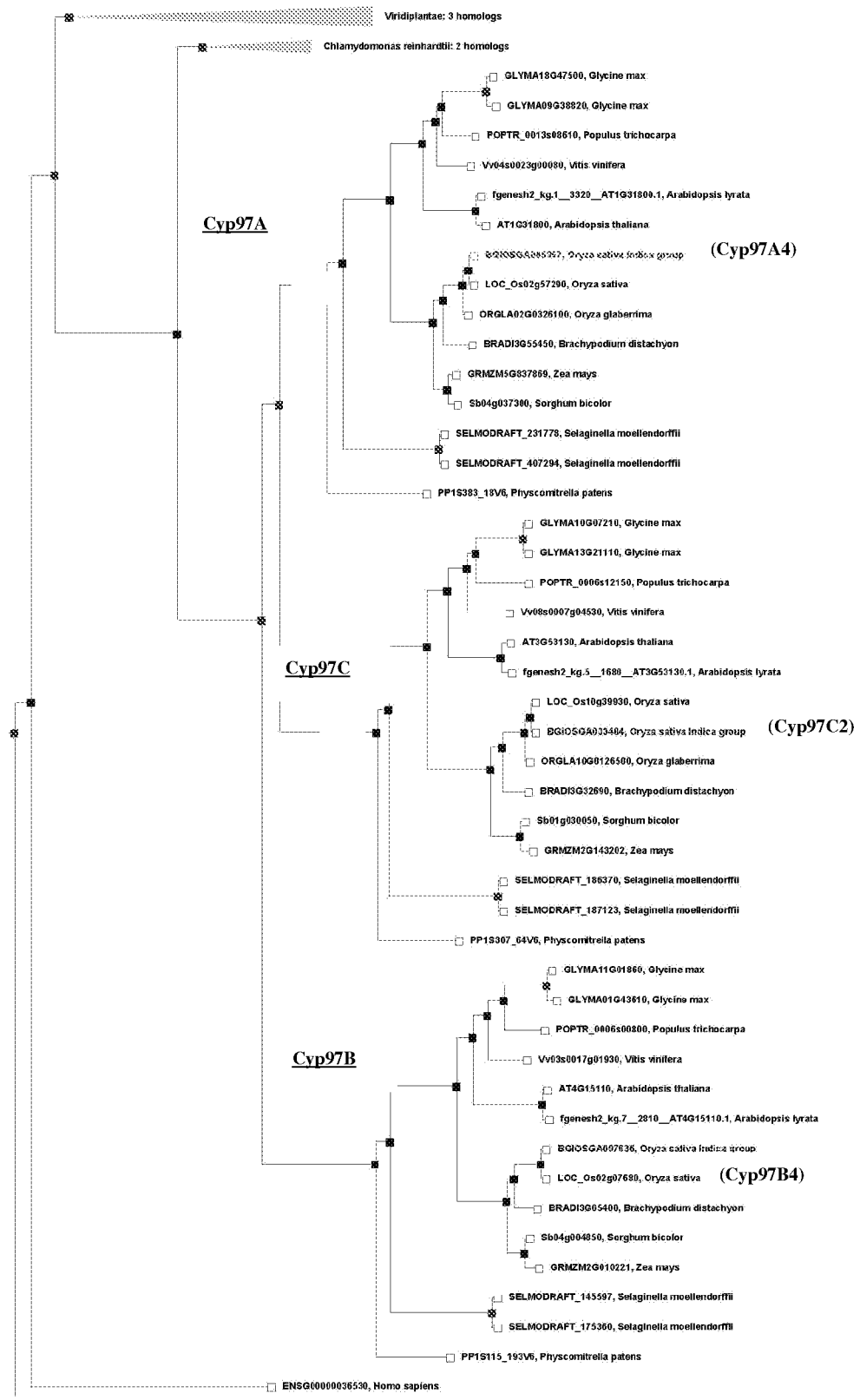
FIG. 2 is a phylogenetic tree showing evolutionary relatedness of CYP97A, CYP97B, and CYP97C genes from various plant species. The plant genomic sequences indicated can be found at the Gramene website. The genomic sequences of CYP97A4, CYP97C2, and CYP97B4 are indicated.
Figure 14:
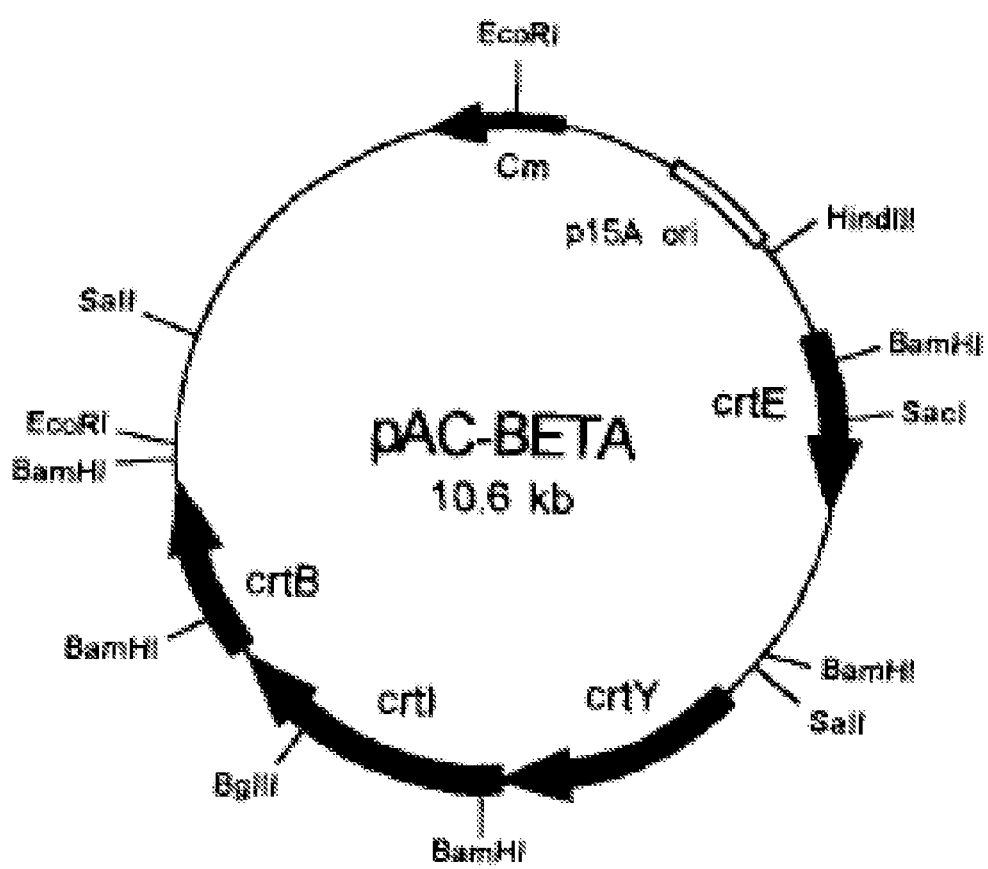
FIG. 14 is a map of the pAC-BETA-At plasmid ("pAC-BETA") showing the location of the p15A origin of replication sequence (ori); the *E. herbicola* geranylgeranyl pyrophosphatase synthase (CrtE), *E. herbicola* phytoene synthase (CrtB), *E. herbicola* phytoene desaturase (CrtI), and *E. herbicola* lycopene β-cyclase (CrtY), the chloramphenicol resistance gene (Cm) from T9, and various restriction endonuclease recognition sites.

Non-limiting examples of nucleic acid sequences that encode a wild type CYP97A protein are shown in FIG. 2 (the CYP97A sequences shown are publicly available on the Gramene website and/or the NCBI website). In some embodiments, the nucleic encodes that encodes a CYP97A protein that is at least 80% identical (e.g., 80%, 85%, 90%, 95%, or 100% identical) to SEQ ID NOS: 1, 7, 9, or 11. In some embodiments, the nucleic acid contains a sequence that is at least 80% identical (e.g., at least 85%, 90%, 95%, or 100%) identical to any one of SEQ NO: 2, 8, 10, and 12.

```
CYP97A4 nucleic acid O. sativa
                                                                        (SEQ ID NO: 2)
atgagctcagcgacgtcagtgagtgcctttgccatggcggctacctcctctgcggccgccgctgctccacctccgtgccgcttactc
ggctccggtcaggcacacctgcgccttcctccttctgctgctgctgctgcttcagctcgtcgccgctgctcctccgctgcgccg
cctcgggcggcaacgggaaaggcggtggtggcgacggctccggctccgaccggttcttgaggagcggcggcggcggcgcca
ggctgagctggcggcgcgcattgcgtccggcgagttcaccgccaaggcccgcgtggattgctcccctcgcggtggggcttgcc
aagctcggccaccggggagctcgccgccgcgctgctcaccaaggtcgccggtggcggcggaccggagataccgcaggcgg
tggggtctatgagtgcggtgacagggcaggctttcttcatcccgctctatgatctcttccttacctatggcggcatctttcgcctcaatttc
ggccctaagtcttcctcattgtctctgatccagctatagctaagcacatcctgagggacaactccaaggcttattccaagggtattctggc
agaaattttagagtttgtgatgggtacgggtttgatccctgctgatggggagatttggcgtgttaggaggcgcgccattgtaccagcaatg
caccagaagtacgttaccgcaatgataagtctcttcggatatgcttcagatcggctctgccagaagttggacaaggcagcaacggatgg
ggaggatgtggagatgaatctttgttctctcgactaacactggatgtcattgggaaggcagtcttcaattatgatttcgactcattgtcttac
gataatggaatagttgaggcagtgtatgtgacactgcgagaagcagaaatgcggagcacttctcctataccaacttgggaaataccata
tggaaagatatttccccgcgggcagaagaaggtcaatgaagcctcttcgcctgataaataagacttcttgatgaactaattgacatctgcaaga
gattggtcgaggaagaagatctgcagtttcatgaagaatacatgaatgagcaagacccccattaccctccacttttcttttggcatctggagat
gatgtctccagcaagcaactccgtgatgatctgatgacaatgctcattgctggccatgagacctctgcagcagtcttgacatggacatttta
tcttctatctaagtatccaaatgtaatggccaaactccaagatgaggctgatactgttctaggtgaccgtttaccaacaattgaggatgtgaag
aaattgaagtatactactagagtaattaacgaatcattgagactctatccacagccaccagttttaattcgtcgctctattgaggaggatatgct
gggagggtacccaattggccggggagaagacattttcatatccgtgtggaacctacatcattgcccaaagcattgggatggtgcagatgtt
tttaatccagaaagatggcctttggatggaccaaatccaaatgaaacaaaccaaaatttcagttacttgccatttggtggcggaccaaggaa
atgtgtaggtgacatgtttgccacttttcgagactgtggtggcaactgcaatgcttgtcaggcgctttgattttcaaatggctccaggagctcct
ccggttgagatgacaactggagcaacgattcacacaactgagggggttgaaaatgactgttactcggaggacaaagccacctgtaatccca
aacctagagatgaaagtcatttctgattcaccagaaaacatgagtactactacatcaatgcccgtttctgctgctagtattgcttcaggagaag
atcaacaagggcaagtctcagcaactcgaatctga CYP97A3 nucleic acid A. thaliana
                                                                        (SEQ ID NO: 8)
   1 gctctgtgat ttgagttttt attttgcggt ggcgttgtat ggctatggcc tttcctcttt
  61 cttatactcc gacgattact gttaaaccag taacgtactc tcggagatcg aactttgtag
 121 ttttctcgtc gagttctaat ggacgagatc ctttagagga gaattcagta cctaatggtg
 181 tgaaaagctt ggagaagctt caagaagaga agcgtcgtgc tgagttatct gctaggattg
 241 cttctggagc tttcactgta cggaaatcta gttttccatc tacagtgaag aatggtttat
 301 ctaagattgg aataccaagc aatgttcttg atttcatgtt tgattggact ggttctgacc
 361 aagactaccc caaggttcct gaggctaaag gctcgattca ggcggtccgg aacgaagctt
 421 tcttcatccc tttgtatgag cttttcctta cttatggtgg aattttcagg ttgacctttg
 481 ggcctaagtc attcttgatc gtgtcggatc cttctattgc taaacatata ttgaaggaca
 541 atgcaaaagc ttactccaag gggattttag ctgaaattct agatttttgt atgggaaaag
 601 gactcattcc tgctgatggg gagatatggc gtagacgaag gcgtgccatt gttcctgcat
 661 tgcatcaaaa gtatgtagca gctatgatta gtttattcgg agaagcttca gataggcttt
 721 gtcagaagct tgatgctgct gcattgaaag gggaagaagt agagatgaaa tcactcttct
 781 ctcgtttgac acttgatatt attggcaagg cggtttcaa ttacgacttt gactccctta
 841 ctaatgatac cggtgtgatc gaggcagtgt acactgttct aagagaagct gaagacagaa
 901 gtgtttcacc tattcctgtt tgggacatac ccatttggaa agatatttcc ccacgtcaga
 961 ggaaagttgc tacttccttg aaattaatca atgacacact tgatgatttg attgcaacat
1021 gcaagagaat ggtagaagaa gaggagttgc agtttcacga ggagtatatg aacgaaagag
1081 atcctagcat ccttcacttt cttttagctt caggagatga tgtctctagt aagcagcttc
1141 gtgatgactt gatgacaatg cttatagccg gacatgaaac atcggcggca gtattaacat
1201 ggacctttta cctttaaca acggaaccaa gtgtagttgc caaacttcaa gaagaggttg
1261 attctgtaat tggagataga ttcccaacca tacaagatat gaaaaagctg aaatacacta
1321 ctcgagtcat gaatgagtca ttgagattat atccacaacc accagtactg atccgtcgtt
1381 ctatagataa tgatatactt ggagagtatc cgataaaaag gggagaggat atcttcatct
1441 cggtttggaa tctacatcga agtcctctgc attgggatga tgcagagaag ttcaatcccg
1501 agagatggcc tttggatgga ccaaacccaa atgagacaaa ccaaaacttc agttacttac
1561 ctttcggtgg aggaccgcgg aaatgtatag gcgacatgtt tgcttccttt gagaatgtgg
1621 tagcaatcgc aatgctttatt cgaagattta actttcagg tgcaccagga gctcctccgg
1681 tgaaaatgac tacaggagct acaatacaca ccacagaagg attgaaattg acagtaacaa
1741 agaggacaaa acctctggac ataccatccg taccgatact tccaatggat acttcacggg
1801 atgaagtttc atctgctctt tcttaagtct tcatctttac aaaactgaaa acaaacaagc
1861 tcagatgaag aagcaaaaat cttgtgttag aacagcaaat gttgaattgt tggaacatga
1921 ccaatgcttt ctgattattt atctgcactg taaaatgcag acaagtaaaa tgagaagatt
1981 tattattctt tggaaaaaaa aatgttttg tctgcacagt gaagataata taacttctgg
2041 gttctatgta agttcaaata ttttctagga TC101515 nucleic acid M. truncatula
                                                                       (SEQ ID NO: 10)
FLKRKDELNCLLKLPQVNSRVKQESGLPSILKKSLSNLGVSNEILEFLFGLYPKIPEAKG
SISAIRSEAFFIPLYELYITYGGIFRLNFGPKSFLIVSDPAIAKHILKDNSKAYSKGILA
EILDFVMGKGLIPADGEIWRVRRRTIVPALHLKFVAAMIGLFGQATDRLCQKLDTAASDG
EDVEMESLFSRLTLDVIGKAVFNYDFDSLSNDTGIIEAVYTVLREAEDRSISPIPVWDLP
IWKDISPRQRKVTAALKLVNDTLNNLIAICKRMVDEEELQFHEEYMNEQDPSISFTFLLA
SGDDVTSKQLRDDLMTMLIAGHETSAAVLTWTFYLLSKEPSVMSKLQEEVDSVLGDRFPT
```

```
                                                -continued
IEDMKKLKYTTRVINESLRLYPQPPVLIRRSIEDDVLGEYPIKRGEDIFISVWNLHRSPT
LWNDADKFEPERWPLDGPNPNETNQGFKYLPFGGGPRKCIGDMFASYEVVVALAMLVRRF
NFQMAVGAPPVVMTTGATIHTTQGLNMTVTRRIKPPIVPSLQMSTLEVDPSVSISDKTEE
IGQKDQVYQAQ TC76166 nucleic acid H. vulgare
                                                                        (SEQ ID NO: 12)
MGTGLIPADGEVWRVRRRAIVPALHQKYVTAMIGLFGNASDRLCQKLDKAASDGEDVEMESLFSRLTLDVIGKAV
FNYDFDSLSYDNGIVEAVYVTLREAEMRSTSPIPTWEIPIWKDISPRQRKVNEALALINNILDELIATCKRMVDE
EDLQFHEEYMNEKDPSILHFLLASGDDVSSKQLRDDLMTMLIAGHETSAAVLTWTFYLLSKYPNVMSKLQAEADA
VLGDGLPTIDDVKKLKYTTRVINESLRLYPQPPVLIRRSLEDDMLGEYPIGKGEDIFISIWNLHRCPKHWDDADV
FNPERWPLDGPNPNETNQKFSYLPFGGGPRKCVGDMFATFETVVATAMLVKRFDFQMAPGAPPVEMTTGATIHTT
KGLNMTVTRRIKPPVIPNLEMKIVSDPEGSTSSTASVAVSTASIASGEGQQVEVSTSQV
```

Methods for introducing one or more nucleic acids that encode a CYP97A protein into a bacterium or yeast cell are described herein.

CYP97B

Non-limiting examples of CYP97B proteins are described herein (see, FIGS. 2-4 and 6). Additional examples of CYP97B proteins are known in the art. Methods for that may be used to determine the ability of a CYP97B protein to hydroxylate the β-ring of α-carotene are described herein. Additional methods for determining the ability of CYP97B protein to hydroxylate the β-ring of α-carotene are known in the art.

Wild type CYP97B proteins are known to share a number of conserved residues, including for example, the conserved amino acid residues shown in FIG. 3 (see, Clan B), and the conserved amino acid residues present in the oxygen-binding motif and the heme-binding motif. The conserved heme-binding motif in plant P450 proteins has a consensus sequence of FXXGXXXCXG. Wild type CYP97B proteins are also conserved at a number of other residues (see, for example, the aligned wild type CYP97B sequences in FIG. 6).

In some embodiments, a CYP97B protein can contain one or more (e.g., two, three, four, five, six, seven, eight, nine, or ten) additions, insertions, substitution, or deletions as compared to a corresponding wild type CYP97B protein. For example, a CYP97B protein can contain one or more substitutions at amino acid positions that are not present within the conserved heme-binding motif or within the oxygen-binding motif, or at amino acid positions that are not conserved among wild type CYP97B proteins (see, e.g., the amino acid positions that are not conserved in FIG. 6).

In some embodiments, the CYP97B protein is at least 80% identical (e.g., at least 85%, 90%, 95%, or 100%) identical to any one of SEQ NO: 3, 13, 15, and 17.

```
CYP97B1 protein P. sativum
                                                                        (SEQ ID NO: 13)
   1mvaapistvk ltdanlhtrf hssssstpst lslplslhfh fsshskrfss ircqsvngek
  61rkqssrnvfd nasnlltsll sganlgsmpi aegavtdlfd rplffslydw flehgsvykl
 121afgpkafvvv sdpivarhil renafsydkg vladilepim gkglipadle twkqrrrvia
 181pgfhtsylea mvqlftscse rtvlkvnell egegrdgqks veldleaefs nlaleiiglg
 241vfnydfgsvt nespvikavy gtlfeaehrs tfyipywkfp larwivprqr kfqddlkvin
 301tcldglirna kesrqetdve klqqrdysnl kdasllrflv dmrgvdvddr qlrddlmtml
 361iaghettaav ltwavfllaq npdkmkkaqa evdlvlgmgk ptfellkkle yirlivvetl
 421rlypqpplli rrslkpdvlp gghkgdkdgy tipagtdvfi svynlhrspy fwdrpndfep
 481erflvqnnne evegwagfdp srspgalypn eiisdfaflp fgggprkcvg dqfalmestv
 541alvccyrism wn CYP97B2 protein G. max
                                                                        (SEQ ID NO: 15)
MSVDTSSTLSTVTDANLHSRFHSRLVPFTHHFSLSQPKRISSIRCQSINTDKKKSSRNLLGNASNLLTDLLSGGS
IGSMPIAEGAVSDLLGRPLFFSLYDWFLEHGAVYKLAFGPKAFVVVSDPIVARHILRENAFSYDKGVLADILEPI
MGKGLIPADLDTWKQRRRVIAPAFHNSYLEAMVKIFTTCSERTILKFNKLLEGEGYDGPDSIELDLEAEFSSLAL
DIIGLGVFNYDFGSVTKESPVIKAVYGTLFEAEHRSTFYIPYWKIPLARWIVPRQRKFQDDLKVINTCLDGLIRN
AKESRQETDVEKLQQRDYLNLKDASLLRFLVDMRGADVDDRQLRDDLMTMLIAGHETTAAVLTWAVFLLAQNPSK
MKKAQAEVDLVLGTGRPTFESLKELQYIRLIVVEALRLYPQPPLLIRRSLKSDVLPGGHKGEKDGYAIPAGTDVF
ISVYNLHRSPYFWDRPDDFEPERFLVQNKNEEIEGWAGLDPSRSPGALYPNEVISDFAFLPFGGGPRKCVGDQFA
LMESTVALTMLLQNFDVELKGTPESVELVTGATIHTKNGMWCRLKKRSNLR CYP97B3 protein A. thaliana
                                                                        (SEQ ID NO: 17)
MVAAMAFPAAATYPTHFQGGALHLGRTDHCLFGFYPQTISSVNSRRASVSIKCQSTEPKTNGNILDNASNLLTNF
LSGGGSLGSMPTAEGSVSDLFGKPLFLSLYDWFLEHGGIYKLAFGPKAFVVISDPIIARHVLRENAFSYDKGVLAE
ILEPIMGKGLIPADLDTWKLRRRAITPAFHKLYLEAMVKVFSDCSEKMILKSEKLIREKETSSGEDTIELDLEAE
FSSLALDIIGLSVFNYDFGSVTKESPVIKAVYGTLFEAEHRSTFYFPYWNFPPARWIVPRQRKFQSDLKIINDCL
DGLIQNAKETRQETDVEKLQERDYTNLKDASLLRFLVDMRGVDIDDRQLRDDLMTMLIAGHETTAAVLTWAVFLL
SQNPEKIRKAQAEIDAVLGQGPPTYESMKKLEYIRLIVVEVLRLFPQPPLLIRRTLKPETLPGGHKGEKEGHKVP
KGTDIFISVYNLHRSPYFWDNPHDFEPERFLRTKESNGIEGWAGFDPSRSPGALYPNEIIADFAFLPFGGGPRKC
IGDQFALMESTVALAMLFQKFDVELRGTPESVELVSGATIHAKNGMWCKLKRRSK CYP97B4 protein O. Sativa
                                                                        (SEQ ID NO: 3)
MAITAATAAAAATPHPWQADASPRRHAACPALRGRR
RLPVVRCQSSSVDDKPKSKRGLLDNASNLLTNLLSG
GSLGAMPVAEGAVTDLFGRPLFFSLYDWFLEHGSVY
KLAFGPKAFVVVSDPIVARHILRENAFCYDKGVLAE
ILKPIMGKGLIPADLDTWKQRRKVITPGFHALFIDA
```

-continued

```
MVGVFTKCSERTIFKLEELIERGEHGEKYTIVDLEA
EFSNLALDIIGLGVFNDFDSVTKESPVIKAVYGTL
FEAEHRSTFYIPYWNLPLTRWIVPRQRKFHSDLKVI
NDCLDSLIKNAKETRQEADVEKLQQRDYSSLKDASL
LRFLVDMRGADVDDRQLRDDLMTMLIAGHETTAAVL
TWSVFLLAQNPSKMRKAQAEVDSVLSNETINVDQLK
KLEYIRLIIVEALRLYPQPPLLIRRALRPDKLPGGY
NGAKEGYEIPAGTDIFLSIYNLHRSPYFWDRPDEFE
PERFSVPKKDESIEGWAGFDPDRSPGAMYPNEILAD
FAFLPFGGGPRKCVGDQFALLESTVALALLLQKFDV
ELRGSPDEVEMVTGATIHTKSGLWCRVRRRT
```

In some embodiments, a nucleic acid encoding a CYP97B protein can be any nucleic acid containing a nucleic acid sequence that is at least 80% (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type CYP97B protein (e.g., SEQ ID NO: 4, 14, 16, and 18). As noted above, percent identity can be determined using a number of molecular biology tools, e.g., BLAST program available at the NCBI website. In some embodiments, the CYP97B protein contains the sequence of a wild type CYP97B protein (e.g., a protein containing the sequence of SEQ ID NO: 3, 13, 15, and 17).

Non-limiting examples of nucleic acid sequences that encode a wild type CYP97A protein are shown in FIG. 2 (the CYP97B sequences shown are publicly available on the Gramene website and/or the NCBI website). In some embodiments, the nucleic encodes that encodes a CYP97B protein contains a sequence that encodes a CYP97B protein that is at least 80% identical (e.g., 85%, 90%, 95%, or 100% identical) to one of SEQ ID NOS: 3, 13, 15, and 17. In some embodiments, the nucleic acid contains a sequence that is at least 80% identical (e.g., at least 85%, 90%, 95%, or 100%) identical to any one of SEQ NO: 4, 14, 16, and 18.

```
CYP97B4 nucleic acid O. sativa
                                                    (SEQ ID NO: 4)
atggcgatcaccgcggccaccgccgccgccgccgcacgccccaccegtggcaggccgacgcc
tgccgcgtcgccacgccgcgtgccccgctctccgcgggaggaggcgcctcccegtcgtcaggtg
ccagtcgtccagcgtcgacgacaagcccaagtccaagcggggcctgctcgacaacgccagcaa
cctgctcaccaacctgctcagcggcgggagcctcggcgcgatgcccgtcgccgagggcgccgtc
accgacctcttcggccggccactcttcttctcgctctacgactggttcctcgagcatggctctgtgtacaa
actcgcttttggaccccaaggcatttgttgttgtctccgatccaattgttgctagacatatcctgcgagaaa
atgctttctgttatgataagggagttcttgctgaaattttaaaaccaataatggggaagggtcttatacct
gctgaccttgatacctggaagcaaaggagaaaagttataaccccgggttccatgcettattcatag
atgctatggtgggagtatttactaagtgttcagagagaacaatatttaagcttgaagagcttattgaaa
ggggcgaacatggggaaaagtataccatagtggaccttgaagctgagttttctaatttggctctc
gacataattggcttgggcgtgttcaattttgattttgattcggttaccaaagaatctcctgtgatcaagg
cagtatacggaactcttttttgaagctgagcacagatccacttttttacattccctattggaatcttcctttaa
ctagatggatagttccaaggcaacgcaagttccacagtgacctcaaggttattaatgattgccttga
tagtctcataaaaaatgcaaaagagacaagacaggaagctgatgtcgaaaagctccagcaa
agagattactcatcattgaaggatgccagcttgctgaggttccttgttgatatgcggggagctgatgt
tgacgatcgccagcttcgagatgaccttatgacaatgcttattgctgggcatgaaacaactgctgct
gttttgacatggtctgttttttctactagcccagaatccctccaagatgagaaaagcacaggcagagg
ttgattctgtactcagcaatgagacaattaatgtggaccagctcaagaaattggagtacataagact
gataattgttgaagctcttcgcttgtatcccagccaccattgttaatcaggcgtgctctgcggccaga
taaattgccaggtgggtacaatggtgcaaaagaaggatatgaaataccagctggaaccgatata
tttctttcgatatacaacctccatagatctccatactttttgggatcggccagatgagtttgaaccagag
agattttcagtaccaaaaaaggatgagagcatagaagggtgggctggttttgatcctgaccggag
tcctggtgctatgtatcctaacgagattttagcagactttgctttccttccttttggcggaggacccccgc
aaatgcgtgggagaccagtttgcactcctcgagtcgacagtagccctggccctgctattgcaaa
agtttgatgtggagctgcgaggatcaccegatgaagtggagatggtgacaggcgcaacaattc
acacgaagagcgggttatggtgcagagtgaggagaaggacctga CYP97B1 nucleic acid P. sativum
                                                    (SEQ ID NO: 14)
The coding sequence is from 64 . . . 1722 in the following:
CATCACTTACCACTAACTGAAACTTGCAAGCACCATTCTCAACTTAACACCGTCGTCACC
GCCATGGTTGCCGCCCCTATCTCAACCGTCAAACTTACCGATGCCAATCTTCACACCAGA
TTTCATTCCTCTTCTTCTTCTACACCATCCACCCTCAGTCTTCCACTCTCTCTTCATTTT
CACTTTTCTTCTCACTCCAAACGCTTTTCTTCTATCAGATGTCAATCGGTTAATGGTGAA
AAGCGAAAACAAAGTAGTAGAAATGTGTTTGACAATGCTAGCAACCTCCTTACAAGCTTG
TTAAGTGGTGCAAATTTAGGGTCCATGCCCATAGCTGAAGGTGCCGTCACAGATCTGTTT
GACCGGCCGCTGTTTTTCTCACTATATGATTGGTTCTTAGAGCATGGTTCTGTGTATAAA
CTGGCGTTTGGACCGAAAGCATTTGTTGTTGTATCAGATCCCATTGTTGCAAGACATATT
CTGCGAGAAAATGCATTTTCTTATGACAAGGGAGTACTTGCTGATATCCTAGAACCAATT
ATGGGAAAAGGACTCATACCTGCAGACCTTGAGACATGGAAGCAAAGGAGAAGAGTGATT
GCTCCGGGTTTCCATACCTCATACTTGGAAGCTATGGTACAACTATTCACTTCATGTTCA
GAAAGAACTGTGTTAAAGGTCAATGAGCTTCTTGAAGGAGAGGGGCGTGATGGACAGAAG
TCAGTTGAATTGGACCTTGAGGCAGAATTTTCAAATTTGGCTCTTGAGATTATTGGGCTA
GGTGTGTTCAACTATGACTTTGGTTCTGTCACCAATGAATCTCCCGTTATTAAGGCTGTC
TATGGCACTCTTTTTGAAGCCGAACATAGATCCACTTTCTATATTCCATATTGGAAATTT
CCATTAGCAAGGTGGATTGTGCCCAGGCAAAGGAAGTTTCAGGATGACCTTAAAGTCATT
AATACTTGTCTTGATGGACTTATCAGAAATGCAAAAGAGAGCAGGCAGGAAACAGATGTT
GAGAAACTGCAGCAAAGGGATTACTCAAATTTGAAGGATGCAAGTCTTCTGCGTTTCCTA
```

-continued
```
GTTGATATGCGGGGAGTTGATGTTGATGATCGTCAGTTGAGGGATGATTTAATGACAATG
CTTATTGCTGGTCATGAGACGACGGCTGCAGTTCTTACATGGGCAGTTTTCCTGCTAGCT
CAAAATCCTGACAAAATGAAGAAGGCTCAAGCAGAGGTAGATTTGGTGCTGGGGATGGGG
AAGCCAACTTTTGAATTGCTTAAAAAGTTGGAGTACATTAGGTTAATTGTTGTGGAGACT
CTTCGATTATATCCACAACCACCTCTGCTGATTAGACGTTCACTCAAACCTGATGTTTTG
CCAGGTGGACATAAAGGTGACAAAGATGGTTATACAATTCCTGCTGGGACTGATGTCTTC
ATTTCTGTATATAATCTCCATCGATCTCCATATTTTTGGGACCGCCCTAATGACTTCGAG
CCTGAACGATTTCTAGTGCAAAACAATAATGAAGAAGTTGAAGGGTGGGCTGGTTTTGAC
CCATCTCGAAGTCCTGGAGCCTTGTATCCAAACGAGATTATATCAGATTTTGCATTCTTG
CCTTTTGGTGGTGGACCACGAAAATGCGTTGGAGACCAATTTGCTCTCATGGAATCCACT
GTAGCGCTAGTATGCTGCTACAGAATTTCGATGTGGAACTGAAGGGGACCCCTGAATCGG
TTGAACTAGTTACTGGGCAACTATCCATACCAAAAATGGATTGTGGTGCAATTTGAGGA
AGAGATCTAGTTTACATTGACATGTTAACTGCAACATTTTTCTTATGCAGAATGATGTAC
AAAATATTTATCATTTAAAATGACATTAACATTGAATAGTGTCTAATACAGCTAAAGGGT
ATTTAC
```

CYP97B2 nucleic acid *G. max*
(SEQ ID NO: 16)
The coding sequence is from: 20 ... 1750 in the following:
```
   1 caacactcgc agtaccgcca tgagtgtcga cacttcctcc accctctcca ccgtcaccga
  61 tgccaatctt cactccagat ttcattctcg tcttgttcca ttcactcatc atttctcact
 121 ttctcaaccc aaacggattt cttcaatcag atgccaatca attaataccg ataagaagaa
 181 atcaagtaga aatctgctgg gcaatgcaag taacctcctc acggacttat taagtggtgg
 241 aagtataggg tctatgccca tagctgaagg tgcagtctca gatctgcttg tcgacctct
 301 ctttttctca ctgtatgatt ggttcttgga gcatggtgcg gtgtataaac ttgcctttgg
 361 accaaaagca tttgttgttg tatcagatcc catagttgct agacatattc tgcgagaaaa
 421 tgcattttct tatgacaagg gagtacttgc tgatatcctt gaaccaataa tgggcaaagg
 481 actcatacca gcagaccttg atacttggaa gcaaaggaga gagtcattg ctccggcttt
 541 ccataactca tacttggaag ctatggttaa atatattcaca acttgttcag aaagaacaat
 601 attgaagttt aataagcttc ttgaaggaga gggttatgat ggacctgact caattgaatt
 661 ggatcttgag gcagagtttt ctagtttggc tcttgatatt attgggcttg gtgtgttcaa
 721 ctatgacttt ggttctgtca ccaaagaatc tccagttatt aaggcagtct atggcactct
 781 ttttgaagct gaacacagat ccactttcta cattccatat tggaaaattc cattggcaag
 841 gtggatagtc ccaaggcaaa gaaagtttca ggatgaccta aaggtcatca atacttgtct
 901 tgatggactt atcagaaatt caaaagagag cagacaggaa acagatgttg agaaattgca
 961 gcagagggat tacttaaatt tgaaggatgc aagtcttctg cgtttcctgg ttgatatgcg
1021 gggagctgat gttgatgatc gtcagttgag ggatgattta atgacaatgc ttattgccgg
1081 tcatgaaaca acggctgcag ttcttacttg gcagttttc ctcctagctc aaaatcctag
1141 caaaatgaag aaggctcaag cagaggtaga tttggtgctg ggtacggga ggccaacttt
1201 tgaatcactt aaggaattgc agtacattag attgattgtt gtggaggctc ttcgtttata
1261 cccccaacca cctttgctga ttagacgttc actcaaatct gatgttttac caggtgggca
1321 caaaggtgaa aaagatggtt atgcaattcc tgctgggact gatgtcttca tttctgtata
1381 taatctccat agatctccat attttgggga ccgccctgat gacttcgaac cagagagatt
1441 tcttgtgcaa aacaagaatg aagaaattga aggatgggct ggtcttgatc catctcgaag
1501 tcccggagcc ttgtatccga acgaggttat atcggatttt gcattcttac cttttggtgg
1561 cggaccacga aaatgtgttg ggaccaatt tgctctgatg gagtccactg tagcgttgac
1621 tatgctgctc cagaattttg acgtggaact aaaagggacc cctgaatcgg tggaactagt
1681 tactggggca actattcata ccaaaaatgg aatgtggtgc agattgaaga agagatctaa
1741 tttacgttga catatgtact gtggccatt tccttataca gaataatgta tattattatt
1801 ctttgagaat aaatatgaata aattcctaga c
```

CYP97B3 nucleic acid *A. thaliana*
(SEQ ID NO: 18)
```
   1 atctaacttt agagcttctc tttttcatttg aagatggtag cagccatggc ttttcctgcc
  61 gctgctactt atcccaccca tttccaaggc ggcgctcttc atctgggtag gaccgatcat
 121 tgcctcttcg gtttctaccc tcaaaccatt tcctctgtga attctcggag agcttctgtt
 181 tccatcaagt gccaatctac ggagccaaag acgaatggta acatattgga caatgcgagc
 241 aacccttttga caaattttttt aagtggtgga agtttgggt caatgcctac tgctgaaggc
 301 tctgtctctg atttgtttgg aaagcctctc ttttatctc tttacgactg gttcttggag
 361 catggaggaa tttataaact tgcgtttggt ccaaaagcct tgttgtcat ctcagatccc
 421 attattgcaa ggcatgtcct ccgggaaaat gcttttttctt atgacaaggg agttcttgct
 481 gagatcttag agccgattat gggaaaaggg ttaataccgg ctgatctaga tacgtggaag
 541 ttaagaagaa gagctatcac tcccgcattc cataaattgt atctagaggc catggtcaaa
 601 gtatttagtg actgttcgga gaaaatgata ttgaaatctg agaaactcat aagggagaaa
 661 gaaacttcaa gcggggagga caccattgag ttggatctgg aagcagaatt ctcgagtctg
 721 gctcttgata ttataggtct tagcgtgttc aactacgatt ttggctctgt cacaaaagag
 781 tcccctgtga tcaaggcagt ttatggaact cttttcgagg cagagcatcg gtctactttc
 841 tacttccctt attggaactt tcctccagct agatggataa ttccgaggca acgaaagttc
 901 caaagcgatc tgaagattat aaacgattgc cttgatggcc tcattcaaaa tgctaaagag
 961 acaagacagg aaacagatgt tgagaagctc aggaaaggg actacactaa tctcaaggat
1021 gcaagtcttt tgcggttctt agtcgatatg cgcggtgttg acattgatga ccggcagctg
1081 agggatgact tgatgactat gctaattgct gtcatgaga caacagcagc agtacttact
1141 tgggctgttt tccttctgtc acaaaatcct gaaaaaatta ggaaagctca agctgagatt
1201 gatgctgtgc ttggtcaagg tccacccact tatgaatcaa tgaaaagct cgagtacata
1261 cgactgatcg ttgtagaagt ccttcgtctc tttcctcagc caccttttgct catcagacgc
1321 actctcaaac cagaaacatt acccggagga cacaagggga aaaagaagg tcataaagtt
1381 ccaaaaggga ctgatatctt catttctgtg tataatctcc atagatctcc atactttggg
1441 gataatcccc acgatttga gcctgagagg tttttaagaa caaggagag caatggaatt
1501 gaaggatggg ctggctttga tccatctcgt agccccgggg cactatatcc gaatgagata
1561 atagcagact ttgcattctt accattggt ggaggaccaa gaaaatgcat tggagaccag
1621 tttgcactaa tggaatcgac cgtcgcacta gctatgttgt ttcagaaatt cgatgtggag
```

```
                              -continued
1681 ctgcgtggaa cgccagaatc tgtttgaactc gtgagcggcg caacgattca tgccaaaaat
1741 gggatgtggt gcaaactaaa gagaagatca aagtgaaatt tatggatagg caaaaagact
1801 caattttaac ttgaaggaag ctgagtgtaa atgagagatg atatgcttat gattcactaa
1861 acgtacattc ttgagatttt gaaaatgcaa aaaagctaat acagagattg gatctgttgg
1921 t
```

Methods for introducing one or more nucleic acids that encode a CYP97B protein into a bacterium or yeast cell are described herein.

CYP97C

Non-limiting examples of CYP97C proteins are described herein (see, FIGS. 2-4 and 7). Additional examples of CYP97C proteins are known in the art. Methods for determining the ability of a CYP97C protein to hydroxylate the ε-ring of α-carotene are described herein. Additional methods for determining the ability of CYP97C protein to hydroxylate the ε-ring of α-carotene are known in the art.

Wild type CYP97C proteins are known to share a number of conserved residues, including for example, the conserved amino acid residues shown in FIG. 3 (see, Clan C), and the conserved amino acid residues present in the oxygen-binding motif and the heme-binding motif (see, FIG. 4). The conserved heme-binding motif corresponds to amino acids 488 to 497 (FSGGPRKCVG) in CYP97C2 from O. sativa (SEQ ID NO: 5). The conserved oxygen-binding motif in wild type CYP97C proteins has a consensus sequence of AGHETT, and the conserved heme-binding motif in wild type CYP97C proteins has a consensus sequence of FSGGPRKCVG (see, FIG. 4). Wild type CYP97C proteins are also conserved at a number of other residues (see, for example, the aligned wild type CYP97A sequences in FIG. 7).

In some embodiments, a CYP97C protein can contain one or more (e.g., two, three, four, five, six, seven, eight, nine, or ten) additions, insertions, substitution, or deletions as compared to a corresponding wild type CYP97C protein. For example, a CYP97C protein can contain one or more substitutions at amino acid positions that are not present within the conserved heme-binding motif or within the oxygen-binding motif, or at amino acid positions that are not conserved among wild type CYP97C proteins (see, e.g., the amino acid positions that are not conserved in FIG. 7).

In some embodiments, the CYP97C protein is at least 80% identical (e.g., at least 85%, 90%, 95%, or 100%) identical to any one of SEQ NO: 5, 19, 21, and 23.

BT012891protein L. esculentum (SEQ ID NO: 19)

FTITMPISVTISSFSLLTNPHHRTTVLRPKNPLQNRSQLTIKSSIDNKKPPSTKPTSWVSPDWLTKLTRSLTLGQ
NDDSNIPIASAELDDVSELLGGALFLPLYRWMNLYGPIYRLAAGPRNFVIVSDPAIAKHVLKNYGKYGKGLVAEV
SEFLFGSGFAIAEGPLWTARRRAVVPSLHKKYLSVIVDRVFCRCAERMVEKLLPDAISGSAVNMEAKFSQLTLDV
IGLALFNYNFDSLTTDSPVIDAVYTALKEAELRSTDLLPYWQIKALCKFIPRQIKAENAVSLIRQTVEELIAKCR
EIVETEGERINEDEYVNDRDPSILRFLLASREEVSSVQLRDDLLSMLVAGHETTGSVLTWTAYLLSKDPSSLEKA
HEEVDRVLGGRSPTYEDMKNLKFLTRCITESLRLYPHPPVLIRRAQVADVLPGNYKVNVGQDIMISVYNIHHSSE
VWDRAEEFDPERFDLEGPVPNETNTDFRFIPFSGGPRKCVGDQFALLEATIALAIFVQNFSFELIPDQTISMTTG
ATIHTTNGLYMKVKQREKASVLAAAPILSQEKVILILTLYTSLVDYENHHYCVMSYFFSGIIAFFSFFLYIRIYC
ASFKNNLSMSTRYRGRVRTDQTLCAQDPTLKIYCMYCCISEYAFVVGKKKK

TC109838 protein M. truncatula (SEQ ID NO: 21)

MPSCSCSCSCSLPLSHLSLSSFSKTPLPQKRYPLHPRILTKSSTNKNPETTKSTSWVSPD
WLTSLSKSLTTSKNDDSNIPIASAKLDDVSDLLGGALFLPLFKWMNEYGPIYRLAAGPRN
FVVVSDPAIAKHVLKNYGKYGKGLVAEVSEFLFGDGFAIAEGPLWTARRRAVVPSLHKRY
LSIMVDRVFCKCAERLVEKLQADAVNGTAVNMEDKFSQLTLDVIGLSVFNYNFDALNSDS
PVIEAVYTALKEAEARSTDLLPYWKIDFLCKIIPRQIKAENAVTVIRKTVEDLIEQCKEI
VESEGERIDADEYVNDADPSILRFLLASREEVSSVQLRDDLLSMLVAGHETTGSVLTWTL
YLLSKDSSSLAKAQEEVDRVLQGRRPTYEDMKDLKFLNRCIIESLRLYPHPPVLIRRSQI
PDELPGDYKIDAGQDIMISVYNIHHSSKVWDRAEEFLPERFDLGPVPNETNTDFRFIPF
RGGPRKGVGDQFALLEATVAFAVFLQHMNFELVPDQNIGMTTGATIHTTNGLYMKMSQRL
KKLTSTFFSHRWQNLLANNYQQD

CYP97C2 protein O. sativa (SEQ ID NO: 5)

AVPCVPFLCPPPPPLVSPRLRRGHVRLRL
RPPRSSGGGGGGAGGDEPPITTSWVSPDWLTALSR
SVATRLGGGDDSGIPVASAKLDDVRDLLGGALFLPL
FKWFREEGPVYRLAAGPRDLVVVSDPAVARHVLRGY
GSRYEKGLVAEVSEFLFGSGFAIAEGALWTVRRRSV
VPSLHKRFLSVMVDRVFCKCAERLVEKLETSALSGK
PVNMEARFSQMTLDVIGLSLFNYNFDSLTSDSPVID
AVYTALKEAELRSTDLLPYWKIDLLCKIVPRQIKAE
KAVNIIRNTVEDLITKCKKIVDAENEQIEGEEYVNE
ADPSILRFLLASREEVTSVQLRDDLLSMLVAGHETT
GSVLTWTIYLLSKDPAALRRAQAEVDRVLQGRLPRY
EDLKELKYLMRCINESMRLYPHPPVLIRRAIVDDVL
PGNYKIKAGQDIMISVYNIHRSPEVWDRADDFIPER
FDLEGPVPNETNTEYRFIPFSGGPRKCVGDQFALLE
AIVALAVVLQKMDIELVPDQKINMTTGATIHTTNGL
YMNVSLRKVDREPDFALSGSR

CYP97C1 protein *A. thaliana*

(SEQ ID NO: 23)

```
  1 messlfspss ssysslftak ptrllspkpk ftfsirssie kpkpkletns sksqswvspd
 61 wltttltrtls sgkndesgip ianaklddva dllggalflp lykwmneygp iyrlaagprn
121 fvivsdpaia khvlrnypky akglvaevse flfgsgfaia egplwtarrr avvpslhrry
181 lsvivervfc kcaerlvekl qpyaedgsav nmeakfsqmt ldviglslfn ynfdslttds
241 lpvieavytal keaelrstdl lpywkidalc kivprqvkae kavtliretv edliakckei
301 veregerind eeyvndadps ilrfllasre evssvqlrdd llsmlvaghe ttgsvltwtl
361 yllsknssal rkaqeevdrv legrnpafed ikelkyitrc inesmrlyph ppvlirraqv
421 pdilpgnykv ntgqdimisv ynihrssevw ekaeeflper fdidgaipne tntdfkfipf
481 sggprkcvgd qfalmeaiva lavflqrlnv elvpdqtism ttgatihttn glymkvsqr
```

In some embodiments, a nucleic acid encoding a CYP97C protein can be any nucleic acid containing a nucleic acid sequence that is at least 80% (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type CYP97C protein (e.g., SEQ ID NO: 6, 20, 22, and 24). Percent identity can be determined using a number of molecular biology tools, e.g., BLAST program available at the NCBI website. In some embodiments, the CYP97C protein contains the sequence of a wild type CYP97C protein (e.g., a protein containing the sequence of SEQ ID NO: 5, 19, 21, and 23).

Non-limiting examples of nucleic acid sequences that encode a wild type CYP97C protein are shown in FIG. 2 (the CYP97C sequences shown are publicly available on the Gramene website and/or the NCBI website). In some embodiments, the nucleic encodes that encodes a CYP97C protein contains a sequence that encodes a CYP97C protein that is at least 80% identical (e.g., 85%, 90%, 95%, or 100% identical) to one of SEQ ID NOS: 5, 19, 21, or 23. In some embodiments, the nucleic acid contains a sequence that is at least 80% identical (e.g., at least 85%, 90%, 95%, or 100%) identical to any one of SEQ NO: 6, 20, 22, or 24.

BT012891 nucleic acid *L. esculentum*

(SEQ ID NO: 20)

```
   1 ttcaccatca ccatgccaat ttcggtcacc atttcttcct tctctcttct cactaaccct
  61 caccaccgga ccaccgtgct ccgcccaaaa aacccactcc aaaatcgttc acaactcacc
 121 attaaatcct ccattgacaa caagaaacca ccttcaacta agcctacttc atgggtcagt
 181 ccagattggc ttactaaact taccaggtca cttactttag gccaaaatga tgattctaac
 241 atacccattg cgagtgctga gcttgatgat gtttcggaac ttctgggcgg tgctcttttt
 301 cttccattgt atagatggat gaatttgtat ggacctattt atcgtcttgc tgctgggccg
 361 aggaattttg ttattgttag tgatcctgct attgctaagc atgttttgaa gaattatggg
 421 aagtatggga aagggcttgt tgctgaagtt tctgagtttt tgtttggttc tggttttgct
 481 attgctgaag gtcctctttg gacggcaagg cgaagggctg tggttccatc tcttcacaag
 541 aagtacttgt cagtaatagt tgatcgggtc ttttgcagat gtgctgagag aatggtggaa
 601 aaactttac ctgatgcaat ttctggctct gcagtgaata tggaggcaaa gttttctcaa
 661 ctaacacttg atgttattgg ccttgcactc ttcaattaca attttgattc ccttactact
 721 gacagtccag ttattgatgc agtttacact gcactaaaag aagcagaact ccgttcaact
 781 gatttgttgc catattggca gatcaaagct ttatgtaagt tcatcccacg acaaataaag
 841 gctgagaatg cagtgtcatt aatcagacaa acagttgaag aacttattgc aaagtgcaga
 901 gagattgtag aaactgaggg tgagaggatt aatgaagatg agtacgtgaa tgatagagat
 961 ccaagcatcc ttcgattctt gcttgctagc cgtgaggagg tttcaagtgt acaacttcga
1021 gatgatcttc tgtcaatgct agttgctggg catgaaacca caggttcagt tttgacttgg
1081 acggcatacc tgctgagtaa ggatccttcc tctttggaaa aagcacatga ggaagtagac
1141 agagttttgg gaggacgctc tccgacttat gaagacatga agaatctcaa gttcttaaca
1201 cggtgcataa ctgagtcact cagactctat ccacatccac ctgtcctaat aagaagagct
1261 caagtagctg atgtcctccc cgggaattac aaagtcaatg ttggtcagga tataatgatt
1321 tcggtatata acattcatca ttcttcagag gtatgggata gagctgaaga atttgatcct
1381 gaaagattcg acttggaagg tcccgtccca aatgaaacaa atactgactt tagattcatc
1441 ccgtttagtg gagggccacg aaaatgcgtt ggtgatcaat ttgccttgtt ggaagctaca
1501 attgctctcg cgatatttgt acagaacttc tcattcgagt tgattccaga tcaaactatt
1561 agcatgacta ctggagcaac cattcatacg acaaacggtt tatacatgaa agtgaagcaa
1621 agggagaaag catctgtttt ggctgctgca ccgtaaattt tgtcacagga gaaagtaatc
1681 ttgattcttt gaacattata tacatctttg gtagactatg agaatcatca ttattgcgtt
1741 atgtcctatt ttttctctgg cattattgcc tttttttctt tcttttctata tattagaata
1801 tattgcgcct ctttcaaaaa taacctctct atgtctacga ggtatagggg tagagtgtag
1861 cgtacagatc aaactctctg cgcccaagat cctaccttga aaatatactg tatgtattgt
1921 tgtatatcag aatatgcctt ttaagttgtt ggaaaaaaaa aaaaaaa
```

TC109838 nucleic acid *M. truncatula*

(SEQ ID NO: 22)

```
  1 cgtaaaccca aaacaatgc catcatgttc atgttcatgt tcatgttcac tccctctctc
 61 tcatctttct ctctcttcct tctccaaaac accactccca caaaaacgtt atccacttca
121 tcctcgtatc ttaacaaaat cctcaactaa caaaaacct gaaacaacaa aatccacttc
181 atgggtaagt ccagattggc tcacatcact ttcaaaatcc ttaacaacat caaaaaatga
241 tgattccaac attcctatag caagtgctaa gcttgatgat gtttctgatc ttttgggtgg
301 tgctcttttt cttcctttgt ttaaatggat gaatgagtat ggtcctattt atcgtttagc
361 tgctggtcca agaaactttg ttgttgttag tgatcctgct attgctaaac atgttcttaa
421 gaattatggt aaatatggta aaggtcttgt tgctgaggtt tctgagtttt tgtttgggga
481 tggttttgct attgctgaag gacctctttg gacggcaagg cgcagggctg tggttccatc
541 tcttcacaaa cggtacttgt ctattatggt ggatagggtg ttctgtaaat gtgcagagag
601 attagtagag aagctacaag ccgatgcagt taatggaact gctgttaaca tggaagacaa
661 gttttctcag ttaaccttg atgttattgg tttatccgtg ttcaactaca actttgacgc
```

-continued

```
 721 actaaattca gatagtcctg ttattgaagc cgtttacact gcactgaaag aggcggaggc
 781 tcggtcaacc gatcttttgc cctattggaa gattgatttt ctttgtaaga taatcccgag
 841 acaaataaag gctgaaaatg ctgttactgt tatcaggaaa actgtagaag acctattga
 901 acaatgtaaa gagattgtag agtccgaggg tgaaagaatt gatgctgatg aatatgtgaa
 961 tgacgctgac cctagtattc ttcgattttt gcttgccagc agagaagagg tttctagtgt
1021 gcaattaagg gatgatcttt tgtcaatgtt agttgctggt catgagacca ccggttcggt
1081 gctgacttgg acactttatc ttctaagtaa ggattcttcc tcattggcaa aagctcaaga
1141 agaggtagac agagttttac agggaaggcg tcctacctat gaagatatga aagatcttaa
1201 gttcttgaat cgctgtatta tcgagtcact ccgactttat ccacatcctc ctgtattgat
1261 aagaagatct caaattcctg atgagcttcc gggtgattac aaaatcgatg ccggtcaaga
1321 tattatgatt tctgtgtaca acatacatca ttcttctaag gtttgggata gagctgaaga
1381 gttttttgcc agaaagattt gtttggatgg tccagtacca aatgaaacaa atacagattt
1441 cagattcatt ccattcaggg gaggccctcg aaagggtgtc ggtgatcagt ttgcattatt
1501 ggaagctacc gttgcttttg cagttttttt acagcacatg aactttgagc tggtacctga
1561 tcagaatatt ggcatgacta cgggagcaac aatacataca acaaatggct tgtacatgaa
1621 aatgagccaa cggttgaaaa agttgacatc cactttttt tcacataggt ggcaaaattt
1681 attggctaat aactatcagc aagattaaat tattttttg agaagcaa tattaaattc
1741 ttaagaggct tatttgtgcc atttcgtaca ccccaagtaa gtagtaaata tcgcatttga
1801 tagaaaatat ttct
```

CYP97C2 nucleic acid *O. sativa*
(SEQ ID NO: 5)

```
gccgtcccgtgcgtaccattcctgtgcccgcctcctccgccattggtctcgccgcgtctccgccgtgg
ccacgtccgcctccgcctgcggccgccaaggagcagcggcggtggaggcggaggcggagc
gggggagacgagccgcccatcaccacctcgtgggtgagcccgactggctcacggcgctctc
ccgctcggtggcaacccgcctcggcggggcgacgactcggggatccccgtcgcctccgcca
agctcgacgacgtgcgggacctcctcggcggcgcgctcttcctccctctcttcaagtggttccgcga
ggaaggccccgtctaccgcctcgcggcggggccgcgggatctcgtcgtcgtcagcgatcccg
ccgttgccaggcacgtgctgcgtgggtacggttcgaggtacgagaaggggctcgtcgccgag
gtttccgagttcctcttcggctccgggttcgccatcgccgagggcgctctctggacggtgagacg
tcgatcagttgtaccatctctacacaaacgatttctctcgggtggttgacagattttttttgtaaatg
tgctgagagattagtgtgagaagcttgagacatctgctttaagtggcaaacctgtaaatatggaa
gcaagttctctcaaatgactttagatgtgattggtttgtccttgttcaattacaattttgattccctcacat
cagatagccctgttattgatgctgttttacactgcactcaaggaagcagaacttcgttctacagatc
ttttaccatactggaagattgatttgctgtgcaagattgttcctagacaaataaaagcagaaaag
gcagttaacatcatcaggaataccgttgaggacctaattaccaaatgcaagaagattgtagat
gctgagaatgaacaaattgagggtgaggaatatgtaaatgaggcagaccctagcatcctgc
gattcctacttgctagccgtgaagaggtaaccagtgtgcagttacgtgatgatctattgtcaatgtt
agttgctggtcatgaaacaacaggctctgtactgacgtggactatttatcttctcagtaaggatcc
agcagcgctgaggagagctcaagcagaggttgaccgtgttctacaaggtagactccccag
atatgaagatctcaaaagagctgaagtacttgatgcgctgtataaatgagtctatgcggctttat
ccacacccacctgtgttgatacggcgagccatagttgatgatgtgcttcccggaaactataag
atcaaagctggtcaagatattatgatttcagtgtacaatatacacaggtcacctgaggtttggg
acagagctgatgattttattcctgagagatttgatttagagggacctgttccaaatgagacaaa
cactgaatacagatttatcccattcagtggaggtcctcggaaatgtgttggagatcagtttgctc
tcttggaagcaattgtggcacttgctgttgtgttgcagaagatggacattgagcttgtgccaga
tcaaaaaattaacatgactactggggccacaattcatacaaccaatggcctgtatatgaatgta
agtctgcgtaaagttgacagggaacctgattttgcactcagtgggtccagatga
```

CYP97C1 nucleic acid *A. thaliana*
(SEQ ID NO: 24)

```
   1 atggagtctt cactctttc tccatcttcc tcttcttact cttctctctt cactgcaaaa
  61 cctacgcgtc ttttatcacc aaaacccaaa ttcacattct ccatcagatc ctccattgag
 121 aaacccaaac ccaaactcga gaccaattca tcgaaatccc aatcatgggt cagtcccgat
 181 tggctcacaa cactcactcg tacccttcc tcaggaaaaa acgacgagtc aggtatacca
 241 atcgcgaacg cgaagctcga cgatgtcgct gatctcctcg gaggtgctct cttcttacct
 301 ctctacaaat ggatgaatga gtacggaccc atttaccgtc tcgctgctgg tcctcgtaat
 361 ttcgtaattg tgagcgaccc agcgatagct aaacatgttt tgaggaatta tccaaagtac
 421 gctaaaggct tagtcgctga agtctctgaa tttctatttg gttcgggttt cgctatcgct
 481 gaaggacctc tttggacagc gaggcgtaga gcggtggttc catcgcttca caggaggtat
 541 ttgtctgtga ttgtggagag agtattctgc aaatgtgcag agaggcttgt tgagaagttg
 601 cagccttatg cagaagacgg aagtgctgtg aatatgaag cgaagttctc tcagatgaca
 661 cttgatgtca ttgggttgtc tctttttaac tacaatttcg attcttgac tactgatagt
 721 cctgtcattg aagctgttta cactgctctt aaagaagctg agcttcgttc tactgatctt
 781 ctgccatatt ggaagatcga tgcattgtgt aagatagtcc cgagacaggt gaaagctgaa
 841 aaggctgtaa ctttgataag ggaaactgtt gaagacctta ttgctaagtg taaagaaatt
 901 gtcgaaagag aaggcgaaag aatcaatgat gaggagtgta taaatgatgc tgacccaagt
 961 atcctgcgtt tcttgcttgc aagcagagaa gaggtatcaa gtgtgcagtt acgggatgat
1021 cttctctcaa tgctcgtagc gggtcatgaa accactggat ctgtcctcac ttggacactt
1081 tatctcctaa gtaagaactc atctgcatta aggaaagcac aagaagaagt agacagagtg
1141 ttagaaggaa gaaacccggc tttcgaggat ataaggagt gaagtacat cactcgttgt
1201 ataaacgagt caatgcgtct ctatcctcat cctcctgtct tgataagaag agctcaagtt
1261 ctgacattc ttcctgggaa ctataaggtc aataccgaac aagacattat gatttcagtc
1321 tataacatcc atcgttcttc cgaggtatgg gaaaaagctg aggaatttct gcctgaacga
1381 ttcgacatag atgcgcaat ccctaacgaa acaaacactg atttcaaatt catcccattc
1441 agtggagggc ctagaaaatg tgtaggcgat cagtttgcat tgatggaggc aattgtggca
1501 ctcgcggtgt tcttcagcg gttaaacgtt gagctggttc ctgatcagac cattagcatg
1561 accacaggag caaccataca caccaccaat ggattgtata tgaaggtgag ccaaaggtaa
```

Methods for introducing one or more nucleic acids that encode a CYP97C protein into a bacterium or yeast cell are described herein.

Geranylgeranyl Pyrophosphate Synthase (CrtE)

Non-limiting examples of geranylgeranyl pyrophosphate synthase proteins are described herein (see, FIG. 8). Additional examples of geranylgeranyl pyrophosphate synthase proteins are known in the art. Methods for determining the ability of a geranylgeranyl pyrophosphate synthase protein to produce geranylgeranyl pyrophosphate from farnesyl pyrophosphate (FPP) and isopentenyl pyrophosphate (IPP) are known in the art (see, e.g., Okada et al., *Plant Physiol.* 122:1045-1056, 2000).

In some embodiments, a geranylgeranyl pyrophosphate synthase protein can contain one or more (e.g., two, three, four, five, six, seven, eight, nine, or ten) additions, insertions, substitution, or deletions as compared to a corresponding wild type geranylgeranyl pyrophosphate synthase protein. For example, a geranylgeranyl pyrophosphate synthase protein can contain one or more substitutions at amino acid positions that are not conserved among wild type geranylgeranyl pyrophosphate synthase proteins (see, e.g., the amino acid positions that are not conserved in FIG. 8).

In some embodiments, the geranylgeranyl pyrophosphate synthase protein is at least 80% identical (e.g., at least 85%, 90%, 95%, or 100%) identical to any one of SEQ NO: 25, 27, 29, and 57.

In some embodiments, a nucleic acid encoding a geranylgeranyl pyrophosphate synthase protein can be any nucleic acid containing a nucleic acid sequence that is at least 80% (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type geranylgeranyl pyrophosphate synthase protein (e.g., SEQ ID NO: 26, 28, 30, and 58). As described above, percent identity can be determined using a number of molecular biology tools, e.g., BLAST program available at the NCBI website. In some embodiments, the geranylgeranyl pyrophosphate synthase protein contains the sequence of a wild type geranylgeranyl pyrophosphate synthase protein (e.g., a protein containing the sequence of SEQ ID NO: 25, 27, 29, and 57).

Non-limiting examples of nucleic acid sequences that encode a wild type geranylgeranyl pyrophosphate synthase protein are shown herein (e.g., SEQ ID NOS: 26, 28, 30, and 58). Additional examples of nucleic acid sequences that encode a wild type geranylgeranyl pyrophosphate synthase are known in the art. In some embodiments, the nucleic acid encodes a geranylgeranyl pyrophosphate synthase protein that contains a sequence that is at least 80% identical (e.g., 85%, 90%, 95%, or 100% identical) to one of SEQ ID NOS: 25, 27, 29, and 57. In some embodiments, the nucleic acid contains a sequence that is at least 80% identical (e.g., at least 85%, 90%, 95%, or 100%) identical to any one of SEQ NO: 26, 28, 30, and 58.

```
Geranylgeranyl pyrophosphate synthase protein A. thaliana
                                                              (SEQ ID NO: 25)
    1masvtlgswi  vvhhhnhhhp  ssiltksrsr  scpitltkpi  sfrskrtvss  sssivsssvv
   61tkednlrqse  pssfdfmsyi  itkaelvnka  ldsavplrep  lkiheamsys  llaggkrvrp
  121vlciaacelv  ggeestampa  rcavemihtm  slihddlpcm  dnddlrrgkp  tnhkvfgedv
  181avlagdalls  fsfehlasat  ssdvvspvrv  vravgelaka  igteglvagq  vvdissegld
  241lndvglehle  fihlhktaal  leasavlgai  vgggsddeie  rlrkfarcig  llfqvvddil
  301dvtksskelg  ktagkdliad  kltypkimgl  eksrefaekl  nreardqllg  fdsdkvapll
  361alanyiayrq  n Geranylgeranyl pyrophosphate synthase protein O. sativa
                                                              (SEQ ID NO: 27)
    1mhvlaqstav  akvaasgclr  rspnpsvtfq  rspslllspa  acrrrcrrgc  svsvdvrcsl
   61gamvtpelng  gdvgvgvggg  sfdfqrylsa  radavhdald  ramprgfper  lcesmrysvl
  121aggkrvrpvl  alaacelvgg  daaaatpvac  avemihtmsl  ihddmpcmdd  dalrrgrpsn
  181hvafgeftal  lagdalhala  fehvargcgd  hgvpadrtlr  avaelgsasg  tggvaagqva
  241dkeseglpvs  lamleyihvh  ktarlleaaa  vsgaivggga  daevervrry  arcvgllfqv
  301vddvldmtst  seqlgktagk  dveadkatyp  kllgvdkare  yaadllamae  aeldgfdaer
  361aaplrhlarf  iayrqh Geranylgeranyl pyrophosphate synthase Catharanthus roseus
                                                              (SEQ ID NO: 29)
    1mrsnlchplk  nqlpisffls  gtirkpifsc  srlsisaiit  keqtqeeses  kskkevafss
   61sssfdfkaym  igkansvnka  ledavlvrep  lkihesmrys  llaggkrvrp  mlciaacelf
  121ggtesvamps  acavemihtm  slmhddlpcm  dnddlrrgkp  tnhkvfgedv  avlagdalla
  181fafehiatat  kgvsserivr  vvgelakcig  seglvagqvv  dvcsegiadv  glehlefihi
  241hktaallegs  vvlgaivgga  ndeqisklrk  farcigllfq  vvddildvtk  ssqelgktag
  301kdlvadkvty  pkllgidksr  efaeklnrea  qeqlaefdpe  kaaplialan  yiayrdn Geranylgeranyl pyrophosphate synthase E. herbicola
                                                              (SEQ ID NO: 57)
MVSGSKAGVSPHREIEVMRQSIDDHLAGLLPETDSQDIVSLAMREGVMAPGKRIRPL
LMLLAARDLRYQGSMPTLLDLACAVELTHTASLMLDDMPCMDNAELRRGQPTTHK
KFGESVAILASVGLLSKAFGLIAATGDLPGERRAQAVNELSTAVGVQGLVLGQFRDL
NDAALDRTPDAILSTNHLKTGILFSAMLQIVAIASASSPSTRETLHAFALDFGQAFQLL
DDLRDDHPETGKDRNKDAGKSTLVNRLGADAARQKLREHIDSADKHLTFACPQGG
AIRQFMHLWFGHHLADWSPVMKIA
```

Geranylgeranyl pyrophosphate synthase nucleic acid A. thaliana (SEQ ID NO: 26)

```
   1 ggtgagaatt tcagatttca gaaatcgcca tggcttcagt gactctaggt tcatggattg
  61 ttgttcacca ccacaatcat catcatccat cttcaatcct taccaaatcc agatccagat
 121 cttgtcctat aactcttact aaacccatct cctttcgatc aaaacgcacc gtttcatcat
 181 cttcttcaat cgtttcttct tccgttgtta caaaagaaga caatctaccg caatctgaac
 241 catcctcttt cgatttcatg tcgtacatca tcaccaaagc cgaattagtc aacaaagctt
 301 tagattcagc tgttcctctc cgtgagccac tcaagatcca cgaagcgatg agttactctc
 361 ttctcgccgg tggcaaaaga gttagaccag ttctctgcat cgctgcttgt gaactcgtcg
 421 gaggtgaaga atcaaccgct atgccagcag cagttgcgcc gt cgagatgat cacaccatgt
 481 cgttgatcca cgacgatctc ccttgtatgg ataacgacga tctccgccgt ggaaaaccga
 541 ccaaccacaa agtgtttggt gaagacgtcg ctgttttagc cggagacgcg cttctctctt
 601 tctctttcga gcatttagct tcggcgacga gttctgatgt gtttctccg gtgagagtgg
 661 ttcgagccgt tggagaattg gctaaagcga taggaacaga agggttagtg gcgggtcaag
 721 tcgtggatat tagtagtgaa gggttagatt taaacgacgt cggtttagag catttggagt
 781 ttatccattt gcataaaacg gcggcgttgc ttgaagcttc tgctgttttg ggagctattg
 841 ttggtggagg aagtgatgat gagattgaga ggttaagaaa gtttgcgaga tgtattggtt
 901 tgttgtttca ggtggttgat gatatcttgg atgtgacgaa atcgtcgaaa gagttaggga
 961 aaactgctgg gaaagatttg attgctgata agttgacgta tccta agatt atgggtttgg
1021 agaaatcgag agagtttgct gagaaattga atagagaggc tcgtgatcag cttttagggt
1081 ttgattctga taaggttgct cctttgttgg ctttggctaa ttacattgcc tatagacaga
1141 actgatttgt gttcgattcc ttttgtcggg aatcattatt agattggaat gtagaaaatc
1201 tcggacaggt tctctagagt ttgttggtgt aatcgtatcc gg
```

Geranylgeranyl pyrophosphate synthase nucleic acid O. sativa (SEQ ID NO: 28)

```
atgcacgt cctcgctcaa tccacggccg tggccaaggt cgccgcctcc
ggctgcctcc gacgaagccc gaacccctcc gtgacgttcc agatcccc ttcccttctt
ctctcgccgg ccgcgtgccg ccgccgctgc cgccgcgggt gctccgtctc cgtcgacgtg
aggtgctccc tgggcgccat ggtcacgccg gagctgaacg gcggcgacgt cggcgtcggc
gtcggcggtg gtagcttcga cttcagcgg tatctgctcg ccaggccgca cgccgtgcac
gacgcgctgg accgggccat gccgcgcggc ttccccgagc ggctctgcga gtccatgcgc
tactccgtcc tcgccggcgg caagcgggtg cgccccgtgc tcgcgctggc cgcgtgcgag
ctcgtcggcg gggacgccgc ggcggccacg cccgtcgcct cgcggtcga gatgatccac
accatgtcgc tcatccacga cgacatgccg tcatgacg acgacgccct ccgccggggc
cgccctccca accacgtcgc cttcggcgag ttcaccgccc tcctcgccgg cgacgcgctc
cacgccctcg cgttcgagca cgtgcgcgcg gctgcggcg accacggcgt ccccgcggac
cgcacgctcc gggcggtcgc cgagctcggg agcgcctcgg caccggcgg ggtcgccgcc
gggcaggtcg ccgacaagga gagcgagggc ctccccgtca gcctcgccat gctggagtac
atccacgtgc acaagacggc gaggctcctc gaggccgccg ccgtgtccgg gccatcgtc
ggcggggg cg gcgacgccga ggtggagagg tccggcggt acgcgcgctg cgtcgggctc
ctcttccagg tggtcgacga cgtgctcgac atgacgagca catcggagca gctcgggaag
acggcgggga aggacgtcga ggccgacaag gccacttacc cgaagctgct cggcgtcgac
aaggcccgcg agtacgccgc cgacctcctc gccatgacgg aggcggagtc cgacgggttc
gacgccgagc gcgccgcgcc gctgcgacac ctcgcgcggt catcgcccta caggcagcat
taa
```

Geranylgeranyl pyrophosphate synthase Catharanthus roseus (SEQ ID NO: 30)

```
   1 gaattcaatt acaacatggg ttccagccca atcaatttat tgtttggaga atggcagatc
  61 cagttctatg cgctctaatc tttgtcaccc tctcaaaaat caacttccca tttctttttt
 121 tctttcgggc acaatccgaa agcccatttt cagttgttct cgtctctcaa tttctgccat
 181 tataacgaaa gaacaaaccc aagaagagag cgaaagcaaa agcaagaaag aggtagcctt
 241 ttcttcctca tcttcatttg atttcaaggc atatatgatt ggaaaggcca attctgttaa
 301 taaggcattg gaagatgcag tcttggttag ggaacctttg aaaattcatg aatctatgag
 361 gtactcactt ctagctggtg gtaaaagagt tcgtcctatg ctctgtattg ctgcttgtga
 421 acttttggt ggaacagaat ctgttgccat gccttctgct tgtgctgttg agatgattca
 481 tactatgtct ctgatgcacg atgaccttcc ctgtatggat aatgatgatt tgagaagagg
 541 gaagccgaca aatcataagg tttttgggga ggatgttgct gttttagctg gggatgccct
 601 tcttgcattt gccttttgaac atatagcaac tgctaccaaa ggtgtctctt ccgaaagaat
 661 tgtgagagta gttggggaat tggctaagtg tattggttca gaagggctgg tggctggaca
 721 ggttgttgat gtgtgctctg agggcattgc tgatgtaggg cttgagcatt tagagttcat
 781 ccatattcac aagactgcag ctttattaga agggtctgtg gttttagggg caattgtggg
 841 ttggtgctaat gatgaacaaa tttccaaatt gaggaaattt gctaggtgta tgggggttgtt
 901 gtttcaggtt gtagatgata ttcttgatgt tactaaatct tctcaagaat taggaaaaac
 961 tgcaggaaa gacttggtgg cagataaggt cacttatcct aaacttcttg gtattgataa
1021 gtccagaaa tttgctgaga gttgaataga gaagctcaa gaacaacttg ctgagtttga
1081 tcctgaaaag gctgctccat taattgtct agcaaattac atagcctaca gagataacta
1141 ataatatgtt gtttaagtta taagagaatt tcacatttga gatagactat accaatgaaa
1201 ttagatattg ttgtcacaca agatatgagc tggtaattct ttcacattgt taatgaaat
1261 gatccgaatt c
```

Geranylgeranyl pyrophosphate synthase E. herbicola (SEQ ID NO: 58)

```
atggtg agtggcagta aagcgggcgt ttcgcctcat cgcgaaatag aagtaatgag acaatccatt gacgatcacc
tggctggcct gttacctgaa accgacagcc aggatatcgt cagccttcg atgcgtgaag gcgtcatggc acccggtaaa
cggatccgtc cgctgctgat gctgctggcc gcccgcgacc tccgctacca gggcagtatg cctacgctgc tcgatctcgc
ctgcgccgtt gaactgaccc ataccgcgtc gctgatgctc gacgacatgc cctgcatgga caacgccgag ctgcgccgcg
gtcagcccac tacccacaaa aatttggtg agagcgtggc gatccttgcc tccgttggc tgctctctaa agcctttggt
ctgatcgccg ccaccggcga tctgccgggg gagaggcgtg cccaggcggt caacgagctc tctaccgccg tgggcgtgca
gggcctggta ctgggcagt ttcgcgatct aacgatgcc gccctcgacc gtaccctga cgctatcctc agcaccaacc
```

-continued

```
acctcaagac cggcattctg ttcagcgcga tgctgcagat cgtcgccatt gcttccgcct cgtcgccgag cacgcgagag
acgctgcacg ccttcgccct cgacttcggc caggcgtttc aactgctgga cgatctgcgt gacgatcacc cggaaaccgg
taaagatcgc aataaggacg cgggaaaatc gacgctggtc aaccggctgg gcgcagacgc ggcccggcaa aagctgcgcg
agcatattga ttccgccgac aaacacctca cttttgcctg tccgcagggc ggcgccatcc gacagtttat gcatctgtgg
tttggccatc accttgccga ctggtcaccg gtcatgaaaa tcgcctga
```

Methods for introducing one or more nucleic acids that encode a geranylgeranyl pyrophosphate synthase protein into a bacterium or yeast cell are described herein.

Phytoene Synthase (CrtB)

Non-limiting examples of phytoene synthase proteins are described herein (see, FIG. 9). Additional examples of phytoene synthase proteins are known in the art. Methods for determining the ability of a phytoene synthase protein to convert geranylgeranyl pyrophosphate to phytoene are known in the art (see, e.g., Fraser et al., *Plant Cell* 19:3194-3211, 2007).

In some embodiments, a phytoene synthase protein can contain one or more (e.g., two, three, four, five, six, seven, eight, nine, or ten) additions, insertions, substitution, or deletions as compared to a corresponding wild type phytoene synthase protein. For example, a phytoene synthase protein can contain one or more substitutions at amino acid positions that are not conserved among wild type phytoene synthase proteins (see, e.g., the amino acid positions that are not conserved in FIG. 9).

In some embodiments, the phytoene synthase protein is at least 80% identical (e.g., at least 85%, 90%, 95%, or 100%) identical to any one of SEQ NO: 31, 33, 35, and 59.

In some embodiments, a nucleic acid encoding a phytoene synthase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type phytoene synthase protein (e.g., SEQ ID NO: 32, 34, 36, and 60). Percent identity can be determined using a number of molecular biology tools, e.g., BLAST program available at the NCBI website. In some embodiments, the phytoene synthase protein contains the sequence of a wild type phytoene synthase protein (e.g., a protein containing the sequence of SEQ ID NO: 31, 33, 35, and 59).

Non-limiting examples of nucleic acid sequences that encode a wild type phytoene synthase protein are shown herein (e.g., SEQ ID NOS: 32, 34, 36, and 60). Additional examples of nucleic acid sequences that encode a wild type phytoene synthase are known in the art. In some embodiments, the nucleic encodes that encodes a phytoene synthase protein that contains a sequence that is at least 80% identical (e.g., at least 85%, 90%, 95%, or 100% identical) to one of SEQ ID NOS: 31, 33, 35, and 59. In some embodiments, the nucleic acid contains a sequence that is at least 80% identical (e.g., at least 85%, 90%, 95%, or 100%) identical to any one of SEQ NO: 32, 34, 36, and 60.

Phytoene synthase protein *A. thaliana*

(SEQ ID NO: 31)
```
msssvavlwv atsslnpdpm nncglvrvle ssrlfspcqn qrlnkgkkkq
iptwsssfvr nrsrrigvvs sslvaspsge ialsseekvy nvvlkqaalv
nkqlrsssyd ldvkkpqdvv lpgslsllvg eaydrcgevc aeypktfylg
tllmtperrk aiwaiywcr rtdelvdgpn ashitpmald rwearledlf
rgrpfdmlda aladtvaryp vdiqpfrdmi egmrmdlkks ryqnfddlyl
ycyyvagtvg lmsvpvmgid pkskattesv ynaalalgia nqltnilrdv
gedarrgrvy lpqdelaqag lsdedifagk vtdkwrnfmk mqlkrarmff
deaekgvtel saasrwpvwa slllyrrild eieandynnf tkrayvgkvk
kiaalplaya ksvlktsssr lsi
```

Phytoene synthase protein *O. sativa*

(SEQ ID NO: 33)
```
  1 maaitllrsa slpglsdala rdaaavqhvc ssylpnnkek krrwilcslk yaclgvdpap
 61 geiartspvy ssltvtpage avisseqkvy dvvlkqaall krhlrpqpht ipivpkdldl
121 prnglkqayh rcgeiceeya ktfylgtmlm tedrrraiwa iyvwcrrtde lvdgpnashi
181 tpsaldrwek rlddlftgrp ydmldaalsd tiskfpidiq pfrdmiegmr sdlrktrykn
241 fdelymycyy vagtvglmsv pvmgiapesk attesvysaa lalgianqlt nilrdvgeda
301 rrgriylpqd elaeaglsde difngvvtnk wrsfmkrqik rarmffeeae rgvtelsqas
361 rwpvwaslll yrqildeiea ndynnftkra yvgkakklla lpvaygrsll mpyslrnsqk
```

Phytoene synthase protein *P. trichocarpa*

(SEQ ID NO: 35)
```
  1 leeayercrn icaeyaktfy lgtrlmteer qkatwaiyvw crrtdelvdg pnavlmstav
 61 ldrweerlqd ifdgrpydml daaltdtisk fpldikpfrd miegmrmdtr kfrydnfqel
121 ylycyyvagt vglmsvpvmg iaaeseasaq siynaalylg ignqltnilr dvgedalrgr
181 vylpqdelaq fglcdqdvfa rkvtdgwref mkeqiirarf yfnlaeegas klekasrwpv
241 wssllvyqki ldaiedndyd nftkrayvgr tkklltlpla ytka
```

Phytoene synthase protein *E. herbicola*

(SEQ ID NO: 59)
```
MSQPPLLDHATQTMANGSKSFATAAKLFDPATRRSVLMLYTWCRHCDDVIDDQTH
GFASEAAAEEEATQRLARLRTLTLAAFEGAEMQDPAFAAFQEVALTHGITPRMALD
HLDGFAMDVAQTRYVTFEDTLRYCYHVAGVVGLMMARVMGVRDERVLDRACDL
GLAFQLTNIARDIIDDAAIDRCYLPAEWLQDAGLTPENYAARENRAALARVAERLID
AAEPYYISSQAGLHDLPPRCAWAIATARSVYREIGIKVKAAGGSAWDRRQHTSKG
EKIAMLMAAPGQVIRAKTTRVTPRPAGLWQRPV
```

Phytoene synthase nucleic acid *A. thaliana*

(SEQ ID NO: 32)

```
   1 cttccgaccg tgtacatata ttacagtaag cgttgcaaca caacttcttg aggatcttct
  61 cacattaatg ggtcaaacct tttgctcttc cttttgatta atttagtgtt tgacaatctc
 121 ctcctccttc tccttcttct tcaaagtttt gtcgcagtat ctattgttct tacagagaga
 181 aaggaaagct ttagtctttt accagtttga tccaattctg ggtttcactg aaaaaaagtt
 241 gggagtttga ttcttctaac tgtagaagaa acagagtcaa cagaagaaaa ctaaaaaagt
 301 tgagattttt ctctcacgcg ctcaagaact tgagtatgtc ttcttctgta gcagtgttat
 361 gggttgctac ttcttctcta aatccagacc caatgaacaa ttgtgggttg gtaagggttc
 421 tagaatcttc tagactgttc tctccttgtc agaatcagag actaaacaaa ggtaagaaga
 481 agcagatacc aacttggagt tcttctttg taaggaaccg aagtagaaga attggtgttg
 541 tgtcttcaag cttagtagca agtccttctg gagagatagc tctttcatct gaagagaagg
 601 tttacaatgt tgtgttgaaa caagctgctt tggtgaacaa acagctaagg tcttcttctt
 661 atgaccttga tgtgaagaaa ccacaagatg ttgttcttcc tgggagtttg agtttgttgg
 721 tgggtgaagc ttatgatcga tgcggtgaag tttgcgctga atatcctaag acgttttatc
 781 ttggaacttt gctatgaca cccgaaaggc gaaaggcgat ttgggcaatc tacgtttggt
 841 gtagaagaac tgatgaactt gtggatgggc caaatgcttc acatataact cccatggctt
 901 tagatagatg ggaagcaagg ttagaagatc ttttccgtgg tcgtccttc gatatgcttg
 961 atgctgctct cgctgataca gttgctagat acccggtcga tattcagcca tttcgagaca
1021 tgatcgaagg aatgagaatg gacttgaaga aatcgagata ccagaacttc gatgatctat
1081 acctttactg ctactacgtc gctggaaccg tcggattgat gagcgttccg gttatgggaa
1141 tcgatcctaa gtccgaaagca caaaccgaaa gtgtttacaa cgctgccttg gcccttggta
1201 tagccaatca gcttactaac atactcagag acgtaggcga agatgcgaga agaggaaggg
1261 tttatctgcc tcaggatgaa ttggctcagg ctggtctttc agatgaagac atattcgccg
1321 gaaaagtaac tgataaatgg agaaacttca tgaaaatgca gcttaaacga gcaagaatgt
1381 tcttcgacga agctgagaaa ggcgtcaccg agctcagtgc cgctagcaga tggcctgtat
1441 gggcttcatt gctattgtac aggagaatac tggacgagat tgaagcgaat gattacaaca
1501 attttactaa gagagcttat gtggggaaag tcaagaaaat tgcagctttg ccattggctt
1561 atgctaaatc agtactaaag acttcaagtt caagactatc gatatgagag cgagaggaaa
1621 gtggaacaaa aacaacctaa gagcgctttt tgtgattaag aaaaaaactta ggctcgaatt
1681 tcttatgtta actaatatat acatattaat ggggaagcaa attcttataa tgttacatta
1741 tctttctgaa tgtaaaaaag tattttttt
```

Phytoene synthase nucleic acid *O. sativa*

(SEQ ID NO: 34)

```
   1 atggcggcca tcacgctcct acgttcagcg tctcttccgg gcctctccga cgccctcgcc
  61 cgggacgctg ctgccgtcca acatgtctgc tcctcctacc tgcccaacaa caaggagaag
 121 aagaggaggt ggatcctctg ctcgctcaag tacgcctgcc ttggcgtcga ccctgccccg
 181 ggcgagattg cccggacctc gccggtgtac tccagcctca ccgtcacccc tgctggagag
 241 gccgtcatct cctcggagca gaaggtgtac gacgtcgtcc tcaagcaggc agcattgctc
 301 aaacgccacc tgcgccaca accacacacc attcccatcg ttcccaagga cctgacctg
 361 ccaagaaacg gcctcaagca ggcctatcat cgctgcggag agatctgcga ggagtatgcc
 421 aagacctttt accttggaac tatgctcatg acggaggacc gacggcgcgc catatgggtg
 481 atctatgtgt ggtgtaggag acagatgag cttgtagatg gaccaaatgc ctcgcacatc
 541 acaccgtcag ccctggaccg gtgggagaag aggcttgatg atctcttcac cggacgcccc
 601 tacgacatgc ttgatgctgc actttctgat accatctcca agtttcctat agatattcag
 661 ccttttcaggg acatgataga agggatgcgc tcagacctca gaaagactag atacaagaac
 721 ttcgacgagc tctacatgta ctgctactat gttgctggaa ctgtggggct aatgagtgtt
 781 cctgtgatgg gtattgcacc cgagtcgaag gcaacaactg aaagtgtgta cagtgctgct
 841 ttggctctcg gcattgcaaa ccagctcaca aatatactcc gtgacgttgg agaggacgcg
 901 agaagaggga ggatatattt accacaagat gaacttgcag aggcagggcct ctcgatgag
 961 gacatcttca tggcgttgt gactaacaaa tggagaagct tcatgaagag acagatcaag
1021 agagctagga tgttttttga ggaggcagag agaggggtga ccgagctcag ccaggcaagc
1081 cggtggccgc tctgggcgtc tctgttgtta taccggcaaa tccttgacga gatagaagca
1141 aacgattaca acaacttcac aaagagggcg tacgttggga aggcgaagaa attgctagcg
1201 cttccagttg catatggtag atcattgctg atgcccact cactgagaaa tagccagaag
1261 tag
```

Phytoene synthase nucleic acid *P. trichocarpa*

(SEQ ID NO: 36)

```
   1 cttgaagaag cctatgaaag gtgcagaaac atttgcgccg aatatgccaa gactttctat
  61 ctaggaactc ggctgatgac agaggagcga cagaaagcca catgggcaat ttatgtatgg
 121 tgcaggagga cagatgagct ggtcgatgga cctaatgcag tgctcatgag cactgctgtt
 181 cttgataggt gggaagagag gctgcaagac atctttgatg agccccta tgactgctc
 241 gatgctgcac ttactgatac aatttccaag ttccctttag acattaagcc tttagggac
 301 atgattgaag gtatgagaat ggatacgaga aaattccgtt acgataattt tcaagagctc
 361 tatctttatt gctattacgt tgcgggcaca gtcggcctaa tgagcgttcc agtgatggga
 421 attgcagcag aatctgaagc ttctgctcaa agtatttata atgcggcact gtacttggt
 481 attggaaacc agcttacaaa cattcttaga gatgtgggag aggatgcttt gagagggaga
 541 gttttatctac cacaagatga gcttgcacag tttgggctat gcgaccaaga tgttttcgca
 601 agaaaagtca ctgatggatg agagagttc atgaaggagc agataataag ggcaagattc
 661 tatttcaacc ttgcagaaga aggggcttca aagcttcaaa aggctagccg gtggccagta
 721 tggtcatccc tactagtata ccaaaaaatc ttggatgcaa ttgaggataa tgattatgat
 781 aacttcacaa aacgagctta tgttggaaga caaagaaaac ttctcacatt gccctggca
 841 tacacaaaag ct
```

Phytoene synthase nucleic acid *E. herbicola*

(SEQ ID NO: 60)

```
atgagccaac cgccgctgct tgaccacgcc acgcagacca tggccaacgg ctcgaaaagt tttgccaccg ctgcgaagct
gttcgacccg gccaccccgcc gtagcgtgct gatgctctac acctggtgcc gccactgcga tgacgtcatt gacgaccaga
cccacggctt cgccagcgag gccgcggcgg aggaggaggc cacccagcgc ctggcccggc tgcgcacgct
```

-continued

```
gaccctggcg gcgtttgaag gggccgagat gcaggatccg gccttcgctg cctttcagga ggtggcgctg acccacggta
ttacgccccg catggcgctc gatcacctcg acggctttgc gatggacgtg gctcagaccc gctatgtcac ctttgaggat
acgctgcgct actgctatca cgtggcgggc gtggtgggtc tgatgatggc cagggtgatg ggcgtgcggg atgagcgggt
gctggatcgc gcctgcgatc tggggctggc cttccagctg acgaatatcg cccgggatat tattgacgat gcggctattg
accgctgcta tctgcccgcc gagtggctgc aggatgccgg gctgaccccg gagaactatg ccgcgcggga gaatcgggcc
gcgctggccgc gggtggcgga gcggcttatt gatgccgcag agccgtacta catctcctcc caggccgggc tacacgatct
gccgccgcgc tgcgcctggg cgatcgccac cgcccgcagc gtctaccggg agatcggtat taaggtaaaa gcggcgggag
gcagcgcctg ggatcgccgc cagcacacca gcaaaggtga aaaaattgcc atgctgatgg cggcaccggg gcaggttatt
cgggcgaaga cgacgagggt gacgccgcgt ccggccggtc tttggcagcg tcccgtttag
```

Methods for introducing one or more nucleic acids that encode a phytoene synthase protein into a bacterium or yeast cell are described herein.

Phytoene Desaturase (Crtl)

Non-limiting examples of phytoene desaturase proteins are described herein (see, FIG. 10). Additional examples of phytoene desaturase proteins are known in the art. Methods for determining the ability of a phytoene desaturase protein to convert phytoene to lycopene are known in the art (see, e.g., Xu et al., *Microbiology* 153:1642-1652, 2007).

In some embodiments, a phytoene desaturase protein can contain one or more (e.g., two, three, four, five, six, seven, eight, nine, or ten) additions, insertions, substitution, or deletions as compared to a corresponding wild type phytoene desaturase protein. For example, a phytoene desaturase protein can contain one or more substitutions at amino acid positions that are not conserved among wild type phytoene desaturase proteins (see, e.g., the amino acid positions that are not conserved in FIG. 10).

In some embodiments, the phytoene desaturase protein is at least 80% identical (e.g., at least 85%, 90%, 95%, or 100%) identical to any one of SEQ NO: 37 and 39.

In some embodiments, a nucleic acid encoding a phytoene desaturase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type phytoene desaturase protein (e.g., SEQ ID NO: 38, 40, 42, and 62). Percent identity can be determined using a number of molecular biology tools, e.g., BLAST program available at the NCBI website. In some embodiments, the phytoene desaturase protein contains the sequence of a wild type phytoene desaturase protein (e.g., a protein containing the sequence of SEQ ID NO: 37 or 39).

Non-limiting examples of nucleic acid sequences that encode a wild type phytoene desaturase protein are shown herein (e.g., SEQ ID NOS: 38 and 40). Additional examples of nucleic acid sequences that encode a wild type phytoene desaturase are known in the art. In some embodiments, the nucleic encodes a phytoene desaturase protein that contains a sequence that is at least 80% identical (e.g., at least 85%, 90%, 95%, or 100% identical) to one of SEQ ID NOS: 37 or 39. In some embodiments, the nucleic acid contains a sequence that is at least 80% identical (e.g., at least 85%, 90%, 95%, or 100%) identical to any one of SEQ NO: 38 and 40.

```
Phytoene desaturase protein E. longus
                                                               (SEQ ID NO: 37)
    1 mnadqniatg lnfapantge rginpviaek ykgrtacvig sgfgglalal rlqshgiqtt
   61 iveardkpgg rayfwekdgf tfdagptvit dppclkelwe ltghdisedv elmkvhpfyr
  121 lnwpdgtnfd ysnvdeelna eiaklnpddv igyqkfleys arvheegyvk lgtvpfldfk
  181 smlkaapalv kerawrsvyd mvssyikder lreafsfhtl lvggspmkts aiyalihkle
  241 kdggvwwarg gtnrliagmv rhferlggtm rigdpvvqvh tqgtkateve tksgwkerfd
  301 avcsnadimh sykellgesd rgrkyaksla rksyspslfv vhfglegswp giahhmilfg
  361 prykelvddi ykhgvlpqdf siylhhptvt dpsmapkgms tfyalvpvah lgkmpidwdv
  421 egpkfekail deigrrlipd ihdrivtkfs yapkdfqadl nahmgsafsl etvlwqsaym
  481 rghnrddvid nfylvgagth pgagipgvvg sakataglml edlsvk Phytoene desaturase protein E. herbicola
                                                               (SEQ ID NO: 39)
MKKTVVIGAGFGGLALAIRLQAAGIPTVLLEQRDKPGGRAYVWHDQGFTFDAGPTV
ITDPTALEALFTLAGRRMEDYVRLLPVKPFYRLCWESGKTLDYANDSAELEAQITQF
NPRDVEGYRRFLAYSQAVFQEGYLRLGSVPFLSFRDMLRAGPQLLKLQAWQSVYQS
VSRFIEDEHLRQAFSFHSLLVGGNPFTTSSIYTLIHALEREWGVWFPEGGTGALVNGM
VKLFTDLGGEIELNARVEELVVADNRVSQVRLADGRIFDTDAVASNADVVNTYKKL
LGHHPVGQKRAAALERKSMSNSLFVLYFGLNQPHSQLAHHTICFGPRYRELIDEIFTG
SALADDFSLYLHSPCVTDPSLAPPGCASFYVLAPVPHLGNAPLDWAQEGPKLRDRIF
DYLEERYMPGLRSQLVTQRIFTPADFHDTLDAHLGSAFSIEPLLTQSAWFRPHNRDSD
IANLYLVGAGTHPGAGIPGVVASAKATASL Phytoene desaturase protein R. sphaeroides
                                                               (SEQ ID NO: 41)
    1 mpsispasda dralvigsgl gglaaamrlg akgwrvtvid kldvpggrgs sitqeghrfd
   61 lgptivtvpq slrdlwktcg rdfdadvelk pidpfyevrw pdgshftvrq steamkaeva
  121 rlspgdvagy ekflkdsekr ywfgyedlgr rsmhklwdli kvlptfgmmr adrtvyqhaa
  181 lrvkderlrm alsfhplfig gdpfnvtsmy ilvsqlekef gvhyaiggva aiaaamakvi
  241 egqggsfrmn tevdeilvek gtatgvrlas gevlraglvv snadaghtym rllrnhprrr
  301 wtdahvksrr wsmglfvwyf gtkgtkgmwp dvghhtivna prykglvedi flkgklakdm
  361 slyihrpsit dptvapegdd tfyalspvph lkqaqpvdwq avaepyresv levleqsmpg
  421 igerigpslv ftpetfrdry lspwgagfsi eprilqsawf rphniseeva nlflvgagth
  481 pgagvpgvig saevmaklap daprarreae paerlaae
```

Phytoene desaturase nucleic acid *E. longus*

(SEQ ID NO: 38)

```
   1 atgaacgccg atcaaaacat cgctacaggg ctcaactttg cgccagccaa tactggcgag
  61 cgcggcatta atccggtgat cgccgaaaaa tacaaaggcc gcaccgcctg tgtgatcggt
 121 tccggttttg gcggcttggc gctagcactg cggctgcaat cgcatggcat tcaaacgacc
 181 atcgtcgaag cgcgcgacaa gcccggtggc cgcgccatt tctgggaaaa agacggcttt
 241 accttcgatg ctggccccac ggtcatcacc gacccgccgt gtttgaaaga actgtgggag
 301 ctgaccggcc acgacatttc cgaagatgtc gagctgatga aggttcaccc tttctaccgc
 361 ctcaactggc ccgatggcac aaacttcgat tattcgaacg ttgatgagga attgaacgcc
 421 gaaatcgcga agctcaatcc tgacgatgtg atcgcctatc aaaaattcct cgaatattcg
 481 gcgcgcgtgc acgaggaagg ctatgtgaag cttggcacgg tgccgttcct cgatttcaag
 541 tcgatgctga agccgccccc tgcccttgtt aaagagcgcg catggcgcag cgtttacgat
 601 atggtctcaa gctacatcaa ggatgagcgc ctgcgcgaag cgttcagctt ccacacgctg
 661 cttgtcggcg gctcgccgat gaagaccagc gccatttatg cgttgatcca caagcttgaa
 721 aaagacggcg tgtctggtg ggcgcgcggc gggaccaacc ggttgatcgc cggaatggtg
 781 cgccattttg aacgcctcgg cggcacgatg cgcatcggcg atccggtggt tcaggtccac
 841 acccaaggga ccaaagcgac cgaggttgaa acgaagagcg gttggaaaga gcgctttgac
 901 gcggtgtgtt caaacgccga catcatgcac tcttacaagg aacttctggg cgaatccgac
 961 cgtggcagaa aatacgctaa gtcattggct cgcaaaagct attcgccttc gctattcgtc
1021 gtacactttg gcttgagggg gtcgtggccc ggtattgccc accacatgat cctgtttggc
1081 ccacgttaca aggaactggt cgacgacatc tacaagcacg cgttctgcc gcaggatttt
1141 tcgatctatc ttcaccaccc gaccgtcacc gacccatcga tggcgccaa gggcatgag
1201 acattctacg cgcttgtccc cgtcgcccac cttggcaaga tgccgattga ttgggacgtc
1261 gaaggaccca agtttgaaaa ggcgattttg gacgagatcg gtcgccgcct gatccccgac
1321 atccacgacc ggatcgtcac caaattcagc tacgcaccaa aggactttca ggcagacctc
1381 aacgccata tgggcagcgc gttcagcctt gagacggtcc tgtggcaaag cgcctacatg
1441 cgcggccaca accgcgacga tgtgatcgac aatttctacc tcgtgggcgc agggacacac
1501 ccgggcgctg gtatcccgg agtggtcggt agcgcgaagg caacggcggg gctgatgctt
1561 gaagatctgt cggtcaaata a
```

Phytoene desaturase nucleic acid *E. herbicola*

(SEQ ID NO: 40)

```
atgaa aaaaaccgtt gtgattggcg caggctttgg tggcctggcg ctggcgattc gcctgcaggc ggcagggatc
ccaaccgtac tgctggagca gcgggacaag cccggcggtc gggcctacgt ctggcatgac cagggcttta cctttgacgc
cgggccgacg gtgatcaccg atcctaccgc gcttgagcgc tgttcaccca tggccggcag gcgcatggag gattacgtca
ggctgctgcc ggtaaaaccc ttctaccgac tctgctggga gtccgggaag acctgcgact atgctaacga cagcgccgag
cttgaggcgc agattaccca gttcaaacccc gcgacgtcg agggctaccg gcgctttctg gcttactccc aggcggtatt
ccaggaggga tatttgcgcc tcggcagcgt gccgttcctc tcttttcgcg acatgctgcg cgccgggccg cagctgctta
agctccaggc gtggcagagc gtctaccagt cggtttcgcg ctttattgag gatgagcatc tgcggcaggc cttctcgttc
cactccctgc tggtaggcgg caaccccttc accacctcgt ccatctacac cctgatccac gccttgagc ggagtgggg
ggtctggttc cctgagggcg gcaccggggc gctggtgaac ggcatggtga gctgtttac cgatctgggc ggggagatcg
aactcaacgc ccgggtcgaa gagctggtgg tgccgataa ccgcgtaagc caggtccggc tggcggatgg tcggatcttt
gacaccgacg ccgtagcctc gaacgctgac gtggtgaaca cctataaaaa gctgctggcc caccatccgg tggggcagaa
gcgggcggca cgctggagc gcaagagcat gagcaactcg ctgtttgtgc tctacttcgg cctgaaccag cctcattccc
agctggcgca ccataccatc tgttttggtcccgctaccg ggagctgatc gacagagatct ttaccggcag cgcgctggcg
gatgacttct cgctctacct gcactcgccc tgcgtgaccg atccctcgct cgcgcctccc ggctgcgcca gcttctacgt
gctgccccg gtgccgcatc ttggcaacgc gccgctgac tgggcgcag aggggcgaa gctgcgcgac cgcatctttg
actaccttga agagcgctat atgccggcc tgcgtagcca gctggtgacc cagcggatct ttaccccggc agacttccac
gacacgctga atgcgcatct gggatcggcc ttctccatcg agccgctgct gacccaaagc gcctggttcc gcccgcacaa
ccgcgacagc gacattgcca acctctacct ggtgggcgca ggtactcacc ctggggcggg cattcctggc gtagtggcct
cggcgaaagc caccgccagc ctga
```

Phytoene desaturase nucleic acid *R. sphaeroides*

(SEQ ID NO: 42)

```
ttgt aaacctgact agacagtcta ttgtatgggg catgttgaca agcactgcag gagttcgcgc catgccttcg atctcgcccg
cctccgacgc cgaccgcgcc cttgtgatcg gctccggact gggggggcctt gcggctgcga tgcgcctcgg cgccaagggc
tggcgcgtga cggtcatcga caagctcgac gttccgggcg gccgcggctc ctcgatcacg caggagggc
accggttcga tctgggaccc accatcgtga cggtgccgca gagcctcgcg gacctgtgga agacctgcgg gcgggacttc
gacgccgatg tcgagctgaa gccgatcgat ccgttctacg aggtgcgctg gccggacggg tcgcacttca cggtgcgcca
gtcgaccgag gcgatgaagg ccgagctcgc gcgcctctcg gcgcgcgtgt tggccggtca cgagaagttc ctgaaggaca
gcgaaaagcg ctactggttc ggttacgagg atctcggccg ccgctcgatg cacaagctgt gggatctcat caaggtgctg
cccaccttcg gatgatgcg ggccgaccgt acggtctacc agcacgccgc gcttcgggtg aaggacgagc ggctgcgcat
ggcgctctcg ttccacccgc tcttcatcgg cggcgacccc ttcaacgtga cctcgatgta tatccttgtg agccagctcg
agaaggagtt cggcgtccat tatgccgatc gcggcgtggc ggccatcgcc gcggccatgg cgaaggtgat cgagggcgaa
ggcggcagct tccgcatgaa caccgaggtg gacgagatcc tcgtcgagaa gggcaccgcc accggtgtgc ggctcgcctc
gggcgaggtg ctgcgggcgg tctcgtggt ctcgaatgcg gatgcggcc atacctacat gcggcttctg cgtaaccatc
cgcgcccgcc ctggaccgac gccccatgtga agagccggcg ctggtcgatg gggctgttcg tctggtattt cggaacgaag
gggacgaagg gcatgtggcc cgacgtcggc caccacacga tcgtcaatgc gccgcgctac aagggcgtga tcgaaggaca
cttcctcaag ggcaagctcg cgaaggacat gagcctctat atccaccggc cctcgatcac cgatccgacc gtgcgcccg
aggggggatga cacgttctat cgcgctctcg ccgtgccgca tctgaaacag gcgcaaccgg tggactggca ggctgtggcc
gagcccctacc gcgaaagcgt gctcgaggtg ctcgaacagt cgatgccggg gatcgggaa cggatcgggc cctcgctcgt
cttcacccccc gagaccttcc gcgaccgcta cctcagccgc tcgggcgtag gcttctcgat cgagccgcag atcctgcagt
cggcctggtt ccgccgcac aacatttccg aggaggtggc gaacctgttc ctcgtgggcg cgggcacccca tcccggtgg
ggcgtgcccg cgtgatcgg ttcggccgaa gtgatggcca gcttgccccc cgatgcgcca cgtgcgcgcc gcgaggccga
acctgctgaa aggcttgccg cggaatgatt gcctctgccg atctcgatgc ctgccggag atgatccgca ccggctccta
ttccttccat gccgcgtccc gcctgctgcc cgagccgcgt cgcgccgtgc cgctggcgct ctatgccttc tgccgcgtgg
ccgacgatgc ggtcgacgag gcggtgaacg atggacgatg cgaggaggat gccgaggtca agccgccgc
cgtcctgagc ctgcgcgacc ggctggacct cgtctatggc ggccgccgc gcaatgcgcc ggcgaccgc gccttcgccg
cggtggtcga ggagttcgag atgccccggg cgctgcccga ggcgctgctc gagggggctcg cctgggacgc
ggtgggggcgg agctacgaca gtttctcggg cgtgctcgac tattcggcgc gggtggccgc ggcggtgggg gcgatgatgt
gcgtcctcat gcgggtgcgc gatccgacg tgctggcccg ggcctgcgat ctgggcctcg ccatgcagct caccaacatc
```

-continued
```
gcccgcgacg tggggaccga cgcgcgctcg ggacggatct atctgccgcg cgactggatg gaggaggagg
ggctgccggt cgaggagttc ctcgcccggc cggtggtcga cgaccgcatc cgcgcggtga cgcaccgcct
gctgcgcgcg gccgaccggc tctatctgcg ttcggaagcg ggggtctgcg gcctgcctct ggcctgccgg cccggcatct
atgccgcgcg ccacatctat gcgggtatcg gcgacgagat cgcgcggaac ggctatgaca gcgtgacgcg ccgcgccttc
accacgcggc gccagaagct cgtctggctc gggctctctt ccacacgcgc ggccctcagc ccgttcggcc ccggctgcgc
cacgctgcat gcggcgcccg agcccgaagt ggccttcctc gtcaatgccg ccgcccgggc ccggccgcag cgcggccgct
ccgaggcgct gatctcggtt ctggcccagc tcgaggcgca ggatcggcag atctcgcggc agcgactggg gaaccgggcc
aacccgatct aggttctcat gccggtatac cggagtaacg atgatgaaca tggactgggc tctttcctc accttcctcg
ctgcctgcgg cgcgcccgcg acgacggggg cgttgctgaa gcccgatgaa tggtacgaca atctgaacaa gccctggtgg
```

Methods for introducing one or more nucleic acids that encode a phytoene synthase protein into a bacterium or yeast cell are described herein.

Lycopene β-Cyclase (CrtY)

Non-limiting examples of lycopene β-cyclase proteins are described herein (see, FIGS. 11 and 12). Additional β-cyclase proteins (see, e.g., the amino acid positions that are not conserved in FIGS. 11 and 12).

In some embodiments, the lycopene β-cyclase protein is at least 80% identical (e.g., at least 85%, 90%, 95%, or 100%) identical to any one of SEQ NO: 45, 47, 49, 63, 65, and 66).

Lycopene β-cyclase protein A. thaliana
(SEQ ID NO: 45)
```
  1 mdtllktpnk ldffipqfhg ferlcsnnpy hsrvrlgvkk raikivssvv sgsaalldlv
 61 petkkenldf elplydtsks qvvdlaivgg gpaglavaqq vseaglsvcs idpspkliwp
121 nnygvwvdef eamdlldcld ttwsgavvyv degvkkdlsr pygrvnrkql kskmlqkcit
181 ngvkfhqskv tnvvheeans tvvcsdgvki qasvvldatg fsrclvqydk pynpgyqvay
241 givaevdghp fdvdkmvfmd wrdkhldsyp elkernskip tflyampfss nrifleetsl
301 varpglrmed iqermaarlk hlginvkrie edercvipmg gplpvlpqrv vgiggtagmv
361 hpstgymvar tlaaapivan aivrylgsps snslrgdqls aevwrdlwpi errrqreffc
421 fgmdillkld ldatrrffda ffdlqphywh gflssrlflp ellvfglslf shasntsrle
481 imtkgtvpla kminnlvqdr d
```

Lycopene β-cyclase protein O. sativa
(SEQ ID NO: 47)
```
  1 mattalllra hpsckppppp spsprptral vcraaaagea lrslappsrp ellsldlpry
 61 dparstpvdl avvgggpagl avaqrvaeag lsvcaidpsp alvwpnnygv wvdefdamgl
121 shcldavwps atvfthddga akslhrpyar varrklkstm mdrcvahgvt fhkarvvkav
181 hgeasslllic ddgvavpatv vldatgfsrc lvqydkpydp gyqvaygila evdghpfdid
241 kmlfmdwrda hlpegseire rnrriptfly ampfsptrif leetslvarp glamddiqer
301 maarlrhlgi rvraveeder cvipmggplp vlpqrvvgig gtagmvhpst gymvartlat
361 apivadaivr fldtgsgdsa fagdalsaev wrelwpaqrr rqreffcfgm dillkldldg
421 trrffdaffd leprywhgfl ssrlflpela mfglslfaka sntsrleima kgtaplakmi
481 gnliqdrdr
```

Lycopene β-cyclase protein N. tabacum
(SEQ ID NO: 49)
```
  1 mdtllktpnk leflhpvhgf svkassfnsv kphkfgsrki cenwgkgvcv kakssallel
 61 vpetkkenld felpmydpsk glvvdlavvg ggpaglavaq qvseaglsvv sidpspkliw
121 pnnygvwvde feamdlldcl datwsgtvvy idddnttkdld rpygrvnrkq lkskmmqkci
181 lngvkfhhak vikviheeak smlicndgvt iqatvvldat gfsrclvqyd kpykpgyqva
241 ygilaeveeh pfdtskmvlm dwrdshlgnn melkernrkv ptflyampfs snkifleets
301 lvarpglrmd diqermvarl nhlgikvksi eedehcvipm ggslpvipqr vvgtggtagl
361 vhpstgymva rtlaaapvva naiihylgse kdllgnelsa avwkdlwpie rrrqreffcf
421 gmdillkldl patrrffdaf fdleprywhg flssrlylpe liffglslfs rasntsriei
481 mtkgtlplvn minnllqdte
```

Lycopene β-cyclase protein E. herbicola
(SEQ ID NO: 63)
```
MRDLILVGGGLANGLIAWRLRQRYPQLNLLLIEAGEQPGGNHTWSFHEDDLTPGQH
AWLAPLVAHAWPGYEVQFPDLRRRLARGYYSITSERFAEALHQALGENIWLNCSVS
EVLPNSVRLANGEALLAGAVIDGRGVTASSAMQTGYQLFLGQQWRLTQPHGLTVPI
LMDATVAQQQGYRFVYTLPLSADTLLIEDTRYANVPQRDDNALRQTVTDYAHSKG
WQLAQLEREETGCLPITLAGDIQALWADAPGVPRSGMRAGLFHPTTGYSLPLAVAL
ADAIADSPRLGSVPLYQLTRQFAERHWRRQGFFRLLNRMLFLAGREENRWRVMQRF
YGLPEPTVERFYAGRLSLFDKARILTGKPPVPLGEAWRAALNHFPDRRDKG
``` examples of lycopene cyclase proteins are known in the art. Methods for determining the ability of a lycopene cyclase protein to convert lycopene to β-carotene are known in the art (see, e.g., Yu et al., J. Biol. Chem. 285:12109-12120, 2010).

In some embodiments, a lycopene β-cyclase protein can contain one or more (e.g., two, three, four, five, six, seven, eight, nine, or ten) additions, insertions, substitution, or deletions as compared to a corresponding wild type lycopene β-cyclase protein. For example, a lycopene β-cyclase protein can contain one or more substitutions at amino acid positions that are not conserved among wild type lycopene In some embodiments, a nucleic acid encoding a lycopene β-cyclase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type lycopene β-cyclase protein (e.g., SEQ ID NO: 46, 48, 50, and 64). Percent identity can be determined using a number of molecular biology tools, e.g., BLAST program available at the NCBI website. In some embodiments, the lycopene β-cyclase protein contains the sequence of a wild type lycopene β-cyclase protein (e.g., a protein containing the sequence of SEQ ID NO: 45, 47, 49, 63, 65, and 66).

Non-limiting examples of nucleic acid sequences that encode a wild type lycopene β-cyclase protein are shown herein (e.g., SEQ ID NOS: 46, 48, 50, and 64). Additional examples of nucleic acid sequences that encode a wild type lycopene β-cyclase are known in the art. In some embodiments, the nucleic encodes a lycopene β-cyclase protein that contains a sequence that is at least 80% identical (e.g., at least 85%, 90%, 95%, or 100% identical) to one of SEQ ID NOS: 45, 47, 49, 63, 65, and 66. In some embodiments, the nucleic acid contains a sequence that is at least 80% identical (e.g., at least 85%, 90%, 95%, or 100% identical) to any one of SEQ NO: 46, 48, 50, and 64.

Lycopene β-cyclase nucleic acid A. thaliana (SEQ ID NO: 46)

```
   1 gagtttgaaa gatttgcttt tgtgttcaaa atccactctt ttatcttatt acattttgcc
  61 tctagttttg gatttacaag agttggtgaa acacaatgca gcacaaagta ttaattttaa
 121 tgaactagta gtaacaattt gatttcacaa ggattcaggt tatgatctgt ggtttataca
 181 caattatcca acgacttgca atgcggatat actactggtc aagaaccaaa gaacagatgt
 241 acttatatgt ctaagtttct ggtccttagt ctctatcttg taccaaattg ttgatcatct
 301 tagcaagagg aacagtcccc tttgtcatga tctccaatct tgaggtattg gaagcgtgtg
 361 agaagagcga caacccgaag accaacagtt ccgggagaaa cagcctggaa gacaagaatc
 421 cgtgccagta atgaggttgc agatcaaaga atgcatcaaa gaaccttcta gtagcgtcta
 481 aatcgagttt cagcagaata tccattccaa aacagaagaa ctccctctgt ctacgccgtt
 541 cgataggcca caagtctctc caaacctcag cagagagttg atctcctctc aggctattac
 601 tacttggtga accgaggtat ctcacaatgg catttgccaa tattggtgca gctgcaagag
 661 tcctagcaac catgtaacca gttgaaggat gaaccattcc tgctgtccca ccaatcccca
 721 caacccgttg aggtaagact ggtaaaggac cgcccatcgg gatcacacaa cgctcgtctt
 781 cctcaatcct cttcacattg atccccagat gtttcagtct agcagccatt ctttcttgga
 841 tatcttccat tctcagacca ggtctagcaa ctaaagaagt ttcttcaaga aatattcggt
 901 tggaagaaaa tggcatagcg tacaagaacg ttgggatctt gctgttccgt tctttcagct
 961 caggatatga gtccagatgt ttgtctctcc aatccatgaa caccattttg tctacatcga
1021 atgggtgacc atcaacttca gctacaatcc cgtaagctac ttggtaccca gggttgtaag
1081 gtttgtcata ctgaaccaag catcgggaaa acccagtggc atcaagaacc acggaagcct
1141 gaatctttac accgtcactg cagaccacag tggagtttgc ctcctcgtga accacattag
1201 tgaccttaga ctgatgaaat ttaacaccgt tggtaataca tttctgaagc attttggatt
1261 tgagctgttt ccggttaact ctcccataag gccggctcaa atccttcttg acaccttcat
1321 cgacatagac aacagcacca gaccatgtgg tatccaggca gtctagtaaa tccatagcct
1381 caaactcatc aacccaaact ccataattgt taggccatat gagcttagga gaaggatcaa
1441 tggaacaaac agagagtcca gcttcagaaa cctgctgagc cacggctaaa ccagcaggac
1501 caccaccaac aatagccaaa tcaacaactt gactcttgga agtgtcgtac aaaggaagct
1561 caaagtcaag attctccttc ttagtttcag gaacaagatc caaaagagca gcgctaccac
1621 tcactacact agagacaatt ttgatagccc ttttcttcac accaagccta acccttgaat
1681 ggtatggatt gttactgcat aatctctcaa acccatgaaa ctgagggatg aaaaaatcga
1741 gcttgttggg tgttttcaac agagtatcca tcgaattccc ccaaaatcga agaaaacacc
1801 aaaaggatat aattcaaaaa tcaccggaca cgatttctaa ccagagggat tgagaaaatg
1861 gaatactaaa ttgctagaga aaagatgaac gaagaccaca aaacttaccc agaagcagta
1921 gcttcatgga gatggagaca attatcttct tcccagaaag agag
```

Lycopene β-cyclase nucleic acid O. sativa (SEQ ID NO: 48)

```
tcacc tatctctgtc ctggatgagg ttgccgatca tcttggcgag agggggcggtg cccttggcca tgatctcgag
gcgcgacgtg ttggaggcct tggcgaagag ggagaggccg aacatggcga gctccggcaa gaagagcctc
gacgacagga agccgtgcca gtagcgcggc tccaggtcga agaaggcgtc gaagaatcgc cgcgtgccgt cgaggtcgag
cttgaggagg atgtccatgc cgaagcagaa gaactccctc tgcctcctcc tctgcgccgg ccacagctcc ctccacacct
ccgccgacag cgcgtcgccg gcgaacgcgc tgtcgccgct gccggtgtcg aggaagcgca cgatggcgtc cgccacgatg
ggcgcagtgg cgagggtgcg cgccaccatg tagcccgtgg acgggtgcac catcccggcg gtgccgccga tgccgacgac
ccgctgcggg agcaccggga gcgggccgcc catgggatg acgcaccgct cgtcctcctc cacggcgcgg acgcgtatcc
cgaggtggcg cagcctcgcc gccatgcgct cctggatgtc gtccatgccg aggcccggc gcgccacgag ggaggtctcc
tcgaggaaga tcctcgtcgg ggagaagggc atggcgtaga ggaacgtcgg gatgcggcgg ttgcgctccc tgatctcgga
ccccctcgggg aggtgcgcgt cgcgccagtc catgaacagc atcttgtcga tgtcgaacgg gtgtccgtcc acctcggcga
ggatgccata ggcgacctgg tacccccgggt cgtacggctt gtcgtactgg acgaggcacc gggagaaccc cgtggcgtcg
agcacgacgg tggccgggac ggcgacgccg tcgtcgcaga tgaggaggga ggatgcctcg ccgtgacgg
ccttgacgac cctggccttg tggaacgtga cgccatgggc gacgcgggg tccatcatgg tggacttgag cttgcggcgg
gcgacgcggg cgtaggggcg gtggagcgac ttggcggcgc cgtcgtcgtg ggtgaagacg gtggcggagg
gccagacggc gtcgaggcag tgggagagtc ccatgcgtc gaactcgtcg acccagacgc cgtagttgtt gggccagacg
agggcggggg agggtcgat ggcgcagacg gagaggcccg cctccgcgac gcgctgcgcg acgcgaggc
cggcgggcc gccgccgacg acggcgaggt cgacggggt ggcgggcgg gggtcgtagc ggggggagctc
gagggagagc agctcgggc gtgacgcgg ggccagcgac cgcagcgcct cgccggcggc ggcggcggg
cagacgagcg cgcgcgtggg gcgcggcgac ggcgagggag ggggaggggg cttgcaggag gggtgggcgc
ggaggaggag ggcggtggtg gccat
```

Lycopene β-cyclase nucleic acid N. tabacum (SEQ ID NO: 50)

```
   1 ggaactttct tgaaatcctg tttgtagttt tcaaaaaaaa ttgaacccct gttggaagat
  61 atggatacat tgttgaaaac cccaaataag cttgagtttc tgcacccagt tcatggattt
 121 tctgttaaag ctagctcctt taactctgta aagccccata agtttggttc taggaaaatt
 181 tgtgaaaatt ggggtaaagg ggtttgtgtt aaggctaaga gtagtgccct tttggagctt
 241 gtacctgaga ccaaaaagga aaatcttgat tttgagcttc ctatgtatga cccttcaaaa
 301 ggtcttgttg tagatctagc tgtggttggt ggtggacccg ctggacttgc agttgcacag
 361 caggttcgg aggctggact atcgttgtt tcaatcgatc catcgccgaa attgatatgg
 421 cccaataact atggtgtttg ggtggatgaa tttgaggcca tggatttgtt ggattgcctc
 481 gacgccacat ggtcaggtac tgttgttat attgatgaca atacaactaa agatcttgat
```

-continued

```
 541 agaccttatg gaaggttaa tcggaaacaa cttaagtcca aaatgatgca gaaatgcata
 601 ctaaacggtg ttaaattcca ccacgccaaa gttataaagg taattcacga ggaagctaaa
 661 tctatgctga tttgcaatga tggtgtaact attcaggcaa cggtggtgct tgatgcaact
 721 ggcttctcaa gatgtcttgt tcagtatgat aagccatata aacctggata tcaagtagct
 781 tatggcatat tggcagaagt ggaggaacat cccttttgata caagtaagat ggttctcatg
 841 gattggcgag attcgcatct tggtaataat atggagctga aggagagaaa tagaaaagtt
 901 ccaacttttt tgtatgccat gccattttca tcaaataaaa tatttcttga agaaacctca
 961 cttgttgctc gtcctggatt acgtatggac gatattcaag aaagaatggt ggctcgttta
1021 aatcacttgg gtataaaagt taagagcatt gaagaggacg agcattgtgt aattccgatg
1081 ggaggctccc ttcctgtaat acctcagaga gttgttggaa ctggtggtac agctggtctg
1141 gttcatccct caacaggtta tatggtagca aggaccctag ctgcagctcc ggtcgtcgct
1201 aatgcaataa ttcactacct tggttctgag aaagacctttt taggtaatga gttatctgca
1261 gctgtttgga aagatttgtg gcccatagaa aggagacgtc aacgagagtt cttttgtttc
1321 ggtatggata ttcttctgaa gcttgattta cccgctacaa gaaggttttt cgatgccttt
1381 tttgatctag aacctcgtta ttggcatggc ttcttgtcat ctcgcctgta tcttcctgag
1441 cttatatttt tcgggctgtc ccttttctct cgcgcttcaa atacttctag aatagagatt
1501 atgacaaagg gaactcttcc tttggtaaat atgatcaaca atttgttaca ggatacagaa
1561 tgacttacca ggaatcttgt tcaatattac atagcatgtg ttaatacact gctc
```

Lycopene β-cyclase nucleic acid *E. herbicola*

(SEQ ID NO: 64)

```
gt gagggatctg atttttagtcg gcggcggcct ggccaacggg ctgatcgcct ggcgtctgcg ccagcgctac ccgcagctta
acctgctgct gatcgaggcc ggggagcagc ccggcgggaa ccatacctgg tcattccatg aagacgatct gactcccggg
cagcacgcct ggctggcccc gctggtggcc cacgcctggc cgggctatga ggtgcagttt cccgatcttc gccgtcgcct
cgcgcgcggc tactactcca ttacctcaga gcgctttgcc gaggccctgc atcaggcgct gggggagaac atctggctaa
actgttcggt gagcgaggtg ttacccaata gcgtgcgcct tgccaacggt gaggcgctgc ttgccggagc ggtgattgac
ggacgcggcg tgaccgccag ttcggcgatg caaaccggct atcagctctt tcttggtcag cagtggcggc tgacacagcc
ccacggcctg accgtaccga tcctgatgga tgccacggtg gcgcagcagc agggctatcg ctttgtctac acgctgccgc
tctccgccga cacgctgctg atcgaggata cgcgctacgc caatgtcccg cagcgtgatg ataatgccct acgccagacg
gttaccgact atgctcacag caaagggtgg cagctggccc agcttgaacg cgaggagacc ggctgtctgc cgattaccct
ggcgggtgac atccaggctc tgtgggccga tgcgccgggc gtgccgcgct cgggaatgcg ggctgggcta tttcacccta
ccactggcta ttcgctgccg ctggcggtgg cccttgccga cgcgattgcc gacagcccgc ggctgggcag cgttccgctc
tatcagctca cccggcagtt tgccgaacgc cactggcgca ggcagggatt cttccgcctg ctgaaccgga tgcttttcct
ggccgggcgc gaggagaacc gctggcgggt gatgcagcgc ttttatgggc tgccggagcc caccgtagag cgcttttacg
ccgtcggct ctctctcttt gataaggccc gcattttgac gggcaagcca ccggttccgc tgggcgaagc ctggcgggcg
gcgctgaacc attttcctga cagacgagat aaaggatga
```

Methods for introducing one or more nucleic acids that encode a lycopene β-cyclase protein into a bacterium or yeast cell are described herein.

Lycopene ε-Cyclase

Non-limiting examples of lycopene ε-cyclase proteins are described herein (see, FIG. 13). Additional examples of lycopene ε-cyclase proteins are known in the art. Methods for determining the ability of a lycopene ε-cyclase protein to convert lycopene to α-carotene (together with a lycopene β-cyclase) are known in the art (see, e.g., Cunningham et al., *Plant Cell* 8:1613-1626, 1996).

In some embodiments, a lycopene ε-cyclase protein can contain one or more (e.g., two, three, four, five, six, seven, eight, nine, or ten) additions, insertions, substitution, or deletions as compared to a corresponding wild type lycopene ε-cyclase protein. For example, a lycopene ε-cyclase protein can contain one or more substitutions at amino acid positions that are not conserved among wild type lycopene ε-cyclase proteins (see, e.g., the amino acid positions that are not conserved in FIG. 13).

In some embodiments, the lycopene ε-cyclase protein is at least 80% identical (e.g., at least 85%, 90%, 95%, or 100%) identical to any one of SEQ NO: 51, 53, and 55.

Lycopene ε-cyclase protein *A. thaliana*

(SEQ ID NO: 51)

```
  1mecvgarnfa amavstfpsw scrrkfpvvk rysyrnirfg lcsvrasggg ssgsescvav
 61redfadeedf vkaggseilf vqmqqnkdmd eqsklvdklp pisigdgald lvvigcgpag
121lalaaesakl glkvgligpd lpftnnygvw edefndlglq kciehvwret ivyldddkpi
181tigraygrvs rrllheellr rcvesgvsyl sskvdsitea sdglrlvacd dnnvipcrla
241tvasgaasgk llqyevggpr vcvqtaygve vevenspydp dqmvfmdyrd ytnekvrsle
301aeyptflyam pmtksrlffe etclaskdvm pfdllktklm lrldtlgiri lktyeeewsy
361ipvggslpnt eqknlafgaa asmvhpatgy svvrslseap kyasviaeil reettkqins
421nisrqawdtl wpperkrqra ffllfglaliv qfdtegirsf frtffrlpkw mwqgflgstl
481tsgdlvlfal ymfvispnnl rkglinhlis dptgatmikt ylkv
```

Lycopene ε-cyclase protein *L. sativa*

(SEQ ID NO: 53)

```
  1mecfgarnmt atmavftcpr ftdcnirhkf sllkqrrftn lsasssslrqi kcsaksdrcv
 61vdkqgisvad eedyvkaggs elffvqmqrt ksmesqskls eklaqipign cildlvvigc
121gpaglalaae saklglnvgl igpdlpftnn ygvwqdefig lglegciehs wkdtlvyldd
181adpirigray grvhrdllhe ellrrcvesg vsylsskver iteapngysl iecegnitip
241crlatvasga asgkfleyel ggprvcvqta ygievevenn pydpdlmvfm dyrdfskhkp
301esleakyptf lyvmamsptk iffeetclas reampfnllk sklmsrlkam giritrtyee
361ewsyipvggs lpnteqknla fgaaasmvhp atgysvvrsl seapnyaavi akilrqdqsk
421emislgkytn iskqawetlw plerkrqraf flfglshivl mdlegtrtff rtffrlpkwm
481wwgflgssls stdliifaly mfviaphslr melvrhllsd ptgatmvkay lti
```

Lycopene ε-cyclase protein *B. napus*

(SEQ ID NO: 55)

```
  1 mecvgarnla atavtafpsw sssrknypvd nrysfsnlrc glcrvkasgg gagsgiescv
 61 avredfadee dfvkaggsei lyvqmqqnkd mdeheqsklv dklppistge gggaldlvvi
121 gcgpaglala aesaklglkv gligpdlpft nnygvwedef ndlglqkcie hvwrdtlvyl
181 dddnpitigr aygrvsrrll heellrrcve sgvsylsskv esiteapdgl rlvsceqntl
241 vpcrlatvas gaasgkllqy evggprvcvq taygleveve kspydpeqmv fmdyrdytke
301 kirsleaeyp tflyampmtk trvffeetcl askdvmpfdl lkkklmlrle tlgirilkty
361 eeewsyipvg gslpnteqkn lafgaaasmv hpatgysvvr slseapkyas vianilkhet
421 ttsftrhint nisrqawdtl wpperkrqra fflfglaliv qldiegircf fhtffrlpkw
481 mwrgflgstl tsgdlvlfaf ymfiiapnnl rkglinhlis dptgatmikt ylkv
```

In some embodiments, a nucleic acid encoding a lycopene ε-cyclase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type lycopene ε-cyclase protein (e.g., SEQ ID NO: 52, 54, and 56). Percent identity can be determined using a number of molecular biology tools, e.g., BLAST program available at the NCBI website. In some embodiments, the lycopene ε-cyclase protein contains the sequence of a wild type lycopene ε-cyclase protein (e.g., a protein containing the sequence of SEQ ID NO: 51, 53, and 55).

Non-limiting examples of nucleic acid sequences that encode a wild type lycopene ε-cyclase protein are shown herein (e.g., SEQ ID NOS: 52, 54, and 56). Additional examples of nucleic acid sequences that encode a wild type lycopene ε-cyclase are known in the art. In some embodiments, the nucleic encodes a lycopene ε-cyclase protein that contains a sequence that is at least 80% identical (e.g., at least 85%, 90%, 95%, or 100% identical) to one of SEQ ID NOS: 51, 53, and 55. In some embodiments, the nucleic acid contains a sequence that is at least 80% identical (e.g., at least 85%, 90%, 95%, or 100%) identical to any one of SEQ NO: 52, 54, and 56.

Lycopene ε-cyclase nucleic acid *A. thaliana*

(SEQ ID NO: 52)

```
   1 acaaaaggaa ataattagat tcctctttct gcttgctata ccttgataga acaatataac
  61 aatggtgtaa gtcttctcgc tgtattcgaa attatttgga ggaggaaaat ggagtgtgtt
 121 ggggctagga atttcgcagc aatggccggtt tcaacatttc cgtcatggag ttgtcgaagg
 181 aaatttccag tggttaagag atacagctat aggaatattc gtttcggttt gtgtagtgtc
 241 agagctagcg gcggcggaag ttccggtagt gagagttgtg tagcggtgag agaagatttc
 301 gctgacgaag aagattttgt gaaagctggt ggttctgaga ttctatttgt tcaaatgcag
 361 cagaacaaag atatggatga acagtctaag cttgttgata agttgcctcc tatatcaatt
 421 ggtgatggtg ctttgatca tgtggttatt ggttgtggtc ctgctggttt agccttggct
 481 gcagaatcac ctaagcttgg attaaaagtt ggactcattg gtccagatct tcctttact
 541 aacaattacg gtgtttggga agatgaattc aatgatcttg ggctgcaaaa atgtattgag
 601 catgtttgga gagagactat tgtgtatctg gatgatgaca agcctattac cattggccgt
 661 gcttatggaa gagttagtcg acgtttgctc catgaggagc ttttgaggag gtgtgtcgag
 721 tcaggtgtct cgtaccttag ctcgaaagtt gacagcataa cagaagcttc tgatggcctt
 781 agacttgttg cttgtgacga caataacgtc attccctgca ggcttgccac tgttgcttct
 841 ggagcagctt cgggaaagct cttgcaatac gaagttggtg gacctagagt ctgtgtgcaa
 901 actgcatacg gcgtggaggt tgaggtggaa aatagtccat atgatccaga tcaaatggtt
 961 ttcatggatt acagagatta tactaacgag aaagttcgga gcttagaagc tgagtatcca
1021 acgtttctgt acgccatgcc tatgacaaag tcaagactct tcttcgagga gacatgtttg
1081 gcctcaaaag atgtcatgcc ctttgatttg ctaaaaacga agctcatgtt aagattagat
1141 acactcggaa ttcgaattct aaagacttac gaagaggagt ggtcctatat cccagttggt
1201 ggttccttgc caaacaccga acaaaagaat ctcgcctttg gtgctgccgc tagcatggta
1261 catcccgcaa caggctattc agttgtgaga tctttgtctg aagctccaaa atatgcatca
1321 gtcatcgcag agatactaag agaagagact accaaacaga tcaacagtaa tatttcaaga
1381 caagcttggg atactttatg gccaccagaa aggaaaagac agagagcatt ctttctcttt
1441 ggtcttgcac tcatagttca attcgatacc gaaggcatta gaagcttctt ccgtactttc
1501 ttccgccttc caaaatggat gtggcaaggg tttctaggat caacattaac atcaggagat
1561 ctcgttctct ttgctttata catgttcgtc atttccaccaa acaatttgag aaaaggtctc
1621 atcaatcatc tcatctctga tccaaccgga gcaaccatga taaaaaccta tctcaaagta
1681 tgatttactt atcaactctt aggtttgtgt atatatatgt tgatttatct gaataatcga
1741 tcaaagaatg gtatgtgggt tactaggaag ttggaaacaa acatgtatag aatctaagga
1801 gtgatcgaaa tggagatgga aacgaaaaga aaaaaatcag tctttgtttt gtggttagtg
```

Lycopene ε-cyclase nucleic acid *L. sativa*

(SEQ ID NO: 54)

```
   1 gaaacaaatg acgtgaaagt tcttcaaaat tgaattaatt gtaatcctga aaacttgatt
  61 tgtgatagaa gaatcaatgg agtgctttgg agctcgaaac atgacggcaa caatggcggt
 121 ttttacgtgc cctagattca cggactgtaa tatcaggcac aaatttttcgt tactgaaaca
 181 acgaagattt actaatttat cagcatcgtc ttcgttgcgt caaattaagt gcagcgctaa
 241 aagcgaccgt tgtgtagtgg ataaacaagg gatttccgta gcagacgaag aagattatgt
 301 gaaggccggt ggatcggagc tgttttttgt tcaaatgcag cggactaagt ccatggaaag
 361 ccagtctaaa ctttccgaaa agctagcaca gataccaatt ggaaattgca tacttgatct
 421 ggttgtaatc ggttgtggcc ctgctggcct tgctcttgct gcagatcag ccaaactagg
 481 gttgaacgtt ggactcattg gccctgatct tcctttaca aacaattatg gtgtttggca
 541 ggatgaattt ataggtcttg gacttgaagg atgcattgaa cattcttgga aagatactct
 601 tgtataccttt gatgatgctg atcccatccg cataggtcgt gcatatggca gagttcatcg
 661 tgatttactt catgaagagt tgttaagaag gtgtgtggaa tcaggtgttt catatctaag
 721 ctccaaagta gaaagaatca ctgaagctcc aaatggctat agtctcattg aatgtgaagg
```

-continued

```
 781 caatatcacc attccatgca ggcttgctac tgttgcatca ggggcagctt cagggaaatt
 841 tctggagtat gaacttgggg gtccccgtgt ttgtgtccaa acagcttatg gtatagaggt
 901 tgaggttgaa aacaacccct atgatccaga tctaatggtg ttcatggatt atagagactt
 961 ctcaaaacat aaaccggaat ctttagaagc aaaatatccg actttcctct atgtcatggc
1021 catgtctcca acaaaaatat tcttcgagga aacttgttta gcttcaagag aagccatgcc
1081 tttcaatctt ctaaagtcca aactcatgtc acgattaaag gcaatgggta tccgaataac
1141 aagaacgtac gaagaggaat ggtcgtatat ccccgtaggt ggatcgttac ctaatacaga
1201 acaaaagaat ctcgcatttg gtgctgcagc tagtatggtg caccctgcca cagggtattc
1261 agttgttcga tctttgtcag aagctcctaa ttatgcagca gtcattgcta agattttaag
1321 acaagatcaa tctaaagaga tgatttctct tggaaaatac actaacattt caaaacaagc
1381 atgggaaaca ttgtgccac ttgaaaggaa aagacagcga gccttctttc tattcggact
1441 atcacacatc gtgctaatgg atctagaggg aacacgtaca tttttccgta ctttctttcg
1501 tttgcccaaa tggatgtggt ggggatttt ggggtcttct ttatcttcaa cggatttgat
1561 aatatttgcg ctttatatgt ttgtgatagc acctcacagc ttgagaatgg aactggttag
1621 acatctactt tctgatccga caggggcaac tatggtaaaa gcatatctca ctatatagat
1681 ttagattata taaataatac ccatatcttg catatatata agccttattt atttcttttg
1741 tatccttaca acaacatact cgttaattat atgtttttta
```

Lycopene ε-cyclase protein B. napus (SEQ ID NO: 56)

```
   1 atggagtgtg ttggtgctcg caatctcgct gcaacggcgg tcacagcttt tccgtcctgg
  61 agttcttcgc gtaaaaacta tcccgtggat aatagataca gctttagtaa tctccggtgc
 121 ggtttgtgta gagtcaaagc tagcggcggc ggagcaggtt ccggtataga gagttgcgtg
 181 gcggtgagag aggacttcgc cgacgaggaa gacttcgtga aggctggtgg ttcggagatt
 241 ctatacgttc aaatgcagca gaacaaagac atggatgaac atgaacagtc taagcttgtt
 301 gataaggtaa gtcaacgttt tgccgttgac ttgtttgtga agataacgaa ctatctatct
 361 cctttgatct tacatttgct tcagacagtt cacgtctgag ttttgaagcc tttgtcttat
 421 tgattgtgtg tgtgtgtgtt tttttttta atataacagt tacctcctat atcaactggt
 481 gaaggtggtg gtgctttgga cctagtggtt attgggtgtg gtcctgctgg tttagccttg
 541 gcggctgaat cagctaagtt aggacttaaa gttggactga ttggtcctga ccttcctttc
 601 actaacaact acggtgtttg ggaagatgag ttcaacggta atgatctagc agttactatc
 661 tccatggtca tattataata aatctatttt gtgtttattg ttttactctt tgcagatctt
 721 ggcttgcaaa aatgtattga gcatgtttgg agagatccc ttgtgtatct ggacgatgac
 781 aatcctatta ccattggtcg tgcttatgga agagttagtc gacgtttact tcacgaggag
 841 ctcttgagga ggtaattaaa aaaatgctcc cactcttcag agagacattt cactagagtt
 901 attattgttc atctcctgac aattgatttt ctgataggtg tgtggagtca ggtgtctcgt
 961 atcttagctc caaagttgag agcataacag aagctcctga tggccttagg cttgtttcct
1021 gtgaacagaa caccccttgtt ccgtgcaggt actctttctt aagtccaaca aaaacgtgct
1081 tgggtacagt gtcaatggtt ccgacattct agacaaatgc aggcttgcca ctgttgcttc
1141 tggagcagct tctgggaagc tcttgcaata cgaagttgga ggacctagag tctgtgtcca
1201 aactgcttac ggcttggagg ttgaggtata gtaatcaaat tatgatattc cagagtaatt
1261 aatacacata ttcctgtaag gaatttgtat taatctctgt ttgaaaactc tttgtaggtg
1321 gaaaagagtc catatgatcc agagcagatg gtgttcatgg attacagaga ttatacaaaa
1381 gagaaaatcc ggagcttaga agctgaatat ccaacgtttc tctacgccat gcctatgaca
1441 aagacaagag tcttctttga ggttccttct ctcttcttct gttttaatca tttttagcac
1501 taaaagtcta ttgcttatta ttggctggag tttctttgca ggagacatgt cttgcttcaa
1561 aagatgtcat gcccttttgat ctgctaaaaa agaagctcat gttgagatta gagacactcg
1621 gaatccgaat actaaagact tatgaagagg taaatctata taaacaaaaa gaagtagagc
1681 ttcacttgtt gagcaaacaa tataaacttc tttggttggt gcataaaaaa caggaatggt
1741 cttatatccc agtaggtggt tccttgccga acacggaaca aaagaatctc gcctttggtg
1801 ctgcagctag catggtacat cctgcaacag gctattcagt tgtgagatct ttgtctgaag
1861 ctccaaaata cgcatcagtc atcgctaata tactaaaaca tgagaccact acttccttca
1921 ccagacacat caacaccaat atttcaagac aaggtgaggc tctatataaa ccaccactga
1981 gttcacatct ttcagacaat ttataaaaac ttgtgagctt gttattctgt gccagcttgg
2041 gatactttat ggccaccaga aaggaaacga caaagacat tctttctctt tggtcttgcg
2101 ctcatagttc aactcgacat cgaaggcatt agatgcttct tccacacttt cttccgcctt
2161 ccaaaatggt aagccatcga ctgatattct tgattcagtt aacaaacaat gtatggaaaa
2221 atcaagaaag tgatgttttt gttttcttt gctcaggatg tggagagggt ttctaggatc
2281 aacattaaca tcaggagacc tcgttctgtt tgctttctac atgttcatca ttgcaccaaa
2341 caacttgaga aaaggtctca tcaatcatct tatctctgat ccaaccggag caaccatgat
2401 taaaacctat cttaaagtat ga
```

Methods for introducing one or more nucleic acids that encode a lycopene ε-cyclase protein into a bacterium or yeast cell are described herein.

D-1-Deoxyxylulose 5-Phosphate Synthase Protein

Non-limiting examples of D-1-deoxyxylulose 5-phosphate synthase proteins are described herein (see, FIG. 20). Additional examples of D-1-deoxyxylulose 5-phosphate synthase proteins are known in the art. Methods for determining the ability of a D-1-deoxyxylulose 5-phosphate synthase protein to produce D-1-deoxyxylulose 5-phosphate from pyruvate and glyceraldehyde 3-phosphate are known in the art (see, e.g., Matthews et al., *Appl. Microbiol. Biotechnol.* 53:396-400, 2000).

In some embodiments, a D-1-deoxyxylulose 5-phosphate synthase protein can contain one or more (e.g., two, three, four, five, six, seven, eight, nine, or ten) additions, insertions, substitution, or deletions as compared to a corresponding wild type D-1-deoxyxylulose 5-phosphate synthase. For example, a D-1-deoxyxylulose 5-phosphate synthase protein can contain one or more substitutions at amino acid positions that are not conserved among wild type D-1-deoxyxylulose 5-phosphate synthase proteins (see, e.g., the amino acid positions that are not conserved in FIG. 20).

In some embodiments, the D-1-deoxyxylulose 5-phosphate synthase protein is at least 80% identical (e.g., at least 85%, 90%, 95%, or 100%) identical to any one of SEQ NO: 95, and 97.

D-1-deoxyxylulose 5-phosphate synthase protein *E. coli*

(SEQ ID NO: 95)

```
  1 msfdiakypt lalvdstqel rllpkeslpk lcdelrryll dsvsrssghf asglgtvelt
 61 valhyvyntp fdqliwdvgh qayphkiltg rrdkigtirq kgglhpfpwr geseydvlsv
121 ghsstsisag igiavaaeke gknrrtvcvi gdgaitagma feamnhagdi rpdmlvilnd
181 nemsisenvg alnnhlaqll sgklyssIre ggkkvfsgvp pikellkrte ehikgmvvpg
241 tlfeelgfny igpvdghdvl glittlknmr dlkgpqflhi mtkkgrgyep aekdpitfha
301 vpkfdpssgc lpkssgglps yskifgdwlc etaakdnklm aitpamregs gmvefsrkfp
361 dryfdvaiae qhavtfaagl aiggykpiva iystflqray dqvlhdvaiq klpvlfaidr
421 agivgadgqt hqgafdlsyl rcipemvimt psdenecrqm lytgyhyndg psavryprgn
481 avgveltple klpigkgivk rrgeklailn fgtlmpeaak vaeslnatlv dmrfvkplde
541 alilemaash ealvtveena imggagsgvn evlmahrkpv pvlniglpdf fipqgtqeem
601 raelgldaag meakikawla
```

D-1-deoxyxylulose 5-phosphate synthase protein *L. esculentum*

(SEQ ID NO: 97)

```
  1 malcayafpg ilnrtgvvsd sskatplfsg wihgtdlqfl fqhklthevk krsrvvqasl
 61 sesgeyytqr pptpildtvn ypihmknlsl kelkqladel rsdtifnvsk tgghlgsslg
121 vveltvalhy vfnapqdril wdvghqsyph kiltgrrdkm stlrqtdgla gftkrsesey
181 dcfgtghsst tisaglgmav grdlkgrnnn viavigdgam tagqayeamn nagyldsdmi
241 vilndnrqvs lptatldgpv apvgalssal srlqsnrplr elrevakgvt kqiggpmhel
301 aakvdeyarg misgsgstlf eelglyyigp vdghniddli ailkevrstk ttgpvlihvv
361 tekgrgypya eraadkyhgv akfdpatgkq fkasaktqsy ttyfaealia eaeadkdiva
421 ihaamgggtg mnlfhrrfpt rcfdvgiaeq havtfaagla cegikpfcai yssfmqrayd
481 qvvhdvdlqk lpvrfamdra glvgadgpth cgafdvtyma clpnmvvmap sdeaelfhmv
541 ataaaiddrp scfryprgng igvelpagnk giplevgkgr iliegerval lgygsavqnc
601 ldaaivlesr glqvtvadar fckpldhali rslakshevl itveegsigg fgshvvqfma
661 ldglldgklk wrpivlpdry idhgspvdql aeagltpshi aatvfnilgq trealevmt
```

In some embodiments, a nucleic acid encoding a D-1-deoxyxylulose 5-phosphate synthase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type D-1-deoxyxylulose 5-phosphate synthase protein (e.g., SEQ ID NO: 95 and 97). Percent identity can be determined using a number of molecular biology tools, e.g., BLAST program available at the NCBI website. In some embodiments, the D-1-deoxyxylulose 5-phosphate synthase protein contains the sequence of a wild type D-1-deoxyxylulose 5-phosphate synthase protein (e.g., a protein containing the sequence of SEQ ID NO: 95 and 97).

Non-limiting examples of nucleic acid sequences that encode a wild type D-1-deoxyxylulose 5-phosphate synthase protein are shown herein (e.g., SEQ ID NOS: 96 and 98). Additional examples of nucleic acid sequences that encode a wild type D-1-deoxyxylulose 5-phosphate synthase protein are known in the art. In some embodiments, the nucleic encodes a D-1-deoxyxylulose 5-phosphate synthase protein that contains a sequence that is at least 80% identical (e.g., at least 85%, 90%, 95%, or 100% identical) to one of SEQ ID NOS: 95 and 97. In some embodiments, the nucleic acid contains a sequence that is at least 80% identical (e.g., at least 85%, 90%, 95%, or 100%) identical to any one of SEQ NO: 96 and 98.

D-1-deoxyxylulose 5-phosphate synthase nucleic acid *E. coli*

(SEQ ID NO: 96)

```
   1 atgagttttg atattgccaa atacccgacc ctggcactgg tcgactccac ccaggagtta
  61 cgactgttgc cgaaagagag tttaccgaaa ctctgcgacg aactgcgccg ctatttactc
 121 gacagcgtga gccgttccag cgggcacttc gcctccgggc tgggcacggt cgaactgacc
 181 gtggcgctgc actatgtcta caacaccccg tttgaccaat tgatttggga tgtggggcat
 241 caggcttatc cgcataaaat tttgaccgga cgccgcgaca aaatcggcac catccgtcag
 301 aaaggcggtc tgcacccgtt cccgtggcgc ggcgaaagcg aatatgacgt attaagcgtc
 361 gggcattcat caacctccat cagtgccgga attggtattg cggttgctgc cgaaaaagaa
 421 ggcaaaaatc gccgcaccgt ctgtgtcatt ggcgatggcg cgattaccgc aggcatggcg
 481 tttgaagcga tgaatcacgc gggcgatatc cgtcctgata tgctggtgat tctcaacgac
 541 aatgaaatgt cgatttccga aaatgtcggc gcgctcaaca accatctggc acagctgctt
 601 tccggtaagc tttactcttc actgcgcgaa ggcgggaaaa aagttttctc tggcgtgccg
 661 ccaattaaag agctgctcaa acgcaccgaa gaacatatta aaggcatggt agtgcctggc
 721 acgttgtttg aagagctggg ctttaactac atcggcccgg tggacggtca cgatgtgctg
 781 gggcttatca ccacgctaaa gaacatgcgc gacctgaaag gcccgcagtt cctgcatatc
 841 atgaccaaaa aaggtcgtgg ttatgaaccg gcagaaaaag acccgatcac tttccacgcc
 901 gtgcctaaat ttgatccctc cagcggttgt ttgccgaaaa gtagcggcgg tttgccgagc
 961 tattcaaaaa tctttggcga ctggttgtgc gaaacggcag cgaaagacaa caagctgatg
1021 gcgattactc cggcgatcg tgaaggttcc ggcatggtcg agttttcacg taaattcccg
1081 gatcgctact tcgacgtggc aattgccgag caacacgcgg tgaccttttgc tgcgggtctg
1141 gcgattggtg gtacaaacc cattgtcgcg atttactcca ctttcctgca acgcgcctat
1201 gatcaggtgc tgcatgacgt ggcgattcaa aagcttccgg tcctgttcgc catcgaccgc
1261 gcgggcattg ttggtgctga cggtcaaacc catcaggtg ctttttgatct ctcttacctg
1321 cgctgcatac cggaaatggt cattatgacc ccgagcgatg aaaacgaatg tcgccagatg
1381 ctctataccg gctatcacta taacgatggc ccgtcagcgg tgcgctaccc gcgtggcaac
1441 gcggtcggcg tggaactgac gccgctggaa aaactaccaa ttggcaaagg cattgtgaag
1501 cgtcgtggcg agaaactggc gatccttaac tttggtacgc tgatgccaga agcggcgaaa
1561 gtcgccgaat cgctgaacgc cacgctggtc gatatgcgtt ttgtgaaacc gcttgatgaa
1621 gcgttaattc tggaaatggc cgccagccat gaagcgctgg tcaccgtaga agaaaacgcc
1681 attatgggcg cgcgcaggcag cggcgtgaac gaagtgctga tggcccatcg taaaccagta
```

```
                                        -continued
1741 cccgtgctga acattggcct gccggacttc tttattccgc aaggaactca ggaagaaatg
1801 cgcgccgaac tcggcctcga tgccgctggt atggaagcca aaatcaaggc ctggctggca
1861 taa
```

D-1-deoxyxylulose 5-phosphate synthase nucleic acid *L. esculentum*

(SEQ ID NO: 96)

```
   1 catcttcata aacaacattt tagtgacagt agcaccaaca cacccacta gaattttctt
  61 gaagtaaacc ccttttttca agaatcaaga aaccacttat aaaatttgtg ggttttcatt
 121 gaaacaaagg aaaaaaaaca gttgaattga ctaatcatgg ctttgtgtgc ttatgcattt
 181 cctgggattt tgaacaggac tggtgtggtt tcagattctt ctaaggcaac cccttttgttc
 241 tctggatgga ttcatggaac agatctgcag tttttgttcc aacacaagct tactcatgag
 301 gtcaagaaaa ggtcacgtgt ggttcaggct tccttatcag aatctggaga atactacaca
 361 cagagaccgc caacgcctat tttggacact gtgaactatc ccattcatat gaaaaatctg
 421 tctctgaagg aacttaaaca actagcagat gaactaaggt cagatacaat tttcaatgta
 481 tcaaagactg ggggtcacct tggctcaagt cttggtgttg ttgagctgac tgttgctctt
 541 cattatgtct tcaatgcacc gcaagatagg attctctggg atgttggtca tcagtcttat
 601 cctcacaaaa tcttgactgg tagaagggac aagatgtcga cattaaggca gacagatggt
 661 cttgcaggat ttactaagcg atcggagagt gaatatgatt gctttggcac cggccacagt
 721 tccaccacca tctcagcagg cctagggatg gctgttggta gagatctaaa aggaagaaac
 781 aacaatgtta ttgccgtaat aggtgatggt gccatgacag caggtcaagc ttatgaagcc
 841 atgaataatg ctggttacct ggactctgac atgattgtta tcttaaacga caatagacaa
 901 gtttctttac ctactgctac tctggatggg ccagttgctc ctgttggagc tctaagtagt
 961 gctttgagca ggttacagtc taataggcct ctcagagaac taagagaagt cgcaaaggga
1021 gttactaagc agattggtgg tcctatgcat gagcttgctg caaaagttga tgaatatgct
1081 cgtggcatga ttagtggttc tggatcaaca ttgtttgaag aacttggact ttactatatt
1141 ggtcctgtgg atggtcacaa cattgatgat ctaattgcca ttctcaaaga ggttagaagt
1201 actaaaacaa caggtccagt actgatccat gttgtcactg agaaaggcag aggttatcca
1261 tatgctgaga gagctgcaga taagtatcat ggagttgcca agtttgatcc agcaacagga
1321 aagcaattca aagccagtgc caagacacag tcctatacaa catatttttgc cgaggcttta
1381 attgcagaag cagaagcaga taaagacatt gttgcaatcc atgctgccat gggggtggg
1441 accggaatga acctttttcca tcgtcgcttc ccaacaaggt gttttgatgt tggaatagca
1501 gaacaacatg cagtaacctt tgctgctgga ttggcttgtg aaggcattaa acctttctgt
1561 gcaatctatt cgtctttcat gcagagggct tatgaccagg tagtgcatga cgttgatttg
1621 caaaagctgc ccgtgaggtt tgcaatggac agagcaggtc ttgttggagc agatggtcca
1681 acacattgtg gtgcatttga tgttacttac atggcaatgc ttcctaacat ggttgtaatg
1741 gctccttctg atgaagcgga gctatttcac atggtagcaa ctgctgccgc cattgatgac
1801 agaccaagtt gtttttagata cccaagagga aatgggatcg tgtagagct tccggctgga
1861 aacaaaggaa ttcctcttga ggttggtaaa ggtaggatat tgattgaggg ggagagagtg
1921 gctctattgg gatatggctc agcagtgcag aactgttttgg atgctgctat tgtgctagaa
1981 tcccgcggct tacaagtaac agttgcagat gcacgtttct gcaaaccact ggaccatgcc
2041 ctcataagga gccttgcaaa atcacatgaa gtgctaatca ctgtcgaaga aggatcaatt
2101 ggaggttttg gatctcatgt tgttcagttc atggcttag atgggcttct tgatggcaag
2161 ttgaagtgga gaccaatagt tcttcctgat cgatacattg accatggatc tcctgttgat
2221 cagttggcgg aagctggcct aacaccatct cacattgcag caacagtatt taacatactt
2281 ggacaaacca gagaggctct agaggtcatg acataagatg gaagaagcgt agaaagatat
2341 atagtatatt gtaaaatata gttttaggtc atgacataag cagattaaca tatactttat
2401 cctccaaaat atgtttaaag tttccatggc tgagttcaag ccctcctctt agtctccacc
2461 atgacttatg attaactcat atggtttctg attgtgtaac cggttcttga tttttcgagt
2521 tatgaagatg aatgaaaatg aaagatttta ctttcaaaaa aaaaaaaa
```

Methods for introducing one or more nucleic acids that encode a D-1-deoxyxylulose 5-phosphate synthase protein into a bacterium or yeast cell are described herein.

Isopentenyl Pyrophosphate Isomerase Protein

Non-limiting examples of isopentenyl pyrophosphate isomerase proteins are described herein (see, FIG. 21). Additional examples of isopentenyl pyrophosphate isomerase proteins are known in the art. Methods for determining the ability to convert isopentenyl pyrophosphate to dimethylallyl diphosphate are known in the art (see, e.g., Spurgeon et al., *Arch. Biochem. Biophys.* 230:446-454, 1984).

In some embodiments, an isopentenyl pyrophosphate isomerase protein can contain one or more (e.g., two, three, four, five, six, seven, eight, nine, or ten) additions, insertions, substitution, or deletions as compared to a corresponding wild type isopentenyl pyrophosphate isomerase protein. For example, an isopentenyl pyrophosphate isomerase protein can contain one or more substitutions at amino acid positions that are not conserved among wild type isopentenyl pyrophosphate isomerase proteins (see, e.g., the amino acid positions that are not conserved in FIG. 21).

In some embodiments, the isopentenyl pyrophosphate isomerase protein is at least 80% identical (e.g., at least 85%, 90%, 95%, or 100%) identical to any one of SEQ NO: 99 and 101.

Isopentenyl pyrophosphate isomerase protein *E. coli*

(SEQ ID NO: 99)

```
  1 menvilidhn dcetgiaekl ythkkgilhr avsvyicnsd gklllqqral gkyhspglws
 61 ntscthpfpg esnlsaanrr lreemgiecp lskllkiyyn vyvggdlteh eiahifygis
121 ddepdlnsle amsykyvslt elsseikfnn dafsrwfvyc fpyiknafln esnytnlli
```

Isopentenyl pyrophosphate isomerase protein *Z mays*

(SEQ ID NO: 101)

```
  1 maaavvddag mdavqkrlmf edecilvdeq dnvvghesky nchlmekids enllhrafsv
 61 flfnskyell lqqrsatkvt fplvwtntcc shplyresel iqenylgvrn aaqrklldel
121 gipaedapvd qftplgrmly kapsdgkwge heldyllfiv rdvkvqpnpd evadvkyvnr
181 delkelirka dagedgvkis pwfrlvvdnf lmgwwdhvek gtlgeavdme tihklke
```

In some embodiments, a nucleic acid encoding an isopentenyl pyrophosphate isomerase protein can be any nucleic acid containing a nucleic acid sequence that is at least 80% identical (e.g., at least 85%, 90%, 95%, 96%, 97%, 98%, 99%, or 100% identical) to a contiguous sequence (e.g., at least 150, 300, 450, 600, 750, or 900 nucleotides) present within a nucleic acid that encodes a wild type isopentenyl pyrophosphate isomerase protein (e.g., SEQ ID NO: 100 and 102). Percent identity can be determined using a number of molecular biology tools, e.g., BLAST program available at the NCBI website. In some embodiments, the isopentenyl pyrophosphate isomerase protein contains the sequence of a wild type isopentenyl pyrophosphate isomerase protein (e.g., a protein containing the sequence of SEQ ID NO: 99 and 101).

Non-limiting examples of nucleic acid sequences that encode a wild type isopentenyl pyrophosphate isomerase protein are shown herein (e.g., SEQ ID NOS: 100 and 102). Additional examples of nucleic acid sequences that encode a wild type isopentenyl pyrophosphate isomerase protein are known in the art. In some embodiments, the nucleic encodes an isopentenyl pyrophosphate isomerase protein that contains a sequence that is at least 80% identical (e.g., at least 85%, 90%, 95%, or 100% identical) to one of SEQ ID NOS: 99 and 101. In some embodiments, the nucleic acid contains a sequence that is at least 80% identical (e.g., at least 85%, 90%, 95%, or 100%) identical to any one of SEQ NO: 100 and 102.

In any of the embodiments described herein (e.g., any of the recombinant bacteria and yeast, and any of the methods described herein) the one or more of: a nucleic acid encoding a CYP97A, a nucleic acid encoding a CYP97B, a nucleic acid encoding a CYP97C, a nucleic acid encoding a geranylgeranyl pyrophosphate synthase, a nucleic acid encoding a phytoene synthase, a nucleic acid encoding a lycopene β-cyclase, and a nucleic acid encoding a lycopene ε-cyclase can be from or derived from a plant, a bacterium, algae, or a fungus that naturally produces one or more carotenoid products (e.g., lycopene, α-carotene, β-carotene, α-carotene, zeinoxanthin, β-cryptoxanthin, zeaxanthin, and lutein). In any of the embodiments described herein, a nucleic acid encoding a phytoene desaturase can be derived from any bacterium that naturally produces one or more carotenoid products (e.g., lycopene). Non-limiting examples of such plants include: *A. thaliana, O. sativa, P. trichocarpa, C. moschata, N. tabacum, Sorghum bicolor, Vitis vinifera, Triticum aestivum, Brachypodium distachyon, Medicago truncatula, Glycine max, Physcomitrella patens, Solanum lycopersicum, Pinus taeda, Pharus lappulaceus, Vitis vinifera, Ricinus communis, Populus trichocarpa, Physcomitrela patens, Selaginella moellendorffi, Bambusa vulgaris, Hordeum muticum, Secale cereal, Aristida adscensionis, Phragmites australis, Zeugites pittieri, Pennisetum tristachyum, Tripsacum zopilotense*, and *Trichodesmium erythraeum*. Non-limiting examples of such bacterium include: *Pantoea ananatis* (formerly *Erwinia uredovora*)

```
Isopentenyl pyrophosphate isomerase nucleic acid E. coli
                                                 (SEQ ID NO: 100)
ctaaa tcaataaatt ggtataatta ctctcattca ggaaagcatt tttaatatat gggaaacaat
agacgaacca acgagaaaaa gcatcgttat tgaattttat ttcagaactt aactctgtca
aggaaacata tttataactc atagcttcca aactatttaa atctggctca tcatcactaa
taccatagaa aatatgtgca atctcatgtt ctgttaaatc accgccgaca taaacattat
agtagatctt taatagttta gataaggggc attctatccc catttcctcc cttaatcttc
tgttagctgc agataaattc gattctcccg ggaagggatg tgtacaagag gtattgctcc
aaaggccggg agaatgatat tttccaagtg ctctttgctg taacaataat tttccatcgc
tattacatat ataaacagaa acagcccgat gtaaaatacc ttttttgtgg gtatataatt
tttcggcaat ccccgtttca caatcattat ggtcaattaa aataacattc tccataaatt Isopentenyl pyrophosphate isomerase nucleic acid Z. mays
                                                 (SEQ ID NO: 102)
   1 cgcacacccc ggcagccgca aacgccttcg ccgtcgcgtc ccgctcctcc gcccgcccga
  61 cgcgacccct aggacctgga gagagaggtc ggcatggctg ccgcagtggt cgacgacgct
 121 ggtatggacg ccgtccagaa gcgcctcatg ttcgaagacg aatgcatttt ggtggacgag
 181 caggacaatg ttgttggcca tgagtcaaag tacaactgcc atttgatgga aaagattgat
 241 tctgagaatc tgctacatag ggcattcagt gtgttccttt tcaactcaaa atatgagctg
 301 ctacttcagc aaaggtccgc gacaaaggtt acctttcctt tagtttggac caatacctgc
 361 tgcagccacc ctctgtaccg tgagtctgag cttatccagg agaactacct tggtgtgaga
 421 aatgcagcac agaggaagct actggatgag ctgggcatcc cagcagaaga tgccccagtt
 481 gaccaattca cccctctggg ccgaatgctt tacaaggcac catctgacgg gaaatgggag
 541 gagcatgagc ttgactacct gctgttcatc gtccgggacg tgaaggtgca gccgaaccca
 601 gatgaagtcg ctgacgtgaa gtacgtgaac cgcgacgagc tcaaggagct catccggaag
 661 gctgacgctg gcgaggacgg ggtgaagatc tccccctggt tcaggctggt ggtggacaac
 721 ttcctcatgg gctggtggga ccatgtcgag aaaggcaccc tcggcgaggc cgtggacatg
 781 gagaccatcc ataagctgaa ggagtgaggg gccgccggcc ggccggctcc gatgacctca
 841 ccacctgttg atgttgctgc tgctgctgca ctgcatgttt atcaaaagtt atcgctcctg
 901 ctcgcggaaa gtgagcttga ctgttgccgg ggtggaagtg tcgttttgga ctgaagatga
 961 gtgccgcgga ggggttttgtt gtttgtttgt ttgtttgttc ggtgaccgaa tcgcgagttg
1021 gacgcctgtt taatccgtgc ttatacatcg tctgagtaaa cagcaataag agggacatcc
1081 gtaagctctt tccgt
```

Methods for introducing one or more nucleic acids that encode a lycopene ε-cyclase protein into a bacterium or yeast cell are described herein.

Additional Exemplary Sequences

The nucleic sequences described herein can be obtained or derived from any organism (e.g., a plant, a bacterium, algae, or a fungus) that produces one or more carotenoid products (e.g., lycopene, α-carotene, β-carotene, α-carotene, zeinoxanthin, β-cryptoxanthin, zeaxanthin, and lutein).

and *Erwinia herbicola*. Non-limiting examples of such algae include: *Synechococcus* and *Synechocystis* spp. Non-limiting examples of such fungi include: *Blakeslea trispora, Glomus intraradices*, and *Glomus deserticola*.

In some embodiments, the one or more of a nucleic acid encoding a CYP97A, a nucleic acid encoding a CYP97B, a nucleic acid encoding a CYP97C, a nucleic acid encoding a geranylgeranyl pyrophosphate synthase, a nucleic acid encoding a phytoene synthase, a nucleic acid encoding a phytoene desaturase, a nucleic acid encoding a lycopene β-cyclase, and a nucleic acid encoding a lycopene ε-cyclase is derived from a wild type sequence present in a plant, a bacterium, algae, or a fungus that naturally produces one or more carotenoid products (e.g., lycopene, α-carotene, β-carotene, α-carotene, zeinoxanthin, β-cryptoxanthin, zeaxanthin, and lutein), wherein the wild type sequence has been optimized for bacterial or yeast cell codon usage (codon-optimized).

Recombinant Cells

Provided herein are recombinant cells (e.g., recombinant bacteria, yeast, mammalian, plant, or insect cells) that contain a nucleic acid encoding a CYP97A protein (e.g., any of the CYP97A proteins described herein or known in the art) and/or a nucleic acid encoding a CYP97B protein (e.g., any of the CYP97B proteins described herein or known in the art), a nucleic acid encoding a CYP97 protein (e.g., any of the CYP97C proteins described herein or known in the art), a nucleic acid encoding a geranylgeranyl pyrophosphate synthase protein (e.g., any of the geranylgeranyl pyrophosphate synthase proteins described herein or known in the art), a nucleic acid encoding a phytoene synthase protein (e.g., any of the phytoene synthase proteins described herein or known in the art), a nucleic acid encoding a phytoene desaturase protein (e.g., any of the phytoene desaturase proteins described herein or known in the art), a nucleic acid encoding a lycopene β-cyclase protein (e.g., any of the lycopene β-cyclase proteins described herein or known in the art), and a nucleic acid encoding a lycopene ε-cyclase protein (e.g., any of the lycopene ε-cyclase proteins described herein or known in the art). Some embodiments further include a nucleic acid encoding a D-1-deoxyxylulose 5-phosphate synthase protein and/or a nucleic acid encoding an isopentenyl pyrophosphate isomerase protein.

In some embodiments, the recombinant cell (e.g., the recombinant bacterium or yeast cell) contains a nucleic acid encoding a CYP97A protein. In some embodiments, the CYP97A is a wild type protein (e.g., one of SEQ ID NO: 1, 7, 9, and 11) or a polypeptide that contains a sequence of a CYP97A wild type protein (e.g., a polypeptide containing the sequence of one of SEQ ID NO: 1, 7, 9, and 11). In some embodiments, the CYP97A protein contains a sequence at least 80% (e.g., at least 85%, 90%, 95%, 96%, 97%, 98%, 99%, or 100%) identical to SEQ ID NO: 1, 7, 9, or 11. Additional non-limiting examples of CYP97A proteins and nucleic acids encoding a CYP97A protein are described herein.

In some embodiments, the recombinant cell (e.g., the recombinant bacterium or yeast cell) contains a nucleic acid encoding a CYP97B protein. In some embodiments, the CYP97B protein is a wild type protein (e.g., one of SEQ ID NO: 3, 13, 15, and 17) or a polypeptide that contains a sequence of a CYP97B wild type protein (e.g., a polypeptide containing the sequence of one of SEQ ID NO: 3, 13, 15, and 17). In some embodiments, the CYP97B protein contains a sequence at least 80% (e.g., at least 85%, 90%, 95%, 96%, 97%, 98%, 99%, or 100%) identical to SEQ ID NO: 3, 13, 15, or 17. Additional non-limiting examples of CYP97B proteins and nucleic acids encoding a CYP97B protein are described herein.

In some embodiments, the CYP97C protein is a wild type protein (e.g., one of SEQ ID NO: 5, 19, 21, and 23) or a polypeptide that contains a sequence of a CYP97C wild type protein (e.g., a polypeptide containing the sequence of one of SEQ ID NO: 5, 19, 21, and 23). In some embodiments, the CYP97C protein contains a sequence at least 80% (e.g., at least 85%, 90%, 95%, 96%, 97%, 98%, 99%, or 100%) identical to SEQ ID NO: 5, 19, 21, or 23. Additional non-limiting examples of CYP97C proteins and nucleic acids encoding a CYP97C protein are described herein.

In some embodiments, the geranylgeranyl pyrophosphate synthase protein is a wild type protein (e.g., one of SEQ ID NO: 57, 25, 27, and 29) or a polypeptide that contains a sequence of a geranylgeranyl pyrophosphate synthase wild type protein (e.g., a polypeptide containing the sequence of one of SEQ ID NO: 57, 25, 27, and 29). In some embodiments, the geranylgeranyl pyrophosphate synthase protein contains a sequence at least 80% (e.g., at least 80%, 85%, 90%, 95%, 96%, 97%, 98%, 99%, or 100%) identical to SEQ ID NO: 57, 25, 27, or 29. Additional non-limiting examples of geranylgeranyl pyrophosphate synthase proteins and nucleic acids encoding a geranylgeranyl pyrophosphate synthase protein are described herein.

In some embodiments, the phytoene synthase protein is a wild type protein (e.g., one of SEQ ID NO: 59, 31, 33, and 35) or a polypeptide that contains a sequence of a phytoene synthase wild type protein (e.g., a polypeptide containing the sequence of one of SEQ ID NO: 59, 31, 33, and 35). In some embodiments, the phytoene synthase protein contains a sequence at least 80% (e.g., at least 85%, 90%, 95%, 96%, 97%, 98%, 99%, or 100%) identical to SEQ ID NO: 59, 31, 33, or 35. Additional non-limiting examples of phytoene synthase proteins and nucleic acids encoding a phytoene synthase protein are described herein.

In some embodiments, the phytoene desaturase protein is a wild type protein (e.g., one of SEQ ID NO: 37 and 39) or a polypeptide that contains a sequence of a phytoene desaturase wild type protein (e.g., a polypeptide containing the sequence of one of SEQ ID NO: 37 and 39). In some embodiments, the phytoene desaturase protein contains a sequence at least 80% (e.g., at least 85%, 90%, 95%, 96%, 97%, 98%, 99%, or 100%) identical to SEQ ID NO: 37 or 39. Additional non-limiting examples of phytoene desaturase proteins and nucleic acids encoding a phytoene desaturase protein are described herein.

In some embodiments, the lycopene β-cyclase protein is a wild type protein (e.g., one of SEQ ID NO: 45, 47, 49, 63, 65, and 66) or a polypeptide that contains a sequence of a lycopene β-cyclase wild type protein (e.g., a polypeptide containing the sequence of one of SEQ ID NO: 45, 47, 49, 63, 65, and 66). In some embodiments, the lycopene β-cyclase protein contains a sequence at least 80% (e.g., at least 85%, 90%, 95%, 96%, 97%, 98%, 99%, or 100%) identical to SEQ ID NO: 45, 47, 49, 63, 65, and 66. Additional non-limiting examples of lycopene β-cyclase proteins and nucleic acids encoding a lycopene β-cyclase protein are described herein.

In some embodiments, the lycopene ε-cyclase protein is a wild type protein (e.g., one of SEQ ID NO: 51, 53, and 55) or a polypeptide that contains a sequence of a lycopene ε-cyclase wild type protein (e.g., a polypeptide containing the sequence of one of SEQ ID NO: 51, 53, and 55). In some embodiments, the lycopene ε-cyclase protein contains a sequence at least 80% (e.g., at least 85%, 90%, 95%, 96%, 97%, 98%, 99%, or 100%) identical to SEQ ID NO: 51, 53, or 55. Additional non-limiting examples of lycopene ε-cyclase proteins and nucleic acids encoding a lycopene ε-cyclase protein are described herein.

In some embodiments, the D-1-deoxyxylulose 5-phosphate synthase protein is a wild type protein (e.g., one of SEQ ID NO: 95 and 97) or a polypeptide that contains a sequence of a D-1-deoxyxylulose 5-phosphate synthase wild type protein (e.g., a polypeptide containing the sequence of one of SEQ ID NO: 95 and 97). In some embodiments, the D-1-deoxyxylulose 5-phosphate synthase protein contains a sequence at least 80% (e.g., at least 85%, 90%, 95%, 96%, 97%, 98%, 99%, or 100%) identical to SEQ ID NO: 95 and 97. Additional non-limiting examples of D-1-deoxyxylulose 5-phosphate synthase proteins and nucleic acids encoding a D-1-deoxyxylulose 5-phosphate synthase protein are described herein.

In some embodiments, the isopentenyl pyrophosphate isomerase protein is a wild type protein (e.g., one of SEQ ID NO: 99 and 101) or a polypeptide that contains a sequence of a D isopentenyl pyrophosphate isomerase wild type protein (e.g., a polypeptide containing the sequence of one of SEQ ID NO: 99 and 101). In some embodiments, the isopentenyl pyrophosphate isomerase protein contains a sequence at least 80% (e.g., at least 85%, 90%, 95%, 96%, 97%, 98%, 99%, or 100%) identical to SEQ ID NO: 99 or 101. Additional non-limiting examples of isopentenyl pyrophosphate isomerase proteins and nucleic acids encoding an isopentenyl pyrophosphate isomerase protein are described herein.

In some embodiments, one or more (e.g., 2, 3, 4, 5, 6, 7, 8, 9, or 10) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and a nucleic acid encoding an isopentenyl pyrophosphate isomerase protein is located on one or more vectors (e.g., two, three, or four vectors) (one or more vectors present within the bacterium or yeast cell). In some embodiments, the one or more vector is selected from the group of plasmids (e.g., yeast integrating plasmids and yeast episomal plasmids), cosmids, bacterial artificial chromosomes, and yeast artificial chromosomes. A variety of empty vectors, that can be genetically manipulated to include one or more of the nucleic acids described herein, are commercially available and can be used to transform a bacterial or yeast cell (e.g., from Sigma Aldich and Promega). In some embodiments, the vector is a plasmid or an artificial chromosome. In some embodiments, the vector (e.g., a plasmid or artificial chromosome) comprises at least one inducible promoter (inducible promoter sequence). In some embodiments, the vector comprises at least one selection marker (e.g., an antibiotic resistance gene).

In some embodiments, one or more (e.g., 2, 3, 4, 5, 6, 7, 8, 9, and 10) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and a nucleic acid encoding an isopentenyl pyrophosphate isomerase protein is integrated in a chromosome in the bacterium or yeast cell. In some embodiments, one or more (e.g., 2, 3, 4, 5, 6, 7, or 8) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and the nucleic acid encoding an isopentenyl pyrophosphate isomerase protein is operably expressed from an inducible promoter (inducible promoter sequence) present within the chromosome. In some embodiments, the chromosome in the bacterium or yeast cell further comprises a selection marker.

In some embodiments, one or more (e.g., 2, 3, 4, 5, 6, 7, or 8) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and the nucleic acid encoding an isopentenyl pyrophosphate isomerase protein is integrated in a chromosome in the bacterium or yeast cell, and one or more (e.g., 2, 3, 4, 5, 6, 7, or 8) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and the nucleic acid encoding an isopentenyl pyrophosphate isomerase protein is located in one or more (e.g., two, three, four, or five) vectors (e.g., plasmid or artificial chromosome) (present within the same bacterial or yeast cell). In some embodiments, one or more (e.g., 2, 3, 4, 5, 6, 7, or 8) of the nucleic acid encoding a CYP97A protein, the nucleic acid encoding a CYP97B protein, the nucleic acid encoding a CYP97 protein, the nucleic acid encoding a geranylgeranyl pyrophosphate synthase protein, the nucleic acid encoding a phytoene synthase protein, the nucleic acid encoding a phytoene desaturase protein, the nucleic acid encoding a lycopene β-cyclase protein, the nucleic acid encoding a lycopene ε-cyclase protein, the nucleic acid encoding a D-1-deoxyxylulose 5-phosphate synthase protein, and the nucleic acid encoding an isopentenyl pyrophosphate isomerase protein is operably expressed from an inducible promoter (inducible promoter sequence) present within the chromosome and/or the one or more vectors (present within the same cell). In some embodiments, the chromosome in the bacterium or yeast cell and/or the one or more vectors further contains a selection marker.

In some embodiments, the recombinant cell can be a mammalian cell (e.g., an epithelial cell or any other mammalian cell type known in the art). In some embodiments, the recombinant cell can be a plant cell (e.g., any of the plant species described herein or known in the art).

Methods for introducing one or more nucleic acids described herein or one or more vectors described herein into a bacterial cell or yeast cell are known in the art. For example, one or more of the nucleic acids described herein or one or more of the vectors described herein can be introduced into a yeast or bacterial cell using transformation. A number of different methods for performing transformation are known in the art (e.g., $CaCl_2$ transformation and electroporation). (See, e.g., the Protocol Online website, protocol-online.org; Xiao, Yeast Protocols (Methods in Molecular Biology), Humana Press Inc., 2010; and Ausubel et al., Short Protocols in Molecular Biology, Fifth Edition, John Wiley & Sons, Inc., 2002.)

In some embodiments, the cell is a recombinant bacterium. Non-limiting examples of bacteria include *Lactobacillus* (including but not limited to *L. casei* and *L. brevis*), *Clostridium, E. coli, Actinotalea fermentans, Cellulomonas* spp., *Lactococcus lactis* subspecies *cremoris, L. delbrueckii* subspecies *lactis, L. lactis* subspecies *lactis* biovar *diacetylactis, Leuconostoc mesenteroides* subspecies *cremoris, Streptococcus salivarius* subspecies *thermophiles (S. thermophiles), Lactobacillus delbrueckii* subspecies *bulgaricus, L. delbrueckii* subspecies *lactis, L. casei, L. helveticus, L. plantarum, Lactobacillus delrueckii* subspecies *bulgaricus, Streptococcus salivarius* subspecies *thermophiles, Lactobacillus acidophilus,* bifidobacteria, *Lactobaccilus* spp., *Leuconostoc* spp., *Pediococcus* spp., *Lactococcus* spp., *Streptococcus, Aerococcus* spp., *Carnobacterium* spp., *Enterococcus* spp., *Oenococcus* spp., *Sporolactobacillus* spp., *Tetragenococcus* spp., *Vagococcus* spp., and *Weisella* spp., *Leuconostoc mesenteroides,* and *Lactobacillus plantarum.* Additional non-limiting examples of bacteria belong to the order of Lactobacillales.

In some embodiments, the cell is a recombinant yeast cell. Non-limiting examples of yeast include Ascomycota and Basidiomycota, including but not limited to: *S. cerevisiae, S. carlsbergensis, Leucosporidium frigidum, S. telluris,* baker's yeast, brewer's yeast, *S. exiguous,* and *Mucor miehei.* Additional non-limiting examples of yeast include yeast from a genus selected from *Saccharomyces, Pichia, Hansenula, Kluyveromyces, Yarrowia, Trichoderma,* and *Scizosacchromyces, Saccharomyces pastorianus, Dekkera/Brettanomyces, Brettanomyces bruxellensis, Brettanomyces anomalus, Brettanomyces custersianus, Brettanomyces naardenesis,* and *Brettanomyces nanus.*

In some embodiments, the recombinant bacterium or yeast cell can be present in a culture (e.g., a liquid or solid culture).

In some embodiments, the recombinant bacteria or yeast cells described herein can produce at least 500 µg of lutein per gram (e.g., at least 600, 800, 1000, 1200, 1400, 1600, or 1800 µg lutein per gram) of pelleted cells (e.g., dry weight of pelleted cells). In some embodiments, the recombinant bacteria or yeast cells described can produce a synergistic or greater than additive amount of lutein production compared to the sum of the amount of lutein produced by (i) recombinant bacteria or yeast cells that contain a nucleic acid encoding one of a CYP97A or CYP97B protein, and a nucleic acid encoding a geranylgeranyl phosphate synthase protein, a nucleic acid encoding a phytoene synthase protein, a nucleic acid encoding a phytoene desaturase protein, a nucleic acid encoding a lycopene β-cyclase protein, and a nucleic acid encoding a phytoene ε-cyclase protein, and (ii) recombinant bacteria or yeast cells that contain a nucleic acid encoding a CYP97C protein, and a nucleic acid encoding a geranylgeranyl phosphate synthase protein, a nucleic acid encoding a phytoene synthase protein, a nucleic acid encoding a phytoene desaturase protein, a nucleic acid encoding a lycopene β-cyclase protein, and a nucleic acid encoding a phytoene ε-cyclase protein.

Methods of Producing Lutein

Also provided herein are methods of producing lutein that include culturing a recombinant cell (e.g., any of the recombinant cells described herein, e.g., any of the recombinant bacterium or yeast cells described herein) (e.g., under conditions that allow for the production of lutein). In some embodiments, the recombinant cell (e.g., the recombinant bacterium or yeast cell) is cultured in a liquid medium. In some embodiments, the recombinant cell (e.g., the recombinant bacterium or yeast cell) is cultured in or on a solid medium. Non-limiting examples of culture medium that can be used in these methods are known in the art (e.g., LB medium). For additional examples of culture media, see, e.g., Yeast Protocols (Methods in Molecular Biology), Humana Press Inc., 2010; and Ausubel et al., Short Protocols in Molecular Biology, Fifth Edition, John Wiley & Sons, Inc., 2002). Additional non-limiting examples of growth media that can be used in these methods are described in the Examples. As one skilled in the art will appreciate, a variety of different culture media can be used in these methods without significantly altering the amount of lutein produced by the recombinant cell (e.g., the recombinant bacteria or yeast cells). In some embodiments, wherein a selection marker is incorporated in a chromosome of the recombinant cell or a selection is incorporated in one or more vector(s) present within the recombinant cell, a antibiotic is added to the culture medium.

Some embodiments further include lysing the recombinant cells (e.g., recombinant bacterial cell(s) or yeast cell (s)), and isolating (e.g., make at least 60% pure by dry weight (e.g., at least 70%, 75%, 80%, 85%, 90%, 95%, or 100% pure by dry weight)) the lutein from the lysate. Some embodiments further include isolating the lutein from the liquid medium.

In some embodiments, lutein can be isolated directly from a cell pellet (e.g., a pellet of any of the recombinant cells (e.g., recombinant bacteria or yeast cells) described herein), or from a lysate or the liquid medium using a number of different techniques including one or more of solvent extraction (e.g., alcohol (e.g., methanol) extraction), centrifugation, and/or chromatography (e.g., HPLC) (see, e.g., the methods described in the Examples). Additional methods of isolating lutein from a variety of different types of cells are described in Kumar et al., *J. Food Process Engineering* 33:1065, 2010; U.S. Pat. Nos. 6,737,552 and 5,382,714 (incorporated herein by reference), and Li et al., *J. Chromatography A* 905:151-155, 2001. Additional methods of isolating lutein from a variety of different cell types are known in the art.

In some embodiments, the methods provided herein allow for a high yield of lutein production to be achieved per culture volume (e.g., milligrams of lutein produced per liter of liquid culture medium) or a high yield of lutein production to be achieved per gram of pelleted recombinant bacterial or yeast cells. For example, the methods provided herein result in the production of at least 500 µg of lutein per gram (e.g., at least 600, 800, 1000, 1200, 1400, 1600, or 1800 µg lutein per gram) of pelleted cells (e.g., dry weight of pelleted cells). In some embodiments, the methods provide a synergistic or greater than additive amount of lutein production compared to the sum of the amount of lutein produced by (i) recombinant bacteria or yeast cells that contain a nucleic acid encoding one of a CYP97A or CYP97B protein, and a nucleic acid encoding a geranylgeranyl phosphate synthase protein, a nucleic acid encoding a phytoene synthase protein, a nucleic acid encoding a phytoene desaturase protein, a nucleic acid encoding a lycopene β-cyclase protein, and a nucleic acid encoding a lycopene ε-cyclase protein, and (ii) recombinant bacteria or yeast cells that contain a nucleic acid encoding a CYP97C protein, and a nucleic acid encoding a geranylgeranyl phosphate synthase protein, a nucleic acid encoding a phytoene synthase protein, a nucleic acid encoding a phytoene desaturase protein, a nucleic acid encoding a lycopene β-cyclase protein, and a nucleic acid encoding a phytoene ε-cyclase protein.

Compositions

Also provided is lutein produced by any of the methods described herein. Also provided are pharmaceutical compositions, food supplements, food products, and cosmetic compositions that contain lutein produced by any of the methods described herein. In some embodiments, the pharmaceutical composition can be formulated for oral administration. In some embodiments, the food supplement or food product is formulated as a liquid or a solid. In some embodiments, the cosmetic compositions can be a powder, lotion, liquid, gel, or shampoo. In some embodiments, the cosmetic composition can further include one or more (e.g., two, three, four, or five) additional moisturizers, fragrances, sunscreen, pigments, or lubricants.

The invention is further described in the following example, which does not limit the scope of the invention described in the claims.

EXAMPLES

Example 1. Functional Complementation Test in *E. coli* for CYP97 and HYD Substrate Specificities CYP97A, CYP97B, and CYP97C enzymes were previously observed to have low activity in bacterial systems. A series of experiments were performed to investigate: whether the reason for the low activity of CYP97 proteins involved in the synthesis of lutein was due to a low or insufficient amount of the optimal substrate, α-carotene (which contains both β- and ε-rings); or whether the CYP97 enzymes did not function optimally as individual enzymes, but required co-expression and interaction to allow for efficient hydroxylation of α-carotene to produce lutein.

Materials and Methods

GenBank Accession Numbers

Rice (*O. sativa*): CYP97A4, #AK068163; CYP97C2, #AK065689. Maize (*Z. mays*): HYD4, #BG320875/AY844956.

Cloning of CYP97A4, CYP97C2, and HYD4

Amplification of ORFs for cloning was performed by Platinum PCR Supermix High Fidelity master mix (Invitrogen) according to manufacturer instructions. PCR conditions: 1 cycle, 95° C., 3 min; 35-40 cycles: 95° C., 45s; 58° C., 45s; 72° C., 2:00-2.30 min; 1 cycle, 72° C., 10 min. The primer sequence used in these experiments are listed in Table 1.

TABLE 1

Primers

| Vector used for cloning | Primer # | Sequence 5'-> 3' | Restriction sites incorporated in primers |
|---|---|---|---|
| pCDFDuet-1 | 2370 | ACCGCATATGGCCGTCCCGTGCGTA (SEQ ID NO: 67) | NdeI |
|  | 2371 | GAGAGGTACCTCATCTGGACCCACTGAG (SEQ ID NO: 68) | Acc65I |
| pCOLADuet-1 | 1932 | GAGAGAATTCAATGGCCGCCGGT CTGT (SEQ ID NO: 69) | EcoRI |
|  | 1933 | ACCGAAGCTTTTCAGATGGTCCGGCCG (SEQ ID NO: 70) | HindIII |
| pTnT | 2175 | ACCGCTCGAGGCCACCATGAGCTCAGCG ACGTCAGTGAGTG (SEQ ID NO: 71) | XhoI |
|  | 2176 | GAGATCTAGATCAGATTCGAGTTGCTGAG ACTTGC (SEQ ID NO: 72) | XbaI |
|  | 2140 | GAGACTCGAGAATCCATCTCGAATCCCTA GC (SEQ ID NO: 72) | XhoI |
|  | 2168 | ACCGTCTAGATCATCTGGACCCACTGAGT G (SEQ ID NO: 73) | XbaI |
|  | 2165 | ACCGCTCGAGGCCACCATGGCCGCCGGTC TGTCC (SEQ ID NO: 74) | XhoI |
|  | 2166 | GAGATCTAGATCAGATGGTCCGGCCGATT (SEQ ID NO: 75) | XbaI |
| pUC35S-sGFP-Nos | 2634 | ACCGTCTAGAATGAGCTCAGCGACGTCAG TGAG (SEQ ID NO: 76) | XbaI |
|  | 2635 | GAGAGGATCCGATTCGAGTTGCTGAGACT TGCC (SEQ ID NO: 77) | BamHI |
|  | 2879 | ACCGTCTAGAATGGCCGCCGCCGCCGCCG CCGCC (SEQ ID NO: 78) | XbaI |
|  | 2880 | GAGATGATCATCTGGACCCACTGAGTGCA AAATCAG (SEQ ID NO: 79) | BclI |
|  | 2640 | ACCGTCTAGAATGGCCGCCGGTCTGTCC (SEQ ID NO: 80) | XbaI |
|  | 2641 | GAGAGGATCCGATGGTCCGGCCGATTCG (SEQ ID NO: 81) | BamHI |

TABLE 1-continued

Primers

| Vector used for cloning | Primer # | Sequence 5'-> 3' | Restriction sites incorporated in primers |
|---|---|---|---|
| pSAT | 2455 | ACCGCTCGAGGCAACAATGAGCTCAGCG ACGTCAGTGAG (SEQ ID NO: 82) | XhoI |
| | 2456 | GAGAGAATTCGATTCGAGTTGCTGAGACT TGCC (SEQ ID NO: 83) | EcoRI |
| | 3025 | ACCGCTCGAGATGGCCGCCGCCGCCGCCG CCGCC (SEQ ID NO: 84) | XhoI |
| | 3026 | GAGAGAATTCTCTGGACCCACTGAGTGCA AAATCAG (SEQ ID NO: 85) | EcoRI |
| | 2469 | ACCGCTCGAGATGGCC GCCGGTCTGTCC (SEQ ID NO: 86) | XhoI |
| | 2470 | GAGAGAATTCGATGGTCCGGCC GAT TCG (SEQ ID NO: 87) | EcoRI |
| | 3023 | ACCGCTCGAGATGAGCTCAGCGACGTCA GTGAG (SEQ ID NO: 88) | XhoI |
| | 3024 | GAGAGAATTCGATTCGAGTTGCTGAGACT TGCC (SEQ ID NO: 89) | EcoRI |
| | 2459 | ACCGCCATGGCCGCCGCCGCC (SEQ ID NO: 90) | NcoI |
| | 2460 | GAGAGAATTCTCTGGACCCACTGAGTGC (SEQ ID NO: 91) | EcoRI |
| | 2848 | ACCGTCATGATGGCCGCCGGTCTGTCCGG (SEQ ID NO: 92) | BspHI |
| | 2849 | GAGAGAATTCGATGGTCCGGCCGATTCGC G (SEQ ID NO: 93) | EcoRI | pColaDuet and pCDFDuet Constructs

For cloning into pCOLADuet™-1 vector (Novagen), full copies of cDNA of CYP97A4 and CYP97C2 were amplified from rice cDNA (Quinlan et al., Arch. Biochem. Biophysics 458:146-157, 2007). pCOLADuet™-1-CYP97A4 was renamed pRT-A4. CYP97C2 was amplified from pCOLA-Duet-1 using primers 2370 & 2371, cloned into NdeI and Acc65I sites of pCDFDuet-1 vector (Novagen) and renamed pRQ-C2. HYD4 was amplified from pTHYD4 (Vallabhaneni et al., Plant Physiol. 151:1635-1645, 2009) using primers 1932 & 1933, and cloned into pCOLADuet-1. pCOLADuet-1-HYD4 was renamed pRQ-H4. The corresponding protein and nucleic acid (mRNA) sequence of rice (O. sativa) CYP97A4 used in these experiments are SEQ ID NOs: 1 and 2, respectively. The corresponding protein and nucleic acid (mRNA) sequence of rice (O. sativa) CYP97C2 used in these experiments are SEQ ID NOs: 5 and 6.

Functional Analysis of Hydroxylases in E. coli

For testing of substrate specificity for individual enzymes, pRT-A4, pRQ-C2, or pRQ-H4 were respectively transformed into E. coli BL21 (DE3) cells (Novagen) harboring either of the following plasmids:

1) pAC-BETA-At (Cunningham et al., 2007) only, which confers β-carotene accumulation, 2) pAC-BETA-At+plasmid y2 (Cunningham Jr. et al., 1996) which together confer accumulation of α- and β-carotene.

For testing of substrate specificity for enzyme combinations the pRT-A4+pRQ-C2 and pRQ-C2+pRQ-H4 constructs were co-transformed into E. coli BL21 (DE3) cells (Novagen) harboring both pAC-BETA-At+plasmid y2. For negative controls, α- and β-carotene accumulating cells were transformed with empty vectors.

For carotenoid analyses, overnight cultures in LB medium were diluted 50-fold into 50 mL fresh medium in 500-mL flasks, then grown in the dark at 250 rpm at 37° C. until OD 0.6, and induced with 10 mM IPTG, and further cultured for a total of three days. Negative controls never generated any hydroxylated products.

Extraction of Carotenoids from E. coli Cells, and HPLC and LC-MS Analysis 50-mL cultures were centrifuged at 3000 g, 10 minutes. The bacterial cell pellets were extracted in 5 mL of methanol using a Sonicator (Vibra Cell), and pelleted down by centrifugation at 3000 g for 10 minutes. The supernatants were transferred to 100-mL Pyrex flasks, and evaporated under nitrogen gas. Once dried, 300 µL of methanol was added to dissolve the samples. The samples were then frozen at −80° C. for 30 minutes, pelleted down using an Eppendorf centrifuge at maximum speed at 4° C., and the supernatants were transferred to HPLC vials (Waters).

HPLC separation was carried out using a Waters system equipped with a 2695 Alliance separation module, a 996 photodiode array detector, a column heater, a fraction collector II, Empower software (Millipore), and a Develosil C30 RP-Aqueous (5 µm, 250×4.6 mm) column (Phenomenex), with a Nucleosil $C_{18}$ (5 µm, 4×3 0 mm) guard column (Phenomenex), with a mobile phase consisting of mixtures of acetonitrile:methanol:water (84:2:14 v/v/v (A)) and methanol:ethyl acetate (68:32 v/v (B)), with a gradient to obtain 100% B at 60 minutes (flow rate 0.6 mL/min), 100% B at 71 minutes with the flow rate changing to 1.2 mL/min, followed by 100% A (flow rate 1.2 mL/min) at 110 minutes. The peaks were identified on the basis of retention times/spectra matching those of authentic standards (Indofine), and standards purified from bacteria expressing genes encoding carotenoid biosynthetic enzymes (Cunningham Jr. et al., Plant Cell 8:1613-1626 1996; Cunningham et al., Eukaryot. Cell 6:533-545, 2007). Integrated peak areas for extracted metabolites were calculated and carotenoids were quantified as a percentage of total carotenoids. All data were collected at lambda max of 450 nm.

LC-MS was performed on a Waters 2695 HPLC equipped with a 2998 PDA detector coupled to a Waters LCT Premiere XE Time of Flight (TOF) Mass Spectrometer system using electrospray ionization in positive ion mode. Separation was performed using a Develosil C30 RP-Aqueous (5 µm, 250×4

6 mm) column (Phenomenex), with mobile phase consisting of mixtures of acetonitrile:methanol:water (84:2:14 v/v/v (A)) and methanol:ethyl acetate (68:32 v/v (B)), with a gradient to obtain 100% B at 60 minutes (flow rate 0.6 mL/minute), 100% B at 71 minutes with flow rate changing to 1.2 mL/min, followed by 100% A (flow rate 1.2 mL/minute) at 110 minutes.

Figure 15:
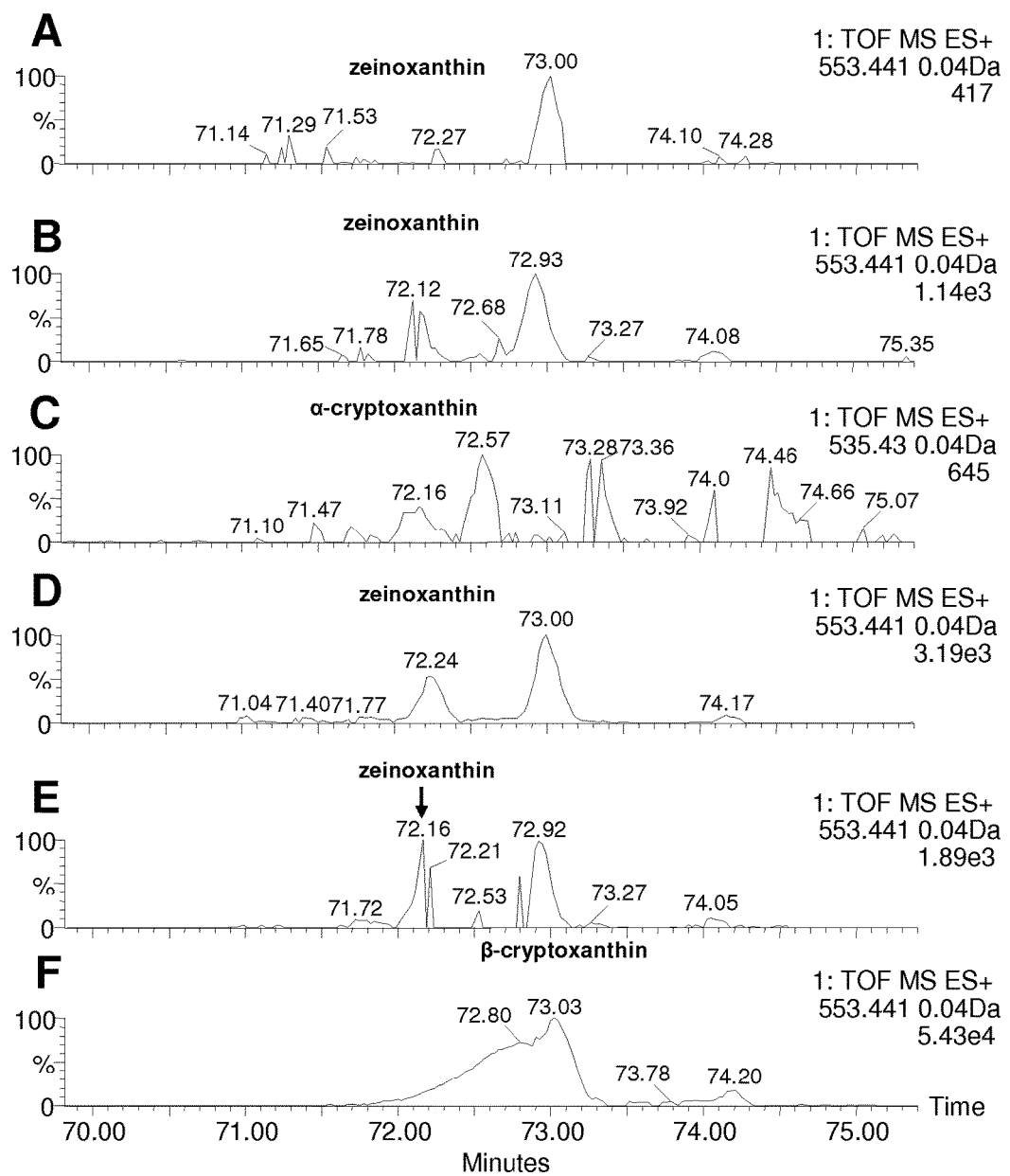
FIG. 15 is a set of six reversed phase HPLC chromatographs of carotenoid extracts from *E. coli* accumulating α- and β-carotene or a purified control (A: bacteria overexpressing CYP97C2+HYD4; B: bacteria overexpressing CYP97C2+CYP97A4; C: bacteria overexpressing CYP97C2; D: bacteria overexpressing HYD4; E: bacteria overexpressing CYP97A4; and F: a purified β-cryptoxanthin standard). The peaks were identified as described in Kim et al., *Phytochemistry* 71:168-178, 2010). The masses of the major quasimolecular ions for the indicated carotenoids are: zeinoxanthin ([MH+]=553.4), β-cryptoxanthin ([MH+]=553.4), and α-cryptoxanthin ([MH+−H2O]= 535.4).

The accumulated carotenoids and the standards for lutein, zeaxanthin, β-cryptoxanthin, and α- and β-carotene were analyzed using HPLC. Alpha-cryptoxanthin, β-cryptoxanthin and zeinoxanthin were identified/confirmed by LC-MS. Cryptoxanthin isomers were identified as described (Kim et al., *Proc. Natl. Acad. Sci. U.S.A.* 103:3474-3479, 2006) (FIG. 15).

Results

Figure 16:
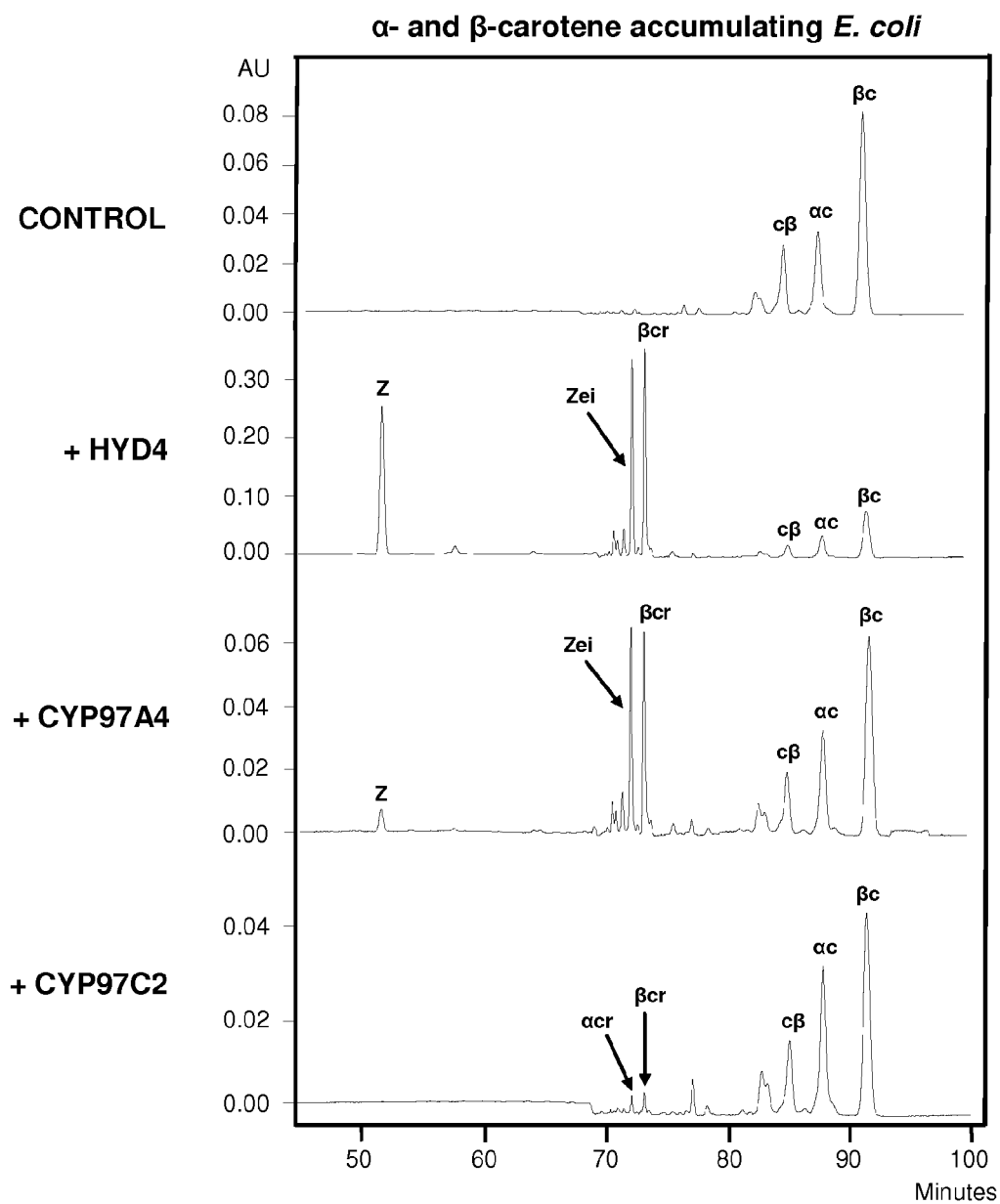
FIG. 16 is a set of four reversed phase HPLC chromatographs from *E. coli* cells accumulating both α-carotene and β-carotene following transformation with a control plasmid (empty pColaDuet) or with test plasmids encoding HYD4 (+HYD4), CYP97A4 (+CYP97A4), or CYP97C2 (+CYP97C2). The spectra shown were extracted at 450 nm Z, zeaxanthin; Zei, zeinoxanthin; acr, α-cryptoxanthin; βcr, β-cryptoxanthin; cβ, 13-cis β-carotene; αc, α-carotene; and βc, β-carotene

A first set of experiments was performed to determine whether the CYP proteins had low activity in bacterial systems due to deficient production of α-carotene as a substrate. Alpha-carotene can only be produced by engineering bacteria to synthesize both β-carotene and α-carotene. In these experiments, CYP97A4 and CYP97C2 (Quinlan et al., *Arch. Biochem. Biophys.* 458:146-157 2007) and maize HYD4 (Vallabhaneni et al., *Plant Physiol.* 151:1635-1645, 2009) were expressed in *E. coli* that accumulated both α-carotene (β-ε rings) and β-carotene (β-β rings). The carotenoid products were analyzed by HPLC and/or LC/MS. In cells accumulating both α- and β-carotene, the expectation was that hydroxylation of both β-rings in β-carotene by the β-ring hydroxylases (CYP97A and HYD) would lead to formation of the monohydroxylated intermediate, β-cryptoxanthin, as well as the end product, zeaxanthin. This was the case for HYD4: cells expressing this enzyme accumulated ~30% zeaxanthin. By contrast, cells expressing CYP97A4 mainly accumulated the intermediate β-cryptoxanthin (17% total carotenoids) while only 3% zeaxanthin was generated (FIG. 16, Table 2). Similar results were observed when cells were engineered to accumulate β-carotene only (Table 3). It was also expected that these β-ring hydroxylases would hydroxylate α-carotene to form zeinoxanthin, and indeed this product was detected in cells expressing both CYP97A and HYD4, although the HYD4 enzyme was twice as active as CYP97A. In addition, it was expected that cells transformed with the ε-ring hydroxylase CYP97C2 would accumulate the monohydroxylated product α-cryptoxanthin. However, this compound was barely detected (~0.7% total carotenoids). These results show that HYD4 was most effective in producing a di-hydroxylated carotene, in this case zeaxanthin, which was produced from β-carotene. The above results only partially confirmed the hypothesis that P450 carotene hydroxylases (CYP97A and CYP97C) require α-carotene as a substrate. CYP97A appeared to function as a monohydroxylase for either β-carotene or α-carotene, but CYP97C was marginally functional, regardless of the substrate. These experiments also show that CYP97C could not efficiently hydroxylate carotene β-rings, which is in disagreement with the opposite conclusion made in prior studies on the basis of lutein-accumulating *Arabidopsis* mutants carrying only CYP97C, but not CYP97A or HYD enzymes (Kim et al., *Plant Cell Physiol* 50:463-479 2009). The triple mutant phenotype is better explained by activity of another endogenous P450 hydroxylase with which CYP97C may partner (Kim et al., *Proc. Natl. Acad. Sci. U.S.A.* 103: 3474-3479 2010). Further experiments were performed to determine whether both CYP97A and CYP97C must be both co-expressed and physically interact to efficiently convert α-carotene to lutein.

TABLE 2

% Major Products in α- and β-carotene accumulating *E. coli* with individually expressed hydroxylases

| Hydroxylase | zeaxanthin | α-cryptoxanthin | zeinoxanthin | β-cryptoxanthin |
|---|---|---|---|---|
| CYP97A4 | 3.38 ± 0.27 | ND | 13.63 ± 2.97 | 16.76 ± 2.14 |
| CYP97C2 | ND | 0.71 ± 0.21 | ND | 1.14 ± 0.30 |
| HYD4 | 30.74 ± 1.85 | ND | 23.03 ± 2.72 | 24.03 ± 0.36 |
| Empty vector control | ND | ND | ND | ND |

Carotenoids are expressed as a percentage of total carotenoids. Each value is the mean result of 3 replicates ± SD.
ND, not detectable.

TABLE 3

% Major Products in β-carotene accumulating *E. coli* with individually expressed hydroxylases

| Hydroxylase | zeaxanthin | β-cryptoxanthin |
|---|---|---|
| CYP97A4 | 11.08 ± 1.21 | 26.19 ± 0.53 |
| CYP97C2 | N.D | 0.78 ± 0.12 |
| HYD4 | 29.34 ± 3.86 | 24.14 ± 1.92 |
| Empty vector control | ND | ND |

Carotenoids are expressed as a percentage of total carotenoids. Each value is the mean result of 3 replicates ± SD.
ND, not detectable.

Figure 17:
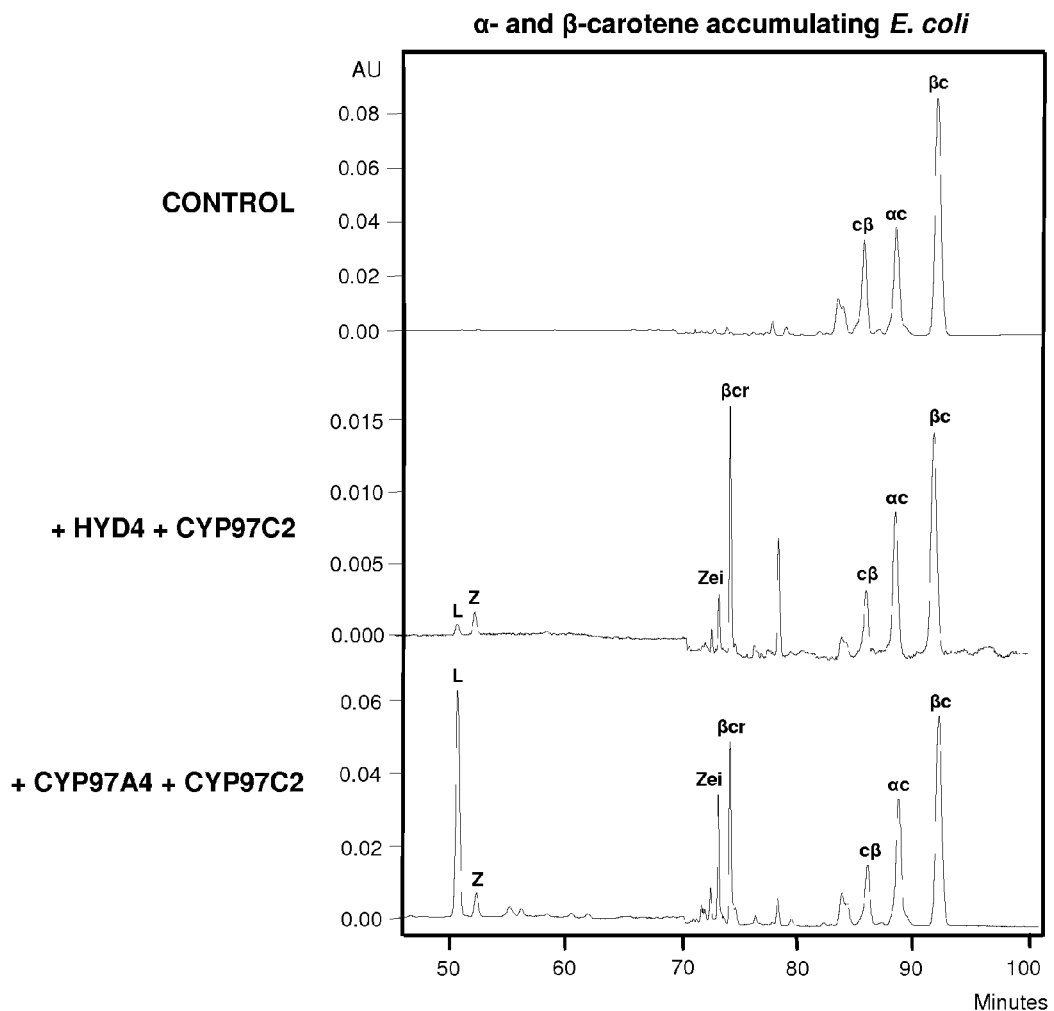
FIG. 17 is a set of three reversed phase HPCL chromatographs from *E. coli* cells accumulating both α-carotene and β-carotene following transformation with a control plasmid (empty pColaDuet) or with combinations of test plasmids HYD4+CYP97C2, or CYP97A4+CYP97C2. The spectra shown were extracted at 450 nm L, lutein; Z, zeaxanthin; Zei, zeinoxanthin; βcr, β-cryptoxanthin; cβ, 13-cis β-carotene; αc, α-carotene; and βc, β-carotene.

When P450 hydroxylases were co-expressed in the presence of α-carotene and β-carotene, their combined activity was dramatically increased as evidenced by formation of lutein (29% of total carotenoids) representing hydroxylation of the ε-ring in α-carotene by CYP97C2 and the β-ring by CYP97A4 (FIG. 17, Table 4). This level of di-hydroxylated pathway end product was comparable to that found for zeaxanthin formation by HYD4 (FIG. 16, Table 2). In contrast, the co-expression of HYD4 with CYP97C2 did not lead to significant levels of hydroxylated carotenes. These data indicate that a synergistic interaction occurs between P450 enzymes that did not occur between HYD4 and CYP97C2, since creating a monohydroxylated substrate by HYD4 was insufficient for CYP97C2 to hydroxylate the remaining ε-ring. These data show that the CYP97 enzymes must be co-expressed in a microbe (e.g., bacteria or yeast) in order for α-carotene to be fully hydroxylated to form lutein.

TABLE 4

% Major products in α- and β-carotene accumulating *E. coli* with co-expressed hydroxylases

| Hydroxylases | lutein | zeaxanthin | α-cryptoxanthin | zeinoxanthin | β-cryptoxanthin |
|---|---|---|---|---|---|
| CYP97A4 + CYP97C2 | 28.99 ± 2.90 | 2.98 ± 0.44 | ND | 7.86 ± 1.28 | 13.32 ± 1.90 |
| HYD4 + CYP97C2 | 1.58 ± 0.14 | 3.16 ± 0.13 | ND | 3.49 ± 0.47 | 17.93 ± 1.57 |
| Empty vector control | ND | ND | ND | ND | ND |

Carotenoids are expressed as a percentage of total carotenoids. Each value is the mean result of 3 replicates ± SD.
ND, not detectable.

The requirement for co-expression suggested that the CYP97 enzymes might need to interact with each other, but not with HYD, in order to efficiently produce the di-hydroxylated carotenes, and the interacting enzymes might require similar patterns of cellular localization (e.g., plastid localization). Additional experiments were performed to test these hypotheses. See, Example 2, below.

Example 2. Plastid Localization of Carotene Hydroxylases Based on Chloroplast Import Studies Recent proteomic methods utilizing LC-MS/MS showed CYP97A and CYP97C localized to the *Arabidopsis* chloroplast envelope (Joyard et al., *Mol Plant* 2:1154-1180, 2009; Ferro et al., *Mol. Cell. Proteomics* 9:1063-1084, 2010). However, no data were available for location of HYD enzymes. Using the online prediction server TMHMM (Krogh et al., *J. Mol. Biol.* 305:567-580 2001), HYD4 was predicted to have four transmembrane helices which would be expected to confer an integral membrane localization. The CYP97 structures were not predicted to have transmembrane helices. In vitro chloroplast import assays were performed to test whether the hydroxylases were integrally or peripherally associated with membranes as described below.

Materials and Methods
pTnT Constructs

A full-length cDNA of CYP97A4 was amplified from the pRT-A4 vector via PCR using primers 2175 & 2176. CYP97C2 was amplified from rice (*Oryza sativa*) cDNA using primers 2140 & 2168. HYD4 was amplified from pRQ-H4 with primers 2165 & 2166. CYP97A4, CYP97C2, and HYD4 were cloned into the XhoI and XbaI sites of the pTnT vector (Promega), and respectively named pTnT-A4, pTnT-C2, and pTnT-H4.

Chloroplast Isolation and In Vitro Import

Chloroplasts used in import assays were isolated from 10-14 day old pea plants as described (Bruce et al., Plant Molecular Biology Manual, Vol J1, Kluwer Academic Publishers, Boston 1994). Approximately, 25 g of leaves were homogenized at 4° C. with a blender in 75 mL of cold grinding buffer (50 mM HEPES pH 8, 0.33 M sorbitol, 1 mM $MgCl_2$, 1 mM $MnCl_2$, 2 mM $Na_2EDTA$, pH 8, 0.1% BSA, 0.1% Na-ascorbate) by 3-5 bursts of 1 second each. All further operations were performed on ice using cold buffers. The homogenate was filtered through 2 layers of cheesecloth and 1 layer of Nylon mesh (60 µm), and the filtrate was centrifuged at 2000 g for 2 minutes. Pellets were carefully resuspended in 1 mL of grinding buffer, and overlaid on top of two 36-mL Percoll gradients (prepared by centrifugation of 50% Percoll (Sigma) in grinding buffer, 40000 g, 30 minutes, at 4° C.), and centrifuged at 12000 g, 11 minutes, at 4° C. The intact chloroplasts in the lower band were gently collected with a pipette, washed with 3 volumes of import buffer (50 mM HEPES, pH 8, 0.33 M sorbitol), and then pelleted at 2000 g, 2 minutes, at 4° C. The washed intact chloroplasts were resuspended in import buffer to yield a chloroplast concentration of 0.5 mg/mL, and kept on ice until use.

The plasmid constructs pTnT-A4, pTnT-C2, and pTnT-H4 were used as templates for in vitro transcription/translation performed with the TnT Coupled Reticulocyte Lysate System (Promega) in the presence of [$^{35}S$]-methionine according to the manufacturer's instructions. The reaction mixtures were prepared containing purified chloroplasts (0.5 mg/mL), 1× import buffer, 4 mM methionine, 4 mM ATP, 4 mM $MgCl_2$, 10 mM KAc, 10 mM $NaHCO_3$, and 10 µL of reticulocyte lysate translation product in a total volume of 150 µL. The reactions mixtures were incubated for 25 minutes at 25° C. in light. The import reactions were stopped by adding 500 µL of 1× import buffer, and samples were centrifuged at 800 g for 2 minutes at 4° C. to obtain pellet of intact chloroplasts. The pellets were resuspended in 200 µL import buffer, supplemented by 1 mM $CaCl_2$, and each reaction mixture was divided into two equal aliquots. Thermolysin was added to one of the two aliquots to a concentration of 125 ng/µL and incubated for 30 minutes at 4° C. The reaction was terminated by addition of EDTA to a concentration of 10 mM. For fractionation experiments after import reaction, the intact chloroplasts were washed twice with import buffer, then diluted with HL buffer (10 mM HEPES-KOH, 10 mM $MgCl_2$, pH=8); the total mixture was frozen in liquid nitrogen/thawed 3 times, and then centrifuged (16000 g, 20 minutes). Alkaline treatment of membrane fractions was performed using 200 mM $Na_2CO_3$, pH>10, for 10 minutes on ice, and the pellets containing the treated membranes were separated from the supernatant by centrifugation (16 000 g, 20 minutes). All fractions, including soluble, membrane, and purified membrane pellets, were analyzed by SDS-PAGE. Radiolabelled protein bands were visualized using a Storm Phosphoimager (Amersham Biosciences).

Isolation and Transformation of Maize Protoplasts

Isolation and transformation of maize protoplasts were performed according to classical protocols (Sheen, *Plant Cell* 3:225-245, 1991; van Bokhoven et al., *J. Gen. Virol.* 74: 2233-2241 1993) with modifications. Maize var. *B*73 plants were grown in the dark at 26° C. for 12 days (12 h day, 12 h night in Avantis growth chamber (Conviron)). The middle parts of $2^{nd}$ leaves of 20 plants were cut into razor thin sections, and transferred to a 500 mL-Erlenmeyer flask containing 50 mL of Ca/mannitol solution (10 mM $CaCl_2$, 0.6M mannitol, 20 mM MES, pH 5.7) to which was added 1% cellulase (*Trichoderma viride*), 0.3% pectinase (*Rhizopus* sp.) (Sigma), 5 mM β-mercaptoethanol (Sigma), and 0.1% BSA (Sigma). A vacuum was applied for 5 minutes, followed by shaking at 60 rpm at RT in the dark for 3 hours. The supernatant was filtered by 60 µm nylon mesh, and collected in a 50-mL Falcon centrifuge tube. The protoplasts were pelleted at 60 g for 5 minutes at room temperature, and then washed with 25 mL Ca/mannitol solution (repeated 3 times). The protoplasts were aliquoted into portions of $10^6$ in 150 µl. To each reaction, 10 µg of ice-cold plasmid DNA was added. The protoplasts were then mixed with 500 µL of polyethylene glycol solution (40% PEG 6000, 0.5 M mannitol, 0.1 M Ca(NO$_3$)$_2$) for 10 seconds, followed by the addition of 4.5 mL of mannitol/MES solution (15 mM MgCl$_2$, 0.1% MES, pH 5.5, 0.5 M mannitol), and incubated at room temperature for 25 minutes. The suspension was then centrifuged at 60 g, 5 minutes, at RT, and the supernatant was discarded. The sediment was washed with Ca/mannitol solution, and pelleted at 60 g, 5 minutes, at room temperature. The supernatant was discarded, and the protoplasts were re-suspended in 1 mL Ca/mannitol solution. The protoplasts were transferred to a 24-well plate, and incubated overnight at 25° C. under dim light. The transformational efficiency for protoplasts was 80-90%.

Results

Figure 18:
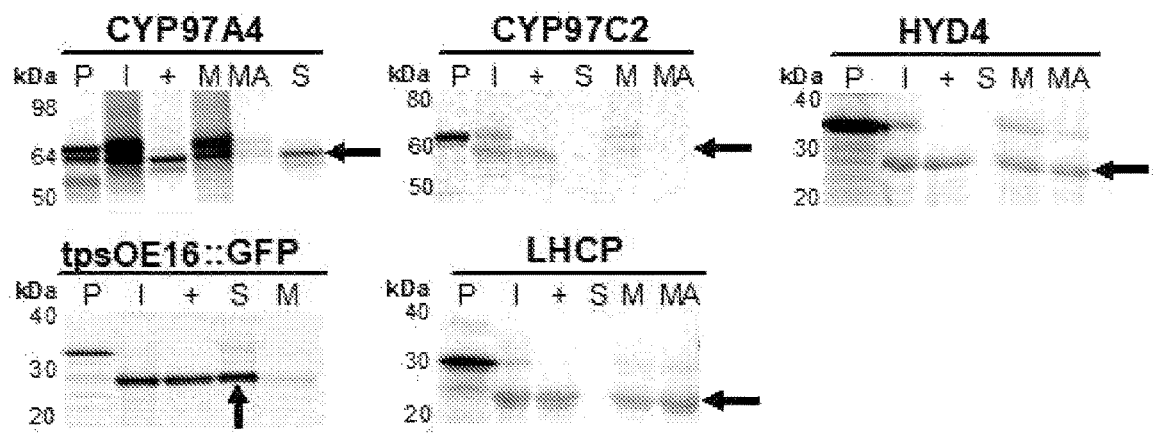
FIG. 18 is a set of five radiographs of the results of an in vitro chloroplast import assay. In these experiments, isolated pea chloroplasts were used for the in vitro import of $^{35}$S-methionine radiolabelled protein precursors. The chloroplasts harboring imported proteins were then re-isolated and subjected to thermolysin treatment to distinguish between proteins that were peripherally-bound to the outer chloroplast envelope, and those that had been imported (processed to remove the transit peptide). The mature proteins were recovered as protease-resistant forms (arrow), confirming import of these proteins into chloroplasts. Chloroplasts containing imported proteins were hypotonically lysed and fractionated into soluble and membrane fractions. The pellet fractions were then treated with an alkaline buffer to wash away peripherally-associated membrane proteins. The purity of the fractions was controlled by import and fractionation analysis of a chloroplast lumen protein, tpsOE16::GFP; and integral membrane-bound protein, LHCP. SDS-PAGE analysis of the above described fractions indicated that the CYP97A4 and CYP97C2 are synthesized as precursors of about 69 kDa and 62 kDa, and then processed to 64 and 59 kDa, respectively. P, translation products; I, imported protein; (+), thermolysin treatment; S, soluble proteins; M, membrane proteins; and MA, alkaline-treated membrane fraction.
Figure 19:
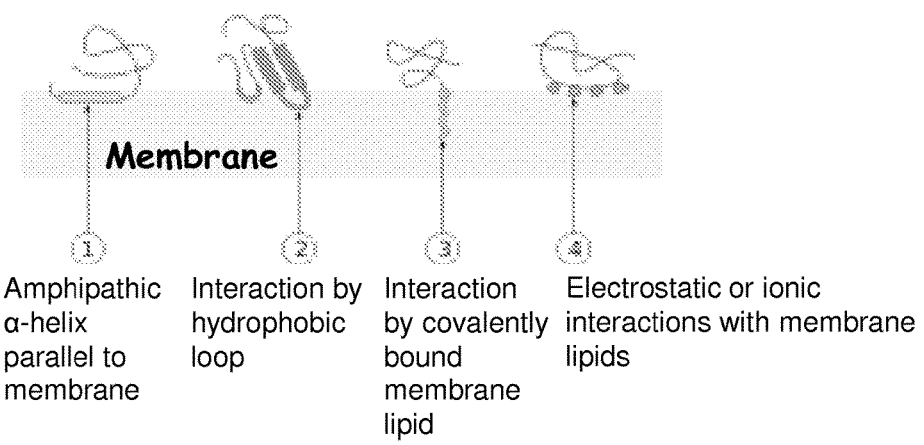
FIG. 19 is a diagram showing the different ways in which a peripheral membrane protein can be associated with a membrane within a cell.
Figure 22:
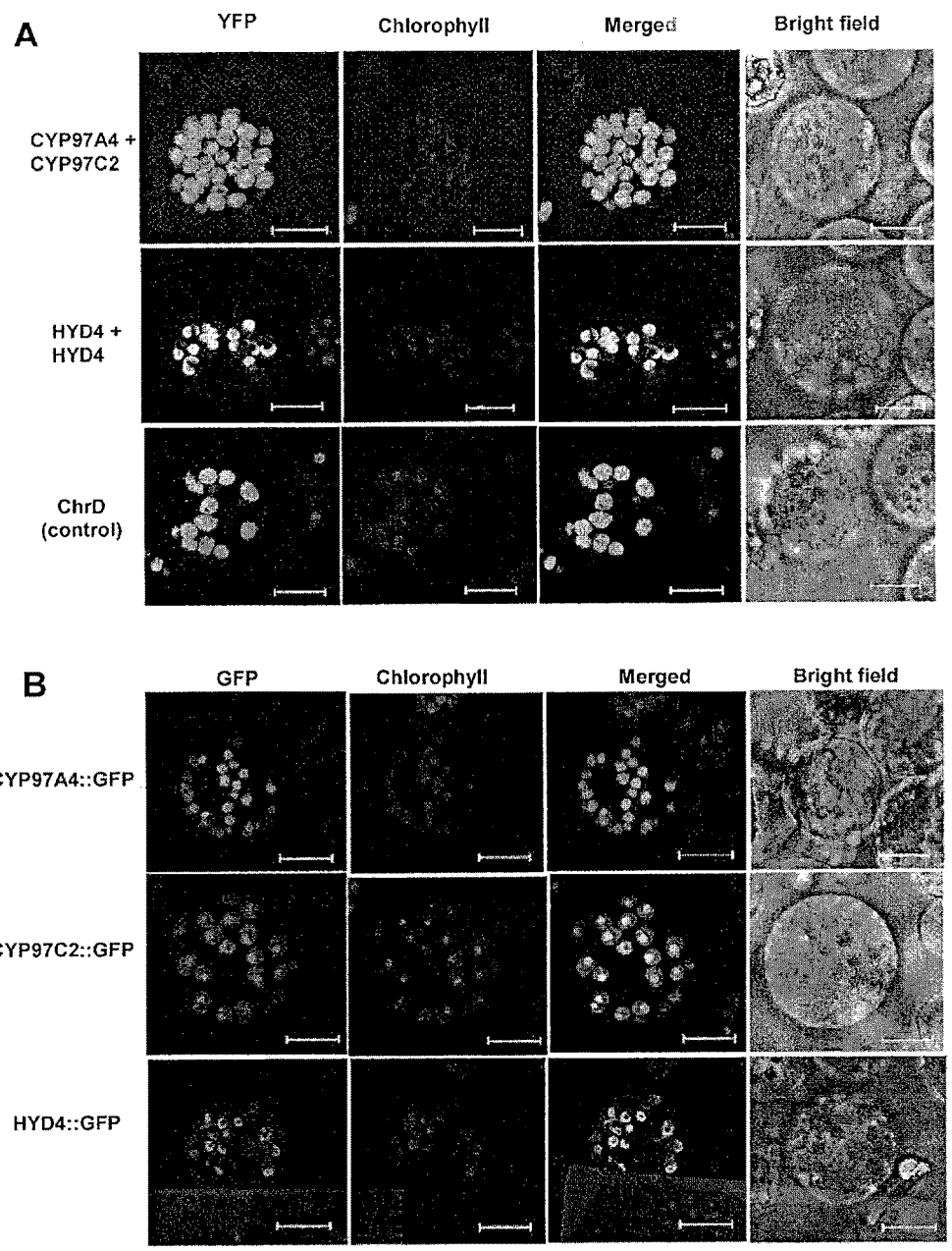
FIG. 22. Interactions and localization of carotene hydroxylases. A, BiFC detection of protein-protein interactions in maize protoplasts. CYP97A4+CYP97C2, HYD4+HYD4 are interacting with each other as seen by restored YFP fluorescence. Fusions of nYFP and cYFP with ChrD protein from cucumber, which is known to form homodimer complexes in plastids (Libal-Weksler et al., 1997), were used as a positive control. B, Transient expression of GFP-fused proteins in maize protoplasts. CYP97 proteins are localized throughout etioplasts, and concentrated at the spot of red chlorophyll autofluorescence of prolamellar bodies, as would be expected for proteins with stromal/weak peripheral membrane association. HYD4 is strictly co-localized with prolamellar bodies consistent with integral thylakoid membrane binding. *Chlorophyll*, chlorophyll autofluorescence. Scale bar=10 μm.
Figure 23:
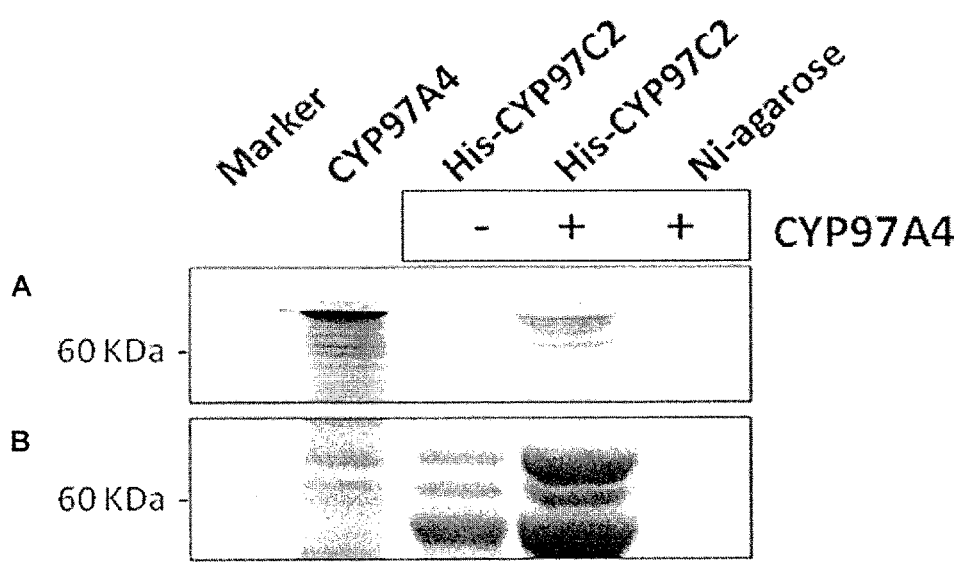
FIG. 23. Pull-down assay. Interaction of CYP97A4 and CYP97C2 was shown in vitro by pull-down assay. CYP97C2 was expressed and purified from *E. coli* cells carrying pET23-CYP97C2, and CYP97A4 (carried by pTnT-A4) was translated in vitro using $^{35}S$ methionine (see Methods). CYP97C2 was bound to Ni-Agarose in a column and used as bait for CYP97A4. Radioactively labeled CYP97A4 interacted with CYP97C2, and interacting proteins eluted from a column together. Control loading of CYP97A4 to pure Ni-Agarose did not show any non-specific binding. A, Autoradiography of SDS-PAGE gel, showing CYP97A4 from in vitro translation reaction and CYP97A4 in the eluate from Ni-Agarose+CYP97C2 column. B. Coomassie staining of the same gel.

Radioactively labeled protein precursors were imported into isolated chloroplasts, and then chloroplasts were fractionated into membrane and soluble fractions. The data show that CYP97A4 and CYP97C2 proteins were found in the membrane fraction and dissociated from it upon alkaline treatment, indicating that these proteins were peripherally associated (FIG. 18). In addition, a significant amount of the CYP97A4 protein was found in the soluble fraction, which also suggested that the peripheral association of this protein is quite weak, allowing the protein to dissociate into a soluble fraction during the fractionation procedure. FIG. 19 is a diagram showing the number of different ways that CYP97A4 and CYP97C2 may be peripherally associated with a membrane in the cell. In contrast to CYP97A4 and CYP97C2, HYD4, found in the membrane fraction as well, proved to be an integral protein as evidenced by resistance to alkaline treatment (FIG. 18).

Example 3. Testing Plastid-Localized Interactions of Partner Hydroxylases

The data described above indicate that a synergistic interaction between CYP97A and CYP97C facilitates lutein formation from α-carotene. Enzyme interactions between CYP97A and CYP97C were further tested in planta using the approach of bimolecular fluorescence complementation (BiFC) (Citovsky et al., *J. Mol. Biol.* 362:1120-1131, 2006) by transient expression in isolated maize protoplasts.

Protoplasts maintain their tissue specificity and reflect in vivo conditions (Faraco et al., *Plant Physiol.* 156:474-478, 2011). In addition, transient expression is an advantageous approach for monitoring localization of low abundance carotenoid biosynthetic enzymes that evade detection in proteomic studies. In BiFC, putative interacting proteins are fused respectively to non-fluorescent N-terminal (nYFP) and C-terminal (cYFP) halves of the yellow fluorescent protein (YFP). The interacting proteins bring together the non-fluorescent fragments, thereby restoring the yellow fluorescence. Various combinations of the CYP97A4, CYP97C2, and HYD4 enzymes were C-terminally fused to the N- and C-terminal halves of YFP. The resulting constructs were transiently co-expressed in maize protoplasts and examined using confocal microscopy.

In additional experiments, the CYP97A4, CYP97C2, and HYD4 enzymes were expressed as GPF fusions in order to further confirm plastid location in the protoplast system.

Materials and Methods pSAT Constructs

For cloning into pSAT-2236 (pSAT4 (A)-nEYFP-N1) (Citovsky et al., *J. Mol. Biol.* 362: 1120-1131, 2006), a full-length cDNA without stop codon of CYP97A4 ORF was amplified from pRT-A4 using primers 2455 and 2426. CYP97C2 was amplified from pRQ-C2 using primers 3025 and 3026. HYD4 was amplified from pRQ-H4 using primers 2469 and 2470. CYP97A4, CYP97C2, and HYD4 were cloned into the XhoI and EcoRI sites of pSAT-2236, and respectively named A4_2236, C2_2236, and H4_2236.

For cloning into pSAT-1476 (pSAT6-cEYFP-N1) (Citovsky et al., *J. Mol. Biol.* 362: 1120-1131, 2006), a full copy of cDNA without stop codon of CYP97A4 was amplified from pRT-A4 using primers 3023 and 3024. CYP97C2 was amplified from pRQ-C2 using primers 2459 and 2460. HYD4 was amplified from pRQ-H4 using primers 2848 and 2849. CYP97A4 was cloned into XhoI and EcoRI sites of pSAT-1476, and named A4_1476. CYP97C2 was cloned into NcoI and EcoRI sites of the pSAT-1476, and named C2_1476. HYD4 was cloned into BspHI and EcoRI sites of pSAT-1476, and named H4_1476.

pUC35S-GUS-Nos Constructs

A full-length cDNA of CYP97A4 without a stop codon was amplified from the pRT-A4 vector with primers 2634 & 2635. CYP97C2 was amplified from pRQ-C2 using primers 2879 & 2880. HYD4 was amplified from the pRQ-H4 using primers 2640 & 2641. CYP97A4, CYP97C2, and HYD4 were cloned in frame into the XbaI and BamHI sites of the pUC35S-sGFP-Nos vector (based on pUC35S-GUS-Nos and pBIG121 vectors (Okada et al., *Plant Physiol.* 122: 1045-1056, 2000)), and respectively named A4-GFP, C2-GFP, and H4-GFP.

Results

The data show that CYP97A4 and CYP97C2 interact with each other, as shown by restored YFP fluorescence (data not shown). The data further show a HYD4+HYD4 interaction, which indicates that HYD4 forms a homodimer (data not shown). Homodimers for CYP97A4 or CYP97C2, or heterodimers for CYP97A4 and HYD4, or CYP97C2 and HYD4 were not observed (data not shown). The enzymes CYP97A4, CYP97C2, and HYD4 were also expressed as GFP fusions in order to confirm plastid localization in the protoplast system. A similar fluorescence pattern was observed, indicating that the interaction does not change the protein localization as seen for the individually expressed proteins (data not shown).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A recombinant bacterium comprising:
   a nucleic acid encoding a cytochrome P450 monooxygenase CYP97A protein or a nucleic acid encoding a cytochrome P450 monooxygenase CYP97B protein;
   a nucleic acid encoding a cytochrome P450 monooxygenase CYP97C protein; a nucleic acid encoding a geranylgeranyl pyrophosphate synthase protein;
   a nucleic acid encoding a phytoene synthase protein; a nucleic acid encoding a phytoene desaturase protein;
   a nucleic acid encoding a lycopene β-cyclase protein; and
   a nucleic acid encoding a lycopene ε-cyclase protein
   wherein the cytochrome P450 monooxygenase CYP97A protein comprises a sequence at least 80% identical to SEP ID NO: 1,
   wherein the cytochrome P450 monooxygenase CYP97B protein comprises a sequence at least 80% identical to SEP ID NO: 3, and
   wherein the cytochrome P45Q monooxygenase CYP97C protein comprises a sequence at least 80% identical to SEP ID NO: 5.

2. The recombinant bacterium of claim 1, further comprising:
   a nucleic acid encoding a D-1-deoxyxylulose 5-phosphate synthase protein; and/or a nucleic acid encoding an isopentenyl pyrophosphate isomerase protein.

3. The recombinant bacterium of claim 1, wherein the bacterium or yeast cell comprises a nucleic acid encoding a cytochrome P450 monooxygenase CYP97A protein.

4. The recombinant bacterium of claim 1, wherein the bacterium or yeast cell comprises a nucleic acid encoding a cytochrome P450 monooxygenase CYP97B protein.

5. The recombinant bacterium of claim 1, wherein the geranylgeranyl pyrophosphate synthase protein comprises a sequence at least 80% identical to SEQ ID NO: 57.

6. The recombinant bacterium of claim 1, wherein the phytoene synthase protein comprises a sequence at least 80% identical to SEQ ID NO: 59.

7. The recombinant bacterium of claim 1, wherein the phytoene desaturase protein comprises a sequence at least 80% identical to SEQ ID NO: 39.

8. The recombinant bacterium of claim 1, wherein the lycopene 0-cyclase protein comprises a sequence at least 80% identical to SEQ ID NO: 45 or SEQ ID NO: 63.

9. The recombinant bacterium of claim 1, wherein the lycopene e-cyclase protein comprises a sequence at least 80% identical to SEQ ID NO: 51.

10. The recombinant bacterium of claim 1, wherein one or more of the nucleic acid encoding a cytochrome P450 monooxygenase GYP97A protein or the nucleic acid encoding a cytochrome P450 monooxygenase CYP97B protein; the nucleic acid encoding a cytochrome P450 monooxygenase CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene P-cyclase protein; and the nucleic acid encoding a lycopene s-cyclase protein is integrated in a chromosome in the bacterium or the yeast cell.

11. The recombinant bacterium of claim 10, wherein one or more of the nucleic acid encoding a cytochrome P450 monooxygenase CYP97A protein or the nucleic acid encoding a cytochrome P450 monooxygenase CYP97B protein; the nucleic acid encoding a cytochrome P450 monooxygenase CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene P-cyclase protein; and the nucleic acid encoding a lycopene 6-cyclase protein is operably expressed from an inducible promoter present within the chromosome.

12. The recombinant bacterium of claim 10, wherein the chromosome in the bacterium or yeast cell further comprises a selection marker.

13. The recombinant bacterium of claim 1, wherein one or more of the nucleic acid encoding a cytochrome P450 monooxygenase CYP97A protein or the nucleic acid encoding a cytochrome P450 monooxygenase CYP97B protein; the nucleic acid encoding a cytochrome P450 monooxygenase CYP97C protein; the nucleic acid encoding a geranylgeranyl pyrophosphate synthase protein; the nucleic acid encoding a phytoene synthase protein; the nucleic acid encoding a phytoene desaturase protein; the nucleic acid encoding a lycopene p-cyclase protein; and the nucleic acid encoding a lycopene e-cyclase protein is present within a vector.

14. The recombinant bacterium of claim 13, wherein the vector is a plasmid.

15. The recombinant bacterium of claim 13, wherein the vector is an artificial chromosome.

16. The recombinant bacterium of claim 13, wherein the vector comprises at least one inducible promoter sequence.

17. The recombinant bacterium of claim 13, wherein the vector comprises at least one selection marker.

18. A method of producing lutein, the method comprising culturing a recombinant bacterium of claim 1 under conditions that allow for the production of lute in.

19. The method of claim 18, further extracting the lutein from the bacterial cell or yeast cell.

20. The method of claim 18, wherein the bacterium is cultured in a liquid medium.

21. The method of claim 20, further comprising isolating lutein from the liquid medium.

22. A method of generating a recombinant bacterium, the method comprising introducing a nucleic acid encoding a CYP97A protein comprising a sequence at least 80% identical to SEQ ID NO: 1 or a nucleic acid encoding a CYP97B protein comprising a sequence at least 80% identical to SEQ ID NO: 3; a nucleic acid encoding a CYP97C protein comprising a sequence at least 80% identical to SEQ ID NO: 5; a nucleic acid encoding a geranylgeranyl pyrophosphate synthase protein; a nucleic acid encoding a phytoene synthase protein; a nucleic acid encoding a phytoene desaturase protein; a nucleic acid encoding a lycopene P-cyclase protein; and a nucleic acid encoding a lycopene e-cyclase protein.

23. The method of claim 22, further comprising introducing a nucleic acid encoding a D-1-deoxyxylulose 5-phosphate synthase protein; and/or a nucleic acid encoding an isopentenyl pyrophosphate isomerase protein.

24. The method of claim 22, wherein the introducing is performed by transformation.

* * * * *

UNITED STATES PATENT AND TRADEMARK OFFICE
CERTIFICATE OF CORRECTION

PATENT NO. : 10,059,974 B2
APPLICATION NO. : 14/377041
DATED : August 28, 2018
INVENTOR(S) : Eleanore T. Wurtzel et al.

Page 1 of 3

It is certified that error appears in the above-identified patent and that said Letters Patent is hereby corrected as shown below:

In the Specification

Column 34, Line 26:
Now reads: "encodes that encodes"
Should read: --acid encodes--

Column 57, Line 17:
Now reads: "a CYP97 protein"
Should read: --a CYP97C protein--

Column 59, Line 24:
Now reads: "a CYP97 protein"
Should read: --a CYP97C protein--

In the Claims

Claim 1, Column 223, Line 43:
Now reads: "a lycopene |3-cyclase protein; and"
Should read: --a lycopene β-cyclase protein; and--

Claim 1, Column 223, Line 44:
Now reads: "a lycopene £-cyclase protein"
Should read: --a lycopene ε-cyclase protein,--

Claim 1, Column 223, Line 47:
Now reads: "SEP ID NO: 1,"
Should read: --SEQ ID NO: 1,"--

Signed and Sealed this
Third Day of September, 2019

Andrei Iancu
*Director of the United States Patent and Trademark Office*

CERTIFICATE OF CORRECTION (continued) Page 2 of 3
U.S. Pat. No. 10,059,974 B2

Claim 1, Column 223, Line 50:
Now reads: "SEP ID NO: 3, and"
Should read: --SEQ ID NO: 3, and"--

Claim 1, Column 223, Line 53:
Now reads: "SEP ID NO: 5."
Should read: --SEQ ID NO: 5.--

Claim 8, Column 224, Line 41:
Now reads: "lycopene 0-cyclase protein"
Should read: --lycopene β-cyclase protein--

Claim 9, Column 224, Line 44:
Now reads: "lycopene e-cyclase protein"
Should read: --lycopene ε-cyclase protein--

Claim 10, Column 224, Line 48:
Now reads: "GYP97A"
Should read: --CYP97A--

Claim 10, Column 224, Line 55:
Now reads: "lycopene P-cyclase protein;"
Should read: --lycopene β-cyclase protein;--

Claim 10, Column 224, Line 56:
Now reads: "lycopene s-cyclase protein"
Should read: --lycopene ε-cyclase protein--

Claim 11, Column 224, Line 67:
Now reads: "lycopene P-cyclase protein;"
Should read: --lycopene β-cyclase protein;--

Claim 11, Column 225, Line 1:
Now reads: "lycopene 6-cyclase protein"
Should read: --lycopene ε-cyclase protein--

Claim 13, Column 225, Line 14:
Now reads: "lycopene p-cyclase protein;"
Should read: --lycopene β-cyclase protein;--

Claim 13, Column 225, Line 15:
Now reads: "lycopene e-cyclase protein"
Should read: --lycopene ε-cyclase protein--

CERTIFICATE OF CORRECTION (continued)
U.S. Pat. No. 10,059,974 B2

Claim 18, Column 225, Line 27:
Now reads: "lute in."
Should read: --lutein--

Claim 22, Column 226, Line 18:
Now reads: "a lycopene P-cyclase"
Should read: --a lycopene β-cyclase--

Claim 22, Column 226, Line 19:
Now reads: "a lycopene e-cyclase."
Should read: --a lycopene ε-cyclase--